US009173964B2

(12) United States Patent
Hochberg et al.

(10) Patent No.: US 9,173,964 B2
(45) Date of Patent: Nov. 3, 2015

(54) DIPHTHERIA TOXIN FIRST OPEN READING FRAME OPERABLY LINKED TO AN H19 PROMOTER AND A DIPHTHERIA TOXIN SECOND OPEN READING FRAME OPERABLY LINKED TO AN IGF-II PROMOTER AS NUCLEIC ACID CONSTRUCT

(75) Inventors: Avraham Hochberg, Jerusalem (IL); Doron Amit, Northern Judea (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 568 days.

(21) Appl. No.: 12/738,620

(22) PCT Filed: Oct. 23, 2008

(86) PCT No.: PCT/IL2008/001405

§ 371 (c)(1), (2), (4) Date: Apr. 22, 2010

(87) PCT Pub. No.: WO2009/053982

PCT Pub. Date: Apr. 30, 2009

(65) Prior Publication Data

US 2010/0256225 A1 Oct. 7, 2010

Related U.S. Application Data

(60) Provisional application No. 60/982,442, filed on Oct. 25, 2007.

(51) Int. Cl.

| | |
|---|---|
| *C12N 15/00* | (2006.01) |
| *A61K 48/00* | (2006.01) |
| *C12N 15/85* | (2006.01) |

(52) U.S. Cl.

CPC ............ *A61K 48/0058* (2013.01); *C12N 15/85* (2013.01); *C12N 2830/001* (2013.01); *C12N 2830/008* (2013.01); *C12N 2830/20* (2013.01); *C12N 2840/20* (2013.01)

(58) Field of Classification Search

CPC ............... A61K 48/0058; C12N 15/85; C12N 2830/001; C12N 2830/008; C12N 2830/20; C12N 2840/20

See application file for complete search history.

(56) References Cited

U.S. PATENT DOCUMENTS

| | | | | |
|---|---|---|---|---|
| 5,955,273 | A | 9/1999 | Hochberg | 435/6 |
| 6,306,833 | B1 | 10/2001 | Hochberg | 514/44 |
| 2004/0082529 | A1 | 4/2004 | Hochberg | 514/44 |
| 2007/0190031 | A1* | 8/2007 | Sidhu et al. | 424/93.2 |

FOREIGN PATENT DOCUMENTS

| | | |
|---|---|---|
| WO | WO 99/18195 | 4/1999 |
| WO | WO 2004/024957 | 3/2004 |
| WO | WO 2004/031359 | 4/2004 |
| WO | WO 2007/007317 | 1/2007 |
| WO | WO 2007/034487 | 3/2007 |
| WO | WO 2008/087641 | 7/2008 |
| WO | WO 2008/087642 | 7/2008 |
| WO | WO 2008/099396 | 8/2008 |

OTHER PUBLICATIONS

Mahairas et al (PNAS, 96(17): 9739-9744, 1999).*

Brandenberger et al (Nat. Biotechnol. 22 (6), 707-716 (2004).*

Yu et al (Molecular, Therapy, 7(6): 827-838, 2003).*

Ariel, I. et al., "The Product of the Imprinted H19 Gene Is an Oncofetal RNA", J. Clin Pathol: Mol Pathol. , vol. 50, pp. 34-44 (1997).

Ariel, I. et al.,"The Imprinted H19 Gene Is a Marker of Early Recurrence in Human Bladder Carcinoma", J. Clin Pathol: Mol Pathol., vol. 53, pp. 320-323 (2000).

Ayesh, B. et al., "Inhibition of Tumor Growth by DT-A Expressed Under the Control of IGF2 P3 and P4 Promotor Sequences". Molecular Therapy, vol. 7, No. 4, pp. 535-541 (2003).

Bennett, M. J. et al., "Refined Structure of Dimeric Diphtheria Toxin at 2.0 Angstrom Resolution", Protein Science, vol. 3, pp. 1444-1463 (1994).

Brannan, Camilynn I., "The Product of the H19 Gene May Function as an RNA", Molecular and Cellular Biology, vol. 10, No. 1, pp. 28-36 (1990).

Brunkow, Mary E. et al., "Ectopic Expression of the H19 Gene in Mice Causes Prenatal Lethality", Genes & Development, vol. 5, pp. 1092-1101 (1991).

Davis, Robert L. et al, "Expression of a Single Transfected cDNA Converts Fibroblasts to Myoblasts", Cell, vol. 51, pp. 987-1000 (1987).

De Groot, Nathan et al., "Genetic Imprinting in Human Embryogenesis H19 and IGF2 Gene Expression", Trophoblast Research, vol. 8, pp. 285-302 (1994).

Glassman, Michael L. et al., "Relaxation of Imprinting in Carcinogenesis", Cancer Genet Cytogenet, vol. 89, pp. 69-73 (1996).

Hassan, A. B.et al., "The Insulin-Like Growth Factor System as a Therapeutic Target in Colorectal Cancer", . Review, Annals of Oncology, vol. 13, pp. 349-356 (2002).

Holthuizen, P. et al., "Transcriptional Regulation of the Major Promoters of the Human IGF-II Gene", Molecular Reproduction and Development, vol. 35, pp. 391-393 (1993).

Hudson, Thomas H. et al., "Quantal Entry of Diphtheria Toxin to the Cytosol", The Journal of Biological Chemistry, vol. 260, No. 5, pp. 2675-2680 (1985).

(Continued)

*Primary Examiner* — Deborah Crouch
*Assistant Examiner* — Magdalene Sgagias
(74) *Attorney, Agent, or Firm* — Winston & Strawn LLP

(57) ABSTRACT

The present invention relates to the field of cancer treatment, particularly to a novel constructs useful for treating tumors expressing H19 and/or IGF-II. More specifically, the invention provides compositions and methods utilizing a nucleic acid construct enabling expression of a cytotoxic gene product directed by more than one tumor specific promoter.

15 Claims, 34 Drawing Sheets

(56) References Cited

OTHER PUBLICATIONS

Hurst, Laurence D. et al., "Imprinted Genes Have Few and Small Introns", Nature Genetics, vol. 12, pp. 234-237 (1996).
Ogawa, Osamu et al., "Relaxation of Insulin-Like Growth Factor II Gene Imprinting Implicated in Wilm's Tumour", Nature, vol. 362, pp. 749-751, (1993).
Ohana, Patricia et al., "Use of H19 Regulatory Sequences for Targeted Gene Therapy in Cancer", International Journal of Cancer, vol. 98, pp. 645-650 (2002).
Ohana, Patricia et al., "Regulatory Sequences of H19 and IGF2 Genes in DNA-Based Therapy of Colorectal Rat Liver Metastases", The Journal of Gene Medicine, vol. 7, pp. 366-374 (2005).
Pachnis, Vassilis et al., "Locus Unlinked to Alpha-Fetoprotein Under the Control of the Murine *raf* and *Rif* Genes", Proc. Natl. Acad Sci., vol. 81, pp. 5523-5527 (1984).
Poirier, Francoise et al., "The Murine H19 Gene Is Activated During Embryonic Stem Cell Differentiation In Vitro and at the Time of Implantation in the Developing Embryo", Development, vol. 113, pp. 1105-1114 (1991).
Raab, Gerhard et al.,"Heparin-Binding EGF-Like Growth Factor", Biochimica et Biophysica Acta, BBA, vol. 1333, pp. F179-F199 (1997).
Rachmilewitz, J. et al., Transcription of the H19 Gene in Differentiating Cytotrophoblasts From Human Placenta, Molecular. Reproduction. and Development, vol. 32, pp. 196-202 (1992).
Rainier, Shirley et al., "Relaxation of Imprinted Genes in Human Cancer", Nature, vol. 362, pp. 747-749 (1993).
Seo, Jin Hye et al., "Different Protein-Binding Patterns in the P3 Promoter Region of the Human Insulin-Like Growth Factor II Gene in the Human Liver Cirrhosis and Hepatocellular Carcinoma Tissues", J. Korean Med Sci., vol. 13, pp. 171-178 (1998).
Zdanovskaia, Marina V. et al.,"Diphtheria Toxin NAD Affinity and ADP Ribosyltransferase Activity are Reduced at Tryptophan 153 Substitutions for Alanine or Phenylalanine", Research in Microbiology, vol. 151, pp. 557-562 (2000).
Zhang, Lin et al., "Gene Expression Profiles in Normal and Cancer Cells", Science, vol. 276, pp. 1268-12772 (1997).
Zhou, Hong-Ke et al., "Construction of a Plasmid Vector of Fused Protein Genes Driven by Human Insulin-Like Growth Factor II P3 Promoter", Zhonghua Yi Xue Za Zhi, vol. 86 (2), pp. 106-110 (translated abstract) (2006).
International Search Report and Written Opinion of PCT/IL2008/001405 mailed Mar. 23, 2009.
(English translation of the relevant part p. 123) Singer, M. and Berg, P.(1998), Genes and Genomes: A Changing Perspective. University Science Books, Mill Valley, Calif., Mir, Moscow, vol. 1, pp. 123.
(English translation of Office Action) Corresponding Russian Patent Application No. 2010119173 Office Action dated Jul. 6, 2012.
Molnar et al., (2004) Factors Influencing the Efficacy, Longevity, and Safety of Electroporation-Assisted Plasmid-Based Gene Transfer Into Mouse Muscles. Molecular Therapy, vol. 10, No. 3, pp. 447-455.
Yin et al., (2005) Investigations of the effect of DNA size in transient transfection assay using dual luciferase system. Analytical Biochemistry, vol. 346(2), pp. 289-294.

\* cited by examiner

SEQUENCE LISTING

<160> NUMBER OF SEQ ID NOS: 24

<210> SEQ ID NO 1
<211> LENGTH: 830
<212> TYPE: DNA
<213> ORGANISM: Homo sapiens

<400> SEQUENCE: 1
ctgcagggcc ccaacaaccc tcaccaaagg ccaaggtggt gaccgacgga cccacagcgg      60
ggtggctggg ggagtcgaaa ctcgccagtc tccactccac tccaaccgt ggtgccccac     120

```
gcgggcctgg gagagtctgt gaggccgccc accgcttgtc agtagagtgc gcccgcgagc    180
cgtaagcaca gcccggcaac atgcggtctt cagacaggaa agtggccgcg aatgggaccg    240
gggtgcccag cggctgtggg gactctgtcc tgcggaaacc gcggtgacga gcacaagctc    300
ggtcaactgg atgggaatcg gcctgggggg ctggcaccgc gcccaccagg ggtttgcgg     360 cacttccctc tgcccctcag caccccaccc ctactctcca ggaacgtgag gtctgagccg    420
tgatggtggc aggaaggggc cctctgtgcc atccgagtcc caggacccg cagctggcc     480 cccagccatg tgcaaagtat gtgcagggcg ctggcaggca gggagcagca ggcatggtgt    540
cccctgaggg gagacagtgg tctgggaggg agaggtcctg gaccctgagg gaggtgatgg    600
ggcaatgctc agccctgtct ccggatgcca aggagggggt gcggggaggc cgtctttgga    660
gaattccagg atgggtgctg ggtgagagag acgtgtgctg gaactgtcca gggcggaggt    720
gggccctgcg ggggccctcg ggagggccct gctctgattg gccggcaggg caggggcggg    780
aattctggcg ggccacccca gttagaaaaa gcccgggcta ggaccgagga              830
```

```
<210> SEQ ID NO 2
<211> LENGTH: 833
<212> TYPE: DNA
<213> ORGANISM: Homo sapiens

<400> SEQUENCE: 2
gacaaccctc accaagggcc aaggtggtga ccgacggacc cacagcgggg tggctggggg     60
agtcgaaact cgccagtctc cactccactc ccaacgtgg tgcccacgc gggcctggga    120 gagtctgtga ggccgcccac cgcttgtcag tagagtgcgc ccgcgagccg taagcacagc    180
ccggcaacat gcggtcttca gacaggaaag tggccgcgaa tgggaccggg gtgcccagcg    240
gctgtgggga ctctgtcctg cggaaaccgc ggtgacgagc acaagctcgg tcaactggat    300
gggaatcggc tgggggggct ggcaccgcgc ccaccagggg tttgcggca cttccctctg    360 cccctcagca ccccacccct actctccagg aacgtgagtt ctgagccgtg atggtggcag    420 gaagggggccc tctgtgccat ccgagtcccc agggacccgc agctggcccc cagccatgtg    480
caaagtatgt gcagggcgct ggcaggcagg agcagcagg catggtgtcc cctgagggga    540
gacagtggtc tgggagggag aagtcctggc cctgagggag gtgatggggc aatgctcagc    600
cctgtctccg gatgccaaag gagggtgcg ggaggccgt cttttggagaa ttccaggatg    660 ggtgctgggt gagagagacg tgtgctggaa ctgtccaggg cggaggtggg ccctgcgggg    720
gccctcggga gggccctgct ctgattggcc ggcaggcag gggcgggaat tctgggcggg    780
gccaccccag ttagaaaaag cccgggctag gaccgaggag caggggtgagg gag         833
```

```
<210> SEQ ID NO 3
<211> LENGTH: 877
<212> TYPE: DNA
<213> ORGANISM: Homo sapiens

<400> SEQUENCE: 3
caaggacatg gaatttcgga ccttctgtcc ccaccctctc tgctgagcct aggaacctct     60
gagcagcagg aaggccttgg gtctagagcc tagaaatgga ccccacgtc cacctgccca    120 gcctagaccc ccagcattga agggtggtca gacttcctgt gagaggaagc cactaagcgg    180
gatggacacc atcgcccact ccacccggcc ctgcccagcc ctgccagtc agcccagtc     240 cagcccagcc ctgcccttcc cagccctgcc cagcccagct catccctgcc ctacccagcc    300
cagccctgtc ctgccctgcc cagcccagcc cagcccagcc ctgccctgcc ctgccctgcc    360
```

| | |
|---|---|
| cttcccagcc ctgaccttcc cagccctgcc cagcccagct catccctgcc ctacccagct | 420 |
| cagccctgcc ctgccctgcc ctgccctgcc cagcccctacc cagcccagcc ctgccctgcc | 480 |
| ctgcccagct cagccctgcc caccccagcc cagcccagcc cagcatgcgt tctctggatg | 540 |
| gtgagcacag gcttgacctt agaaagaggc tggcaacgag ggctgaggcc accaggccac | 600 |
| tgggtgctca cgggtcagac aagcccagag cctgctcccc tgccacgggt cggggctgtc | 660 |
| accgccagca tgctgtggat gtgcatggcc tcagggctgc tggctccagg ctgccccgc | 720 |
| cctggctccc gaggccaccc ctcttatgcc atgaaccctg tgccacaccc acctctgagc | 780 |
| tgtccccgct cctgccgcct gcaccccctg agcagccccc tgtgtgtttc atgggagtct | 840 |
| tagcaaggaa ggggagctcg aattcctgca gcccggg | 877 |

```
<210> SEQ ID NO 4
<211> LENGTH: 1960
<212> TYPE: DNA
<213> ORGANISM: Homo sapiens
<220> FEATURE:
<221> NAME/KEY: misc_feature
<222> LOCATION: (1016)..(1016)
<223> OTHER INFORMATION: n is a, c, g, or t
<220> FEATURE:
<221> NAME/KEY: misc_feature
<222> LOCATION: (1126)..(1126)
<223> OTHER INFORMATION: n is a, c, g, or t

<400> SEQUENCE: 4
```

| | |
|---|---|
| ccgggtaccg agctcccagg aagataaatg atttcctcct ctctagagat gggggtggga | 60 |
| tctgagcact cagagccaag ggcgcagtgg gtccgggcgg gggccctcct cggccctccc | 120 |
| aacatggggg ccaggaggtc agcccctcaa cctggacccc ggctgggtct cagggaatgg | 180 |
| tctcccccag tggcccagct tgcttgtgtt ttcagatggg tgtgcatggg tgtgtgtgtg | 240 |
| tgtgtgtgtg tgtgtgtgtg tgtgtgtgtg tgtgatgcct gacaagcccc agagagccaa | 300 |
| agacctgagt ggagatcttg tgacttctca aaagggggat tggaaggttc gagaaagagc | 360 |
| tgtggtcagc cttgctctcc cttaaggctg tggtaaccac actaggcata gcataggcct | 420 |
| gcgcccgtc cctccttccc tcctccgcgc ctctcctttc tctttctccc ccctctaccc | 480 |
| cgctccctgg cctgctcctg gtgacaccgt tggccccctt ccagggctga gggaagccag | 540 |
| cgggggcccc ttcctgaaag cccacctgca ggccggcttg ctgggaaggg gctgctctcg | 600 |
| cagaggctcc cgcccgccct gcagccgttt cctggaagca gtcgctgtgg gtattctgtt | 660 |
| ccttgtcagc actgtgcttg caaagaaagc agacactgtg ctccttgtcc ttagggagcc | 720 |
| ccgctccatc acccaacacc tggctggaca caggcgggag gccgggtccg cggggagcgg | 780 |
| cgcggggctg gggccggacc attaaacaca cacgggcgcc aggcactgca ggctcctcct | 840 |
| cctcctcctg cccagcgcct ctgctcacag gcacgtgcca agcccctagg ccaggaggcc | 900 |
| agcagtgggt gcagaacaag ctcctgggaa ggggtgcag gcggaccccc ggggagaag | 960 |
| ggctggcagg gctgtggggg acgctgaccg tgggccccac gttgcagaaa actggntgcc | 1020 |
| tggctggaag atgggggaga tgccaagcct ctgaggcagc acgagcaggg tgcatggagg | 1080 |
| ccggggcgcg gggaggctgc actgcagcat gcaccccaaa gcccanaggg agtgagacc | 1140 |
| aggccctgga atcgagaagt agaaaggcgg cttggaggcc tcggaaccgg ctgacctcca | 1200 |
| acagagtggg tctccagcct ggctctgccc tgccgcaggt cccctcccct cattaccagg | 1260 |
| cctagagcct ccagtcccgg tggccccag cccgagggtg aacggcctca ccctgggtcg | 1320 |
| tgggacagag ggcacgttca tcaagagtgg ctcccaaggg acacgtggct gtttgcagtt | 1380 |

| | |
|---|---|
| cacaggaagc attcgagata aggagcttgt tttcccagtg ggcacggagc cagcagggg | 1440 |
| gctgtggggc agcccagggt gcaaggccag gctgtgggc tgcagctgcc ttgggcccca | 1500 |
| ctcccaggcc tttgcgggag gtgggaggcg ggaggcggca gctgcacagt ggccccaggc | 1560 |
| gaggctctca gccccagtcg ctctccgggt gggcagccca agagggtctg gctgagcctc | 1620 |
| ccacatctgg gactccatca cccaacaact taattaaggc tgaatttcac gtgtcctgtg | 1680 |
| acttgggtag acaaagcccc tgtccaaagg ggcagccagc ctaaggcagt ggggacggcg | 1740 |
| tgggtggcgg gcgacggggg agatggacaa caggaccgag ggtgtgcggg cgatggggga | 1800 |
| gatggacaac aggaccgagg gtgtgcggc gatgggggag atggacaaca ggaccgaggg | 1860 |
| tgtgcgggac acgcatgtca ctcatgcacg ccaatggggg gcgtgggagg ctggggagca | 1920 |
| gacagactgg gctgggctgg gcgggaagga cgggcagatg | 1960 |

<210> SEQ ID NO 5
<211> LENGTH: 4085
<212> TYPE: DNA
<213> ORGANISM: Homo sapiens
<220> FEATURE:
<221> NAME/KEY: misc_feature
<222> LOCATION: (1016)..(1016)
<223> OTHER INFORMATION: n is a, c, g, or t
<220> FEATURE:
<221> NAME/KEY: misc_feature
<222> LOCATION: (1126)..(1126)
<223> OTHER INFORMATION: n is a, c, g, or t
<220> FEATURE:
<221> NAME/KEY: misc_feature
<222> LOCATION: (2194)..(2194)
<223> OTHER INFORMATION: n is a, c, g, or t
<220> FEATURE:
<221> NAME/KEY: misc_feature
<222> LOCATION: (3235)..(3235)
<223> OTHER INFORMATION: n is a, c, g, or t

<400> SEQUENCE: 5

| | |
|---|---|
| ccgggtaccg agctcccagg aagataaatg atttcctcct ctctagagat gggggtggga | 60 |
| tctgagcact cagagccaag ggcgcagtgg gtccgggcgg gggccctcct cggccctccc | 120 |
| aacatggggg ccaggaggtc agcccctcaa cctggacccc ggctgggtct cagggaatgg | 180 |
| tctcccccag tggcccagct tgcttgtgtt ttcagatggg tgtgcatggg tgtgtgtgtg | 240 |
| tgtgtgtgtg tgtgtgtgtg tgtgtgtgtg tgtgatgcct gacaagcccc agagagccaa | 300 |
| agacctgagt ggagatcttg tgacttctca aaaggcggat tggaaggttc gagaaagagc | 360 |
| tgtggtcagc cttgctctcc cttaaggctg tggtaaccac actaggcata gcataggcct | 420 |
| gcgccccgtc cctccttccc tcctccgcgc ctctcctttc tctttctccc ccctctaccc | 480 |
| cgctccctgg cctgctcctg gtgacaccgt tggcccccct tccaggctga gggaagccag | 540 |
| cgggggcccc ttcctgaaag cccacctgca ggccggcttg ctgggaaggg gctgctctcg | 600 |
| cagaggctcc cgcccgccct gcagccgttt cctggaagca gtcgctgtgg gtattctgtt | 660 |
| ccttgtcagc actgtgcttg caaagaaagc agacactgtg ctccttgtcc ttagggagcc | 720 |
| ccgctccatc acccaacacc tggctggaca caggcgggag gccgggtccg cggggagcgg | 780 |
| cgcggggctg gggccggacc attaaacaca cacgggcgcc aggcactgca ggctcctcct | 840 |
| cctcctcctg cccagcgcct ctgctcacag gcacgtgcca agccctagg ccaggaggcc | 900 |
| agcagtgggt gcagaacaag ctcctggaa ggggtgcag gcggacccc cggggagaag | 960 |
| ggctggcagg gctgtggggg acgctgaccg tgggccccac gttgcagaaa actggntgcc | 1020 |
| tggctggaag atgggggaga tgccaagcct ctgaggcagc acgagcaggg tgcatggagg | 1080 |

```
ccggggcgcg gggaggctgc actgcagcat gcaccccaaa gcccanaggg agtggagacc    1140
aggccctgga atcgagaagt agaaaggcgg cttggaggcc tcggaaccgg ctgacctcca    1200
acagagtggg gccggccctg gaggcaaaga ggtgcccggg gtccggccct gcctggggga    1260
gctatgtgtc atgggcaagc cacaggatat gtagcccgct ctgagcctat ggacccaggg    1320
cagggctgca aggcagggca ggggagacag cacggggag caaggagcag agaggggcc     1380
tcaggctctc ccaggaggaa cattctcccg acaggaggaa gagacggccc agggtgact    1440
gtggggagcc atggtggcag ctggggtcgt ggcagatggg agagaggctg gcgaggtgaa    1500
ggtgcagggg tcaggctctc tggggcccaca tgcctgtggg agcaggcagg cccagggctc    1560
tccgccactc cccactcccg cttggctcat aggctgggcc caagggtggg gtgggatgag    1620
caggagatgg ggcccagggg gcaagcaggg ccccaaagac atttagaaaa accggtttat    1680
gcaggcagca ttcagagcag gcggcgtgcg tggcggggggcc cctgggagca cagagaggca   1740
cacgtagggc ccccgagggg ctccccattg gccggcagtg acatcacccc tgtgtcaaca    1800
gtgatgtctg cagctccggc cagccagggt ttatggagcg agaccagcc cggcctgggc     1860
cctcactccc caggcccaca cactagccca ctgttcaggg tccggggtgg cggcatggcc    1920
tgggggtcct ggcaccgctg ctcctctgcc caccctaact tccggcatc gcggctgccc     1980
cctctgagcg tccccaacca gtaagtgtgg ggcccagcag gcctgccgtc ctcctcctct    2040
tcccctctag agaaaacgt ggaggtcctg ggctggggg cgctcatagc cctgtgacac      2100
aggtgcatgg ggtcaggggt cccagaatgg cccctgggaa ggacctcagc tgggccggcg    2160
gctctaggct tcaggggtct gtctgcacag gggntagccc ctcccagacc tctgtgaagc    2220
cagtacgggc ctcccctccc tgccccgtgc tctgtccggt gcttcctgga ctgcactgcg    2280
ggccactggt gagagggtgg acagggaagg gccgccgtgg tgcctgttcc tgcccacctg    2340
gctgtgtggt cccctccaag tagggacaac ccttctgagg gcttgggggc accctgggt     2400
tgccagggc tccagagcc ctgtgagccc ctgggggtc tggcctgatg ccccctcca       2460
cgtccagggc cggctgtggc ccagaacccc agcttcccag caggccggtg tgcggtggtg    2520
acccaggaga ggcctcgcct ccactgaggg gccaccgacc tctgtcagac cacagagacc    2580
cccaaggagt ctgaaggctg gagacccggg gctgggacca ggtgggactt tcccacggag    2640
ccgtccccag gcccagctgg ggacacgtcc cccttctctc cagacacacc ctgcctgcca    2700
ccaggacaca ccggcctgtt gggggtctct tttaagtgct tgccactctg aggtgactgt    2760
ccctttccaa agaggtttct ggggcccagg tgggatgcgt cggcctgagc aggaggatct    2820
gggccgccag gggctgggga ctgtctcctg ggaaggaag cgcctgggag cgtgtgtgct     2880
gacccaggac catccaggga ggcccgtctg tggggcaagc gggaagggag cggctggaga    2940
ggcttggccg ccccgccct gcctcccatt ccttagctcc atgcctgtca acctctgtca    3000
cccagtgagt gatgtccagg ggccctggaa aggtcacagc atgtttgagc ggggtgagag    3060
agaggggaaa ggcgggggcg gggaaaagta cgtggaggaa gctttaggcc caaggaagga    3120
gacagggttc tgggagggag ggagccactg gggccgccgg gaaggtccct gcttgctgct    3180
gccacccaga accctcgcct cttagctagc ccccgcagcc ccagccttcc tggcntgtgg    3240
ccctctcccc catcccagg tgtcctgtgc aaccaggcct tggacccaaa ccctcctgcc     3300
ccctcctctc cctcctcacc ctcccaatgc agtggtctcc agcctggctc tgccctgccg    3360
caggtccccct cccctcatta ccaggcctag agcctccagt cccggtggcc cccagcccga    3420
gggtgaacgg cctcaccctg ggtcgtggga cagagggcac gttcatcaag agtggctccc    3480
```

-continued

```
aagggacacg tggctgtttg cagttcacag gaagcattcg agataaggag cttgttttcc   3540
cagtgggcac ggagccagca ggggggctgt ggggcagccc agggtgcaag gccaggctgt   3600
ggggctgcag ctgccttggg ccccactccc aggcctttgc gggaggtggg aggcgggagg   3660
cggcagctgc acagtggccc caggcgaggc tctcagcccc agtcgctctc cgggtgggca   3720
gcccaagagg gtctggctga gcctccccaca tctgggactc catcacccaa caacttaatt   3780
aaggctgaat ttcacgtgtc ctgtgacttg ggtagacaaa gcccctgtcc aaaggggcag   3840
ccagcctaag gcagtgggga cggcgtgggt ggcgggcgac gggggagatg gacaacagga   3900
ccgagggtgt gcgggcgatg ggggagatgg acaacaggac cgagggtgtg cgggcgatgg   3960
gggagatgga caacaggacc gagggtgtgc gggacacgca tgtcactcat gcacgccaat   4020
ggggggcgtg ggaggctggg gagcagacag actgggctgg gctgggcggg aaggacgggc   4080
agatg                                                               4085
```

<210> SEQ ID NO 6
<211> LENGTH: 591
<212> TYPE: DNA
<213> ORGANISM: Corynebacterium diphtheriae

<400> SEQUENCE: 6

```
atggatcctg atgatgttgt tgattcttct aaatcttttg tgatggaaaa cttttcttcg     60
taccacggga ctaaacctgg ttatgtagat tccattcaaa aaggtataca aaagccaaaa    120
tctggtacac aaggaaatta tgacgatgat tggaaagggt tttatagtac cgacaataaa    180
tacgacgctg cgggatactc tgtagataat gaaaacccgc tctctggaaa agctggaggc    240
gtggtcaaag tgacgtatcc aggactgacg aaggttctcg cactaaaagt ggataatgcc    300
gaaactatta agaaagagtt aggtttaagt ctcactgaac cgttgatgga gcaagtcgga    360
acggaagagt ttatcaaaag gttcggtgat ggtgcttcgc gtgtagtgct cagccttccc    420
ttcgctgagg ggagttctag cgttgaatat attaataact gggaacaggc gaaagcgtta    480
agcgtagaac ttgagattaa ttttgaaacc cgtggaaaac gtggccaaga tgcgatgtat    540
gagtatatgg ctcaagcctg tgcaggaaat cgtgtcaggc gatctttgtg a             591
```

<210> SEQ ID NO 7
<211> LENGTH: 196
<212> TYPE: PRT
<213> ORGANISM: Corynebacterium diphtheriae

<400> SEQUENCE: 7

```
Met Asp Pro Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110
```

```
Glu Pro Leu Met Glu Gln Val Gly Thr Glu Phe Ile Lys Arg Phe
        115                 120                 125
Gly Asp Gly Ala Ser Arg Val Val Leu Ser Leu Pro Phe Ala Glu Gly
    130                 135                 140
Ser Ser Val Glu Tyr Ile Asn Asn Trp Glu Gln Ala Lys Ala Leu
145                 150                 155                 160
Ser Val Glu Leu Glu Ile Asn Phe Glu Thr Arg Gly Lys Arg Gly Gln
                165                 170                 175
Asp Ala Met Tyr Glu Tyr Met Ala Gln Ala Cys Ala Gly Asn Arg Val
            180                 185                 190
Arg Arg Ser Leu
        195
```

<210> SEQ ID NO 8
<211> LENGTH: 891
<212> TYPE: DNA
<213> ORGANISM: Homo sapiens

<400> SEQUENCE: 8

```
gagctcggcc atgcaggtag gatttgagct gtgtttcccg ccctgatcct ctctcctctg      60
gcggccggag cctccgtagg ctccaagcct ggcccagatt cggcggcgca gccggccttc    120
cgcgcgtccg cacctagcgg gggctccggg gctccggcgc ggcaccgggg ggcgctcggg    180
atctggctga ggctccaagg cccgcgtggc cggctcctcc tgctggggca ggtggcggct    240
gcgcgccccg cccgagccca ggggccccct cagccgcaac aaccagcaag gaccccccga    300
ctcagcccca agccacctgc atctgcactc agacggggcg cacccgcagt gcagcctcct    360
ggtggggcgc tgggagcccg cctgcccctg cctgcccgga gaccccagct cacgagcaca    420
ggccgcccgg gcaccccaga aacccgggat ggggccctg aattctctag gacgggcatt     480
cagcatggcc ttggcgctct gcggctccct gccccccacc cagcctcgcc ccgcgcacc    540
ccccagcccc tgcgaccgcc gcccccccc cggggcccc agggcccag cccgcacccc      600
ccgccccgct cttggctcgg gttgcgggg cgggccgggg gcggggcgag ggctccgcgg    660
gcgcccattg gcgcgggcgc gaggccagcg gccccgcgcg gccctgggcc gcggctggcg    720
cgactataag agccgggcgt gggcgcccgc agttcgcctg ctctccggcg gagctgcgtg    780
aggcccggcc ggccccggcc ccccccttcc ggccgcccc gctcctggcc cacgcctgc     840
ccgcgctctg cccaccagcg cctccatcgg gcaaggcggc cccgcgtcga c             891
```

<210> SEQ ID NO 9
<211> LENGTH: 785
<212> TYPE: DNA
<213> ORGANISM: Homo sapiens

<400> SEQUENCE: 9

```
acttcccggt cggtctgtgg gtgcaggggg tgccgcctca catgtgtgat tcgtgccttg      60
cgggccctgg cctccggggt gctgggtaac gaggaggggc gcggagccgc agaagcccac    120
cctggtatgt tgacgcggtg ccagcgagac cgcgagagga agacggggt gggcggggcc     180
aggatggaga ggggccgagt tggcaggagt catggcagac gccacattcg cgacatctcc    240
cccacacccc ctctggctct gtccgcaaca tttccaaaca ggagtcccgg agagggggga    300
gaggggctgc tggtctgagg ctaagaaggg cagagccttc gacccggaga gaggccgcgg    360
cccctgccca gtgggcagcg tggaagtttc catacaagga ggtgggaagg accccccc     420
cccccttcac tgccctgtgc agagatgagc cgggggtgca ggatgggagc ccatggcact    480
```

| | |
|---|---:|
| tcgctacggg atggtccagg gctcccggtt gggggtgcag gagagaagag actggctggg | 540 |
| aggagggaga gggcgggagc aaaggcgcgg gggagtggtc agcagggaga ggggtggggg | 600 |
| gtagggtgga gcccgggctg ggaggagtcg gctcacacat aaaagctgag gcactgacca | 660 |
| gcctgcaaac tggacattag cttctcctgt gaaagagact tccagcttcc tcctcctcct | 720 |
| cttcctcctc ctcctcctgc cccagcgagc cttctgctga gctgtagggg gatcttctag | 780 |
| agtcg | 785 |

<210> SEQ ID NO 10
<211> LENGTH: 8837
<212> TYPE: DNA
<213> ORGANISM: Homo sapiens
<220> FEATURE:
<221> NAME/KEY: misc_feature
<222> LOCATION: (238)..(239)
<223> OTHER INFORMATION: n is a, c, g, or t
<220> FEATURE:
<221> NAME/KEY: misc_feature
<222> LOCATION: (733)..(733)
<223> OTHER INFORMATION: n is a, c, g, or t
<220> FEATURE:
<221> NAME/KEY: misc_feature
<222> LOCATION: (3178)..(3203)
<223> OTHER INFORMATION: n is a, c, g, or t
<220> FEATURE:
<221> NAME/KEY: misc_feature
<222> LOCATION: (7393)..(7393)
<223> OTHER INFORMATION: n is a, c, g, or t

<400> SEQUENCE: 10

| | |
|---|---:|
| cccaaccccg cgcacagcgg gcactggttt cgggcctctc tgtctcctac gaagtccgta | 60 |
| gagcaactcg gatttgggaa atttctctct agcgttgccc aaacacactt gggtcggccg | 120 |
| cgcgccctca ggacgtggac agggagggct tcccgtgtc caggaaagcg accgggcatt | 180 |
| gcccccagtc tcccccaaat ttgggcattg tccccgggtc ttccaacgga ctgggcgnng | 240 |
| ctcccggaca ctgaggactg gccccgggt ctcgctcacc ttcagcagcg tccaccgcct | 300 |
| gccacagagc gttcgatcgc tcgctgcctg agctcctggt gcgcccgcgg acgcagcctc | 360 |
| cagcttcgcg gtgagctccc cgccgcgccc atcccctccg cctctgcgcc cctgaccggc | 420 |
| tctcggcccg catctgctgc tgtcccgccg gtgctggcgc tcgtccgctg cgccggggag | 480 |
| gccggcgtgg ggcgcgggac acggctgcgg acttgcggct gcgctgcgct cgctcctgct | 540 |
| gggcgccccg aaatccgcgc cactttcgtt tgctcattgc aaagatctca tttgtgggga | 600 |
| aagcggctgg agggtcccaa agtggggcgg gcagggggct ggggcgaggg acgcggagga | 660 |
| gaggcgctcc cgccgggcgg taaagtgcct ctagcccgcg ggcctaggac tccgccggga | 720 |
| gggcgcgcga gngcgaagt gattgatggc ggaagcgggg gggcaagggg ggcagggggg | 780 |
| cgcgggattc cgccggcgac cccttcccct tggctaggct taggcggcgg ggggctggcg | 840 |
| gggtgcggga ttttgtgcgt ggtttttgac ttggtaaaaa tcacagtgct ttcttacatc | 900 |
| gttcaaactc tccaggagat ggtttcccca gaccccaaa ttatcgtggt ggcccccgag | 960 |
| accgaactcg cgtctatgca agtccaacgc actgaggacg gggtaaccat tatccagata | 1020 |
| ttttgggtgg gccgcaaagg cgagctactt agacgcaccc cggtgagctc ggccatgcag | 1080 |
| gtaggatttg agctgtgttt cccgccctga tcctctctcc tctggcggcc ggagcctccg | 1140 |
| taggctccaa gcctggccca gattcggcgg cgcagccggc cttccgcgcg tccgcaccta | 1200 |
| gcgggggctc cggggctccg gcgcggcacc gggggggcgct cgggatctgg ctgaggctcc | 1260 |
| aaggcccgcg tggccggctc ctcctgctgg ggcaggtggc ggctgcgcgc cccgcccgag | 1320 |

```
cccaggggcc ccctcagccg caacaaccag caaggacccc ccgactcagc cccaagccac    1380
ctgcatctgc actcagacgg ggcgcacccg cagtgcagcc tcctggtggg gcgctgggag    1440
cccgcctgcc cctgcctgcc cggagacccc agctcacgag cacaggccgc ccgggcaccc    1500
cagaaacccg ggatgggggcc cctgaattct ctaggacggg cattcagcat ggccttggcg   1560
ctctgcggct ccctgccccc cacccagcct cgccccgcg caccccccag ccctgcgac     1620 cgccgcccc ccccccgggg ccccagggcc ccagcccgca ccccccgccc cgctcttggc    1680
tcgggttgcg ggggcgggcc gggggcgggg cgagggctcc gcgggcgccc attggcgcgg   1740
gcgcgaggcc agcggccccg cgcggccctg ggccgcggct ggcgcgacta taagagccgg    1800
gcgtgggcgc ccgcagttcg cctgctctcc ggcggagctg cgtgaggccc ggccggcccc    1860 ggccccccc ttccggccgc ccccgcctcc tgcccacgc ctgccgcgc tctgcccacc      1920 agcgcctcca tcgggcaagg cggccccgcg tcgacgccgc ccgctgcctc gctgctgact   1980
cccgtcccgg gcgccgtccg cggggtcgcg ctccgccggg cctgcggatt ccccgccgcc   2040
tcctcttcat ctacctcaac tcccccccatc cccgcttcgc ccgaggaggc ggttcccccc  2100
gcaggcagtc cggctcgcag gccgccggcg ttgtcacccc ccccgcgctc ccctccagc    2160 cctccccccg gcgcgcagcc tcgggccgct ccccttccg cgctgcgtcc cggagcggcc    2220
ccggtgccgc caccgcctgt cccctcccg aggcccgggc tcgcgacggc agagggctcc    2280
gtcggcccaa accgagctgg gcgccgcgg tccgggtgca gcctccactc cgcccccag     2340 tcaccgcctc ccccggcccc tcgacgtggc gcccttccct ccgcttctct gtgctccccg   2400
cgcccctctt ggcgtctggc cccggccccc gctctttctc ccgcaacctt ccttcgctc    2460 cctcccgtcc ccccagctc ctagcctccg actccctccc ccctcacgc ccgccctctc     2520 gccttcgccg aaccaaagtg gattaattac acgctttctg tttctctccg tgctgttctc   2580
tcccgctgtg cgcctgcccg cctctcgctg tcctctctcc ccctcgccct ctcttcggcc   2640
cccccctttc acgttcactc tgtctctccc actatctctg ccccccctcta tccttgatac  2700 aacagctgac ctcatttccc gatacctttt cccccccgaa aagtacaaca tctggcccgc   2760
cccagcccga agacagcccg tcctccctgg acaatcagac gaattctccc ccccccccca   2820
aaaaaaagcc atcccccgc tctgcccgt cgcacattcg gccccgcga ctcggccaga     2880 gcggcgctgg cagaggagtg tccggcagga gggccaacgc ccgctgttcg gtttgcgaca   2940
cgcagcaggg aggtgggcgg cagcgtcgcc ggcttccagg taagcggcgt gtgcgggccg   3000
ggccggggcc ggggctgggg cggcgcgggc ttgcggcgac gcccggccct tcctccgccc   3060
gctcccggcc cggggcctgc ggggctcggc ggggcggctg agccgggggg gaggaggagg   3120
aggaggagga ggacggacgg ctgcgggtcc cgttccctgc gcggagcccg cgctaccnnn   3180 nnnnnnnnn nnnnnnnnnn nnngacgtcc ccgctgaagg gggtcggtct gtgggtgcag   3240
ggggtgccgc ctcacatgtg tgattcgtgc cttgcgggcc ctggcctccg gggtgctggg   3300
taacgaggag gggcgcggag ccgcagaagc ccaccctggt gtcgttgacg ccggtgccag   3360
cgagaccgcg agaggaagac gggggcgggc ggggccagga tggagagggg ccgagttggc   3420
aggagtcatg gcagacgcca cactcgcgac catctcccc acaccctct ggcctctgtc     3480 cgcaacattt ccaaacagga gtcccgggag aggggagag gggctgctgg tctgaggcta    3540
agaagggcag agccttcgac ccggagagag gccgcggccg cctgcccag tggcaacgtt    3600 gaagttttcc atacaacgga ggtcgggaag gagaccccc cccccccttca ctgccctgtg   3660 aagagatgag ccggggggtgc aggatgggag cccatggcac ttcgctacgg gatgtccagg  3720
```

```
gctccggttg ggggtgcagg agagaagaga ctggctggga ggagggagag ggcgggagca    3780
aaggcgcggg ggtgtggtca gagggagagg ggtgggggtt aggtggagcc cgggctggga    3840
ggagtcggct cacacataaa actgaggcac tgaccagcct gcaaactgga tattagcttc    3900
tcctgtgaaa gagacttcca gcttcctcct cctcctcttc ctcctcctcc tcctgcccca    3960
gcgagccttc tgctgagctg taggtaacca gggctgtgga gtgaaggacc cccgctgcca    4020
tcccactcca gcctgaggca gggcagcagg gggcacggcc cacgcctggg cctcgggccc    4080
tgcagccgcc agcccgctgc ctctcggaca gcacccccct cccctcttt tcctctgсссc    4140
tgcccccacc tggcgtctct gctccctcac ctgctccttc cctttctgtt ccttcccttc    4200
ggccccctcc ttgcccagct caggactttt cctgggccct cacctgctcc gcaccgctgc    4260
atgcttcctg tcctgctttc tgccggtccc ctgacccgga cctccaagcg cagagtggtg    4320
gggcttgttg cggaagcgcg gcgagggcta gagtggccag ctggcggagt gtgctcttag    4380
aatttggaag ggggtggcag aggggcggt gagaggactg ccagggtcc gccatgtcaa    4440
ggagatgacc aaggaggctt tcagatcctc ggcgcagtcg cccactagtc tttagagagg    4500
gcatgcaaag ttgtgcttct gtcccactgc ctgctcagtc gctcacataa tttattgcat    4560
caaaaactcc cctgggtctg cggagcaagg ctggggctgc ccgcctggag ggtaccacct    4620
tctgcaggag cagggccaac ttgctgtggt ggctcccggc ctcccacccc cgagtgggta    4680
acccggccct gtgacctgca gcctgtggag ggggtgtgcc taagactggc ctccccttcc    4740
agattgtagt ctggggaacc tggtgtcgga cttcccaggt ggcctgagct ggtctcttca    4800
gctccacggg gagagtttgg tagcgcaaat agggagatgt tctgggcccc tggccttact    4860
ggttcgattt gaggcctgga aaggaggctc tgggcgtgtg tgtgtgtgtt tgggggtacc    4920
caaggcagac tggagttgga gaactgggtg actgggaaaa caaggtttct agagcatggg    4980
tggcgtggtt gtgttaacca ttggagtcgc ttgacccagg cctggctcag ctgcagactg    5040
gaaaggtgga aaagccaggg ggaggggcgg ggctggccca gcaggactgg cctgctgctt    5100
tgagggcgat ggtcctcctg acccccccct gctcagctgg gggttgtggg gaggaagggg    5160
ctggtcctcc ttgagcaca tgctctgtag gggtggggct gtctgccatc ttggcggcgc    5220
tggaggcctg agaagtggcg atgtaacgct gggctggccc tgccccatg tgtgtcatagg    5280
acggaggcag gtcgggtgtc cagcctgggc ccctgcagct gtggatgccg ctgagctcct    5340
gcaataatga ccgtgcagat ggtcacccct cgtgtaaaat tactagtgct tcttgcaaat    5400
ggaaggaact gggcctttc tgtgtgcttc tggacgcttc attctgcaca tggccctgcg    5460
ccctcacctc ggcattatga cctgtgtgtt acttttgtaa taaaataat gtttatagga    5520
aagccgtgct ttcaatttc aactgaattt gtaggttggc aaatttggtt tgggaggggc    5580
acctctggcc tggggcttgg cctggctgcc ccgctcacgc cacttctctc ccgcccccag    5640
acaccaatgg gaatcccaat ggggaagtcg atgctggtgc ttctcacctt cttggccttc    5700
gcctcgtgct gcattgctgc ttaccgcccc agtgagaccc tgtgcggcgg ggagctggtg    5760
gacaccctcc agttcgtctg tggggaccgc ggcttctact tcagtaagta gcagggaggg    5820
gcttcctcag acctggtcag gcccctagag tgacggtga ggatctccca tcctcaagcc    5880
aggggagcac actcctaggt cagcagccca gccgcttgct ctgagacttt gaccttcccg    5940
ccgcgtttct gagcacgtgc ggtgtcccag ggcatccaca ccagctgcct ttcccatcac    6000
acgcctcctt cgaagggtgg gccagaggtg cccctagac gtcaggggca tctacagggg    6060
tctccctggg catcagaatt tctgttgggg gccgtgaggc tcctgctcct gaggcaccgc    6120
```

```
acgcctagtg cagggcttca ggctctggag gaagagcctg cctttcttcc tgcaccttt     6180
ggacattttg acaagggacg tgcgttcggt gaatgatcag aattaaaatc aataaagtga    6240
tttatataat taaaatcaat aagacaagtg cagttggtgg gtggcagggg tgagcggtgc    6300
atgcgcctcc ttgggcccca aggctgccgt gggggtgcc cacctgctga cctcaaggac     6360
gcttcagcct ttcctcatgt ttctctcttg gttctccagc ctggggggctg caggtgggt    6420
gcatggccca ttgtccttga accccaccc ccagataggg gggctgggtg gatgcagagg     6480
caggcatggt gcctgggcat gcctgatggg gcaggggagg ggccgctcct tactggcaga   6540
ggccgcaact tattccacct gacactcacc acgtgacatc tttaccacca ctgcttactc   6600
acgctgtgaa atgggctcac aggatgcaaa tgcacttcaa agcttctctc tgaaaagttc   6660
ctgctgcttg actctggaag cccctgcccg ccctggcctc tcctgtgccc tctctcttgc   6720
ctgccccatt tggggtagg aagtggcact gcagggcctg gtgccagcca gtccttgccc    6780
agggagaagc ttccctgcac caggctttcc tgagaggagg ggaggccaa gcccccactt    6840
gggggcccc gtgacgggc ctcctgctcc ctcctccggc tgatggcacc tgcccttgg      6900
caccccaagg tggagccccc agcgaccttc cccttccagc tgagcattgc tgtggggag    6960
aggggaaga cggaggaaa gaagggagtg gttccatcac gcctcctcag cctcctctcc    7020
tcccgtcttc tcctctcctg cccttgtctc cctgtctcag cagctccagg ggtggtgtgg   7080
gcccctccag cctcccaggt ggtgccaggc cagagtccaa gctcacggac agcagtcctc   7140
ctgtggggc cctgaactgg gctcacatcc cacacatttt ccaaaccact cccattgtga    7200
gcctttggtc ctggtggtgt ccctctggtt gtgggaccaa gagcttgtgc cattttca     7260
tctgaggaag gaggcagcag aagtcacggg ctggtctggg cccactcac ctcccctctc    7320
acctctcttc ttcctgggac gcctctgcct gccggctctc acttccctcc cctgacccgc   7380
agggtggctg cgnccttcca gggcctggcc tgagggcagg ggtggtttgc tggggggttcg  7440
gcctccgggg gctgggggtc ggtgcggtgc taacacggct ctctctgtgc tgtgggactt   7500
ccaggcaggc ccgcaagccg tgtgagccgt cgcagccgtg gcatcgttga ggagtgctgt   7560
ttccgcagct gtgacctggc cctcctggag acgtactgtg ctaccccgc caagtccgag    7620
agggacgtgt cgacccctcc gaccgtgctt ccggtgaggg tcctgggccc ctttcccact   7680
ctctagagac agagaaatag ggcttcgggc gcccagcgtt tcctgtgcc tctgggacct    7740
cttggccagg gacaaggacc cgtgacttcc ttgcttgctg tgtggcccgg gagcagctca   7800
gacgctggct ccttctgtcc ctctgcccgt ggacattagc tcaagtcact gatcagtcac   7860
aggggtggcc tgtcaggtca ggcgggcggc tcaggcggaa gagcgtggag agcaggcacc   7920
tgctgaccag ccccttcccc tcccaggaca acttccccga gatacccctg ggcaagttct    7980
tccaatatga cacctggaag cagtccaccc agcgcctgcg caggggcctg cctgccctcc   8040
tgcgtgcccg ccggggtcac gtgctcgcca aggagctcga ggcgttcagg gaggccaaac   8100
gtcaccgtcc cctgattgct ctacccaccc aagacccgc ccacgggggc gccccccag     8160
agatggccag caatcggaag tgagcaaaac tgccgcaagt ctgcagcccg gcgccaccat   8220
cctgcagcct cctcctgacc acggacgttt ccatcaggtt ccatcccgaa aatctctcgg   8280
ttccacgtcc cctggggctt ctcctgaccc agtccccgtg ccccgcctcc ccgaaacagg   8340
ctactctcct cggccccctc catcgggctg aggaagcaca gcagcatctt caaacatgta   8400
caaaatcgat tggctttaaa cacccttcac atacctcccc cccaaattat ccccaattat   8460
ccccacacat aaaaaatcaa aacattaaac taacccccctt ccccccccc cacaacaacc   8520
```

```
ctcttaaaac taattggctt tttagaaaca ccccacaaaa gctcagaaat tggctttaaa    8580
aaaaacaacc accaaaaaaa atcaattggc taaaaaaaaa aagtattaaa aacgaattgg    8640
ctgagaaaca attggcaaaa taaggaatt tggcactccc cacccccctc tttctcttct     8700
cccttggact ttgagtcaaa ttggcctgga cttgagtccc tgaaccagca aagagaaaag    8760
aagggcccca gaaatcacag gtgggcacgt cgcgtctacc gccatctccc ttctcacggg    8820
aattttcagg gtaaact                                                   8837

<210> SEQ ID NO 11
<211> LENGTH: 6045
<212> TYPE: DNA
<213> ORGANISM: Artificial Sequence
<220> FEATURE:
<223> OTHER INFORMATION: recombinant construct

<400> SEQUENCE: 11
ccctcaccaa gggccaaggt ggtgaccgac ggacccacag cggggtggct gggggagtcg      60
aaactcgcca gtctccactc cactcccaac cgtggtgccc cacgcgggcc tgggagagtc    120
tgtgaggccg cccaccgctt gtcagtagag tgcgcccgcg agccgtaagc acagcccggc    180
aacatgcggt cttcagacag gaaagtggcc gcgaatggga ccggggtgcc cagcggctgt    240
ggggactctg tcctgcggaa accgcggtga cgagcacaag ctcggtcaac tggatgggaa    300
tcggcctggg gggctggcac cgcgcccacc aggggggtttg cggcacttcc ctctgccccct   360 cagcaccca ccctactct ccaggaacgt gagttctgag ccgtgatggt ggcaggaagg       420
ggccctctgt gccatccgag tccccaggga cccgcagctg gccccagcc atgtgcaaag      480 tatgtgcagg gcgctggcag gcagggagca gcaggcatgg tgtccctga ggggagacag      540 tggtctggga gggagaagtc ctggaccctg agggaggtga tggggcaatg ctcagccctg     600
tctccggatg ccaaaggagg ggtgcgggga ggccgtcttt ggagaattcc aggatgggtg     660
ctgggtgaga gagacgtgtg ctggaactgt ccagggcgga ggtgggccct gcgggggccc    720
tcgggagggc cctgctctga ttggccggca gggcaggggc gggaatcctg gcgggggcca    780
ccccagttag aaaagcccg ggctaggacc gaggagcagg gtgagggaga agcttggcat     840
tccggtactg ttggtaaagc caccatggat cctgatgatg ttgttgattc ttctaaatct    900
tttgtgatgg aaaactttt ttcgtaccac gggactaaac ctggttatgt agattccatt    960 caaaaggta tacaaagcc aaaatctggt acacaaggaa attatgacga tgattggaaa     1020 gggtttata gtaccgacaa taaatacgac gctgcgggat actctgtaga taatgaaaac    1080
ccgctctctg gaaaagctgg aggcgtggtc aaagtgacgt atccaggact gacgaaggtt    1140
ctcgcactaa agtgataa tgccgaaact attaagaaag agttaggttt aagtctcact    1200
gaaccgttga tggagcaagt cggaacggaa gagtttatca aaaggttcgg tgatggtgct    1260
tcgcgtgtag tgctcagcct tccccttcgct gaggggagtt ctagcgttga atatattaat   1320
aactgggaac aggcgaaagc gttaagcgta gaacttgaga ttaattttga acccgtggaa    1380
aaacgtggcc aagatgcgat gtatgagtat atggctcaag cctgtgcagg aaatcgtgtc    1440
aggcgatctt tgtgaaggaa ccttacttct gtggtgtgac ataattggac aaactaccta    1500
cagagatttg gggatcctct agagtcgggg cggccggccg cttcgagcag acatgataag    1560
atacattgat gagtttggac aaaccacaac tagaatgcag tgaaaaaaat gctttatttg    1620
tgaaatttgt gatgctattg ctttatttgt aaccattata agctgcaata aacaagttaa    1680
caacaacaat tgcattcatt ttatgtttca ggttcagggg gaggtgtggg aggttttta    1740
```

```
aagcaagtaa aacctctaca aatgtggtaa aatcgataag gatccgtcga ccgatgccct   1800
tgagagcctt caacccagtc agctccttcc ggtgggcgcg gggcatgact atcgtcgccg   1860
cacttatgac tgtcttcttt atcatgcaac tcgtaggaca ggtgccggca gcgctcttcc   1920
gcttcctcgc tcactgactc gctgcgctcg gtcgttcggc tgcggcgagc ggtatcagct   1980
cactcaaagg cggtaatacg gttatccaca gaatcagggg ataacgcagg aaagaacatg   2040
tgagcaaaag gccagcaaaa ggccaggaac cgtaaaaagg ccgcgttgct ggcgtttttc   2100
cataggctcc gcccccctga cgagcatcac aaaaatcgac gctcaagtca gaggtggcga   2160
aacccgacag gactataaag ataccaggcg tttccccctg gaagctccct cgtgcgctct   2220
cctgttccga ccctgccgct taccggatac ctgtccgcct ttctcccttc gggaagcgtg   2280
gcgctttctc atagctcacg ctgtaggtat ctcagttcgg tgtaggtcgt tcgctccaag   2340
ctgggctgtg tgcacgaacc ccccgttcag cccgaccgct gcgccttatc cggtaactat   2400
cgtcttgagt ccaacccggt aagacacgac ttatcgccac tggcagcagc cactggtaac   2460
aggattagca gagcgaggta tgtaggcggt gctacagagt tcttgaagtg gtggcctaac   2520
tacggctaca ctagaagaac agtatttggt atctgcgctc tgctgaagcc agttaccttc   2580
ggaaaaagag ttggtagctc ttgatccggc aaacaaacca ccgctggtag cggtggtttt   2640
tttgtttgca agcagcagat tacgcgcaga aaaaaggat ctcaagaaga tcctttgatc   2700
ttttctacgg ggtctgacgc tcagtggaac gaaaactcac gttaagggat tttggtcatg   2760
agattatcaa aaaggatctt cacctagatc cttttaaatt aaaaatgaag ttttaaatca   2820
atctaaagta tatatgagta aacttggtct gacagttaga aaaactcatc gagcatcaaa   2880
tgaaactgca atttattcat atcaggatta tcaataccat attttgaaa agccgtttc    2940 tgtaatgaag gagaaaactc accgaggcag ttccatagga tggcaagatc ctggtatcgg   3000
tctgcgattc cgactcgtcc aacatcaata caacctatta atttccctc gtcaaaaata   3060 aggttatcaa gtgagaaatc accatgagtg acgactgaat ccgtgagaa tggcaaaagt   3120 ttatgcattt ctttccagac ttgttcaaca ggccagccat tacgctcgtc atcaaaatca   3180
ctcgcatcaa ccaaaccgtt attcattcgt gattgcgcct gagcgagacg aaatacgcga   3240
tcgctgttaa aaggacaatt acaaacagga atcgaatgca accggcgcag gaacactgcc   3300
agcgcatcaa caatatttc acctgaatca ggatattctt ctaatacctg gaatgctgtt   3360
ttcccgggga tcgcagtggt gagtaaccat gcatcatcag gagtacggat aaaatgcttg   3420
atggtcggaa gaggcataaa ttccgtcagc cagtttagtc tgaccatctc atctgtaaca   3480
tcattggcaa cgctaccttt gccatgtttc agaaacaact ctggcgcatc gggcttccca   3540
tacaatcgat agattgtcgc acctgattgc ccgacattat cgcgagccca tttatacca   3600 tataaatcag catccatgtt ggaatttaat cgcggcctag agcaagacgt ttcccgttga   3660
atatggctca tactcttcct ttttcaatat tattgaagca tttatcaggg ttattgtctc   3720
atgagcggat acatatttga atgtatttag aaaaataaac aatagggggt ccgcgcaca    3780 tttccccgaa aagtgccacc tgacgcgccc tgtagcggcg cattaagcgc ggcgggtgtg   3840
gtggttacgc gcagcgtgac cgctacactt gccagcgccc tagcgcccgc tcctttcgct   3900
ttcttccctt cctttctcgc cacgttcgcc ggctttcccc gtcaagctct aaatcggggg   3960
ctccctttag ggttccgatt tagtgcttta cggcacctcg accccaaaaa acttgattag   4020
ggtgatggtt cacgtagtgg gccatcgccc tgatagacgg ttttcgccc tttgacgttg   4080 gagtccacgt tctttaatag tggactcttg ttccaaactg gaacaacact caaccctatc   4140
```

```
tcggtctatt cttttgattt ataagggatt ttgccgattt cggcctattg gttaaaaaat      4200
gagctgattt aacaaaaatt taacgcgaat tttaacaaaa tattaacgct tacaatttgc      4260
cattcgccat tcaggctgcg caactgttgg aagggcgat cggtgcgggc ctcttcgcta       4320
ttacgccagc ccaagctacc atgataagta agtaatatta aggtacggga ggtacttgga     4380
gcggccgcaa taaaatatct ttattttcat tacatctgtg tgttggtttt ttgtgtgaat     4440
cgatagtact aacatacgct ctccatcaaa acaaaacgaa acaaaacaaa ctagcaaaat     4500
aggctgtccc cagtgcaagt gcaggtgcca gaacatttct ctatcgataa cttcccggtc    4560
ggtctgtggg tgcaggggt gccgcctcac atgtgtgatt cgtgccttgc gggccctggc     4620
ctccggggtg ctgggtaacg aggaggggcg cggagccgca gaagcccacc ctggtatgtt    4680
gacgcggtgc cagcgagacc gcgagaggaa gacggggtg ggcggggcca ggatggagag     4740
gggccgagtt ggcaggagtc atggcagacg ccacattcgc gacatctccc ccacaccccc   4800
tctggctctg tccgcaacat ttccaaacag gagtcccggg agaggggag aggggctgct    4860 ggtctgaggc taagaagggc agagccttcg acccggagag aggccgcggc ccctgcccag   4920
tgggcagcgt ggaagtttcc atacaaggag gtgggaagga gaccccccc ccccttcact    4980 gccctgtgca gagatgagcc gggggtgcag gatgggagcc catggcactt cgctacggga   5040
tggtccaggg ctcccggttg ggggtgcagg agagaagaga ctggctggga ggagggagag  5100
ggcgggagca aaggcgcggg ggagtggtca gcagggagag gggtgggggg tagggtggag   5160
cccgggctgg gaggagtcgg ctcacacata aaagctgagg cactgaccag cctgcaaact   5220
ggacattagc ttctcctgtg aaagagactt ccagcttcct cctcctcctc ttcctcctcc  5280
tcctcctgcc ccagcgagcc ttctgctgag ctgtaggggg atcttctaga gtcggctagc 5340
ggcattccgg tactgttggt aaagccacca tggatcctga tgatgttgtt gattcttcta  5400
aatcttttgt gatggaaaac ttttcttcgt accacgggac taaacctggt tatgtagatt  5460
ccattcaaaa aggtatacaa aagccaaaat ctggtacaca aggaaattat gacgatgatt 5520
ggaaagggtt ttatagtacc gacaataaat acgacgctgc gggatactct gtagataatg 5580
aaaacccgct ctctggaaaa gctggaggcg tggtcaaagt gacgtatcca ggactgacga  5640
aggttctcgc actaaaagtg gataatgccg aaactattaa gaaagagtta ggtttaagtc  5700
tcactgaacc gttgatggag caagtcggaa cggaagagtt tatcaaaagg ttcggtgatg   5760
gtgcttcgcg tgtagtgctc agccttccct tcgctgaggg gagttctagc gttgaatata  5820
ttaataactg gaacaggcg aaagcgttaa gcgtagaact tgagattaat tttgaaaccc    5880
gtggaaaacg tggccaagat gcgatgtatg agtatatggc tcaagcctgt gcaggaaatc  5940
gtgtcaggcg atctttgtga aggaaccta cttctgtggt gtgacataat tggacaaact  6000
acctacagag atttggggat ccctcgagac gtagggtacc gacaa                   6045

<210> SEQ ID NO 12
<211> LENGTH: 632
<212> TYPE: DNA
<213> ORGANISM: Homo sapiens

<400> SEQUENCE: 12
gacgggggtg ggcggggcca ggatggagag gggccgagtt ggcaggagtc atggcagacg      60
ccacattcgc gacactctcc ccacaccccc tctggctctg tccgcaacat ttccaaacag     120
gagtcccggg agaggggag aggggctgct ggtctgaggc taagaagggc agagccttcg     180
acccggagag aggccgcggc ccctgcccag tgggcagcgt ggaagtttcc atacaaggag    240
```

| | |
|---|---|
| gtgggaagga gaccccccc ccccttcact gccctgtgca gagatgagcc ggggggtgcag | 300 |
| gatgggagcc catggcactt cgctacggga tggtcagggc tcccggttgg gggtgcagga | 360 |
| gagaagagac tggctgggag gagggagagg gcgggagcaa aggcgcgggg gagtggtcag | 420 |
| cagggagagg ggtggggggt agggtggagc ccgggctggg aggagtcggc tcacacataa | 480 |
| aagctgaggc actgaccagc ctgcaaactg gacattagct tctcctgtga aagagacttc | 540 |
| cagcttcctc ctcctcctct tcctcctcct cctcctgccc cagcgagcct tctgctgagc | 600 |
| tgtaggtaac cagggccgtg gatgagactc tc | 632 |

<210> SEQ ID NO 13
<211> LENGTH: 870
<212> TYPE: DNA
<213> ORGANISM: Homo sapiens

<400> SEQUENCE: 13

| | |
|---|---|
| ggatccccaa aatgtgttcc ttgctttcat ctgccaattt tacgtaatat ggctctacgg | 60 |
| caaaattccc aatttcatat ggagaatttt ctttaactac ccctcctcac aaattggtcc | 120 |
| cccaagctag ctggcccta tttgagacct cttttctctat gttcccaatt gcatggagca | 180 |
| acttctctca tcccccaaac ctgtaatcta tttttctgga gtctcgagtt tagtcattaa | 240 |
| tcacggttcc cacattaacg gagtccccgg ggtcccctcc tccaggacac ccattcgcta | 300 |
| agcccgcaag gcagaaagaa ctctgccttg cgttccccaa aatttgggca ttgttccggc | 360 |
| tcgccggcca cccactgcag cttccccaac cccgcgcaca gcgggcactg gtttcgggcc | 420 |
| tctctgtctc ctacgaagtc cccagagcaa ctcggatttg ggaaatttct ctctagcgtt | 480 |
| gcccaaacac acttgggtcg gccgcgcgcc ctcaggacgt ggacagggag ggcttccccg | 540 |
| tgtccaggaa agcgaccggg cattgccccc agtctccccc aaatttgggc attgtccccg | 600 |
| ggtcttccaa cggactgggc gttgctcccg gacactgagg actggccccg ggtctcgct | 660 |
| caccttcagc agcgtccacc gcctgccaca gagcgttcga tcgctcgctg cctgagctcc | 720 |
| tggtgcgccc gcggacgcag cctccagctt cgcggtgagc tccccgccgc gccgatcccc | 780 |
| tccgcctctg cgccctgac cggctctcgg cccgcatctg ctgctgtccc gccggtgctg | 840 |
| gcgctcgtct ccggctgccg ccggggaggc | 870 |

<210> SEQ ID NO 14
<211> LENGTH: 720
<212> TYPE: DNA
<213> ORGANISM: Homo sapiens

<400> SEQUENCE: 14

| | |
|---|---|
| tcatgagcac cgagagcatg atcagggatg tggagctggc cgaggaggcc ctgcccaaga | 60 |
| aaacaggcgg ccctcagggc agcagaagat gcctgttcct gagcctgttc agcttcctga | 120 |
| tcgtggccgg agccaccacc ctgttctgcc tgctgaactt cggcgtgatc ggccccagda | 180 |
| gagaggagtt cccagagac ctgagcctga tctcccccct ggcccaggct gtgagaagca | 240 |
| gcagcagaac ccccagcgac aagcccgtgg cccacgtggt ggccaacccc caggccgagg | 300 |
| gccagctgca gtggctgaac agaagagcca acgccctgct ggccaacggc gtggagctga | 360 |
| gagacaacca gctggtggtg cccagcgagg gcctgtacct gatctacagc caggtgctgt | 420 |
| tcaagggcca gggctgcccc agcacccacg tgctgctgac ccacaccatc agcagaatcg | 480 |
| ccgtgtccta ccagaccaag gtgaacctgc tgtccgccat caagagccct tgccagagag | 540 |
| agaccccga gggcgccgag gccaagccct ggtacgagcc tatctacctg ggcggcgtgt | 600 |

```
tccagctgga aagggcgac agactgagcg ccgagatcaa cagacccgac tacctggatt    660
tcgccgagag cggccaggtg tacttcggca tcatcgccct gtgataatct agaaccatgg   720
```

<210> SEQ ID NO 15
<211> LENGTH: 233
<212> TYPE: PRT
<213> ORGANISM: Homo sapiens

<400> SEQUENCE: 15

```
Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu Asn Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```

<210> SEQ ID NO 16
<211> LENGTH: 4560
<212> TYPE: DNA
<213> ORGANISM: artificial
<220> FEATURE:
<223> OTHER INFORMATION: recombinant construct

<400> SEQUENCE: 16

```
ggtaccgaca accctcacca agggccaagg tggtgaccga cggacccaca gcggggtggc    60
tgggggagtc gaaactcgcc agtctccact ccactcccaa ccgtggtgcc ccacgcgggc   120
ctgggagagt ctgtgaggcc gcccaccgct tgtcagtaga gtgcgcccgc gagccgtaag   180
cacagcccgg caacatgcgg tcttcagaca ggaaagtggc cgcgaatggg accggggtgc   240
ccagcggctg tggggactct gtcctgcgga aaccgcggtg acgagcacaa gctcggtcaa   300
ctggatggga atcggcctgg ggggctggca ccgcgcccac cagggggttt gcggcacttc   360
```

```
cctctgcccc tcagcacccc acccctactc tccaggaacg tgagttctga gccgtgatgg    420
tggcaggaag gggccctctg tgccatccga gtccccaggg acccgcagct ggcccccagc    480
catgtgcaaa gtatgtgcag ggcgctggca ggcagggagc agcaggcatg tgtcccctg     540 aggggagaca gtggtctggg agggagaagt cctggaccct gagggaggtg atggggcaat    600
gctcagccct gtctccggat gccaaggag gggtgcgggg aggccgtctt tggagaattc     660
caggatgggt gctgggtgag agagacgtgt gctggaactg tccagggcgg aggtgggccc    720
tgcgggggcc ctcgggaggg ccctgctctg attggccggc agggcagggg cgggaatcct    780
gggcggggcc accccagtta gaaaaagccc gggctaggac cgaggagcag ggtgagggag    840
aagcttggca ttccggtact gttggtaaag ccaccatgga tcctgatgat gttgttgatt    900
cttctaaatc ttttgtgatg gaaaacttt cttcgtacca cgggactaaa cctggttatg     960
tagattccat tcaaaaaggt atacaaaagc caaaatctgg tacacaagga aattatgacg   1020
atgattggaa agggttttat agtaccgaca taaatacga cgctgcggga tactctgtag    1080
ataatgaaaa cccgctctct ggaaaagctg gaggcgtggt caaagtgacg tatccaggac   1140
tgacgaaggt tctcgcacta aaagtggata atgccgaaac tattaagaaa gagttaggtt   1200
taagtctcac tgaaccgttg atggagcaag tcggaacgga agagttatc aaaaggttcg    1260 gtgatggtgc ttcgcgtgta gtgctcagcc ttcccttcgc tgaggggagt tctagcgttg   1320
aatatattaa taactgggaa caggcgaaag cgttaagcgt agaacttgag attaattttg   1380
aaacccgtgg aaaacgtggc caagatgcga tgtatgagta tatggctcaa gcctgtgcag   1440
gaaatcgtgt caggcgatct ttgtgaagga accttacttc tgtggtgtga cataattgga   1500
caaactacct acagagattt ggggatcctc tagagtcggg gcggccggcc gcttcgagca   1560
gacatgataa gatacattga tgagtttgga caaaccacaa ctagaatgca gtgaaaaaaa   1620
tgctttattt gtgaaatttg tgatgctatt gctttatttg taaccattat aagctgcaat   1680
aaacaagtta acaacaacaa ttgcattcat tttatgtttc aggttcaggg ggaggtgtgg   1740 gaggttttt aaagcaagta aaacctctac aaatgtggta aaatcgataa ggatccgtcg   1800
accgatgccc ttgagagcct tcaacccagt cagctccttc cggtgggcgc ggggcatgac   1860
tatcgtcgcc gcacttatga ctgtcttctt tatcatgcaa ctcgtaggac aggtgccggc   1920
agcgctcttc cgcttcctcg ctcactgact cgctgcgctc ggtcgttcgg ctgcggcgag   1980
cggtatcagc tcactcaaag gcggtaatac ggttatccac agaatcaggg gataacgcag   2040
gaaagaacat gtgagcaaaa ggccagcaaa aggccaggaa ccgtaaaaag gccgcgttgc   2100
tggcgttttt ccataggctc cgcccccctg acgagcatca caaaaatcga cgctcaagtc   2160
agaggtggcg aaacccgaca ggactataaa gataccaggc gtttccccct ggaagctccc   2220
tcgtgcgctc tcctgttccg accctgccgc ttaccggata cctgtccgcc tttctccctt   2280
cgggaagcgt ggcgctttct catagctcac gctgtaggta tctcagttcg gtgtaggtcg   2340
ttcgctccaa gctgggctgt gtgcacgaac cccccgttca gcccgaccgc tgcgccttat   2400
ccggtaacta tcgtcttgag tccaacccgg taagacacga cttatcgcca ctggcagcag   2460
ccactggtaa caggattagc agagcgaggt atgtaggcgg tgctacagag ttcttgaagt   2520
ggtggcctaa ctacggctac actagaagaa cagtatttgg tatctgcgct ctgctgaagc   2580
cagttacctt cggaaaaaga gttggtagct cttgatccgg caaacaaacc accgctggta   2640
gcggtggttt ttttgtttgc aagcagcaga ttacgcgcag aaaaaaagga tctcaagaag   2700
atcctttgat cttttctacg gggtctgacg ctcagtggaa cgaaaactca cgttaaggga   2760
```

| | |
|---|---|
| ttttggtcat gagattatca aaaaggatct tcacctagat cctttaaat taaaatgaa | 2820 |
| gttttaaatc aatctaaagt atatatgagt aaacttggtc tgacagttag aaaaactcat | 2880 |
| cgagcatcaa atgaaactgc aatttattca tatcaggatt atcaatacca tatttttgaa | 2940 |
| aaagccgttt ctgtaatgaa ggagaaaact caccgaggca gttccatagg atggcaagat | 3000 |
| cctggtatcg gtctgcgatt ccgactcgtc aacatcaat acaacctatt aatttcccct | 3060 |
| cgtcaaaaat aaggttatca agtgagaaat caccatgagt gacgactgaa tccggtgaga | 3120 |
| atggcaaaag tttatgcatt tctttccaga cttgttcaac aggccagcca ttacgctcgt | 3180 |
| catcaaaatc actcgcatca accaaaccgt tattcattcg tgattgcgcc tgagcgagac | 3240 |
| gaaatacgcg atcgctgtta aaaggacaat tacaaacagg aatcgaatgc aaccggcgca | 3300 |
| ggaacactgc cagcgcatca acaatatttt cacctgaatc aggatattct tctaatacct | 3360 |
| ggaatgctgt ttcccgggg atcgcagtgg tgagtaacca tgcatcatca ggagtacgga | 3420 |
| taaaatgctt gatggtcgga agaggcataa attccgtcag ccagtttagt ctgaccatct | 3480 |
| catctgtaac atcattggca acgctacctt tgccatgttt cagaaacaac tctggcgcat | 3540 |
| cgggcttccc atacaatcga tagattgtcg cacctgattg cccgacatta tcgcgagccc | 3600 |
| atttatacccc atataaatca gcatccatgt tggaatttaa tcgcggccta gagcaagacg | 3660 |
| tttcccgttg aatatggctc atactcttcc tttttcaata ttattgaagc atttatcagg | 3720 |
| gttattgtct catgagcgga tacatatttg aatgtattta gaaaataaa caatagggg | 3780 |
| ttccgcgcac atttccccga aaagtgccac ctgacgcgcc ctgtagcggc gcattaagcg | 3840 |
| cggcgggtgt ggtggttacg cgcagcgtga ccgctacact tgccagcgcc ctagcgcccg | 3900 |
| ctcctttcgc tttcttccct tcctttctcg ccacgttcgc cggctttccc cgtcaagctc | 3960 |
| taaatcgggg gctcccttta gggttccgat ttagtgcttt acggcacctc gaccccaaaa | 4020 |
| aacttgatta gggtgatggt tcacgtagtg gccatcgcc ctgatagacg ttttttcgcc | 4080 |
| ctttgacgtt ggagtccacg ttctttaata gtggactctt gttccaaact ggaacaacac | 4140 |
| tcaaccctat ctcggtctat tcttttgatt tataagggat tttgccgatt tcggcctatt | 4200 |
| ggttaaaaaa tgagctgatt taacaaaaat ttaacgcgaa ttttaacaaa atattaacgc | 4260 |
| ttacaatttg ccattcgcca ttcaggctgc gcaactgttg ggaagggcga tcggtgcggg | 4320 |
| cctcttcgct attacgccag cccaagctac catgataagt aagtaatatt aaggtacggg | 4380 |
| aggtacttgg agcggccgca ataaaatatc tttattttca ttacatctgt gtgttggttt | 4440 |
| tttgtgtgaa tcgatagtac taacatacgc tctccatcaa aacaaaacga aacaaaacaa | 4500 |
| actagcaaaa taggctgtcc ccagtgcaag tgcaggtgcc agaacatttc tctatcgata | 4560 |

<210> SEQ ID NO 17
<211> LENGTH: 885
<212> TYPE: DNA
<213> ORGANISM: Artificial Sequence
<220> FEATURE:
<223> OTHER INFORMATION: recombinant construct

<400> SEQUENCE: 17

| | |
|---|---|
| ggccatgcag gtaggatttg agctgtgttt cccgccctga tcctctctcc tctggcggcc | 60 |
| ggagcctccg taggctccaa gcctggccca gattcggcgg cgcagccggc cttccgcgcg | 120 |
| tccgcaccta gcggggctc cggggctccg gcgcggcacc ggggggcgct cgggatctgg | 180 |
| ctgaggctcc aaggcccgcg tggccggctc tcctgctgg ggcaggtggc ggctgcgcgc | 240 |
| cccgcccgag cccaggggcc ccctcagccg caacaaccag caaggacccc ccgactcagc | 300 |

| | |
|---|---|
| cccaagccac ctgcatctgc actcagacgg ggcgcacccg cagtgcagcc tcctggtggg | 360 |
| gcgctgggag cccgcctgcc cctgcctgcc cggagacccc agctcacgag cacaggccgc | 420 |
| ccgggcaccc cagaaacccg ggatggggcc cctgaattct ctaggacggg cattcagcat | 480 |
| ggccttggcg ctctgcggct ccctgccccc cacccagcct cgccccgcg cacccccag | 540 |
| cccctgcgac cgccgccccc ccccgggg ccccagggcc ccagcccgca ccccgccc | 600 |
| cgctcttggc tcgggttgcg ggggcgggcc ggggcgggg cgaggctcc gcgggcgccc | 660 |
| attggcgcgg gcgcgaggcc agcggcccg cgcggccctg ggccgcggct ggcgcgacta | 720 |
| taagagccgg gcgtgggcgc ccgcagttcg cctgctctcc ggcggagctg cgtgaggccc | 780 |
| ggccggcccc ggcccccccc ttccggccgc ccccgcctcc tggcccacgc ctgcccgcgc | 840 |
| tctgcccacc agcgcctcca tcgggcaagg cggccccgcg tcgac | 885 |

<210> SEQ ID NO 18
<211> LENGTH: 6163
<212> TYPE: DNA
<213> ORGANISM: Artificial Sequence
<220> FEATURE:
<223> OTHER INFORMATION: recombinant construct

<400> SEQUENCE: 18

| | |
|---|---|
| ccctcaccaa gggccaaggt ggtgaccgac ggacccacag cggggtggct gggggagtcg | 60 |
| aaactcgcca gtctccactc cactcccaac cgtggtgccc cacgcgggcc tgggagagtc | 120 |
| tgtgaggccg cccaccgctt gtcagtagag tgcgcccgcg agccgtaagc acagcccggc | 180 |
| aacatgcggt cttcagacag gaaagtggcc gcgaatggga ccggggtgcc cagcggctgt | 240 |
| ggggactctg tcctgcggaa accgcggtga cgagcacaag ctcggtcaac tggatgggaa | 300 |
| tcggcctggg gggctggcac cgcgcccacc aggggggtttg cggcacttcc ctctgccct | 360 |
| cagcacccca cccctactct ccaggaacgt gagttctgag ccgtgatggt ggcaggaagg | 420 |
| ggccctctgt gccatccgag tccccaggga cccgcagctg gccccagcc atgtgcaaag | 480 |
| tatgtgcagg gcgctggcag gcagggagca gcaggcatgg tgtcccctga ggggagacag | 540 |
| tggtctggga gggagaagtc ctggaccctg agggaggtga tggggcaatg ctcagccctg | 600 |
| tctccggatg ccaaaggagg ggtgcgggga ggccgtcttt ggagaattcc aggatgggtg | 660 |
| ctgggtgaga gagacgtgtg ctggaactgt ccagggcgga ggtgggccct gcggggccc | 720 |
| tcgggagggc cctgctctga ttggccggca gggcagggc gggaatcctg gcggggcca | 780 |
| ccccagttag aaaaagcccg ggctaggacc gaggagcagg gtgagggaga agcttggcat | 840 |
| tccggtactg ttggtaaagc caccatggat cctgatgatg ttgttgattc ttctaaatct | 900 |
| tttgtgatgg aaaactttc ttcgtaccac gggactaaac ctggttatgt agattccatt | 960 |
| caaaaaggta tacaaaagcc aaaatctggt acacaaggaa attatgacga tgattggaaa | 1020 |
| gggttttata gtaccgacaa taaatacgac gctgcgggat actctgtaga taatgaaaac | 1080 |
| ccgctctctg gaaaagctgg aggcgtggtc aaagtgacgt atccaggact gacgaaggtt | 1140 |
| ctcgcactaa aagtggataa tgccgaaact attaagaaag agttaggttt aagtctcact | 1200 |
| gaaccgttga tggagcaagt cggaacggaa gagtttatca aaaggttcgg tgatggtgct | 1260 |
| tcgcgtgtag tgctcagcct tcccttcgct gaggggagtt ctagcgttga atatattaat | 1320 |
| aactgggaac aggcgaaagc gttaagcgta gaacttgaga ttaatttgga acccgtgga | 1380 |
| aaacgtggcc aagatgcgat gtatgagtat atggctcaag cctgtgcagg aaatcgtgtc | 1440 |
| aggcgatctt tgtgaaggaa ccttacttct gtggtgtgac ataattggac aaactaccta | 1500 |

```
cagagatttg gggatcctct agagtcgggg cggccggccg cttcgagcag acatgataag    1560
atacattgat gagtttggac aaaccacaac tagaatgcag tgaaaaaaat gctttatttg    1620
tgaaatttgt gatgctattg ctttatttgt aaccattata agctgcaata acaagttaa    1680 caacaacaat tgcattcatt ttatgtttca ggttcagggg gaggtgtggg aggtttttta    1740
aagcaagtaa aacctctaca aatgtggtaa aatcgataag gatccgtcga ccgatgccct    1800
tgagagcctt caacccagtc agctccttcc ggtgggcgcg gggcatgact atcgtcgccg    1860
cacttatgac tgtcttcttt atcatgcaac tcgtaggaca ggtgccggca gcgctcttcc    1920
gcttcctcgc tcactgactc gctgcgctcg gtcgttcggc tgcggcgagc ggtatcagct    1980
cactcaaagg cggtaatacg gttatccaca gaatcagggg ataacgcagg aaagaacatg    2040
tgagcaaaag gccagcaaaa ggccaggaac cgtaaaaagg ccgcgttgct ggcgtttttc    2100
cataggctcc gcccccctga cgagcatcac aaaaatcgac gctcaagtca gaggtggcga    2160
aacccgacag gactataaag ataccaggcg tttccccctg gaagctccct cgtgcgctct    2220
cctgttccga ccctgccgct taccggatac ctgtccgcct ttctcccttc gggaagcgtg    2280
gcgctttctc atagctcacg ctgtaggtat ctcagttcgg tgtaggtcgt tcgctccaag    2340
ctgggctgtg tgcacgaacc ccccgttcag cccgaccgct gcgccttatc cggtaactat    2400
cgtcttgagt ccaacccggt aagacacgac ttatcgccac tggcagcagc cactggtaac    2460
aggattagca gagcgaggta tgtaggcggt gctacagagt tcttgaagtg gtggcctaac    2520
tacggctaca ctagaagaac agtatttggt atctgcgctc tgctgaagcc agttaccttc    2580
ggaaaaagag ttggtagctc ttgatccggc aaacaaacca ccgctggtag cggtggtttt    2640
tttgtttgca agcagcagat tacgcgcaga aaaaaaggat ctcaagaaga tcctttgatc    2700
ttttctacgg ggtctgacgc tcagtggaac gaaaactcac gttaagggat tttggtcatg    2760
agattatcaa aaaggatctt cacctagatc cttttaaatt aaaaatgaag ttttaaatca    2820
atctaaagta tatatgagta aacttggtct gacagttaga aaaactcatc gagcatcaaa    2880
tgaaactgca atttattcat atcaggatta tcaataccat attttgaaa agccgtttc     2940 tgtaatgaag gagaaaactc accgaggcag ttccatagga tggcaagatc ctggtatcgg    3000
tctgcgattc cgactcgtcc aacatcaata caacctatta atttcccctc gtcaaaaata    3060
aggttatcaa gtgagaaatc accatgagtg acgactgaat ccggtgagaa tggcaaaagt    3120
ttatgcattt cttttccagac ttgttcaaca ggccagccat tacgctcgtc atcaaaatca    3180
ctcgcatcaa ccaaaccgtt attcattcgt gattgcgcct gagcgagacg aaatacgcga    3240
tcgctgttaa aaggacaatt acaaacagga tcgaatgca accggcgcag gaacactgcc    3300
agcgcatcaa caatattttc acctgaatca ggatattctt ctaatacctg gaatgctgtt    3360
ttcccgggga tcgcagtggt gagtaaccat gcatcatcag gagtacggat aaaatgcttg    3420
atggtcggaa gaggcataaa ttccgtcagc cagtttagtc tgaccatctc atctgtaaca    3480
tcattggcaa cgctaccttt gccatgtttc agaaacaact ctggcgcatc gggcttccca    3540
tacaatcgat agattgtcgc acctgattgc ccgacattat cgcgagccca tttataccca    3600
tataaatcag catccatgtt ggaatttaat cgcggcctag agcaagacgt ttcccgttga    3660
atatggctca tactcttcct ttttcaatat tattgaagca tttatcaggg ttattgtctc    3720
atgagcggat acatatttga atgtatttag aaaaataaac aaatagggggt tccgcgcaca    3780 tttccccgaa aagtgccacc tgacgcgccc tgtagcggcg cattaagcgc ggcgggtgtg    3840
```

```
gtggttacgc gcagcgtgac cgctacactt gccagcgccc tagcgcccgc tcctttcgct   3900
ttcttccctt cctttctcgc cacgttcgcc ggctttcccc gtcaagctct aaatcggggg   3960
ctcccctttag ggttccgatt tagtgcttta cggcacctcg accccaaaaa acttgattag   4020
ggtgatggtt cacgtagtgg gccatcgccc tgatagacgg ttttcgccc tttgacgttg    4080
gagtccacgt tctttaatag tggactcttg ttccaaactg gaacaacact caaccctatc   4140
tcggtctatt cttttgattt ataagggatt ttgccgattt cggcctattg gttaaaaaat   4200
gagctgattt aacaaaaatt taacgcgaat tttaacaaaa tattaacgct tacaatttgc   4260
cattcgccat tcaggctgcg caactgttgg gaagggcgat cggtgcgggc ctcttcgcta   4320
ttacgccagc ccaagctacc atgataagta agtaatatta aggtacggga ggtacttgga   4380
gcggccgcaa taaatatct ttattttcat tacatctgtg tgttggtttt ttgtgtgaat    4440
cgatagtact aacatacgct ctccatcaaa acaaaacgaa acaaaacaaa ctagcaaaat   4500
aggctgtccc cagtgcaagt gcaggtgcca gaacatttct ctatcgatac tcgagggcca   4560
tgcaggtagg atttgagctg tgtttcccgc cctgatcctc tctcctctgg cggccggagc   4620
ctccgtaggc tccaagcctg gcccagattc ggcggcgcag ccggccttcc gcgcgtccgc   4680
acctagcggg ggctccgggg ctccggcgcg gcaccggggg gcgctcggga tctggctgag   4740
gctccaaggc ccgcgtggcc ggctcctcct gctggggcag gtggcggctg cgcgccccgc   4800
ccgagcccag gggcccctc agccgcaaca accagcaagg accccccgac tcagcccaa    4860
gccacctgca tctgcactca gacggggcgc acccgcagtg cagcctcctg gtgggcgct    4920
gggagcccgc ctgcccctgc ctgcccggag accccagctc acgagcacag gccgcccggg   4980
caccccagaa accgggatg gggcccctga attctctagg acgggcattc agcatggcct    5040
tggcgctctg cggctccctg cccccaccc agcctcgccc ccgcgcaccc ccagcccct    5100
gcgaccgccg cccccccccc cggggcccca gggcccagc ccgcaccccc cgccccgctc    5160
ttggctcggg ttgcggggc gggccggggg cggggcgagg gctccgcggg cgcccattgg   5220
cgcgggcgcg aggccagcgg ccccgcgcgg ccctgggccg cggctggcgc gactataaga   5280
gccgggcgtg ggcgcccgca gttcgcctgc tctccggcgg agctgcgtga ggcccggccg   5340
gcccggcc ccccttccg gccgccccg cctcctggcc cacgcctgcc cgcgctctgc      5400
ccaccagcgc ctccatcggg caaggcggcc ccgcgtcgac aagcttagct acgctagcgg   5460
cattccggta ctgttggtaa agccaccatg gatcctgatg atgttgttga ttcttctaaa   5520
tcttttgtga tggaaaactt ttcttcgtac cacgggacta aacctggtta tgtagattcc   5580
attcaaaaag gtatacaaaa gccaaaatct ggtacacaag gaaattatga cgatgattgg   5640
aaagggtttt atagtaccga caataaatac gacgctgcgg gatactctgt agataatgaa   5700
aacccgctct ctggaaaagc tggaggcgtg gtcaaagtga cgtatccagg actgacgaag   5760
gttctcgcac taaaagtgga taatgccgaa actattaaga aagagttagg tttaagtctc   5820
actgaaccgt tgatggagca agtcggaacg gaagagttta tcaaaaggtt cggtgatggt   5880
gcttcgcgtg tagtgctcag ccttcccttc gctgagggga gttctagcgt tgaatatatt   5940
aataactggg aacaggcgaa agcgttaagc gtagaacttg agattaatt tgaaacccgt   6000
ggaaaacgtg gccaagatgc gatgtatgag tatatggctc aagcctgtgc aggaaatcgt   6060
gtcaggcgat ctttgtgaag gaaccttact tctgtggtgt gacataattg gacaaactac   6120
ctacagagat ttggggatcc ctcgagacgt agggtaccga caa                    6163
```

-continued

<210> SEQ ID NO 19
<211> LENGTH: 4657
<212> TYPE: DNA
<213> ORGANISM: Artificial Sequence
<220> FEATURE:
<223> OTHER INFORMATION: recombinant construct

<400> SEQUENCE: 19

| | | | | | |
|---|---|---|---|---|---|
| tctatcgata | ggtaccgaca | accctcacca | agggccaagg | tggtgaccgg | ccatgcaggt | 60 |
| aggatttgag | ctgtgtttcc | cgccctgatc | ctctctcctc | tggcggccgg | agcctccgta | 120 |
| ggctccaagc | ctggcccaga | ttcggcggcg | cagccggcct | tccgcgcgtc | cgcacctagc | 180 |
| gggggctccg | gggctccggc | gcggcaccgg | ggggcgctcg | ggatctggct | gaggctccaa | 240 |
| ggcccgcgtg | gccggctcct | cctgctgggg | caggtggcgg | ctgcgcgccc | cgcccgagcc | 300 |
| caggggcccc | ctcagccgca | acaaccagca | aggaccccc | gactcagccc | caagccacct | 360 |
| gcatctgcac | tcagacgggg | cgcacccgca | gtgcagcctc | ctggtggggc | gctgggagcc | 420 |
| cgcctgcccc | tgcctgcccg | gagacccag | ctcacgagca | caggccgccc | gggcacccca | 480 |
| gaaacccggg | atggggcccc | tgaattctct | aggacgggca | ttcagcatgg | ccttggcgct | 540 |
| ctgcggctcc | ctgcccccca | cccagcctcg | ccccgcgca | cccccagcc | cctgcgaccg | 600 |
| ccgcccccc | cccggggcc | ccagggcccc | agcccgcacc | cccgccccg | ctcttggctc | 660 |
| gggttgcggg | ggcgggccgg | gggcggggcg | agggctccgc | gggcgcccat | ggcgcgggc | 720 |
| gcgaggccag | cggccccgcg | cggccctggg | ccgcggctgg | cgcgactata | agagccgggc | 780 |
| gtgggcgccc | gcagttcgcc | tgctctccgg | cggagctgcg | tgaggccgg | ccggccccgg | 840 |
| ccccccctt | ccggccgccc | ccgcctcctg | gcccacgcct | gcccgcgctc | tgcccaccag | 900 |
| cgcctccatc | gggcaaggcg | gccccgcaag | cttggcattc | cggtactgtt | ggtaaagcca | 960 |
| ccatggatcc | tgatgatgtt | gttgattctt | ctaaatcttt | tgtgatggaa | aacttttctt | 1020 |
| cgtaccacgg | gactaaacct | ggttatgtag | attccattca | aaaaggtata | caaaagccaa | 1080 |
| aatctggtac | acaaggaaat | tatgacgatg | attggaaagg | gttttatagt | accgacaata | 1140 |
| aatacgacgc | tgcgggatac | tctgtagata | tgaaaaccc | gctctctgga | aaagctggag | 1200 |
| gcgtggtcaa | agtgacgtat | ccaggactga | cgaaggttct | cgcactaaaa | gtggataatg | 1260 |
| ccgaaactat | taagaaagag | ttaggtttaa | gtctcactga | accgttgatg | gagcaagtcg | 1320 |
| gaacggaaga | gtttatcaaa | aggttcggtg | atggtgcttc | gcgtgtagtg | ctcagccttc | 1380 |
| ccttcgctga | ggggagttct | agcgttgaat | atattaataa | ctgggaacag | gcgaaagcgt | 1440 |
| taagcgtaga | acttgagatt | aattttgaaa | cccgtggaaa | acgtggccaa | gatgcgatgt | 1500 |
| atgagtatat | ggctcaagcc | tgtgcaggaa | atcgtgtcag | gcgatctttg | tgaaggaacc | 1560 |
| ttacttctgt | ggtgtgacat | aattggacaa | actacctaca | gagatttggg | atcctctag | 1620 |
| agtcggggcg | gccggccgct | tcgagcagac | atgataagat | acattgatga | gtttggacaa | 1680 |
| accacaacta | gaatgcagtg | aaaaaaatgc | tttatttgtg | aaatttgtga | tgctattgct | 1740 |
| ttatttgtaa | ccattataag | ctgcaataaa | caagttaaca | acaacaattg | cattcatttt | 1800 |
| atgtttcagg | ttcaggggga | ggtgtgggag | gttttttaaa | gcaagtaaaa | cctctacaaa | 1860 |
| tgtggtaaaa | tcgataagga | tccgtcgacc | gatgcccttg | agagccttca | acccagtcag | 1920 |
| ctccttccgg | tgggcgcggg | gcatgactat | cgtcgccgca | cttatgactg | tcttctttat | 1980 |
| catgcaactc | gtaggacagg | tgccggcagc | gctcttccgc | ttcctcgctc | actgactcgc | 2040 |
| tgcgctcggt | cgttcggctg | cggcgagcgg | tatcagctca | ctcaaaggcg | gtaatacggt | 2100 |

```
tatccacaga atcaggggat aacgcaggaa agaacatgtg agcaaaaggc cagcaaaagg    2160
ccaggaaccg taaaaaggcc gcgttgctgg cgtttttcca taggctccgc ccccctgacg    2220
agcatcacaa aaatcgacgc tcaagtcaga ggtggcgaaa cccgacagga ctataaagat    2280
accaggcgtt tccccctgga agctccctcg tgcgctctcc tgttccgacc ctgccgctta    2340
ccggatacct gtccgccttt ctcccttcgg gaagcgtggc gctttctcat agctcacgct    2400
gtaggtatct cagttcggtg taggtcgttc gctccaagct gggctgtgtg cacgaacccc    2460
ccgttcagcc cgaccgctgc gccttatccg gtaactatcg tcttgagtcc aacccggtaa    2520
gacacgactt atcgccactg gcagcagcca ctggtaacag gattagcaga gcgaggtatg    2580
taggcggtgc tacagagttc ttgaagtggt ggcctaacta cggctacact agaagaacag    2640
tatttggtat ctgcgctctg ctgaagccag ttaccttcgg aaaaagagtt ggtagctctt    2700
gatccggcaa acaaaccacc gctggtagcg gtggtttttt tgtttgcaag cagcagatta    2760
cgcgcagaaa aaaaggatct caagaagatc ctttgatctt ttctacgggg tctgacgctc    2820
agtggaacga aaactcacgt taagggattt tggtcatgag attatcaaaa aggatcttca    2880
cctagatcct tttaaattaa aaatgaagtt ttaaatcaat ctaaagtata tatgagtaaa    2940
cttggtctga cagttagaaa aactcatcga gcatcaaatg aaactgcaat ttattcatat    3000
caggattatc aataccatat ttttgaaaaa gccgtttctg taatgaagga gaaaactcac    3060
cgaggcagtt ccataggatg gcaagatcct ggtatcggtc tgcgattccg actcgtccaa    3120
catcaataca acctattaat ttcccctcgt caaaaataag gttatcaagt gagaaatcac    3180
catgagtgac gactgaatcc ggtgagaatg gcaaaagttt atgcatttct ttccagactt    3240
gttcaacagg ccagccatta cgctcgtcat caaaatcact cgcatcaacc aaaccgttat    3300
tcattcgtga ttgcgcctga gcgagacgaa atacgcgatc gctgttaaaa ggacaattac    3360
aaacaggaat cgaatgcaac cggcgcagga acactgccag cgcatcaaca atattttcac    3420
ctgaatcagg atattcttct aatacctgga atgctgtttt cccggggatc gcagtggtga    3480
gtaaccatgc atcatcagga gtacggataa aatgcttgat ggtcggaaga ggcataaatt    3540
ccgtcagcca gtttagtctg accatctcat ctgtaacatc attggcaacg ctacctttgc    3600
catgtttcag aaacaactct ggcgcatcgg gcttcccata caatcgatag attgtcgcac    3660
ctgattgccc gacattatcg cgagcccatt tatacccata taaatcagca tccatgttgg    3720
aatttaatcg cggcctagag caagacgttt cccgttgaat atggctcata ctcttccttt    3780
ttcaatatta ttgaagcatt tatcagggtt attgtctcat gagcggatac atatttgaat    3840
gtatttagaa aaataaacaa ataggggttc cgcgcacatt tccccgaaaa gtgccacctg    3900
acgcgccctg tagcggcgca ttaagcgcgg cgggtgtggt ggttacgcgc agcgtgaccg    3960
ctacacttgc cagcgcccta gcgcccgctc ctttcgcttt cttcccttcc tttctcgcca    4020
cgttcgccgg ctttccccgt caagctctaa atcgggggct ccctttaggg ttccgattta    4080
gtgctttacg gcacctcgac cccaaaaaac ttgattaggg tgatggttca cgtagtgggc    4140
catcgccctg atagacggtt tttcgccctt tgacgttgga gtccacgttc tttaatagtg    4200
gactcttgtt ccaaactgga acaacactca accctatctc ggtctattct tttgatttat    4260
aagggatttt gccgatttcg gcctattggt taaaaaatga gctgatttaa caaaaattta    4320
acgcgaattt taacaaaata ttaacgctta caatttgcca ttcgccattc aggctgcgca    4380
actgttggga agggcgatcg gtgcgggcct cttcgctatt acgccagccc aagctaccat    4440
gataagtaag taatattaag gtacgggagg tacttggagc ggccgcaata aaatatcttt    4500
```

| | |
|---|---:|
| attttcatta catctgtgtg ttggtttttt gtgtgaatcg atagtactaa catacgctct | 4560 |
| ccatcaaaac aaaacgaaac aaaacaaact agcaaaatag gctgtcccca gtgcaagtgc | 4620 |
| aggtgccaga acatttctct atcgataggt accgaca | 4657 |

<210> SEQ ID NO 20
<211> LENGTH: 8162
<212> TYPE: DNA
<213> ORGANISM: Artificial Sequence
<220> FEATURE:
<223> OTHER INFORMATION: recombinant construct

<400> SEQUENCE: 20

| | |
|---|---:|
| gacaaccctc accaagggcc aaggtggtga ccgacggacc cacagcgggg tggctggggg | 60 |
| agtcgaaact cgccagtctc cactccactc ccaaccgtgg tgccccacgc gggcctggga | 120 |
| gagtctgtga ggccgcccac cgcttgtcag tagagtgcgc ccgcgagccg taagcacagc | 180 |
| ccggcaacat gcggtcttca gacaggaaag tggccgcgaa tgggaccggg gtgcccagcg | 240 |
| gctgtgggga ctctgtcctg cggaaaccgc ggtgacgagc acaagctcgg tcaactggat | 300 |
| gggaatcggc ctgggggggct ggcaccgcgc ccaccagggg gtttgcggca cttccctctg | 360 |
| ccctcagca ccccaccccct actctccagg aacgtgagtt ctgagccgtg atggtggcag | 420 |
| gaaggggccc tctgtgccat ccgagtcccc agggacccgc agctggcccc cagccatgtg | 480 |
| caaagtatgt gcagggcgct ggcaggcagg gagcagcagg catggtgtcc cctgagggga | 540 |
| gacagtggtc tgggagggag aagtcctggc cctgagggag gtgatggggc aatgctcagc | 600 |
| cctgtctccg gatgccaaag gagggtgcg gggaggccgt cttggagaa ttccaggatg | 660 |
| ggtgctgggt gagagagacg tgtgctggaa ctgtccaggg cggaggtggg ccctgcgggg | 720 |
| gccctcggga gggccctgct ctgattggcc ggcagggcag gggcgggaat tctgggcggg | 780 |
| gccacccag ttagaaaaag cccgggctag gaccgaggag cagggtgagg gaagcttggc | 840 |
| attccggtac tgttggtaaa gccaccatgg aagacgccaa aaacataaag aaaggcccgg | 900 |
| cgccattcta tccgctggaa gatggaaccg ctggagagca actgcataag gctatgaaga | 960 |
| gatacgccct ggttcctgga acaattgctt ttacagatgc acatatcgag gtggacatca | 1020 |
| cttacgctga gtacttcgaa atgtccgttc ggttggcaga agctatgaaa cgatatgggc | 1080 |
| tgaatacaaa tcacagaatc gtcgtatgca gtgaaaactc tcttcaattc tttatgccgg | 1140 |
| tgttgggcgc gttatttatc ggagttgcag ttgcgcccgc gaacgacatt tataatgaac | 1200 |
| gtgaattgct caacagtatg gcatttcgc agcctaccgt ggtgttcgtt tccaaaaagg | 1260 |
| ggttgcaaaa aattttgaac gtgcaaaaaa agctcccaat catccaaaaa attattatca | 1320 |
| tggattctaa aacggattac cagggatttc agtcgatgta cacgttcgtc acatctcatc | 1380 |
| tacctcccgg ttttaatgaa tacgatttg tgccagagtc cttcgatagg gacaagacaa | 1440 |
| ttgcactgat catgaactcc tctggatcta ctggtctgcc taaaggtgtc gctctgcctc | 1500 |
| atagaactgc ctgcgtgaga ttctcgcatg ccagagatcc tattttggc aatcaaatca | 1560 |
| ttccggatac tgcgatttta agtgttgttc cattccatca cggttttgga atgtttacta | 1620 |
| cactcggata tttgatatgt ggatttcgag tcgtcttaat gtatagattt gaagaagagc | 1680 |
| tgtttctgag gagccttcag gattacaaga ttcaaagtgc gctgctggtg ccaaccctat | 1740 |
| tctccttctt cgccaaaagc actctgattg acaaatacga tttatctaat ttacacgaaa | 1800 |
| ttgcttctgg tggcgctccc ctctctaagg aagtcgggga gcggttgcc aagaggttcc | 1860 |
| atctgccagg tatcaggcaa ggatatgggc tcactgagac tacatcagct attctgatta | 1920 |

```
cacccgaggg ggatgataaa ccgggcgcgg tcggtaaagt tgttccattt tttgaagcga      1980
aggttgtgga tctggatacc gggaaaacgc tgggcgttaa tcaaagaggc gaactgtgtg      2040
tgagaggtcc tatgattatg tccggttatg taaacaatcc ggaagcgacc aacgccttga      2100
ttgacaagga tggatggcta cattctggag acatagctta ctgggacgaa gacgaacact      2160
tcttcatcgt tgaccgcctg aagtctctga ttaagtacaa aggctatcag gtggctcccg      2220
ctgaattgga atccatcttg ctccaacacc ccaacatctt cgacgcaggt gtcgcaggtc      2280
ttccccgacga tgacgccggt gaacttcccg ccgccgttgt tgttttggag cacggaaaga      2340
cgatgacgga aaaagagatc gtggattacg tcgccagtca agtaacaacc gcgaaaaagt      2400
tgcgcggagg agttgtgttt gtggacgaag taccgaaagg tcttaccgga aaactcgacg      2460
caagaaaaat cagagagatc ctcataaagg ccaagaaggg cggaaagatc gccgtgtaat      2520
tctagagtcg gggcggccgg ccgcttcgag cagacatgat aagatacatt gatgagtttg      2580
gacaaaccac aactagaatg cagtgaaaaa aatgctttat ttgtgaaatt tgtgatgcta      2640
ttgctttatt tgtaaccatt ataagctgca ataaacaagt taacaacaac aattgcattc      2700
attttatgtt tcaggttcag ggggaggtgt gggaggtttt ttaaagcaag taaaacctct      2760
acaaatgtgg taaaatcgat aaggatccgt cgaccgatgc ccttgagagc cttcaaccca      2820
gtcagctcct tccggtgggc gcggggcatg actatcgtcg ccgcacttat gactgtcttc      2880
tttatcatgc aactcgtagg acaggtgccg gcagcgctct ccgcttcct cgctcactga      2940
ctcgctgcgc tcggtcgttc ggctgcggcg agcggtatca gctcactcaa aggcggtaat      3000
acggttatcc acagaatcag gggataacgc aggaaagaac atgtgagcaa aaggccagca      3060
aaaggccagg aaccgtaaaa aggccgcgtt gctggcgttt ttccataggc tccgcccccc      3120
tgacgagcat cacaaaaatc gacgctcaag tcagaggtgg cgaaacccga caggactata      3180
aagataccag gcgtttcccc ctggaagctc cctcgtgcgc tctcctgttc cgaccctgcc      3240
gcttaccgga tacctgtccg cctttctccc ttcgggaagc gtggcgcttt ctcatagctc      3300
acgctgtagg tatctcagtt cggtgtaggt cgttcgctcc aagctgggct gtgtgcacga      3360
accccccgtt cagcccgacc gctgcgcctt atccggtaac tatcgtcttg agtccaaccc      3420
ggtaagacac gacttatcgc cactggcagc agccactggt aacaggatta gcagagcgag      3480
gtatgtaggc ggtgctacag agttcttgaa gtggtggcct aactacggct acactagaag      3540
aacagtattt ggtatctgcg ctctgctgaa gccagttacc ttcggaaaaa gagttggtag      3600
ctcttgatcc ggcaaacaaa ccaccgctgg tagcggtggt ttttttgttt gcaagcagca      3660
gattacgcgc agaaaaaaag gatctcaaga agatcctttg atcttttcta cggggtctga      3720
cgctcagtgg aacgaaaact cacgttaagg gattttggtc atgagattat caaaaaggat      3780
cttcacctag atccttttaa attaaaaatg aagttttaaa tcaatctaaa gtatatatga      3840
gtaaacttgg tctgacagtt agaaaaactc atcgagcatc aaatgaaact gcaatttatt      3900
catatcagga ttatcaatac catattttg aaaaagccgt ttctgtaatg aaggagaaaa      3960
ctcaccgagg cagttccata ggatggcaag atcctggtat cggtctgcga ttccgactcg      4020
tccaacatca atacaaccta ttaatttccc ctcgtcaaaa ataaggttat caagtgagaa      4080
atcaccatga gtgacgactg aatccggtga gaatggcaaa agtttatgca tttctttcca      4140
gacttgttca acaggccagc cattacgctc gtcatcaaaa tcactcgcat caaccaaacc      4200
gttattcatt cgtgattgcg cctgagcgag acgaaatacg cgatcgctgt taaaaggaca      4260
attacaaaca ggaatcgaat gcaaccggcg caggaacact gccagcgcat caacaatatt      4320
```

-continued

```
ttcacctgaa tcaggatatt cttctaatac ctggaatgct gttttcccgg ggatcgcagt    4380
ggtgagtaac catgcatcat caggagtacg ataaaatgc ttgatggtcg gaagaggcat     4440
aaattccgtc agccagttta gtctgaccat ctcatctgta acatcattgg caacgctacc    4500
tttgccatgt ttcagaaaca actctggcgc atcgggcttc ccatacaatc gatagattgt    4560
cgcacctgat tgcccgacat tatcgcgagc ccatttatac ccatataaat cagcatccat    4620
gttggaattt aatcgcggcc tagagcaaga cgtttcccgt tgaatatggc tcatactctt    4680 ccttttttcaa tattattgaa gcatttatca gggttattgt ctcatgagcg gatacatatt    4740
tgaatgtatt tagaaaaata aacaataggg gttccgcgc acatttcccc gaaaagtgcc     4800
acctgacgcg ccctgtagcg gcgcattaag cgcggcgggt gtggtggtta cgcgcagcgt    4860
gaccgctaca cttgccagcg ccctagcgcc cgctcctttc gctttcttcc cttcctttct    4920
cgccacgttc gccggctttc cccgtcaagc tctaaatcgg gggctccctt tagggttccg    4980
atttagtgct ttacggcacc tcgaccccaa aaaacttgat tagggtgatg gttcacgtag    5040
tgggccatcg ccctgataga cggttttttcg ccctttgacg ttggagtcca cgttctttaa    5100
tagtggactc ttgttccaaa ctggaacaac actcaaccct atctcggtct attcttttga    5160
tttataaggg attttgccga tttcggccta ttggttaaaa aatgagctga tttaacaaaa    5220
atttaacgcg aattttaaca aaatattaac gcttacaatt tgccattcgc cattcaggct    5280
gcgcaactgt tgggaagggc gatcggtgcg ggcctcttcg ctattacgcc agcccaagct    5340
accatgataa gtaagtaata ttaaggtacg gaggtactt ggagcggccg caataaaata     5400
tctttatttt cattacatct gtgtgttggt tttttgtgtg aatcgatagt actaacatac    5460
gctctccatc aaaacaaaac gaaacaaaac aaactagcaa aataggctgt ccccagtgca    5520
agtgcaggtg ccagaacatt tctctatcga tactcgaggg ccatgcaggt aggattttgag   5580 ctgtgttttcc cgccctgatc ctctctcctc tggcggccgg agcctccgta ggctccaagc    5640
ctggcccaga ttcggcggcg cagccggcct tccgcgcgtc cgcacctagc gggggctccg    5700
gggctccggc gcggcaccgg ggggcgctcg ggatctggct gaggctccaa ggcccgcgtg    5760
gccggctcct cctgctgggg caggtggcgg ctgcgcgccc cgcccgagcc caggggcccc    5820
ctcagccgca acaaccagca aggacccccc gactcagccc caagccacct gcatctgcac    5880
tcagacgggg cgcacccgca gtgcagcctc ctggtggggc gctggagcc cgcctgcccc      5940 tgcctgcccg gagacccag ctcacgagca caggccgccc gggcacccca gaaacccggg      6000
atggggcccc tgaattctct aggacgggca ttcagcatgg ccttggcgct ctgcggctcc    6060
ctgcccccca cccagcctcg cccccgcgca cccccagcc cctgcgaccg ccgccccccc      6120
ccccggggcc ccagggcccc agcccgcacc ccccgcccccg ctcttggctc gggttgcggg    6180
ggcgggccgg gggcggggcg agggctccgc gggcgcccat tggcgcgggc gcgaggccag    6240 cggcccccgcg cggccctggg ccgcggctgg cgcgactata agagccgggc gtgggcgccc    6300
gcagttcgcc tgctctccgg cggagctgcg tgaggcccgg ccggcccgg ccccccctt      6360 ccggccgccc ccgcctcctg gcccacgcct gcccgcgctc tgcccaccag cgcctccatc    6420
gggcaaggcg gccccgcgtc gacaagctta gctacgctag cggcattccg gtactgttgg    6480
taaagccacc atggaagacg ccaaaaacat aaagaaaggc ccggcgccat tctatccgct    6540
ggaagatgga accgctggag agcaactgca taaggctatg aagagatacg ccctggttcc    6600
tggaacaatt gcttttacag atgcacatat cgaggtggac atcacttacg ctgagtactt    6660
cgaaatgtcc gttcggttgg cagaagctat gaaacgatat gggctgaata caaatcacag    6720
```

```
aatcgtcgta tgcagtgaaa actctcttca attctttatg ccggtgttgg gcgcgttatt    6780
tatcggagtt gcagttgcgc ccgcgaacga catttataat gaacgtgaat tgctcaacag    6840
tatgggcatt tcgcagccta ccgtggtgtt cgtttccaaa aaggggttgc aaaaaatttt    6900
gaacgtgcaa aaaagctcc caatcatcca aaaaattatt atcatggatt ctaaaacgga    6960
ttaccaggga tttcagtcga tgtacacgtt cgtcacatct catctacctc ccggttttaa    7020
tgaatacgat tttgtgccag agtccttcga tagggacaag acaattgcac tgatcatgaa    7080
ctcctctgga tctactggtc tgcctaaagg tgtcgctctg cctcatagaa ctgcctgcgt    7140
gagattctcg catgccagag atcctatttt tggcaatcaa atcattccgg atactgcgat    7200
tttaagtgtt gttccattcc atcacggttt tggaatgttt actacactcg atatttgat     7260 atgtggattt cgagtcgtct taatgtatag atttgaagaa gagctgtttc tgaggagcct    7320
tcaggattac aagattcaaa gtgcgctgct ggtgccaacc ctattctcct tcttcgccaa    7380
aagcactctg attgacaaat acgatttatc taatttacac gaaattgctt ctggtggcgc    7440 tccctctct aaggaagtcg gggaagcggt tgccaagagg ttccatctgc caggtatcag     7500
gcaaggatat gggctcactg agactacatc agctattctg attacacccg aggggatga     7560 taaaccgggc gcggtcggta aagttgttcc attttttgaa gcgaaggttg tggatctgga    7620
taccgggaaa acgctgggcg ttaatcaaag aggcgaactg tgtgtgagag gtcctatgat    7680
tatgtccggt tatgtaaaca atccggaagc gaccaacgcc ttgattgaca aggatggatg    7740
gctacattct ggagacatag cttactggga cgaagacgaa cacttcttca tcgttgaccg    7800
cctgaagtct ctgattaagt acaaaggcta tcaggtggct cccgctgaat tggaatccat    7860
cttgctccaa caccccaaca tcttcgacgc aggtgtcgca ggtcttcccg acgatgacgc    7920
cggtgaactt cccgccgccg ttgttgtttt ggagcacgga aagacgatga cggaaaaaga    7980
gatcgtggat tacgtcgcca gtcaagtaac aaccgcgaaa aagttgcgcg gaggagttgt    8040
gtttgtggac gaagtaccga aaggtcttac cggaaaactc gacgcaagaa aaatcagaga    8100
gatcctcata aaggccaaga agggcggaaa gatcgccgtg taatctcgag acgtagggta    8160
cc                                                                  8162
```

<210> SEQ ID NO 21
<211> LENGTH: 3579
<212> TYPE: DNA
<213> ORGANISM: Artificial Sequence
<220> FEATURE:
<223> OTHER INFORMATION: recombinant construct

<400> SEQUENCE: 21

```
ctaaattgta agcgttaata tttttgttaaa attcgcgtta aattttttgtt aaatcagctc      60 atttttttaac caataggccg aaatcggcaa aatcccttat aaatcaaaag aatagaccga     120 gataggttg agtgttgttc cagtttggaa caagagtcca ctattaaaga acgtggactc      180
caacgtcaaa gggcgaaaaa ccgtctatca gggctatggc ccactacgtg aaccatcacc     240
ctaatcaagt tttttgggggt cgaggtgccg taaagcacta atcggaacc ctaaagggag     300 ccccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
```

```
taaaacgacg gccagtgagc gcgcgtaata cgactcacta tagggcgaat tgggtaccct    660
acgtctcgag ggatccccaa atctctgtag gtagtttgtc caattatgtc acaccacaga    720
agtaaggttc cttcacaaag atcgcctgac acgatttcct gcacaggctt gagccatata    780
ctcatacatc gcatcttggc cacgtttttcc acgggtttca aaattaatct caagttctac    840
gcttaacgct ttcgcctgtt cccagttatt aatatattca acgctagaac tcccctcagc    900
gaagggaagg ctgagcacta cacgcgaagc accatcaccg aacctttttga taaactcttc    960 cgttccgact tgctccatca acggttcagt gagacttaaa cctaactctt tcttaatagt   1020
ttcggcatta tccactttta gtgcgagaac cttcgtcagt cctggatacg tcactttgac   1080
cacgcctcca gcttttccag agagcgggtt ttcattatct acagagtatc ccgcagcgtc   1140
gtatttattg tcggtactat aaaacccttt ccaatcatcg tcataatttc cttgtgtacc   1200
agattttggc ttttgtatac cttttttgaat ggaatctaca taaccaggtt tagtcccgtg   1260
gtacgaagaa aagttttcca tcacaaaaga tttagaagaa tcaacaacat catcaggatc   1320
catggtggct ttaccaacag taccggaatg ccgctagcgt agctgcggcc gcgagctcca   1380
gcttttgttc cctttagtga gggttaattg cgcgcttggc gtaatcatgg tcatagctgt   1440
ttcctgtgtg aaattgttat ccgctcacaa ttccacacaa catacgagcc ggaagcataa   1500
agtgtaaagc ctggggtgcc taatgagtga gctaactcac attaattgcg ttgcgctcac   1560
tgcccgcttt ccagtcggga aacctgtcgt gccagctgca ttaatgaatc ggccaacgcg   1620
cggggagagg cggtttgcgt attgggcgct cttccgcttc ctcgctcact gactcgctgc   1680
gctcggtcgt tcggctgcgg cgagcggtat cagctcactc aaaggcggta atacggttat   1740
ccacagaatc agggggataac gcaggaaaga acatgtgagc aaaaggccag caaaaggcca   1800
ggaaccgtaa aaaggccgcg ttgctggcgt ttttccatag gctccgcccc cctgacgagc   1860
atcacaaaaa tcgacgctca agtcagaggt ggcgaaaccc gacaggacta taaagatacc   1920
aggcgtttcc ccctggaagc tccctcgtgc gctctcctgt tccgaccctg ccgcttaccg   1980
gatacctgtc cgcctttctc ccttcgggaa gcgtggcgct ttctcatagc tcacgctgta   2040
ggtatctcag ttcggtgtag gtcgttcgct ccaagctggg ctgtgtgcac gaaccccccg   2100
ttcagcccga ccgctgcgcc ttatccggta actatcgtct tgagtccaac ccggtaagac   2160
acgacttatc gccactggca gcagccactg gtaacaggat tagcagagcg aggtatgtag   2220
gcggtgctac agagttcttg aagtggtggc ctaactacgg ctacactaga agaacagtat   2280
ttggtatctg cgctctgctg aagccagtta ccttcggaaa aagagttggt agctcttgat   2340
ccggcaaaca aaccaccgct ggtagcggtg ttttttttgt ttgcaagcag cagattacgc   2400
gcagaaaaaa aggatctcaa gaagatcctt tgatcttttc tacggggtct gacgctcagt   2460
ggaacgaaaa ctcacgttaa gggattttgg tcatgagatt atcaaaaagg atcttcacct   2520
agatcctttt aaattaaaaa tgaagtttta aatcaatcta agtatatat gagtaaactt   2580 ggtctgacag ttaccaatgc ttaatcagtg aggcacctat ctcagcgatc tgtctatttc   2640
gttcatccat agttgcctga ctccccgtcg tgtagataac tacgatacgg gagggcttac   2700
catctggccc cagtgctgca atgataccgc gagaaccacg ctcaccggct ccagatttat   2760
cagcaataaa ccagccagcc ggaagggccg agcgcagaag tggtcctgca actttatccg   2820
cctccatcca gtctattaat tgttgccggg aagctagagt aagtagttcg ccagttaata   2880
gtttgcgcaa cgttgttgcc attgctacag gcatcgtggt gtcacgctcg tcgtttggta   2940
tggcttcatt cagctccggt tcccaacgat caaggcgagt tacatgatcc cccatgttgt   3000
```

| | |
|---|---:|
| gcaaaaaagc ggttagctcc ttcggtcctc cgatcgttgt cagaagtaag ttggccgcag | 3060 |
| tgttatcact catggttatg gcagcactgc ataattctct tactgtcatg ccatccgtaa | 3120 |
| gatgcttttc tgtgactggt gagtactcaa ccaagtcatt ctgagaatag tgtatgcggc | 3180 |
| gaccgagttg ctcttgcccg gcgtcaatac gggataatac cgcgccacat agcagaactt | 3240 |
| taaaagtgct catcattgga aaacgttctt cggggcgaaa actctcaagg atcttaccgc | 3300 |
| tgttgagatc cagttcgatg taacccactc gtgcacccaa ctgatcttca gcatctttta | 3360 |
| ctttcaccag cgtttctggg tgagcaaaaa caggaaggca aaatgccgca aaaagggaa | 3420 |
| taagggcgac acgaaaatgt tgaatactca tactcttcct ttttcaatat tattgaagca | 3480 |
| tttatcaggg ttattgtctc atgagcggat acatatttga atgtatttag aaaaataaac | 3540 |
| aaataggggt tccgcgcaca tttccccgaa aagtgccac | 3579 |

<210> SEQ ID NO 22
<211> LENGTH: 8086
<212> TYPE: DNA
<213> ORGANISM: Artificial Sequence
<220> FEATURE:
<223> OTHER INFORMATION: recombinant construct
<400> SEQUENCE: 22

| | |
|---|---:|
| ggtgcgggcc tcttcgctat tacgccagcc caagctacca tgataagtaa gtaatattaa | 60 |
| ggtacgggag gtacttggag cggccgcaat aaaatatctt tattttcatt acatctgtgt | 120 |
| gttggttttt tgtgtgaatc gatagtacta acatacgctc tccatcaaaa caaaacgaaa | 180 |
| caaaacaaac tagcaaaata ggctgtcccc agtgcaagtg caggtgccag aacatttctc | 240 |
| tatcgataac ttcccggtcg gtctgtgggt gcaggggtg ccgcctcaca tgtgtgattc | 300 |
| gtgccttgcg ggccctggcc tccggggtgc tgggtaacga ggaggggcgc ggagccgcag | 360 |
| aagcccaccc tggtatgttg acgcggtgcc agcgagaccg cgagaggaag acggggtgg | 420 |
| gcggggccag gatggagagg ggccgagttg cggagtca tggcagacgc cacattcgcg | 480 |
| acatctcccc cacacccct ctggctctgt ccgcaacatt tccaaacagg agtcccggga | 540 |
| gaggggaga ggggctgctg gtctgaggct aagaagggca gagccttcga cccgagaga | 600 |
| ggccgcggcc cctgcccagt gggcagcgtg gaagtttcca tacaaggagg tgggaaggag | 660 |
| accccccccc cccttcactg ccctgtgcag agatgagccg ggggtgcagg atgggagccc | 720 |
| atggcacttc gctacgggat ggtccagggc tcccggttgg gggtgcagga gagaagagac | 780 |
| tggctgggag gagggagagg gcgggagcaa aggcgcgggg gagtggtcag cagggagagg | 840 |
| ggtgggggt agggtggagc ccgggctggg aggagtcggc tcacacataa aagctgaggc | 900 |
| actgaccagc ctgcaaactg gacattagct tctcctgtga aagagacttc cagcttcctc | 960 |
| ctcctcctct tcctcctcct cctcctgccc cagcgagcct tctgctgagc tgtaggggga | 1020 |
| tcttctagag tcggctagcg gcattccggt actgttggta aagccaccat ggaagacgcc | 1080 |
| aaaaacataa agaaaggccc ggcgccattc tatccgctgg aagatggaac cgctggagag | 1140 |
| caactgcata aggctatgaa gagatacgcc ctggttcctg gaacaattgc ttttacagat | 1200 |
| gcacatatcg aggtggacat cacttacgct gagtacttcg aaatgtccgt tcggttggca | 1260 |
| gaagctatga acgatatggg gctgaataca aatcacagaa tcgtcgtatg cagtgaaaac | 1320 |
| tctcttcaat ctttatgcc ggtgttgggc gcgttattta tcggagttgc agttgcgccc | 1380 |
| gcgaacgaca tttataatga acgtgaattg ctcaacagta tgggcatttc gcagcctacc | 1440 |
| gtggtgttcg tttccaaaaa ggggttgcaa aaaattttga acgtgcaaaa aaagctccca | 1500 |

```
atcatccaaa aaattattat catggattct aaaacggatt accagggatt tcagtcgatg    1560
tacacgttcg tcacatctca tctacctccc ggttttaatg aatacgattt tgtgccagag    1620
tccttcgata gggacaagac aattgcactg atcatgaact cctctggatc tactggtctg    1680
cctaaaggtg tcgctctgcc tcatagaact gcctgcgtga gattctcgca tgccagagat    1740
cctattttg gcaatcaaat cattccggat actgcgattt taagtgttgt tccattccat    1800
cacggttttg gaatgtttac tacactcgga tatttgatat gtggatttcg agtcgtctta    1860
atgtatagat ttgaagaaga gctgtttctg aggagccttc aggattacaa gattcaaagt    1920
gcgctgctgg tgccaaccct attctccttc ttcgccaaaa gcactctgat tgacaaatac    1980
gatttatcta atttacacga aattgcttct ggtggcgctc ccctctctaa ggaagtcggg    2040
gaagcggttg ccaagaggtt ccatctgcca ggtatcaggc aaggatatgg gctcactgag    2100
actacatcag ctattctgat tacacccgag ggggatgata aaccgggcgc ggtcggtaaa    2160
gttgttccat tttttgaagc gaaggttgtg gatctggata ccgggaaaac gctgggcgtt    2220
aatcaaagag gcgaactgtg tgtgagaggt cctatgatta tgtccggtta tgtaaacaat    2280
ccggaagcga ccaacgcctt gattgacaag gatggatggc tacattctgg agacatagct    2340
tactgggacg aagacgaaca cttcttcatc gttgaccgcc tgaagtctct gattaagtac    2400
aaaggctatc aggtggctcc cgctgaattg gaatccatct gctccaaca ccccaacatc    2460
ttcgacgcag gtgtcgcagg tcttcccgac gatgacgccg tgaacttcc cgccgccgtt    2520
gttgttttgg agcacggaaa gacgatgacg gaaaagaga tcgtggatta cgtcgccagt    2580
caagtaacaa ccgcgaaaaa gttgcgcgga ggagttgtgt ttgtggacga agtaccgaaa    2640
ggtcttaccg gaaaactcga cgcaagaaaa atcagagaga tcctcataaa ggccaagaag    2700
ggcggaaaga tcgccgtgta atctcgaggg ccatgcaggt aggatttgag ctgtgtttcc    2760
cgccctgatc ctctctcctc tggcggccgg agcctccgta ggctccaagc tggcccaga    2820
ttcggcggcg cagccggcct tccgcgcgtc cgcacctagc gggggctccg gggctccggc    2880
gcggcaccgg ggggcgctcg ggatctggct gaggctccaa ggcccgcgtg ccggctcct    2940
cctgctgggg caggtggcgg ctgcgcgccc cgcccgagcc caggggcccc ctcagccgca    3000
acaaccagca aggaccccc gactcagccc caagccacct gcatctgcac tcagacgggg    3060
cgcacccgca gtcagcctc ctggtggggc gctgggagcc cgcctgcccc tgcctgcccg    3120
gagacccag ctcacgagca caggccgccc gggcacccca gaaacccggg atggggcccc    3180
tgaattctct aggacgggca ttcagcatgg ccttggcgct ctgcggctcc ctgcccccca    3240
cccagcctcg ccccgcgca ccccagcc cctgcgaccg ccgcccccc cccggggcc    3300
ccagggcccc agcccgcacc ccgcccg ctcttggctc gggttgcggg gcgggccgg    3360
gggcggggcg agggctccgc gggcgcccat ggcgcgggc gcgaggccag cggccccgcg    3420
cggccctggg ccgcggctgg cgcgactata agagccgggc gtgggcgccc gcagttcgcc    3480
tgctctccgg cggagctgcg tgaggcccgg ccggccccgg ccccccctt ccggccgccc    3540
ccgcctcctg gccacgcct gcccgcgctc tgcccaccag cgcctccatc gggcaaggcg    3600
gccccgcgtc gacaagcttg gcattccggt actgttggta aagccaccat ggaagacgcc    3660
aaaaacataa agaaaggccc ggcgccattc tatccgctgg aagatggaac cgctggagag    3720
caactgcata aggctatgaa gagatacgcc ctggttcctg gaacaattgc ttttacagat    3780
gcacatatcg aggtggacat cacttacgct gagtacttcg aaatgtccgt tcggttggca    3840
gaagctatga aacgatatgg gctgaataca aatcacagaa tcgtcgtatg cagtgaaaac    3900
```

```
tctcttcaat tctttatgcc ggtgttgggc gcgttattta tcggagttgc agttgcgccc    3960
gcgaacgaca tttataatga acgtgaattg ctcaacagta tgggcatttc gcagcctacc    4020
gtggtgttcg tttccaaaaa ggggttgcaa aaattttga acgtgcaaaa aaagctccca     4080
atcatccaaa aaattattat catggattct aaaacggatt accagggatt tcagtcgatg    4140
tacacgttcg tcacatctca tctacctccc ggttttaatg aatacgattt tgtgccagag    4200
tccttcgata gggacaagac aattgcactg atcatgaact cctctggatc tactggtctg    4260
cctaaaggtg tcgctctgcc tcatagaact gcctgcgtga gattctcgca tgccagagat    4320 cctattttg gcaatcaaat cattccggat actgcgattt taagtgttgt tccattccat      4380
cacggttttg gaatgtttac tacactcgga tatttgatat gtggatttcg agtcgtctta    4440
atgtatagat ttgaagaaga gctgtttctg aggagccttc aggattacaa gattcaaagt    4500
gcgctgctgg tgccaaccct attctccttc ttcgccaaaa gcactctgat tgacaaatac    4560
gatttatcta atttcacga aattgcttct ggtggcgctc ccctctctaa ggaagtcggg      4620
gaagcggttg ccaagaggtt ccatctgcca ggtatcaggc aaggatatgg gctcactgag    4680
actacatcag ctattctgat tacacccgag ggggatgata aaccgggcgc ggtcggtaaa    4740
gttgttccat tttttgaagc gaaggttgtg atctgggata ccgggaaaac gctgggcgtt    4800
aatcaaagag gcgaactgtg tgtgagaggt cctatgatta tgtccggtta tgtaaacaat    4860
ccggaagcga ccaacgcctt gattgacaag atggatggc tacattctgg agacatagct      4920
tactgggacg aagacgaaca cttcttcatc gttgaccgcc tgaagtctct gattaagtac    4980
aaaggctatc aggtggctcc cgctgaattg gaatccatct tgctccaaca ccccaacatc    5040
ttcgacgcag gtgtcgcagg tcttcccgac gatgacgccg gtgaacttcc cgccgccgtt    5100
gttgttttgg agcacggaaa gacgatgacg gaaaaagaga tcgtggatta cgtcgccagt    5160
caagtaacaa ccgcgaaaaa gttgcgcgga ggagttgtgt tgtggacga agtaccgaaa      5220 ggtcttaccg gaaaactcga cgcaagaaaa atcagagaga tcctcataaa ggccaagaag    5280
ggcggaaaga tcgccgtgta attctagagt cggggcggcc ggccgcttcg agcagacatg    5340
ataagataca ttgatgagtt tggacaaacc acaactagaa tgcagtgaaa aaatgcttt     5400 atttgtgaaa tttgtgatgc tattgcttta tttgtaacca ttataagctg caataaacaa    5460
gttaacaaca acaattgcat tcattttatg tttcaggttc aggggaggt gtgggaggtt     5520 ttttaaagca agtaaaacct ctacaaatgt ggtaaaatcg ataaggatcc gtcgaccgat    5580
gcccttgaga gccttcaacc cagtcagctc cttccggtgg gcgcggggca tgactatcgt    5640
cgccgcactt atgactgtct tctttatcat gcaactcgta ggacaggtgc cggcagcgct    5700
cttccgcttc ctcgctcact gactcgctgc gctcggtcgt tcggctgcgg cgagcggtat    5760
cagctcactc aaaggcggta atacggttat ccacagaatc aggggataac gcaggaaaga    5820
acatgtgagc aaaaggccag caaaaggcca ggaaccgtaa aaaggccgcg ttgctggcgt    5880
ttttccatag gctccgcccc cctgacgagc atcacaaaaa tcgacgctca agtcagaggt    5940
ggcgaaaccc gacaggacta taaagatacc aggcgtttcc ccctggaagc tccctcgtgc    6000
gctctcctgt tccgaccctg ccgcttaccg gatacctgtc gcctttctc ccttcgggaa      6060 gcgtggcgct ttctcatagc tcacgctgta ggtatctcag ttcggtgtag tcgttcgct      6120 ccaagctggg ctgtgtgcac gaaccccccg ttcagcccga ccgctgcgcc ttatccggta    6180
actatcgtct gagtccaac ccggtaagac acgacttatc gccactggca gcagccactg      6240
gtaacaggat tagcagagcg aggtatgtag gcggtgctac agagttcttg aagtggtggc    6300
```

```
ctaactacgg ctacactaga agaacagtat ttggtatctg cgctctgctg aagccagtta    6360
ccttcggaaa aagagttggt agctcttgat ccggcaaaca aaccaccgct ggtagcggtg    6420 gttttttttgt ttgcaagcag cagattacgc gcagaaaaaa aggatctcaa gaagatcctt   6480
tgatcttttc tacggggtct gacgctcagt ggaacgaaaa ctcacgttaa gggattttgg    6540
tcatgagatt atcaaaaagg atcttcacct agatccttt aaattaaaaa tgaagtttta     6600
aatcaatcta agtatatat gagtaaactt ggtctgacag ttagaaaaac tcatcgagca     6660
tcaaatgaaa ctgcaattta ttcatatcag gattatcaat accatatttt tgaaaaagcc    6720
gtttctgtaa tgaaggagaa aactcaccga ggcagttcca taggatgca agatcctggt     6780 atcggtctgc gattccgact cgtccaacat caatacaacc tattaatttc cctcgtcaa     6840 aaataaggtt atcaagtgag aaatcaccat gagtgacgac tgaatccggt gagaatggca    6900
aaagtttatg catttctttc cagacttgtt caacaggcca gccattacgc tcgtcatcaa    6960
aatcactcgc atcaaccaaa ccgttattca ttcgtgattg cgcctgagcg agacgaaata    7020
cgcgatcgct gttaaaagga caattacaaa caggaatcga atgcaaccgg cgcaggaaca    7080
ctgccagcgc atcaacaata ttttcacctg aatcaggata ttcttctaat acctggaatg    7140
ctgttttccc ggggatcgca gtggtgagta accatgcatc atcaggagta cggataaaat    7200
gcttgatggt cggaagaggc ataaattccg tcagccagtt tagtctgacc atctcatctg    7260
taacatcatt ggcaacgcta cctttgccat gtttcagaaa caactctggc gcatcgggct    7320
tcccatacaa tcgatagatt gtcgcacctg attgcccgac attatcgcga gcccatttat    7380
acccatataa atcagcatcc atgttggaat ttaatcgcgg cctagagcaa gacgtttccc    7440
gttgaatatg gctcatactc ttccttttc aatattattg aagcatttat cagggttatt     7500
gtctcatgag cggatacata tttgaatgta tttagaaaaa taaacaaata ggggttccgc    7560
gcacatttcc ccgaaaagtg ccacctgacg cgccctgtag cggcgcatta agcgcggcgg    7620
gtgtggtggt tacgcgcagc gtgaccgcta cacttgccag cgccctagcg cccgctcctt    7680
tcgctttctt cccttccttt ctcgccacgt tcgccggctt tccccgtcaa gctctaaatc    7740
gggggctccc tttagggttc cgatttagtg ctttacggca cctcgacccc aaaaaacttg    7800
attagggtga tggttcacgt agtgggccat cgccctgata dacggttttt cgccctttga    7860
cgttggagtc cacgttcttt aatagtggac tcttgttcca aactggaaca acactcaacc    7920
ctatctcggt ctattctttt gatttataag ggattttgcc gatttcggcc tattggttaa    7980
aaaatgagct gatttaacaa aaatttaacg cgaattttaa caaatatta acgcttacaa     8040 tttgccattc gccattcagg ctgcgcaact gttgggaagg gcgatc                    8086
```

<210> SEQ ID NO 23
<211> LENGTH: 3843
<212> TYPE: DNA
<213> ORGANISM: Artificial Sequence
<220> FEATURE:
<223> OTHER INFORMATION: recombinant construct

<400> SEQUENCE: 23

```
ctaaattgta agcgttaata tttttgttaaa attcgcgtta aatttttgtt aaatcagctc      60
attttttaac caataggccg aaatcggcaa aatcccttat aaatcaaaag aatagaccga     120
gatagggttg agtgttgttc cagtttggaa caagagtcca ctattaaaga acgtggactc     180
caacgtcaaa gggcgaaaaa ccgtctatca gggctatggc ccactacgtg aaccatcacc     240
ctaatcaagt ttttttgggt cgaggtgccg taaagcacta aatcggaacc ctaaagggag     300
```

```
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tgggtaccct    660
acgtctcgag gtagctgcta ccgactctga aagatccccc tacagctcag cagaaggct    720
cgctggggca ggaggaggag gaggaagagg aggaggagga agctggaagt ctctttcaca    780
ggagaagcta atgtccagtt tgcaggctgg tcagtgcctc agcttttatg tgtgagccga    840
ctcctcccag cccgggctcc accctacccc ccacccctct ccctgctgac cactcccccg    900
cgcctttgct cccgccctct ccctcctccc agccagtctc ttctctcctg cacccccaac    960
cgggagccct ggaccatccc gtagcgaagt gccatgggct cccatcctgc acccccggct   1020
catctctgca cagggcagtg aagggggggg ggggtctcct tcccacctcc ttgtatggaa   1080
acttccacgc tgcccactgg gcaggggccg cggcctctct ccgggtcgaa ggctctgccc   1140
ttcttagcct cagaccagca gccccctctcc ccctctcccg ggactcctgt ttggaaatgt   1200
tgcggacaga gccagagggg gtgtggggga gatgtcgcga atgtggcgtc tgccatgact   1260
cctgccaact cggcccctct ccatcctggc cccgccaccc ccgtcttcc tctcgcggtc    1320
tcgctggcac cgcgtcaaca taccagggtg ggcttctgcg gctccgcgcc cctcctcgtt   1380
acccagcacc ccggaggcca gggcccgcaa ggcacgaatc acacatgtga ggcggcaccc   1440
cctgcaccca cagaccgacc gggaagttat cgatagagaa atgttctggc acctgcactt   1500
gcactgggga cagcctattt tgctagtttg ttttgtttcg ttttgttttg atggagagcg   1560
tatgttagta ctatcgattc acacaaaaaa ccaacacaca gatgtaatga aaataaagat   1620
attttattgc ggccgcgagc tccagctttt gttccctta gtgagggtta attgcgcgct   1680
tggcgtaatc atggtcatag ctgtttcctg tgtgaaattg ttatccgctc acaattccac   1740
acaacatacg agccggaagc ataaagtgta aagcctgggg tgcctaatga gtgagctaac   1800
tcacattaat tgcgttgcgc tcactgcccg ctttccagtc gggaaacctg tcgtgccagc   1860
tgcattaatg aatcggccaa cgcgcgggga gaggcggttt gcgtattggg cgctcttccg   1920
cttcctcgct cactgactcg ctgcgctcgg tcgttcggct gcggcgagcg gtatcagctc   1980
actcaaaggc ggtaatacgg ttatccacag aatcagggga taacgcagga agaacatgt    2040
gagcaaaagg ccagcaaaag gccaggaacc gtaaaaaggc cgcgttgctg gcgttttcc    2100
ataggctccg ccccctgac gagcatcaca aaaatcgacg ctcaagtcag aggtggcgaa    2160
acccgacagg actataaaga taccaggcgt ttccccctgg aagctccctc gtgcgctctc   2220
ctgttccgac cctgccgctt accggatacc tgtccgcctt ctcccttcg ggaagcgtgg    2280
cgctttctca tagctcacgc tgtaggtatc tcagttcggt gtaggtcgtt cgctccaagc   2340
tgggctgtgt gcacgaaccc cccgttcagc ccgaccgctg cgccttatcc ggtaactatc   2400
gtcttgagtc aacccggta agacacgact tatcgccact ggcagcagcc actggtaaca    2460
ggattagcag agcgaggtat gtaggcggtg ctacagagtt cttgaagtgg tggcctaact   2520
acggctacac tagaagaaca gtatttggta tctgcgctct gctgaagcca gttaccttcg   2580
gaaaaagagt tggtagctct tgatccggca acaaaccac cgctggtagc ggtggttttt   2640
ttgtttgcaa gcagcagatt acgcgcagaa aaaaaggatc tcaagaagat cctttgatct   2700
```

-continued

| | |
|---|---|
| tttctacggg gtctgacgct cagtggaacg aaaactcacg ttaagggatt ttggtcatga | 2760 |
| gattatcaaa aaggatcttc acctagatcc ttttaaatta aaatgaagt tttaaatcaa | 2820 |
| tctaaagtat atatgagtaa acttggtctg acagttacca atgcttaatc agtgaggcac | 2880 |
| ctatctcagc gatctgtcta tttcgttcat ccatagttgc ctgactcccc gtcgtgtaga | 2940 |
| taactacgat acgggagggc ttaccatctg gccccagtgc tgcaatgata ccgcgagaac | 3000 |
| cacgctcacc ggctccagat ttatcagcaa taaaccagcc agccggaagg gccgagcgca | 3060 |
| gaagtggtcc tgcaacttta tccgcctcca tccagtctat taattgttgc cgggaagcta | 3120 |
| gagtaagtag ttcgccagtt aatagtttgc gcaacgttgt tgccattgct acaggcatcg | 3180 |
| tggtgtcacg ctcgtcgttt ggtatggctt cattcagctc cggttcccaa cgatcaaggc | 3240 |
| gagttacatg atcccccatg ttgtgcaaaa aagcggttag ctccttcggt cctccgatcg | 3300 |
| ttgtcagaag taagttggcc gcagtgttat cactcatggt tatggcagca ctgcataatt | 3360 |
| ctcttactgt catgccatcc gtaagatgct tttctgtgac tggtgagtac tcaaccaagt | 3420 |
| cattctgaga atagtgtatg cggcgaccga gttgctcttg cccggcgtca atacgggata | 3480 |
| ataccgcgcc acatagcaga actttaaaag tgctcatcat tggaaaacgt tcttcggggc | 3540 |
| gaaaactctc aaggatctta ccgctgttga tccagttc gatgtaaccc actcgtgcac | 3600 |
| ccaactgatc ttcagcatct tttactttca ccagcgtttc tgggtgagca aaaacaggaa | 3660 |
| ggcaaaatgc cgcaaaaaag gaataagggc gacacggaa atgttgaata ctcatactct | 3720 |
| tcctttttca atattattga agcatttatc agggttattg tctcatgagc ggatacatat | 3780 |
| ttgaatgtat ttagaaaaat aaacaaatag gggttccgcg cacatttccc cgaaaagtgc | 3840 |
| cac | 3843 |

<210> SEQ ID NO 24
<211> LENGTH: 6084
<212> TYPE: DNA
<213> ORGANISM: Artificial Sequence
<220> FEATURE:
<223> OTHER INFORMATION: recombinant construct

<400> SEQUENCE: 24

| | |
|---|---|
| gcggccgcaa taaatatct ttattttcat tacatctgtg tgttggtttt tgtgtgaat | 60 |
| cgatagtact aacatacgct ctccatcaaa acaaaacgaa acaaaacaaa ctagcaaaat | 120 |
| aggctgtccc cagtgcaagt gcaggtgcca gaacatttct ctatcgataa cttcccggtc | 180 |
| ggtctgtggg tgcaggggt gccgcctcac atgtgtgatt cgtgccttgc gggccctggc | 240 |
| ctccggggtg ctgggtaacg aggaggggcg cggagccgca gaagcccacc ctggtatgtt | 300 |
| gacgcggtgc cagcgagacc gcgagaggaa gacggggggtg gcggggcca ggatggagag | 360 |
| gggccgagtt ggcaggagtc atggcagacg ccacattcgc gacatctccc ccacacccc | 420 |
| tctggctctg tccgcaacat ttccaaacag gagtcccggg agaggggag aggggctgct | 480 |
| ggtctgaggc taagaagggc agagccttcg acccggagag aggccgcggc ccctgcccag | 540 |
| tgggcagcgt ggaagtttcc atacaaggag gtgggaagga accccccccc cccttcact | 600 |
| gccctgtgca gagatgagcc gggggtgcag gatgggagcc catggcactt cgctacggga | 660 |
| tggtccaggg ctcccggttg ggggtgcagg agagaagaga ctggctggga ggagggagag | 720 |
| ggcgggagca aaggcgcggg ggagtggtca gcagggagag gggtgggggg tagggtggag | 780 |
| cccgggctgg gaggagtcgg ctcacacata aaagctgagg cactgaccag cctgcaaact | 840 |
| ggacattagc ttctcctgtg aaagagactt ccagcttcct cctcctcctc ttcctcctcc | 900 |

-continued

| | |
|---|---|
| tcctcctgcc ccagcgagcc ttctgctgag ctgtaggggg atcttctaga gtcggctagc | 960 |
| ggcattccgg tactgttggt aaagccacca tggatcctga tgatgttgtt gattcttcta | 1020 |
| aatcttttgt gatggaaaac ttttcttcgt accacgggac taaacctggt tatgtagatt | 1080 |
| ccattcaaaa aggtatacaa agccaaaat ctggtacaca aggaaattat gacgatgatt | 1140 |
| ggaaagggtt ttatagtacc gacaataaat acgacgctgc gggatactct gtagataatg | 1200 |
| aaaacccgct ctctggaaaa gctggaggcg tggtcaaagt gacgtatcca ggactgacga | 1260 |
| aggttctcgc actaaaagtg gataatgccg aaactattaa gaaagagtta ggtttaagtc | 1320 |
| tcactgaacc gttgatggag caagtcggaa cggaagagtt tatcaaaagg ttcggtgatg | 1380 |
| gtgcttcgcg tgtagtgctc agccttccct tcgctgaggg gagttctagc gttgaatata | 1440 |
| ttaataactg gaacaggcg aaagcgttaa gcgtagaact tgagattaat tttgaaaccc | 1500 |
| gtggaaaacg tggccaagat gcgatgtatg agtatatggc tcaagcctgt gcaggaaatc | 1560 |
| gtgtcaggcg atctttgtga aggaacctta cttctgtggt gtgacataat tggacaaact | 1620 |
| acctacagag atttggggat ccctcgaggg ccatgcaggt aggatttgag ctgtgtttcc | 1680 |
| cgccctgatc ctctctcctc tggcggccgg agcctccgta ggctccaagc ctggcccaga | 1740 |
| ttcggcggc cagccggcct tccgcgcgtc cgcacctagc gggggctccg ggctccggc | 1800 |
| gcggcaccgg ggggcgctcg ggatctggct gaggctccaa ggcccgcgtg gccggctcct | 1860 |
| cctgctgggg caggtggcgg ctgcgcgccc cgcccgagcc caggggcccc ctcagccgca | 1920 |
| acaaccagca aggaccccc gactcagccc caagccacct gcatctgcac tcagacgggg | 1980 |
| cgcacccgca gtgcagcctc ctggtggggc gctgggagcc cgcctgcccc tgcctgcccg | 2040 |
| gagacccag ctcacgagca caggccgccc gggcacccca gaaacccggg atggggcccc | 2100 |
| tgaattctct aggacgggca ttcagcatgg ccttggcgct ctgcggctcc ctgcccccca | 2160 |
| cccagcctcg ccccgcgca cccccagcc cctgcgaccg ccgcccccc cccggggcc | 2220 |
| ccagggcccc agcccgcacc ccccgcccg ctcttggctc gggttgcggg ggcgggccgg | 2280 |
| gggcggggcg agggctccgc gggcgcccat ggcgcgggc gcgaggccag cggccccgcg | 2340 |
| cggccctggg ccgcggctgg cgcgactata agagccgggc gtgggcgccc gcagttcgcc | 2400 |
| tgctctccgg cggagctgcg tgaggcccgg ccggccccgg cccccccctt ccggccgccc | 2460 |
| ccgcctcctg gccacgcct gcccgcgctc tgcccaccag cgcctccatc gggcaaggcg | 2520 |
| gccccgcgtc gacaagcttg gcattccggt actgttggta aagccaccat ggatcctgat | 2580 |
| gatgttgttg attcttctaa atcttttgtg atggaaaact tttcttcgta ccacgggact | 2640 |
| aaacctggtt atgtagattc cattcaaaaa ggtatacaaa agccaaaatc tggtacacaa | 2700 |
| ggaaattatg acgatgattg gaaagggttt tatagtaccg acaataaata cgacgctgcg | 2760 |
| ggatactctg tagataatga aaacccgctc tctggaaaag ctggaggcgt ggtcaaagtg | 2820 |
| acgtatccag gactgacgaa ggttctcgca ctaaaagtgg ataatgccga aactattaag | 2880 |
| aaagagttag gtttaagtct cactgaaccg ttgatggagc aagtcggaac ggaagagttt | 2940 |
| atcaaaaggt tcggtgatgg tgcttcgcgt gtagtgctca gccttccctt cgctgagggg | 3000 |
| agttctagcg ttgaatatat taataactgg aacaggcga aagcgttaag cgtagaactt | 3060 |
| gagattaatt ttgaaacccg tggaaaacgt ggccaagatg cgatgtatga gtatatggct | 3120 |
| caagcctgtg caggaaatcg tgtcaggcga tctttgtgaa ggaaccttac ttctgtggtg | 3180 |
| tgacataatt ggacaaacta cctacagaga tttggggatc ctctagagtc ggggcggccg | 3240 |
| gccgcttcga gcagacatga taagatacat tgatgagttt ggacaaacca caactagaat | 3300 |

```
gcagtgaaaa aaatgcttta tttgtgaaat ttgtgatgct attgctttat ttgtaaccat    3360
tataagctgc aataaacaag ttaacaacaa caattgcatt cattttatgt ttcaggttca    3420
gggggaggtg tgggaggttt tttaaagcaa gtaaaacctc tacaaatgtg gtaaaatcga    3480
taaggatccg tcgaccgatg cccttgagag ccttcaaccc agtcagctcc ttccggtggg    3540
cgcggggcat gactatcgtc gccgcactta tgactgtctt ctttatcatg caactcgtag    3600
gacaggtgcc ggcagcgctc ttccgcttcc tcgctcactg actcgctgcg ctcggtcgtt    3660
cggctgcggc gagcggtatc agctcactca aaggcggtaa tacggttatc cacagaatca    3720
ggggataacg caggaaagaa catgtgagca aaaggccagc aaaaggccag gaaccgtaaa    3780
aaggccgcgt tgctggcgtt tttccatagg ctccgccccc ctgacgagca tcacaaaaat    3840
cgacgctcaa gtcagaggtg gcgaaacccg acaggactat aaagatacca ggcgtttccc    3900
cctggaagct ccctcgtgcg ctctcctgtt ccgaccctgc cgcttaccgg atacctgtcc    3960
gcctttctcc cttcgggaag cgtggcgctt tctcatagct cacgctgtag gtatctcagt    4020
tcggtgtagg tcgttcgctc caagctgggc tgtgtgcacg aacccccccgt tcagcccgac    4080
cgctgcgcct tatccggtaa ctatcgtctt gagtccaacc cggtaagaca cgacttatcg    4140
ccactggcag cagccactgg taacaggatt agcagagcga ggtatgtagg cggtgctaca    4200
gagttcttga agtggtggcc taactacggc tacactagaa gaacagtatt tggtatctgc    4260
gctctgctga agccagttac cttcggaaaa agagttggta gctcttgatc cggcaaacaa    4320
accaccgctg gtagcggtgg ttttttttgtt tgcaagcagc agattacgcg cagaaaaaaa    4380
ggatctcaag aagatccttt gatcttttct acggggtctg acgctcagtg gaacgaaaac    4440
tcacgttaag ggattttggt catgagatta tcaaaaagga tcttcaccta gatccttttta   4500
aattaaaaat gaagttttaa atcaatctaa agtatatatg agtaaacttg gtctgacagt    4560
tagaaaaact catcgagcat caaatgaaac tgcaatttat tcatatcagg attatcaata    4620
ccatattttt gaaaaagccg tttctgtaat gaaggagaaa actcaccgag gcagttccat    4680
aggatggcaa gatcctggta tcggtctgcg attccgactc gtccaacatc aatacaacct    4740
attaatttcc cctcgtcaaa aataaggtta tcaagtgaga aatcaccatg agtgacgact    4800
gaatccggtg agaatggcaa aagtttatgc atttcttttcc agacttgttc aacaggccag    4860
ccattacgct cgtcatcaaa atcactcgca tcaaccaaac cgttattcat tcgtgattgc    4920
gcctgagcga gacgaaatac gcgatcgctg ttaaaaggac aattacaaac aggaatcgaa    4980
tgcaaccggc gcaggaacac tgccagcgca tcaacaatat tttcacctga atcaggatat    5040
tcttctaata cctggaatgc tgttttcccg gggatcgcag tggtgagtaa ccatgcatca    5100
tcaggagtac ggataaaatg cttgatggtc ggaagaggca taaattccgt cagccagttt    5160
agtctgacca tctcatctgt aacatcattg gcaacgctac ctttgccatg tttcagaaac    5220
aactctggcg catcgggctt cccatacaat cgatagattg tcgcacctga ttgcccgaca    5280
ttatcgcgag cccatttata cccatataaa tcagcatcca tgttggaatt taatcgcggc    5340
ctagagcaag acgtttcccg ttgaatatgg ctcatactct ccttttttca atattattga    5400
agcatttatc agggttattg tctcatgagc ggatacatat ttgaatgtat ttagaaaaat    5460
aaacaaatag gggttccgcg cacatttccc cgaaaagtgc cacctgacgc gccctgtagc    5520
ggcgcattaa gcgcggcggg tgtggtggtt acgcgcagcg tgaccgctac acttgccagc    5580
gccctagcgc ccgctccttt cgctttcttc ccttcctttc tcgccacgtt cgccggcttt    5640
ccccgtcaag ctctaaatcg ggggctccct ttagggttcc gatttagtgc tttacggcac    5700
```

-continued

```
ctcgacccca aaaaacttga ttagggtgat ggttcacgta gtgggccatc gccctgatag    5760
acggtttttc gccctttgac gttggagtcc acgttcttta atagtggact cttgttccaa    5820
actggaacaa cactcaaccc tatctcggtc tattcttttg atttataagg gattttgccg    5880
atttcggcct attggttaaa aaatgagctg atttaacaaa aatttaacgc gaattttaac    5940
aaaatattaa cgcttacaat ttgccattcg ccattcaggc tgcgcaactg ttgggaaggg    6000
cgatcggtgc gggcctcttc gctattacgc cagcccaagc taccatgata agtaagtaat    6060
attaaggtac gggaggtact tgga                                           6084
```

DIPHTHERIA TOXIN FIRST OPEN READING FRAME OPERABLY LINKED TO AN H19 PROMOTER AND A DIPHTHERIA TOXIN SECOND OPEN READING FRAME OPERABLY LINKED TO AN IGF-II PROMOTER AS NUCLEIC ACID CONSTRUCT

This application is a 371 filing of International Patent Application PCT/IL2008/001405 filed Oct. 23, 2008, which claims the benefit of application Ser. No. 60/982,442 filed Oct. 25, 2007.

FIELD OF THE INVENTION

The present invention is directed to the field of cancer treatment, specifically to novel nucleic acid constructs that are particularly useful for treating tumors expressing H19 and/or IGF-II.

BACKGROUND OF THE INVENTION

Neoplasia is a process that occurs in cancer, by which the normal controlling mechanisms that regulate cell growth and differentiation are impaired, resulting in progressive growth. This impairment of control mechanisms allows a tumor to enlarge and occupy spaces in vital areas of the body. If the tumor invades surrounding tissue and is transported to distant sites (metastases) it will likely result in death of the individual.

The desired goal of cancer therapy is to eliminate cancer cells preferentially, without having a deleterious effect on normal cells. Several methods have been used in an attempt to reach this goal, including surgery, radiation therapy and chemotherapy.

Local treatments, such as radiation therapy and surgery, offer a means of reducing the tumor mass in regions of the body that is accessible through surgical techniques or high doses of radiation therapy. However, more effective local therapies with fewer side effects are needed. Moreover, these treatments are not applicable to the destruction of widely disseminated or circulating tumor cells eventually found in most cancer patients. To combat the spread of tumor cells, systemic therapies are used.

One such systemic treatment is chemotherapy. Chemotherapy is the main treatment for disseminated, malignant cancers. However, chemotherapeutic agents are limited in their effectiveness for treating many cancer types, including many common solid tumors. This limitation is in part due to the intrinsic or acquired drug resistance of many tumor cells. Another drawback to the use of chemotherapeutic agents is their severe side effects. These include bone marrow suppression, nausea, vomiting, hair loss, and ulcerations in the mouth. Clearly, new approaches are needed to enhance the efficiency with which a chemotherapeutic agent can kill malignant tumor cells, while at the same time avoiding systemic toxicity.

H19 in Diagnosis and Therapy

The H19 gene is one of several genes known to be imprinted in humans (Hurst et al., 1996, Nature Genetics 12:234 237). At the very beginning of embryogenesis, H19 is expressed from both chromosomal alleles (DeGroot et al., 1994, Trophoblast 8:285 302). Shortly afterwards, silencing of the paternal allele occurs, and only the maternally inherited allele is transcribed.

H19 is abundantly expressed during embryogenesis, and was first identified as a gene that was coordinately regulated with alpha-fetoprotein in liver by the trans-acting locus raf (Pachnis et al., 1984, "Locus unlinked to alpha-fetoprotein under the control of the murine raf and Rif genes", Proc Natl Acad Sci. 81:5523 5527). Additionally, H19 has been independently cloned by several groups using screens aimed at isolating genes expressed during tissue differentiation. For example, the mouse homolog of H19 was identified in a screen for genes that are active early during differentiation of C3H10T1/2 cells (Davis et al., 1987, "Expression of a single transfected cDNA converts fibroblasts to myoblasts", Cell 51:987 1000). Similarly, murine H19 was shown to be expressed during stem cell differentiation and at the time of implantation (Poirier et al., 1991, "The murine H19 gene is activated during embryonic stem cell differentiation in vitro and at the time of implantation in the developing embryo", Development 113:1105 1114). Transcription of the human H19 gene was also discovered in differentiating cytotrophoblasts from human placenta (Rachmilewitz et al., 1992, Molec. Reprod. Dev. 32:196 202).

While transcription of H19 RNA occurs in many different embryonic tissues throughout fetal life and placental development, H19 expression is downregulated postnatally, although low levels of H19 transcription have been reported, for example, in murine adult muscle and liver (Brunkow and Tilghman, 1991, "Ectopic expression of the H19 gene in mice causes prenatal lethality", Genes Dev. 5:1092 1101).

H19 transcription can be re-activated postnatally in cancer cells as demonstrated in tumors derived from tissues expressing H19 prenatally (Ariel et al., 1997, "The product of the imprinted H19 gene is an oncofetal RNA", Mol Pathol. 50:34 44). Additionally, H19 RNA is postnatally expressed in some tumors, in particular astrocytoma and ganglioneuroblastoma, which are derived from neural tissues not known to express H19 (Ariel et al. supra). Given that H19 RNA is expressed in many types of tumors and cancers, Ariel et al. speculated that H19 RNA was an oncofetal RNA, and proposed investigating H19 as a tumor marker for human neoplasia.

H19 is significantly expressed in 84% of human bladder carcinomas, expression decreasing with tumor loss differentiation. Independent of tumor grade, the H19 expression level significantly correlated with early tumor recurrence (Ayesh, B., et al, Mol Ther, 2003. 7(4): p. 535-41).

Comparing patterns of gene expression in two homogeneous cell populations that differ only in the presence or absence of H19 RNA have identified a plethora of downstream effectors of H19 RNA. Among these are group of genes that were previously reported to play crucial roles in some aspects of the tumorigenic process. H19 RNA presence may enhance the invasive, migratory and angiogenic capacity of the cell by up-regulating genes that function in those pathways, and thus could contribute at least to the initial steps of the metastatic cascade. Additional studies highlight the potential role of H19 in promoting cancer progression and tumor metastasis by being a gene responsive to Hepatocyte growth factor/scatter factor (HGF/SF).

Specific expression of the H19 gene in cancer cells has prompted its use in clinical applications for diagnosing cancer. For example, U.S. Pat. No. 5,955,273 teaches the use of H19 gene as a tumor specific marker. PCT Pub. No. WO 2004/024957 discloses the use of H19 for the detection, in a patient suspected of having cancer, of the presence of residual cancer cells or micro-metastases originating from solid tumors.

IGF-II

Insulin-like growth factor-II (IGF-II) is expressed in the majority of bladder carcinomas such as transitional cell carcinomas (TCC; Ariel, I., et al., The imprinted H19 gene is a marker of early recurrence in human bladder carcinoma. Mol Pathol, 2000. 53(6): p. 320-3). The biological activities are mediated by the binding to the cell surface-receptors IGF-I receptor (IGF-1R), IGF-II receptor (IGF-2R) and insulin receptor (IR). The IGF receptors are present almost in all tissues of fetal and adult animals. IGF-2R binds IGF-II with the highest affinity, whereas the IGF-1R and IR possess high, but lower affinity to IGF-II than to their respective ligands. IGF-II is a potent embryonic and tumor growth factor that signals via the IGF1R through the Ras/mitogen-activated protein kinase, phosphatidylinositol 3-kinase/Akt/FOXO, and S6K/mammalian target of rapamycin (mTOR) signaling pathways to modify cell proliferation, cell survival, gene expression, and cell growth.

IGF-II is another imprinted gene whose expression depends upon its parental origin. However in contrast to H19, IGF-II is maternally imprinted in both mice and humans, and is therefore expressed from the paternally inherited allele (Rainier et al., 1993, "Relaxation of imprinted genes in human cancer", Nature 362:747 749). The human IGF-II gene exhibits a complex transcriptional pattern. There are four IGF-II promoters that are activated in a tissue-specific and developmentally specific manner. Only three of the IGF-II promoters (i.e., P2, P3 and P4) are imprinted and active during fetal development and in cancer tissues. The P3 promoter of the IGF-II gene has been implicated in the progression of liver cirrhosis and hepatocellular carcinoma (Seo et al., 1998, "Different protein-binding patterns in the P3 promoter region of the human insulin-like growth factor II gene in the human liver cirrhosis and hepatocellular carcinoma tissues", J Korean Med Sci.13:171 178).

The fourth IGF-II promoter, (i.e., P1) is not imprinted, and is activated in the adult liver and choroid plexus (See Holthuizen et al., 1993, "Transcriptional regulation of the major promoters of the human IGF-II gene", Mol Reprod Dev. 35:391 393).

Loss of imprinting of IGF-II has been implicated in Wilm's tumor (Ogawa et al., 1993, "Relaxation of insulin-like growth factor II gene imprinting implicated in Wilm's tumour", Nature 362:749 751). This observation led many investigators to speculate that the loss of imprinting and biallelic expression of imprinted genes may be involved in growth disorders and the development of cancer (Rainier et al., 1993, Nature 362:747 749; Glassman et al., 1996, "Relaxation of imprinting in carcinogenesis", Cancer Genet Cytogenet. 89:69 73).

Epigenetic modification and mutations of the IGF-II signaling system occur in cancers such as human colorectal tumors (Hassan A B, Macaulay V M. The insulin-like growth factor system as a therapeutic target in colorectal cancer. Ann Oncol 2002; 13:349-56). Supply of IGF-II is frequently up-regulated, and serial analysis of gene expression has shown IGF-II as a commonly overexpressed gene in a number of cancer cell lines and tumors, e.g. human bladder carcinoma and colorectal cancer (Zhang L, Zhou W, Velculescu V E, et al. Gene expression profiles in normal and cancer cells. Science 1997; 276:1268-72).

WO 99/18195 and U.S. Pat. No. 7,041,654 teach the specific expression of heterologous sequences, particularly genes encoding cytotoxic products (e.g. Diphtheria toxin), in tumor cells under the control of a cancer specific promoter (e.g., an H19 promoter and enhancer, IGF-II P3 promoter, IGF-II P4 promoter, or IGF-1 promoter).

WO 04/031359 teaches a method for regulating the expression of angiogenesis-controlling genes in cells that are involved in neo-vascularization, comprising administering to the cells an effective amount of an H19 modulator.

WO 2007/034487 discloses a nucleic acid construct comprising: (i) a first nucleic acid sequence encoding TNF alpha; (ii) a second nucleic acid sequence encoding a Diphtheria toxin; and (iii) at least one additional nucleic acid sequence comprising a cancer specific promoter (e.g. H19, IGF-1, P3, or IGF-II P4 promoters); the TNF alpha and Diphtheria toxin encoding sequences being under an expression control of the cancer specific promoter. Also provided are construct systems and methods and uses of same.

WO 2007/007317 discloses isolated oligonucleotides capable of down-regulating a level of H19 mRNA in cancer cells, articles of manufacture comprising agents capable of downregulating H19 mRNA in combination with an additional anti-cancer treatment as well as methods of treating cancer by administering same. WO 2007/007317 discloses that anti-cancer drugs can be co-administered with the claimed oligonucleotides.

WO 2008/087641 discloses compositions and methods for treating rheumatoid arthritis, utilizing H19-silencing nucleic acid agents such as inhibitory RNA.

WO 2008/087642 discloses compositions and methods for the treatment of cancer and other conditions that are associated with elevated expression of the H19 gene, utilizing H19-silencing nucleic acid agents such as inhibitory RNA.

WO 2008/099396 discloses compositions and methods for treating restenosis, utilizing H19-silencing nucleic acid agents such as inhibitory RNA.

None of the above references discloses or suggests a single construct containing multiple Diphtheria toxin-expressing open reading frames, wherein the Diphtheria toxin is expressed from a plurality of promoters.

Use of a single promoter (e.g. an H19 promoter or an IGF-II P3 or P4 promoter) alone for expression of a cytotoxic or cytostatic gene from an anti-cancer therapeutic construct presents several unresolved problems. For one, not every tumor of a given type of cancer (e.g. bladder carcinoma, superficial bladder cancer, etc.) is positive for expression via the H19 promoter or the IGF-II P3 or P4 promoter. Thus, such therapy is bound to fail in a sizable proportion of patients, even without accounting for tumor mutagenesis. Determination of responsiveness to such constructs would involve the costly and difficult step of genotyping individual tumors.

Tumors are known to exhibit significant genomic instability and heterogeneity. Thus, even individuals with an H19-expressing tumor, for example, are likely to contain a sizable number of cancer cells that have downregulated or abrogated H19 expression via mutation. Therefore, expressing the cytotoxic or cytostatic gene from a single promoter in such patients may result in temporary and partial tumor regression that will rapidly be reversed when the cells containing these mutations survive and rapidly multiply.

There remains an unmet medical need for developing additional safe and effective therapeutic modalities useful in cancer therapy.

The inclusion or description of literary references in this section or any other part of this application does not constitute an admission that the references are regarded as prior art to this invention.

SUMMARY OF THE INVENTION

The present invention relates to the field of cancer treatment, in particular to novel nucleic acid constructs and expression vectors that are particularly useful for treating tumors expressing H19 and/or Insulin-Like Growth Factor-II (IGF-II). The invention further provides compositions, methods and kits utilizing the nucleic acid constructs of the invention.

Specifically, the novel vectors of the invention comprise a nucleic acid construct containing multiple expression cassettes that enable expression of a cytotoxic agent, e.g. a Diphtheria toxin, from a plurality of cancer-specific promoters, selected from H19-, IGF-II P3-, and IGF-II P4-derived sequences.

According to a first aspect of the present invention, there is provided a nucleic acid construct, comprising:
(a) a first open reading frame encoding a cytotoxic or cytostatic gene product, the first open reading frame being operably linked to a first transcription-regulating sequence; and
(b) a second open reading frame encoding the cytotoxic or cytostatic gene product, the second open reading frame being operably linked to a second transcription-regulating sequence;
wherein the first transcription-regulating sequence and the second transcription-regulating sequence are different, and are selected from the group consisting of: i) H19-specific transcription-regulating sequences and ii) IGF-II transcription-regulating sequences selected from IGF-II P3 and IGF-II P4.

For example, the transcription regulating sequences may be:
i) a first transcription-regulating sequence being an H19-specific transcription-regulating sequence, and a second transcription-regulating sequence being an IGF-II P4 transcription-regulating sequence;
ii) a first transcription-regulating sequence being an H19-specific transcription-regulating sequence, and a second transcription-regulating sequence being an IGF-II P3 transcription-regulating sequence; or
iii) a first transcription-regulating sequence being an IGF-II P4 transcription-regulating sequence, and a second transcription-regulating sequence being an IGF-II P3 transcription-regulating sequence.

Optionally, said construct may further comprise a third open reading frame encoding the cytotoxic or cytostatic gene product, the third open reading frame being operably linked to a third transcription-regulating sequence selected from H19-specific transcription-regulating sequences, IGF-II P3 transcription-regulating sequences and IGF-II P4 transcription-regulating sequences.

In another aspect, the invention provides a nucleic acid construct, comprising: a) a first open reading frame encoding a diphtheria toxin, the first open reading frame being operably linked to an H19-specific transcription-regulating sequence, and b) a second open reading frame encoding a diphtheria toxin, the second open reading frame being operably linked to a first IGF-II transcription-regulating sequence selected from IGF-II P4 and IGF-II P3 sequences.

In one embodiment, said nucleic acid construct further comprises a third open reading frame encoding a diphtheria toxin, said third open reading frame being operably linked to a second IGF-II transcription-regulating sequence selected from IGF-II P4 and IGF-II P3 sequences, wherein the first IGF-II transcription-regulating sequence and the second IGF-II transcription-regulating sequence are different. For example, the second open reading frame may be operably linked to an IGF-II P4 transcription regulating sequence and the third open reading frame may be operably linked to an IGF-II P3 transcription regulating sequence, or alternatively the second open reading frame may be operably linked to an IGF-II P3 transcription regulating sequence and the third open reading frame may be operably linked to an IGF-II P4 transcription regulating sequence.

In another aspect, the invention provides a nucleic acid construct, comprising: a) a first open reading frame encoding a diphtheria toxin, said first open reading frame being operably linked to an IGF-II P3 transcription-regulating sequence; and b) a second open reading frame encoding a diphtheria toxin, said second open reading frame being operably linked to an IGF-II P4 transcription-regulating sequence.

In another embodiment, said nucleic acid construct further comprises a third open reading frame encoding a diphtheria toxin, said third open reading frame being operably linked to an H19-specific transcription-regulating sequence.

In the constructs of the invention, the diphtheria toxin may be, for example, a diphtheria toxin A chain (diphtheria toxin A, DTA), e.g. a toxin having an amino acid sequence comprising a sequence as set forth in SEQ ID NO: 7, as detailed hereinbelow.

According to various embodiments, the transcription regulating sequence may be a regulatory sequence (e.g. a promoter or enhancer) that induces or enhances expression selectively (or, in other embodiments, preferentially) in cancer cells, as detailed herein.

The term "IGF-II transcription-regulating sequence" refers, in another embodiment, to a sequence that regulates transcription in a specific (or differential) manner and is found in association with an IGF-II gene on a chromosome, e.g. a human chromosome. According to specific embodiments, "IGF-II P3 transcription-regulating sequence" and "IGF-II P4 transcription-regulating sequence" refer to a P3 or P4 (respectively) promoter. In another embodiment, the terms refer to a transcription-regulating sequence derived from a P3 or P4 (respectively) promoter. In another embodiment, the terms refer to one of the P3- or P4 (respectively)-specific transcription-regulating sequences disclosed herein. Each possibility represents a separate embodiment of the present invention.

For example, without limitation, the IGF-II P4 transcription-regulating sequence may be a promoter comprising a nucleic acid sequence set forth in SEQ ID NO: 9, as detailed hereinbelow. Non-limitative examples of IGF-II P3 promoters include promoters comprising a nucleic acid sequence as set forth in a sequence selected from SEQ ID NO: 8, SEQ ID NO: 12, and SEQ ID NO: 17, as detailed hereinbelow.

"H19-specific transcription-regulating sequence" refers, in another embodiment, to a sequence that regulates transcription in a specific (or differential) manner and is found in association with an H19 gene on a chromosome, e.g. a human chromosome. In another embodiment, the term refers to an H19-specific promoter. In another embodiment, the terms refer to a transcription-regulating sequence derived from an H19 promoter. In another embodiment, the term refers to one of the H19-specific transcription-regulating sequences disclosed herein. Each possibility represents a separate embodiment of the present invention. For example, without limitation, the H19-specific transcription-regulating sequence may be a promoter comprising a nucleic acid sequence set forth in any one of SEQ ID NOS: 1-2, as detailed hereinbelow.

The present invention discloses for the first time that such constructs provide a particularly effective and safe treatment targeted specifically to malignancies expressing H19 and/or expressing IGF-II from the P3 and/or P4 promoter. Advantageously, it is now disclosed that the constructs of the invention elicit responses in a higher number of cells and/or higher proportion of patients, thus providing improved cancer treatment compared to hitherto known therapy.

In another embodiment, said nucleic acid construct is a plasmid. In another embodiment, the present invention provides a eukaryotic expression vector comprising a nucleic acid construct of the present invention.

In another embodiment, the present invention provides a method for treating a tumor in a human subject in need thereof, comprising administering to the human subject a nucleic acid construct (e.g. a therapeutically effective amount of the nucleic acid construct) of the present invention, thereby treating a tumor in a human subject in need thereof.

In another embodiment, the present invention provides a method for inhibiting tumor progression in a human subject in need thereof, comprising administering to the human subject a nucleic acid construct (e.g. a therapeutically effective amount of the nucleic acid construct) of the present invention, thereby inhibiting tumor progression in a human subject in need thereof.

In another embodiment, the present invention provides a method for inhibiting tumor metastasis in a human subject in need thereof, comprising administering to the human subject a nucleic acid construct (e.g. a therapeutically effective amount of the nucleic acid construct) of the present invention, thereby inhibiting tumor progression in a human subject in need thereof.

In another embodiment, the present invention provides a method for reducing or alleviating a symptom associated with a neoplastic disorder in a human subject in need thereof, comprising administering to the human subject a nucleic acid construct (e.g. a therapeutically effective amount of the nucleic acid construct) of the present invention, thereby reducing or alleviating a symptom associated with a neoplastic disorder in a human subject in need thereof.

In the methods of the invention, said subject is afflicted, in one embodiment, with a tumor characterized by expression of H19 RNA in at least a portion of the cells of the tumor, e.g. wherein a cell of said tumor is capable of expressing a transcript directed by the H19 promoter, a transcript directed by the IGF-II P4 promoter and/or a transcript directed by the IGF-II P3 promoter.

The constructs of the invention may also be in form of a kit or a pharmaceutical pack containing one or more courses of treatment for a neoplasm expressing H19 and/or expressing IGF-II from the P3 and/or P4 promoter in a subject in need thereof. Thus, there is provided in another aspect a kit containing i) a nucleic acid construct of the invention; and ii) instructions for administering said nucleic acid construct to a subject in need thereof (e.g. a subject afflicted with cancer).

The compositions, methods and kits of the present invention are useful in the treatment of a variety of malignancies associated with expression of H19 and/or expression of IGF-II from the P3 and/or P4 promoter. In another embodiment, the tumor is a solid tumor. In another embodiment, the tumor is a carcinoma. In various particular embodiments, the tumor includes, but is not limited to, bladder carcinoma, liver neoplasms (e.g. hepatocellular carcinoma), lung adenocarcinoma (small and non-small cell lung cancer), esophageal, ovarian, rhabdomyosarcoma, cervical carcinoma, head and neck squamous cell carcinoma, colorectal, uterus and testicular germ cell tumors, medulloblastoma, glioblastoma and adenocortical tumors.

According to still further features in the described preferred embodiments, the tumor is selected from the group consisting of bladder carcinoma, hepatocellular carcinoma and colon carcinoma. In another embodiment, the tumor is selected from the group consisting of bladder carcinoma, a hepatocellular carcinoma, an ovarian carcinoma, and a pancreatic carcinoma. In another embodiment, the tumor is selected from the group consisting of a bladder carcinoma, a hepatocellular carcinoma, an ovarian carcinoma, a pancreatic carcinoma, a breast carcinoma, a prostate carcinoma, a cervical carcinoma, a colon carcinoma, and a lung carcinoma. In another particular embodiment, the subject is afflicted with superficial bladder cancer. Each possibility represents a separate embodiment of the present invention.

Exemplary metastasizing tumors include e.g. colorectal cancer metastasizing to the liver and metastasizing breast cancer. In a particular embodiment, the combinations of the invention are used to prevent or inhibit the formation of liver metastases.

Other objects, features and advantages of the present invention will become clear from the following description and drawings.

luciferase activity (% of control). X axis (for A): μg plasmid/well. Axes are same as FIG. 2.

Figure 8A:
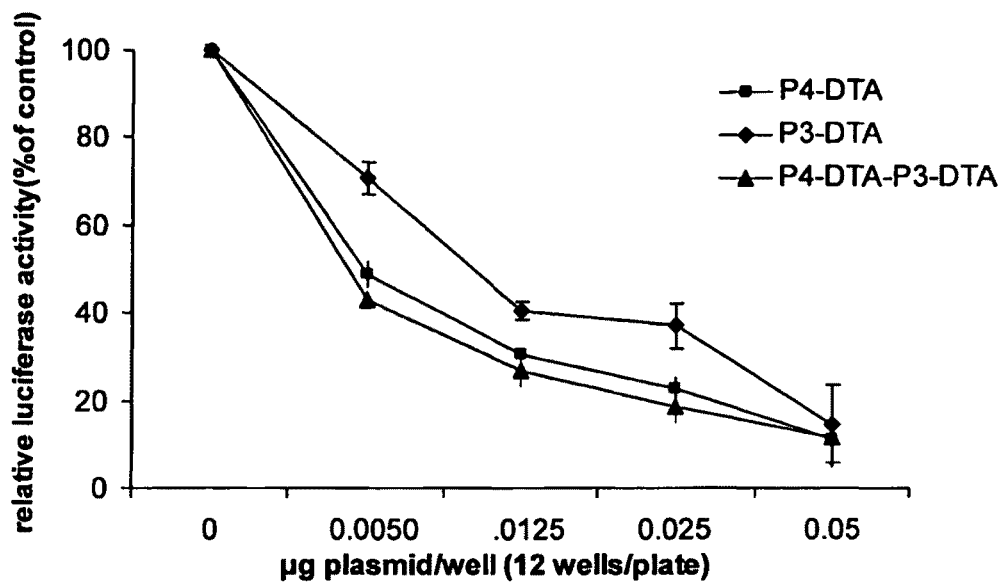
FIG. 8. Relative in-vitro activity of DTA-expressing constructs with P3, P4, and P3+P4 regulatory sequences in T24P cells. Human T24P cells were co-transfected with 2 µg of LucSV40 and the indicated concentrations of P3-DTA, P4-DTA, or P4-DTA-P3-DTA. A. Luciferase activity at various dosages compared to cells transfected with LucSV40 alone. B. Bar graph of 0.005 µg data. Y axis (for A-B)
Figure 8B:
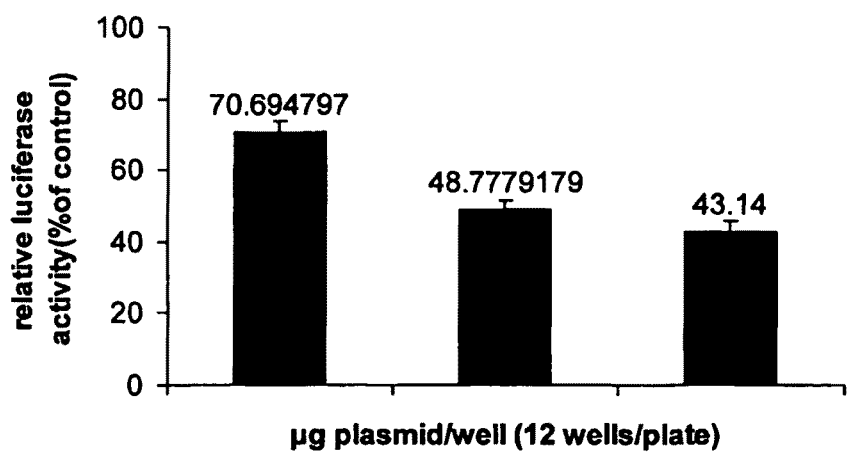

FIG. 9. Relative activity of DTA-expressing constructs in HT-1376 cells. Experiment was performed as described for FIG. 8; axes are same as FIG. 8. A. Luciferase activity at various dosages compared to cells transfected with LucSV40 alone. B. Bar graph of 0.005 μg data.

FIG. 10. Relative activity of DTA-expressing constructs in Hep3B cells. Experiment was performed as described for FIG. 8; axes are same as FIG. 8. A. Luciferase activity at various dosages compared to cells transfected with LucSV40 alone. B. Bar graph of 0.005 μg data.

FIG. 11. Relative activity of DTA-expressing constructs in ES-2 cells. Experiment was performed as described for FIG. 8; axes are same as FIG. 8. A. Luciferase activity at various dosages compared to cells transfected with LucSV40 alone. B. Bar graph of 0.005 μg data.

Figure 12A:
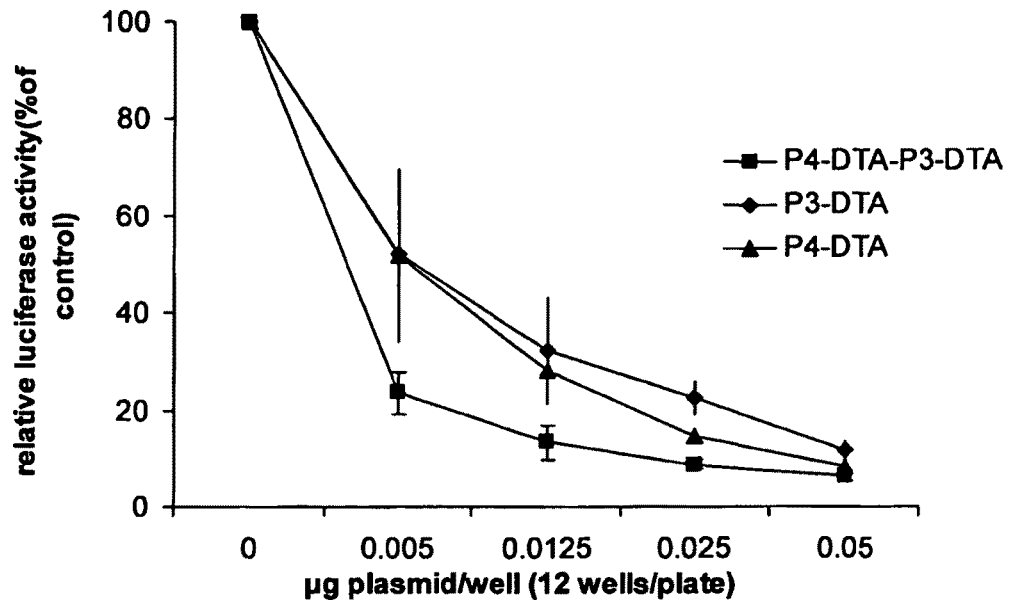
Figure 12B:
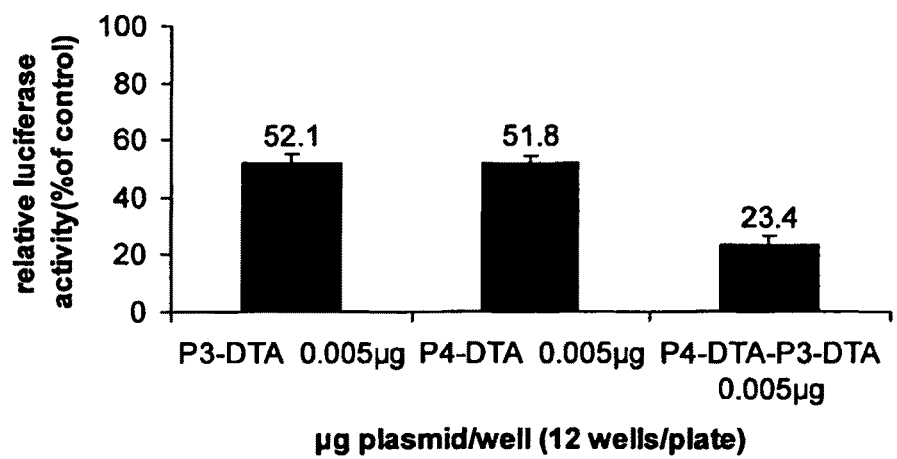

FIG. 12. Relative activity of DTA-expressing constructs in PC-1 cells. Experiment was performed as described for FIG. 8; axes are same as FIG. 8. A. Luciferase activity at various dosages compared to cells transfected with LucSV40 alone. B. Bar graph of 0.005 μg data.

FIG. 13. Relative activity of DTA-expressing constructs in CRL-1469 cells. Experiment was performed as described for FIG. 8; axes are same as FIG. 8. A. Luciferase activity at various dosages compared to cells transfected with LucSV40 alone. B. Bar graph of 0.005 μg data.

FIG. 14. Relative in-vitro activity of DTA expressed from constructs with H19, P3, and H19+P3 regulatory sequences in T24P cells. T24P cells were co-transfected with 2 μg of LucSV40 and the indicated concentrations of H19-DTA, P3-DTA, or H19-DTA-P3-DTA. A. Luciferase activity at various dosages compared to cells transfected with LucSV40 alone. B. Bar graph of 0.005 μg data. Y axis (for A-B): luciferase activity (% of control). X axis (for A): μg plasmid/well. Axes are same as FIG. 2.

FIG. 15. Relative in-vitro activity in T24P cells of H19-DTA-P4-DTA vs. P4-driven and H19-driven constructs in combination. T24P cells were co-transfected with 2 μg of LucSV40 and the indicated concentrations of H19-DTA-P4-DTA or an equal amount of each of P4-DTA+H19-DTA. A. Luciferase activity at various dosages compared to cells transfected with LucSV40 alone. B. Bar graph of 0.005 μg data. Y axis (for A-B): luciferase activity (% of control). X axis (for A): μg plasmid/well.

FIG. 16. Relative in-vitro activity in Hep3B cells of H19-DTA-P4-DTA vs. P4-driven and H19-driven constructs in combination. Experiment was performed as described for FIG. 15; axes are same as FIG. 15. A. Luciferase activity at various dosages compared to cells transfected with LucSV40 alone. B. Bar graph of 0.005 μg data.

Figure 17A:
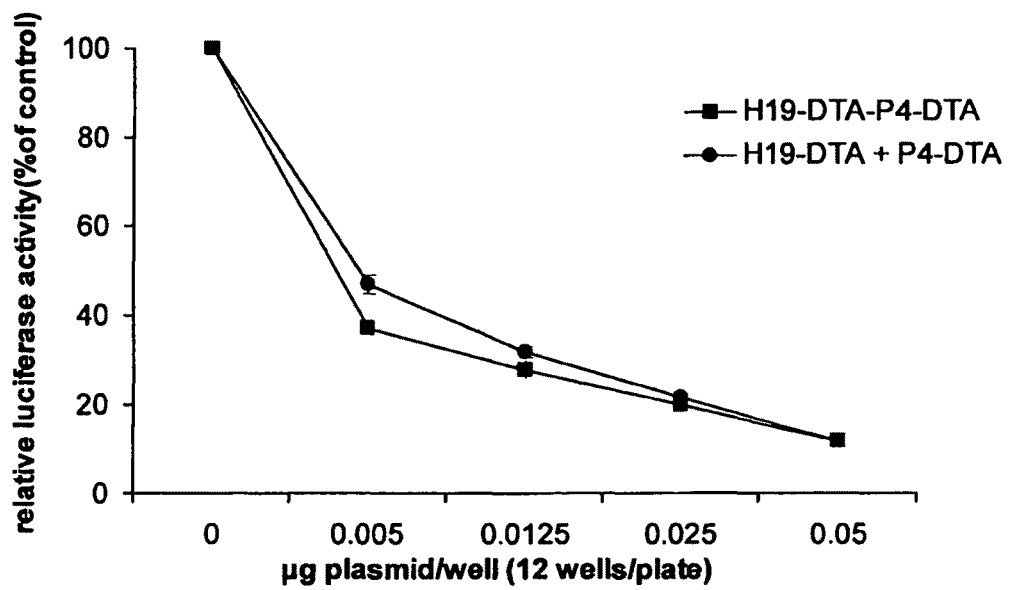
Figure 17B:
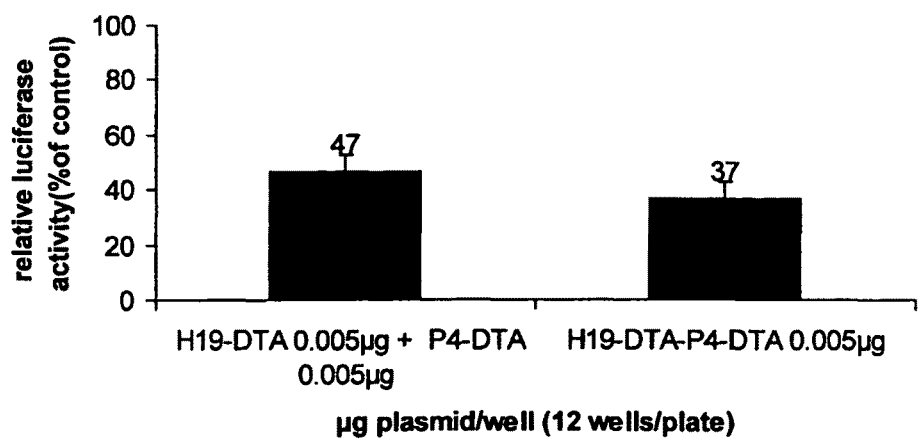

FIG. 17. Relative in-vitro activity in ES-2 cells of H19-DTA-P4-DTA vs. P4-driven and H19-driven constructs in combination. Experiment was performed as described for FIG. 15; axes are same as FIG. 15. A. Luciferase activity at various dosages compared to cells transfected with LucSV40 alone. B. Bar graph of 0.005 μg data.

Figure 18A:
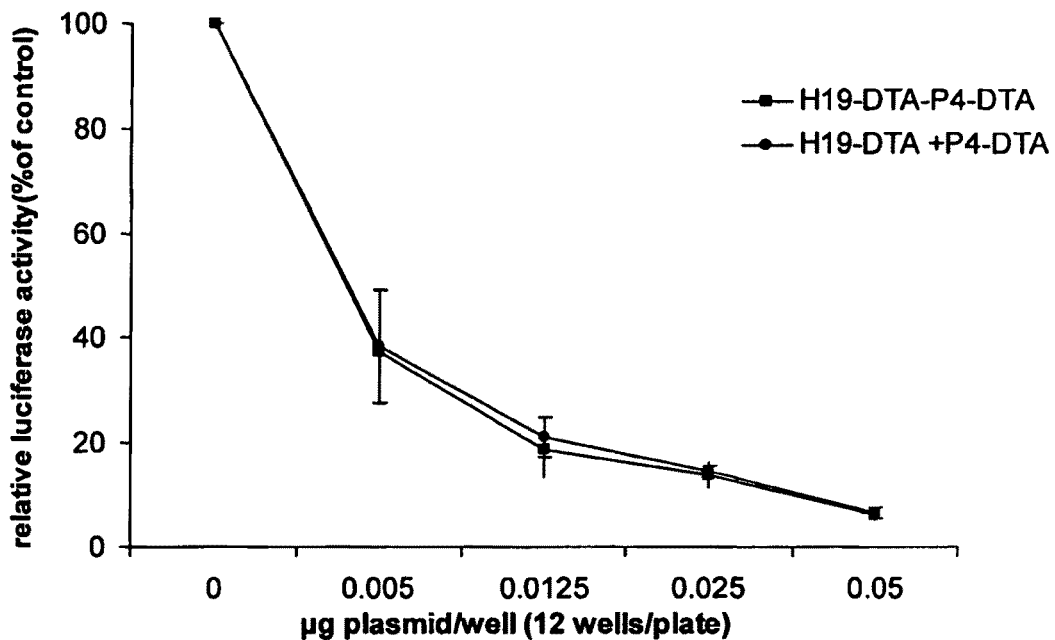
Figure 18B:
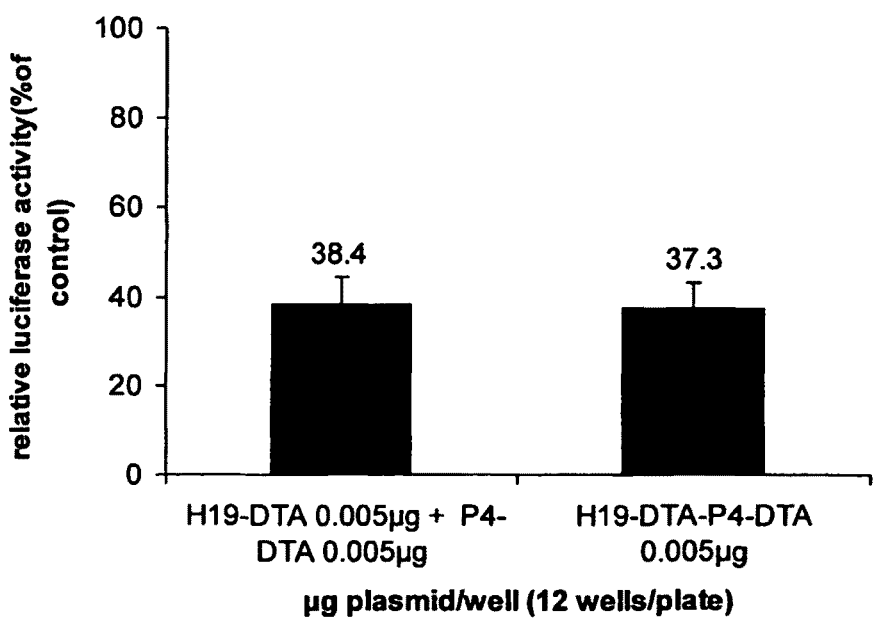

FIG. 18. Relative in-vitro activity in PC-1 cells of H19-DTA-P4-DTA vs. P4-driven and H19-driven constructs in combination. Experiment was performed as described for FIG. 15; axes are same as FIG. 15. A. Luciferase activity at various dosages compared to cells transfected with LucSV40 alone. B. Bar graph of 0.005 μg data.

Figure 19A:
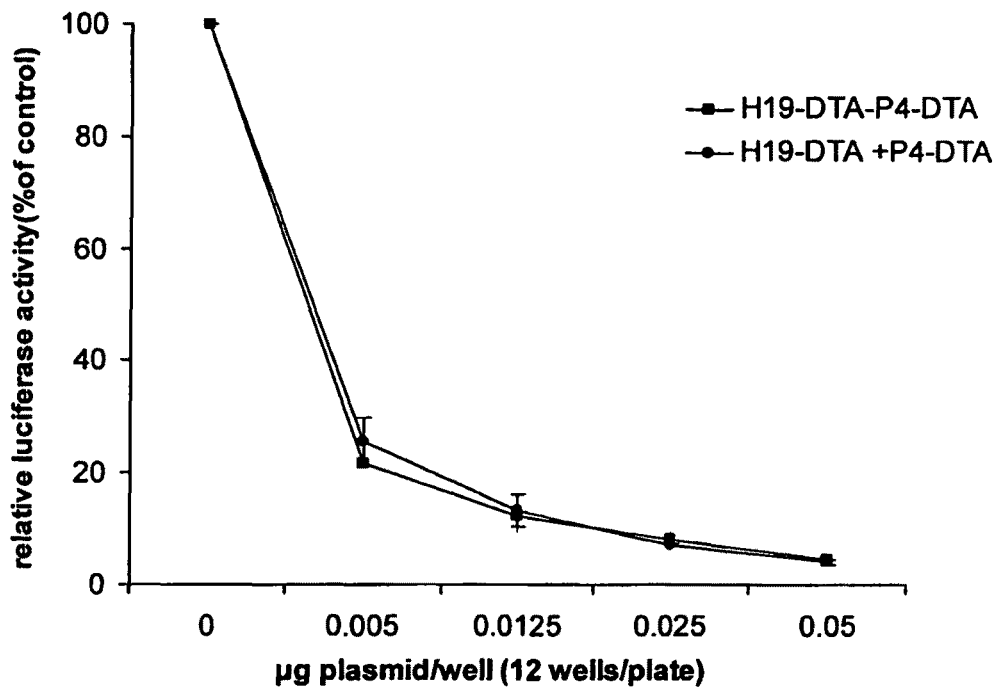
Figure 19B:
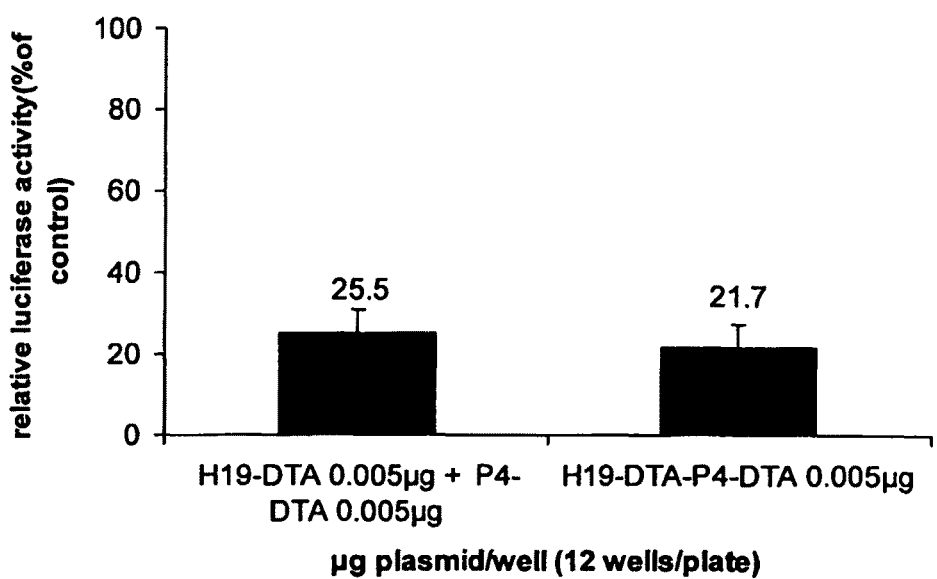

FIG. 19. Relative in-vitro activity in CRL-1469 cells of H19-DTA-P4-DTA vs. P4-driven and H19-driven constructs in combination. Experiment was performed as described for FIG. 15; axes are same as FIG. 15. A. Luciferase activity at various dosages compared to cells transfected with LucSV40 alone. B. Bar graph of 0.005 μg data.

FIG. 20. Relative in-vitro activity in HT-1376 cells of P4-DTA-P3-DTA vs. P3-driven and P4-driven constructs in combination. HT-1376 cells were co-transfected with 2 μg of LucSV40 and the indicated concentrations of P4-DTA-P3-DTA or an equal amount of each of P3-DTA+P4-DTA. A. Luciferase activity at various dosages compared to cells transfected with LucSV40 alone. B. Bar graph of 0.005 μg data. Axes are same as for FIG. 15.

Figure 21A:
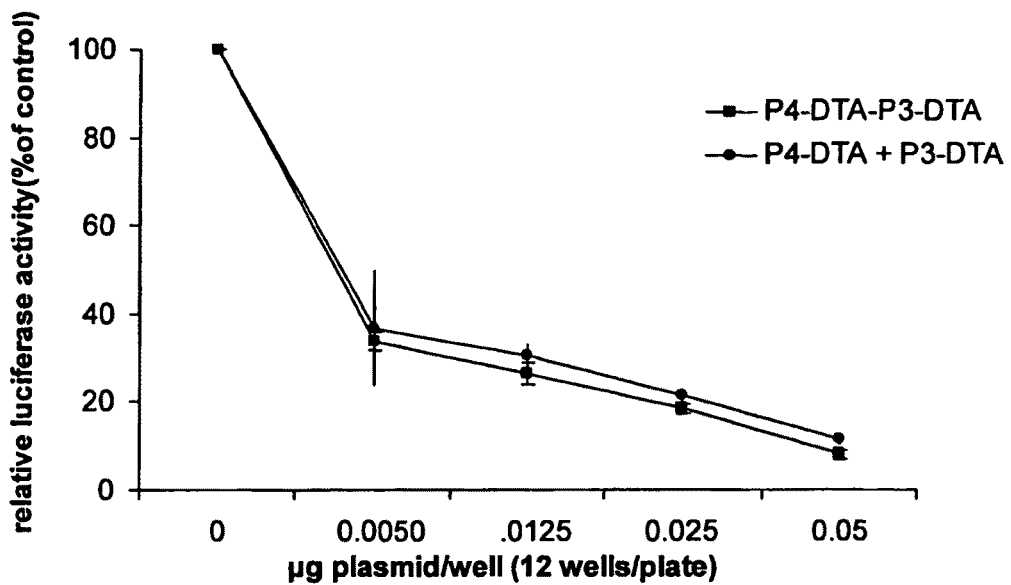
Figure 21B:
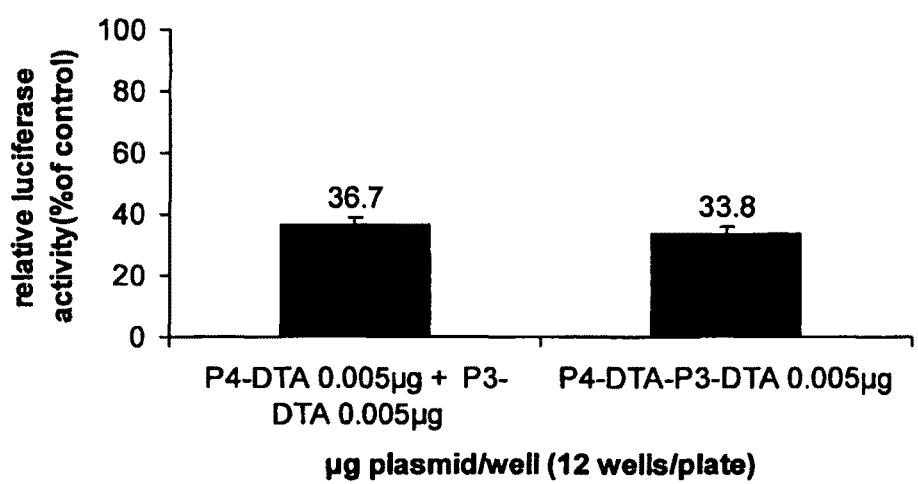

FIG. 21. Relative in-vitro activity in ES-2 cells of P4-DTA-P3-DTA vs. P3-driven and P4-driven constructs in combination. ES-2 cells were co-transfected with 2 μg of LucSV40 and the indicated concentrations of P4-DTA-P3-DTA or an equal amount of each of P3-DTA+P4-DTA. A. Luciferase activity at various dosages compared to cells transfected with LucSV40 alone. B. Bar graph of 0.005 μg data. Axes are same as for FIG. 15

Figure 22:
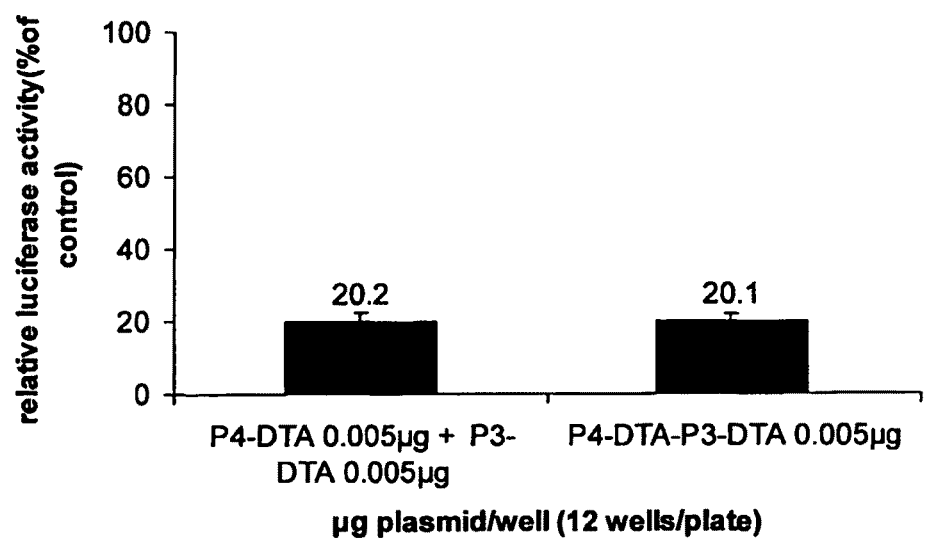

FIG. 22. Relative in-vitro activity in Hep-3B cells of 0.005 μg of P4-DTA-P3-DTA vs. 0.005 μg of each of P3-driven and P4-driven constructs in combination. Experiment was performed as described for FIG. 21. Axes are same as for FIG. 15B.

FIG. 23. Relative activity of DTA-expressing constructs in HT-1376 cells. Experiment was performed as described for FIG. 15; axes are same as FIG. 15. A. Luciferase activity at various dosages compared to cells transfected with LucSV40 alone. B. Additional repetition of the experiment described in (A). C. Bar graph of 0.005 μg data.

FIG. 24. Relative in-vitro activity in CRL-1469 cells of 0.005 μg of P4-DTA-P3-DTA vs. 0.005 μg of each of P3-driven and P4-driven constructs in combination. A. Luciferase activity at various dosages compared to cells transfected with LucSV40 alone. B. Bar graph of 0.005 μg data. Experiment was performed as described for FIG. 21. Axes are same as for FIG. 15.

Figure 25:
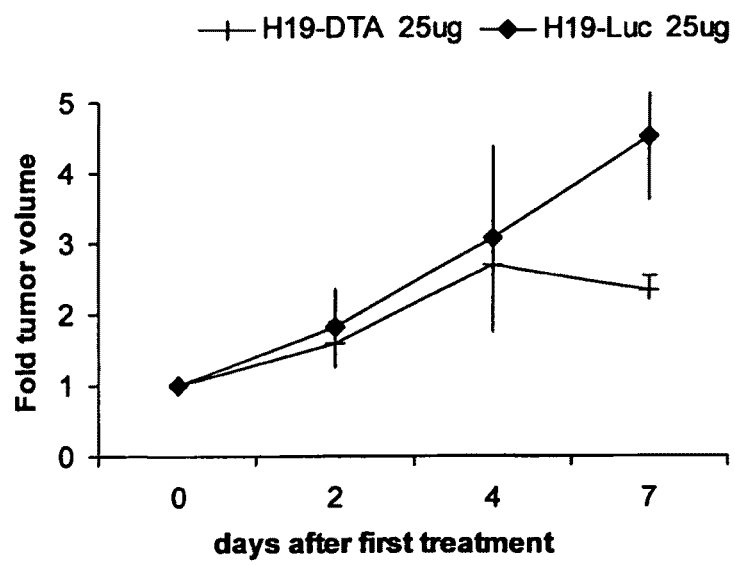

FIG. 25. In vivo anti-tumor effect of injection of 25 μg of H19-DTA. Y-axis: fold-tumor volume increase. X-axis: time (days).

Figure 26:
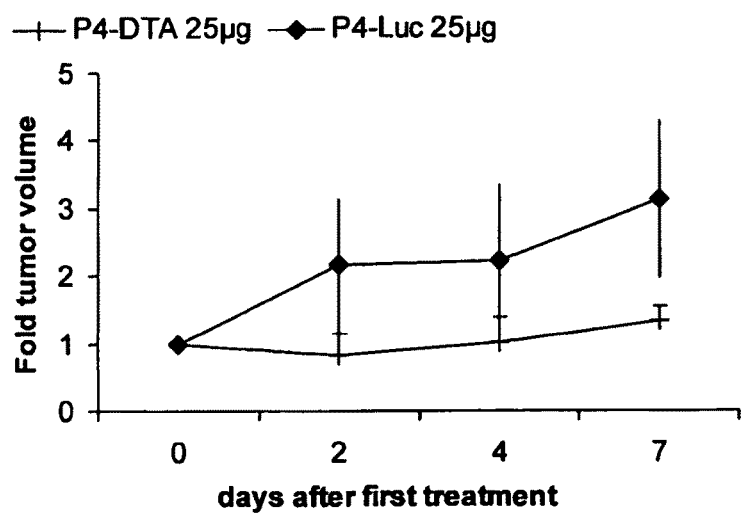

FIG. 26. In vivo anti-tumor effect of injection of 25 μg of P4-DTA. Y-axis: fold-tumor volume increase. X-axis: time (days).

Figure 27:
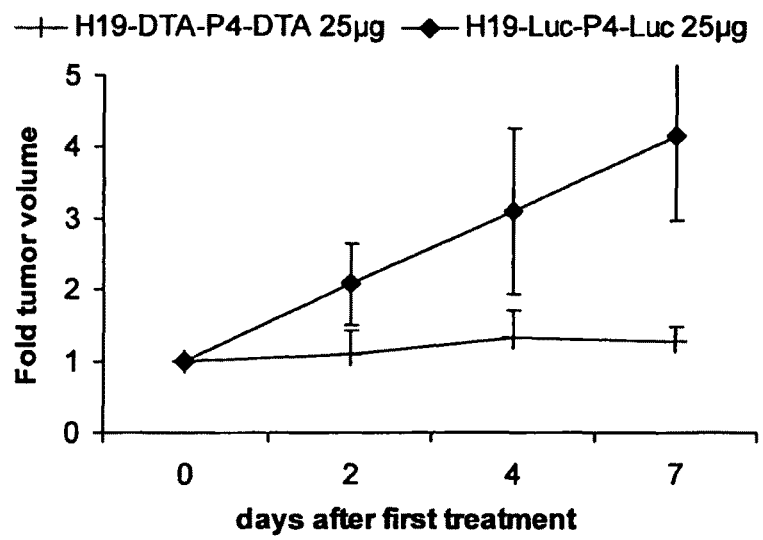

FIG. 27. In vivo anti-tumor effect of injection of 25 μg of H19-DTA-P4-DTA. Y-axis: fold-tumor volume increase. X-axis: time (days).

Figure 28:
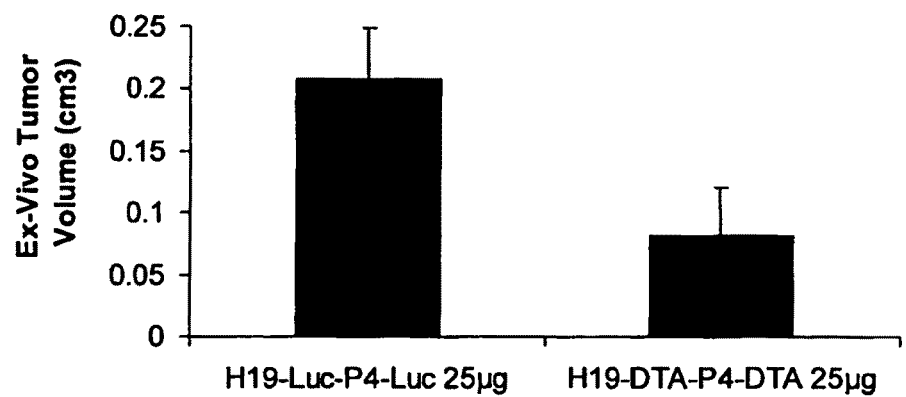

FIG. 28. Ex-vivo volume of tumors from H19-DTA-P4-DTA-treated mice.

Figure 29:
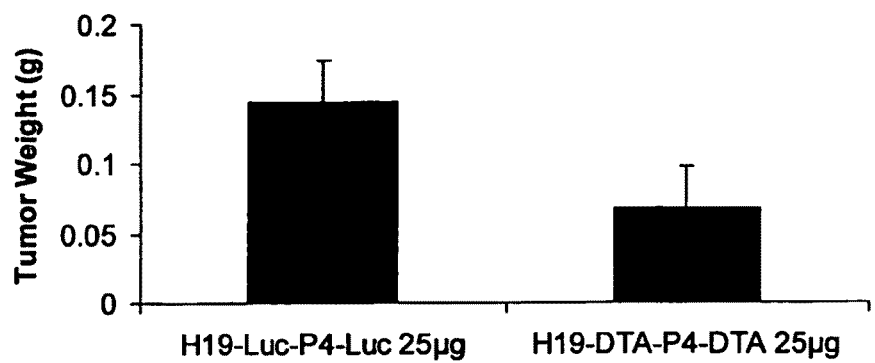

FIG. 29. Ex-vivo weight of tumors from H19-DTA-P4-DTA-treated mice.

Figure 30:
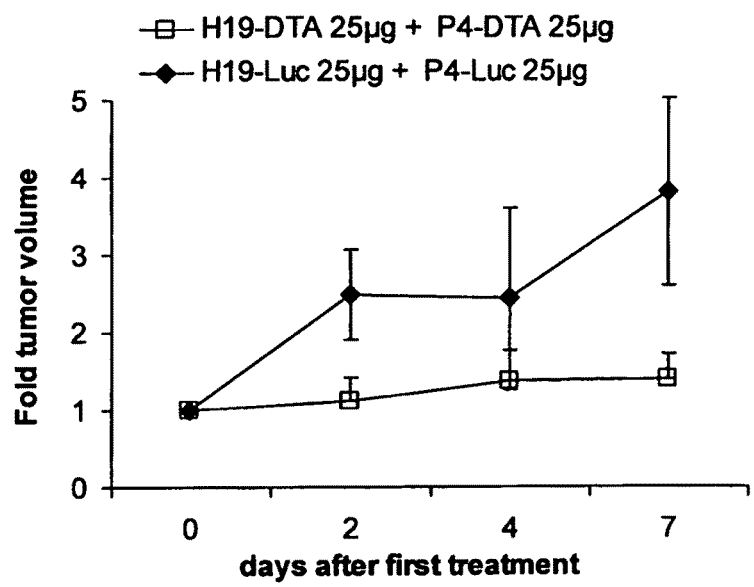

FIG. 30. In vivo anti-tumor effect of injection of 25 μg each of H19-DTA and P4-DTA. Y-axis: fold-tumor volume increase. X-axis: time (days).

Figure 31:
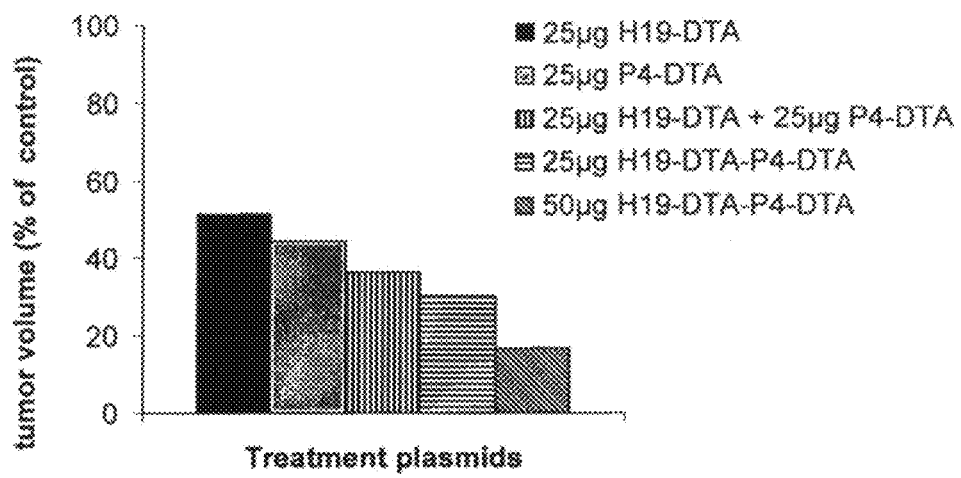

FIG. 31. Summary of T24P bladder cancer model data.

Figure 32:
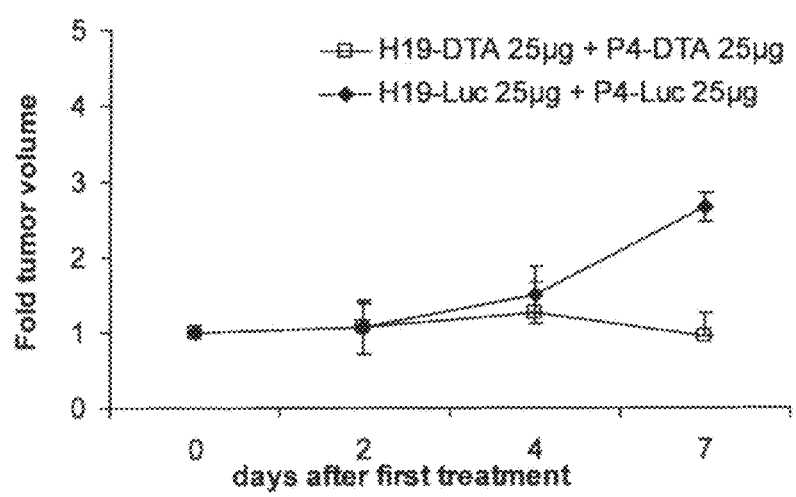

FIG. 32. In vivo anti-tumor effect of injection of 25 μg each of H19-DTA and P4-DTA in the HT-1376 model. Y-axis: fold-tumor volume increase. X-axis: time (days).

Figure 33:
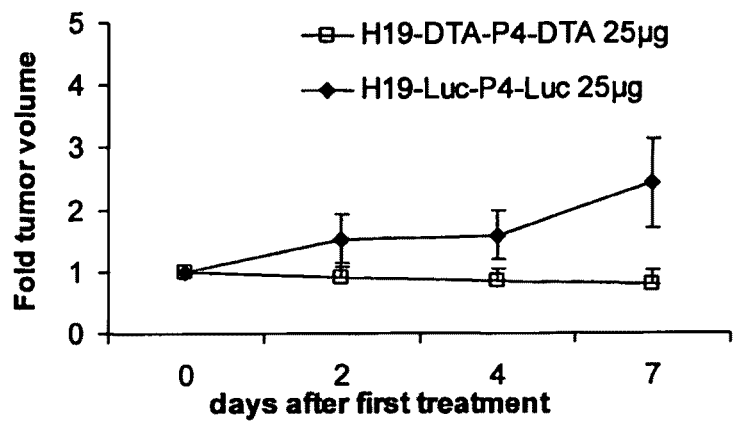

FIG. 33. In vivo anti-tumor effect of injection of 25 μg of H19-DTA-P4-DTA in the HT-1376 model. Y-axis: fold-tumor volume increase. X-axis: time (days).

Figure 34:
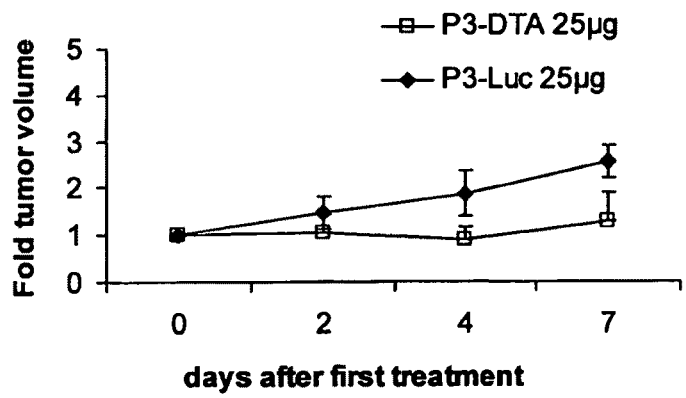

FIG. 34. In vivo anti-tumor effect of injection of 25 μg of P3-DTA. Y-axis: fold-tumor volume increase. X-axis: time (days).

Figure 35:
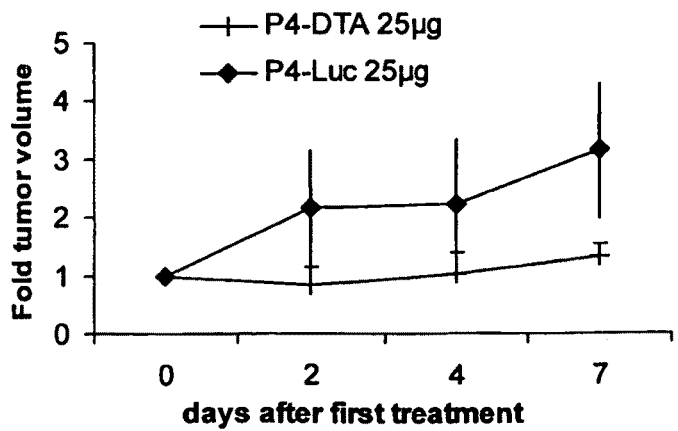

FIG. 35. In vivo anti-tumor effect of injection of 25 μg of P4-DTA. Y-axis: fold-tumor volume increase. X-axis: time (days).

Figure 36:
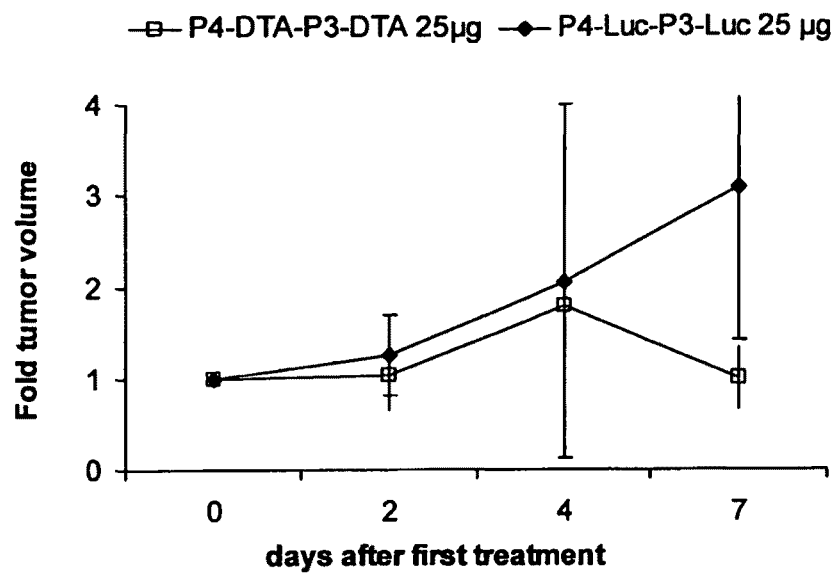

FIG. 36. In vivo anti-tumor effect of injection of 25 μg of P4-DTA-P3-DTA. Y-axis: fold-tumor volume increase. X-axis: time (days).

Figure 37:
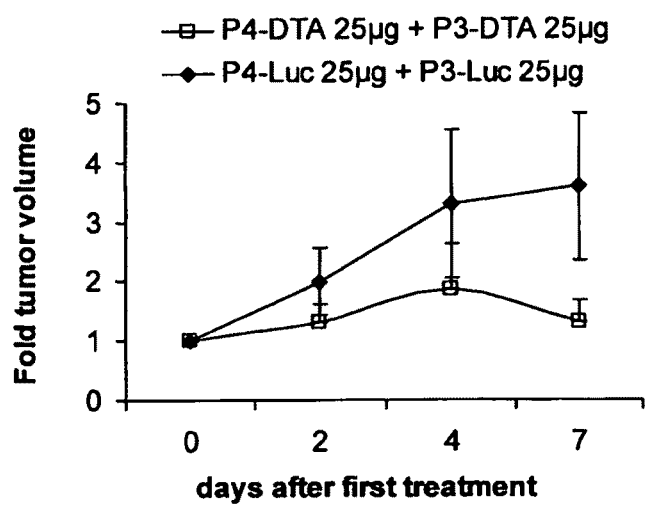

FIG. 37. In vivo anti-tumor effect of injection of 25 μg each of P3-DTA and P4-DTA. Y-axis: fold-tumor volume increase. X-axis: time (days).

Figure 38:
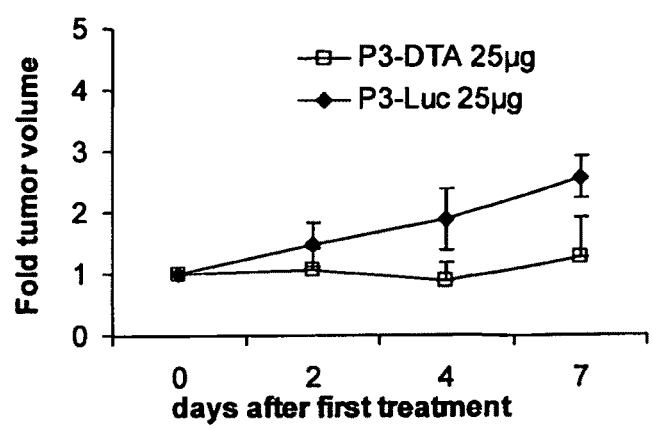

FIG. 38. In vivo anti-tumor effect of injection of 25 μg of P3-DTA. Y-axis: fold-tumor volume increase. X-axis: time (days).

Figure 39:
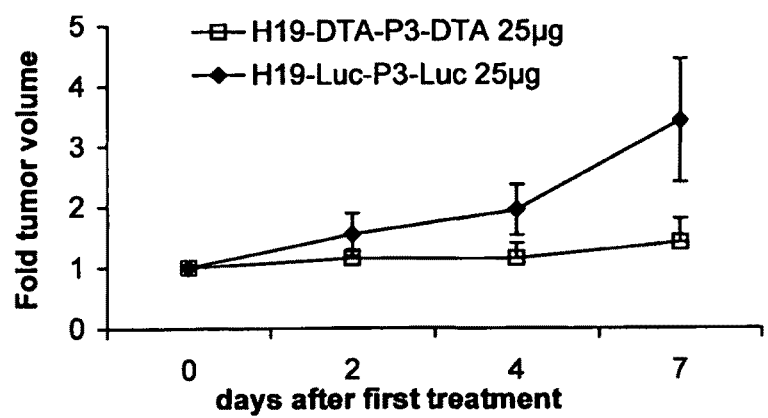

FIG. 39. In vivo anti-tumor effect of injection of 25 μg of H19-DTA-P3-DTA. Y-axis: fold-tumor volume increase. X-axis: time (days).

FIG. 40. Relative activity of DTA-expressing constructs in HT-1376 cells. Experiment was performed as described for FIG. 2; axes are same as FIG. 2. A. Luciferase activity at various dosages compared to cells transfected with LucSV40 alone. B. Bar graph of 0.005 μg data.

DETAILED DESCRIPTION OF THE INVENTION

The present invention relates to the field of cancer treatment, particularly to a novel therapy useful for treating H19-expressing and/or Insulin-Like Growth Factor-II (IGF-II)-expressing tumors.

Specifically, the novel vectors of the invention comprise a nucleic acid construct comprising multiple expression cassettes that enable expression of a cytotoxic agent from a plurality of promoters, selected from H19, IGF-II P3, and IGF-II P4.

Thus, the invention provides in some embodiments a nucleic acid construct comprising:
  (a) a first open reading frame encoding a cytotoxic or cytostatic gene product, the first open reading frame being operably linked to a first cancer-specific transcription-regulating sequence; and
  (b) a second open reading frame encoding the cytotoxic or cytostatic gene product (i.e. the same gene product or a variant thereof), the second open reading frame being operably linked to a second cancer-specific transcription-regulating sequence;
  wherein the first transcription-regulating sequence and the second transcription-regulating sequence are different and selected from the group consisting of i) an H19-specific transcription-regulating sequence (e.g. an H19 promoter) and ii) an IGF-II transcription-regulating sequences (e.g. an IGF-II P3 or IGF-II P4 promoter).

In other words, the construct contains at least two different transcription-regulating sequences, each being derived from a different regulatory sequence (H19, P4 or P3), and each being operably linked to a separate sequence encoding the cytotoxic or cytostatic gene product. For example, the two transcription-regulating sequences may be:
  i) a first transcription-regulating sequence being an H19-specific transcription-regulating sequence, and a second transcription-regulating sequence being an IGF-II P4 transcription-regulating sequence;
  ii) a first transcription-regulating sequence being an H19-specific transcription-regulating sequence, and a second transcription-regulating sequence being an IGF-II P3 transcription-regulating sequence; or
  iii) a first transcription-regulating sequence being an IGF-II P4 transcription-regulating sequence, and a second transcription-regulating sequence being an IGF-II P3 transcription-regulating sequence.

It should be understood, that the multiple expression cassettes are operably linked to distinct transcription-regulating sequences, enabling independent regulation of transcription from each open reading frame encoding the cytotoxic agent. Thus, the arrangement of the open reading frames within the construct may vary in different embodiments of the present invention, for example, the construct may be designed such that the first expression cassette is either upstream or downstream to the second expression cassette.

In one embodiment, the present invention provides a single nucleic acid molecule, comprising a first open reading frame encoding a cytotoxic or cytostatic gene product, the first open reading frame being operably linked to an H19-specific transcription-regulating sequence; and a second open reading frame encoding the cytotoxic or cytostatic gene product, the second open reading frame being operably linked to an IGF-II P3 transcription-regulating sequence. In another embodiment, the nucleic acid molecule further comprises a third open reading frame encoding the cytotoxic or cytostatic gene product, said third open reading frame being operably linked to an IGF-II P4 transcription-regulating sequence. Each possibility represents a separate embodiment of the present invention.

In another embodiment, the present invention provides a single nucleic acid molecule, comprising a first open reading frame encoding a cytotoxic or cytostatic gene product, the first open reading frame being operably linked to an H19-specific transcription-regulating sequence; and a second open reading frame encoding the cytotoxic or cytostatic gene product, the second open reading frame being operably linked to an IGF-II P4 transcription-regulating sequence. In another embodiment, the nucleic acid molecule further comprises a third open reading frame encoding the cytotoxic or cytostatic gene product, said third open reading frame being operably linked to an IGF-II P3 transcription-regulating sequence. Each possibility represents a separate embodiment of the present invention.

In another embodiment, the present invention provides a single nucleic acid molecule, comprising a first open reading frame encoding a cytotoxic or cytostatic gene product, the first open reading frame being operably linked to an IGF-II P4 transcription-regulating sequence; and a second open reading frame encoding the cytotoxic or cytostatic gene product, the second open reading frame being operably linked to an IGF-II P3 transcription-regulating sequence. In another embodiment, the nucleic acid molecule further comprises a third open reading frame encoding the cytotoxic or cytostatic gene product, said third open reading frame being operably linked to an H19-specific transcription-regulating sequence. Each possibility represents a separate embodiment of the present invention.

Figure 1:
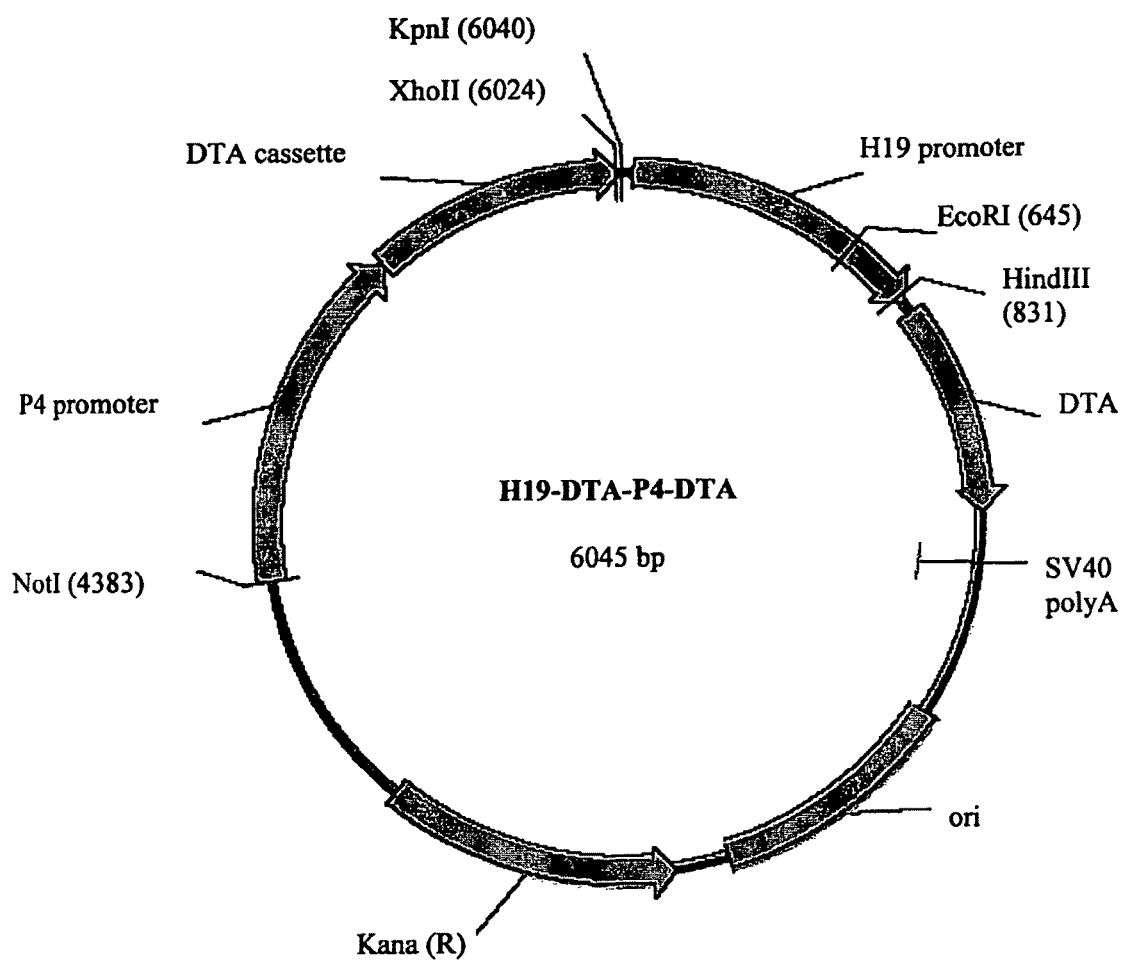
FIG. 1. A schematic illustration depicting the construction of the double promoter H19-DTA-P4-DTA expression vector. The coding sequence of each DTA is under the transcriptional control of both IGF-II-P4 and H19 promoter sequences, respectively, Kana (R)—kanamycin resistance gene.

An exemplary construct of the invention, expressing a cytotoxic agent (DTA) under separate expression control of H19 and P4 promoters, H19-DTA-P4-DTA, is depicted in FIG. 1 and is further described herein (Example 1). Exemplary constructs of the invention expressing DTA under separate expression control of P4 and P3 promoters (P4-DTA-P3-DTA), and of H19 and P3 promoters (H19-DTA-P3-DTA) are described as well in the Experimental Details section in Example 5 and Example 6, respectively. These constructs are represented by the nucleic acid sequences as set forth in SEQ ID NOs: 11, 24 and 18, respectively, as detailed hereinbelow.

As demonstrated herein, administration of a single expression vector comprising two different sequences, each expressing DTA under the transcriptional control of a different tumor-specific promoter, namely, the H19 and IGF-II P4 promoters, resulted in enhanced killing of a wide variety of carcinoma cells, compared to each construct (expressing DTA under control of the H19 or P4 promoter) administered separately (Examples 1-4). Moreover, results were shown to be greater-than additive compared to administering the single-promoter constructs in combination (Example 7). The enhanced ability of the single expression vector comprising the two different genes was borne out by in vivo testing as well (Example 10).

In addition, administration of a single expression vector comprising two different sequences, each expressing DTA under the transcriptional control of a different tumor-specific promoter, namely, the IGF-II P3 and IGF-II P4 promoters, resulted in enhanced killing of a wide variety of carcinoma cells, compared to each construct (expressing DTA under control of the P3 or P4 promoter) administered separately (Example 5). Moreover, results were shown to be greater-than additive compared to administering the single-promoter constructs in combination (Example 8). The enhanced ability of the single expression vector comprising the two different genes was borne out by in vivo testing as well (Example 11).

In addition, administration of a single expression vector comprising two different sequences, each expressing DTA under the transcriptional control of a different tumor-specific promoter, namely, the H19 and IGF-II P3 promoters, resulted in enhanced killing of bladder carcinoma cells, compared to each construct (expressing DTA under control of the P3 or H19 promoter) administered separately (Example 6). The enhanced ability of the single expression vector comprising the two different genes was borne out by in vivo testing as well (Example 12).

The cytotoxic gene product of methods and compositions of the present invention is, according to a currently preferred embodiment of the present invention, a diphtheria toxin. In another embodiment, both sequences encode the same diphtheria toxin. In another embodiment, each sequence encodes a different variant of a diphtheria toxin. In another embodiment, the diphtheria toxin is DTA. Each possibility represents a separate embodiment of the present invention.

In another embodiment, the construct further comprises an additional open reading frame encoding a TNF alpha, the additional open reading frame being operably linked to an additional transcription regulating sequence selected from an H19-specific transcription-regulating sequence, an IGF-II P3 transcription-regulating sequences or an IGF-II P4 transcription-regulating sequence.

In another embodiment, the cytotoxic gene product is thymidine kinase. In another embodiment, the cytotoxic gene product is *Pseudomonas* toxin. In another embodiment, the cytotoxic gene product is ricin. In another embodiment, the cytotoxic gene product is cholera toxin. In another embodiment, the cytotoxic gene product is retinoblastoma gene product. In another embodiment, the cytotoxic gene product is p53. In another embodiment, the cytotoxic gene product is a retinoblastoma gene product.

In another embodiment, the cytotoxic agent is tumoricidal, i.e. of greater toxicity to tumor cells relative to non-tumor cells. Each possibility represents a separate embodiment of the present invention.

The cytostatic gene product of methods and compositions of the present invention is, in another embodiment, p21. In another embodiment, the cytostatic gene product is p27. In another embodiment, the cytostatic gene product is p53. In another embodiment, the cytostatic gene product is p53175P. In another embodiment, the cytostatic gene product is p57. In another embodiment, the cytostatic gene product is p15. In another embodiment, the cytostatic gene product is p16. In another embodiment, the cytostatic gene product is p18. In another embodiment, the cytostatic gene product is p19. In another embodiment, the cytostatic gene product is p73. In another embodiment, the cytostatic gene product is GADD45. In another embodiment, the cytostatic gene product is APC1. In another embodiment, the cytostatic gene product is p73RB1. In another embodiment, the cytostatic gene product is WT1. In another embodiment, the cytostatic gene product is NF1. In another embodiment, the cytostatic gene product is VH. In another embodiment, the cytostatic gene product is p53. In another embodiment, the cytotoxic agent is tumoristatic, i.e. of greater toxicity to tumor cells relative to non-tumor cells. Each possibility represents a separate embodiment of the present invention. A nucleic acid sequence encoding a cytotoxic or cytostatic agent may be obtained by methods well known in the art, e.g. as exemplified hereinbelow.

In another embodiment, the present invention provides a pharmaceutical composition comprising a nucleic acid construct of the present invention and a pharmaceutically acceptable carrier, excipient or diluent. Each possibility represents a separate embodiment of the present invention.

In another embodiment, the present invention provides eukaryotic expression constructs and vectors comprising a nucleic acid construct of the present invention.

In another embodiment, the present invention provides a method for treating a tumor in a human subject in need thereof, comprising administering to the human subject a nucleic acid construct of the present invention, thereby treating a tumor in a human subject in need thereof. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, the cytotoxic gene product is a diphtheria toxin. In another embodiment, a therapeutically effective amount of the nucleic acid construct is administered. In another embodiment, the tumor is characterized by expression of H19 RNA and/or IGF-II from the P3 and/or P4 promoter. Each possibility represents a separate embodiment of the present invention.

In another embodiment, the present invention provides a method for inhibiting tumor progression in a human subject in need thereof, comprising administering to the human subject a nucleic acid construct of the present invention, thereby inhibiting tumor progression in a human subject in need thereof. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, the cytotoxic gene product is a diphtheria toxin. In another embodiment, a therapeutically effective amount of the nucleic acid construct is administered. In another embodiment, the tumor is characterized by expression of H19 RNA and/or IGF-II from the P3 and/or P4 promoter. Each possibility represents a separate embodiment of the present invention.

In another embodiment, the present invention provides a method for inhibiting tumor metastasis in a human subject in need thereof, comprising administering to the human subject a nucleic acid construct of the present invention, thereby inhibiting tumor metastasis in a human subject in need thereof. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, the cytotoxic gene product is a diphtheria toxin. In another embodiment, a therapeutically effective amount of the nucleic acid construct is administered. In another embodiment, the tumor is characterized by expression of H19 RNA and/or IGF-II from the P3 and/or P4 promoter. Each possibility represents a separate embodiment of the present invention.

In another embodiment, the present invention provides a method for reducing or alleviating a symptom associated with a neoplastic disorder in a human subject in need thereof, comprising administering to the human subject a nucleic acid construct of the present invention, thereby reducing or alleviating a symptom associated with a neoplastic disorder in a human subject in need thereof. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, the cytotoxic gene product is a diphtheria toxin. In another embodiment, a therapeutically effective amount of the nucleic acid construct is administered. In another embodiment, the neoplastic disorder is characterized by expression of H19 RNA and/or IGF-II from the P3 and/or P4 promoter. Each possibility represents a separate embodiment of the present invention.

In another embodiment, the present invention provides use of a nucleic acid construct of the present invention for the manufacture of a medicament for treating a tumor in a human subject. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, the cytotoxic gene product is a diphtheria toxin. In another embodiment, a therapeutically effective amount of the nucleic acid construct is administered. In another embodiment, the tumor is characterized by expression of H19 RNA and/or IGF-II from the P3 and/or P4 promoter. Each possibility represents a separate embodiment of the present invention.

In another embodiment, the present invention provides use of a nucleic acid construct of the present invention for the manufacture of a medicament for inhibiting tumor progression in a human subject. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, the cytotoxic gene product is a diphtheria toxin. In another embodiment, a therapeutically effective amount of the nucleic acid construct is administered. In another embodiment, the tumor is characterized by expression of H19 RNA and/or IGF-II from the P3 and/or P4 promoter. Each possibility represents a separate embodiment of the present invention.

In another embodiment, the present invention provides use of a nucleic acid construct of the present invention for the manufacture of a medicament for inhibiting tumor metastasis in a human subject. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, the cytotoxic gene product is a diphtheria toxin. In another embodiment, a therapeutically effective amount of the nucleic acid construct is administered. In another embodiment, the tumor is characterized by expression of H19 RNA and/or IGF-II from the P3 and/or P4 promoter. Each possibility represents a separate embodiment of the present invention.

In another embodiment, the present invention provides use of a nucleic acid construct of the present invention for the manufacture of a medicament for reducing or alleviating a symptom associated with a neoplastic disorder in a human subject. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, a therapeutically effective amount of the nucleic acid construct is administered. In another embodiment, the neoplastic disorder is characterized by expression of H19 RNA and/or IGF-II from the P3 and/or P4 promoter. Each possibility represents a separate embodiment of the present invention.

In another embodiment, the present invention provides a composition for treating a tumor in a human subject, comprising a nucleic acid construct of the present invention. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, a therapeutically effective amount of the nucleic acid construct is administered. In another embodiment, the tumor is characterized by expression of H19 RNA and/or IGF-II from the P3 and/or P4 promoter. Each possibility represents a separate embodiment of the present invention.

In another embodiment, the present invention provides a composition for inhibiting tumor progression in a human subject, comprising a nucleic acid construct of the present invention. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, the cytotoxic gene product is a diphtheria toxin. In another embodiment, a therapeutically effective amount of the nucleic acid construct is administered. In another embodiment, the tumor is characterized by expression of H19 RNA and/or IGF-II from the P3 and/or P4 promoter. Each possibility represents a separate embodiment of the present invention.

In another embodiment, the present invention provides a composition for inhibiting tumor metastasis in a human subject, comprising a nucleic acid construct of the present invention. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, the cytotoxic gene product is a diphtheria toxin. In another embodiment, a therapeutically effective amount of the nucleic acid construct is administered. In another embodiment, the tumor is characterized by expression of H19 RNA and/or IGF-II from the P3 and/or P4 promoter. Each possibility represents a separate embodiment of the present invention.

In another embodiment, the present invention provides a composition for reducing or alleviating a symptom associated with a neoplastic disorder in a human subject, comprising a nucleic acid construct of the present invention. In another embodiment, the construct contains two separate nucleic acid sequences that express the same cytotoxic gene product from an H19 promoter and an IGF-II P4 promoter. In another embodiment, the two separate nucleic acid sequences express the same cytotoxic gene product from an IGF-II P3 promoter and an IGF-II P4 promoter. In another embodiment, the two separate nucleic acid sequences express the same cytotoxic gene product from an H19 promoter and an IGF-II P3 promoter. In another embodiment, a therapeutically effective amount of the nucleic acid construct is administered. In another embodiment, the neoplastic disorder is characterized by expression of H19 RNA and/or IGF-II from the P3 and/or P4 promoter. Each possibility represents a separate embodiment of the present invention.

In some embodiments of the present invention, the neoplastic disorder of methods and compositions of the present invention is a carcinoma, e.g. a bladder carcinoma, a hepatocellular carcinoma, an ovarian carcinoma, and a pancreatic carcinoma. In another embodiment, the neoplastic disorder of methods and compositions of the present invention is a bladder carcinoma. In another embodiment, the neoplastic disorder is a hepatocellular carcinoma. In another embodiment, the neoplastic disorder is an ovarian carcinoma. In another embodiment, the neoplastic disorder is a pancreatic carcinoma. In another embodiment, the neoplastic disorder is a colon carcinoma. In another embodiment, the neoplastic disorder is another type of solid tumor. Each possibility represents a separate embodiment of the present invention.

In another embodiment, the H19-specific transcription-regulating sequence of methods of the present invention is an H19 promoter. In another embodiment, the H19 promoter comprises a nucleic acid sequence as set forth in a sequence disclosed herein. In another embodiment, the H19 promoter comprises a fragment of a nucleic acid sequence as set forth in a sequence disclosed herein. In another embodiment, the H19 promoter consists of a nucleic acid sequence as set forth in a sequence disclosed herein. Each possibility represents a separate embodiment of the present invention.

In another embodiment, the H19-specific transcription-regulating sequence of methods of the present invention comprises an H19 enhancer. In another embodiment, the H19 enhancer comprises a nucleic acid sequence as set forth in a sequence disclosed herein. In another embodiment, the H19 enhancer comprises a fragment of a nucleic acid sequence as set forth in a sequence disclosed herein. In another embodiment, the H19 enhancer consists of a nucleic acid sequence as set forth in a sequence disclosed herein. Each possibility represents a separate embodiment of the present invention.

In another embodiment, the IGF-II P3 transcription-regulating sequence of methods of the present invention is an P3 promoter. In another embodiment, the IGF-II P3 promoter comprises a nucleic acid sequence as set forth in a sequence disclosed herein. In another embodiment, the IGF-II P3 promoter comprises a fragment of a nucleic acid sequence as set forth in a sequence disclosed herein. In another embodiment, the IGF-II P3 promoter consists of a nucleic acid sequence as set forth in a sequence disclosed herein. Each possibility represents a separate embodiment of the present invention.

In another embodiment, the IGF-II P3 transcription-regulating sequence of methods of the present invention comprises an H19 enhancer. In another embodiment, the H19 enhancer comprises a nucleic acid sequence as set forth in a sequence disclosed herein. In another embodiment, the H19 enhancer comprises a fragment of a nucleic acid sequence as set forth in a sequence disclosed herein. In another embodiment, the H19 enhancer consists of a nucleic acid sequence as set forth in a sequence disclosed herein. Each possibility represents a separate embodiment of the present invention.

In another embodiment, the IGF-II P4 transcription-regulating sequence of methods of the present invention is an IGF-II P4 promoter. In another embodiment, the IGF-II P4 promoter comprises a nucleic acid sequence as set forth in a sequence disclosed herein. In another embodiment, the IGF-II P4 promoter comprises a fragment of a nucleic acid sequence as set forth in a sequence disclosed herein. In another embodiment, the IGF-II P4 promoter consists of a nucleic acid sequence as set forth in a sequence disclosed herein. Each possibility represents a separate embodiment of the present invention.

In another embodiment, the IGF-II P4 transcription-regulating sequence of methods of the present invention comprises an H19 enhancer. In another embodiment, the H19 enhancer comprises a nucleic acid sequence as set forth in a sequence disclosed herein. In another embodiment, the H19 enhancer comprises a fragment of a nucleic acid sequence as set forth in a sequence disclosed herein. In another embodiment, the H19 enhancer consists of a nucleic acid sequence as set forth in a sequence disclosed herein. Each possibility represents a separate embodiment of the present invention.

Nucleic Acid Constructs

The term "nucleic acid construct" or "construct" as used herein includes a nucleic acid sequence encoding a cytotoxic or cytostatic gene product (e.g. Diphtheria toxin, DT) according to the present invention, the nucleic acid sequence being operably linked to a promoter and optionally other transcription regulation sequences. In the constructs of the invention, the DT-encoding nucleic acid sequence is operably linked to at least one H19-specific transcription-regulating sequence, P3 transcription-regulating sequence and/or P4 transcription-regulating sequence.

The nucleic acid construct of methods and compositions of the present invention is, in another embodiment, a eukaryotic expression vector. In another embodiment, the nucleic acid construct is a plasmid. In another embodiment, the nucleic acid construct is any other type of expression vector capable of mediating expression in a cancer cell. Each possibility represents a separate embodiment of the present invention.

The phrase "operably linked" refers to a nucleic acid sequence linked a to a transcription control sequence in a manner such that the molecule is able to be expressed when transfected (i.e., transformed, transduced, infected, or transfected) into a host cell. Transcription control sequences are sequences, which control the initiation, elongation, and termination of transcription. Particularly important transcription control sequences are those which control transcription initiation, such as promoter, enhancer, operator and repressor sequences.

In another embodiment, the nucleic acid molecule of methods and compositions of the present invention is a DNA molecule. In another embodiment, the molecule is an RNA molecule. In another embodiment, the molecule is any other type of nucleic acid molecule known in the art. Each possibility represents a separate embodiment of the present invention.

As used herein, the term "vector" refers to a construct, comprising a regulatory sequence operatively linked to a heterologous polynucleotide, that is administered to target cells. The vector can be a viral expression vector, a plasmid or a construct of naked DNA, and, optionally, can include additional sequences required for construction, selection, stability, penetration, etc.

As used herein, the term "variant" refers to a pharmaceutically acceptable salt, homologue, analogue, or fragment of a nucleotide sequence useful for the invention (e.g., vector sequences, transcriptional regulatory sequences, cloned polynucleotides of interest, etc.). Encompassed within the term "variant" are chemically modified natural and synthetic nucleotide molecules. Also encompassed within the term "variant" are conservative substitutions within the nucleotide sequence of the molecule. In addition, non-conservative substitutions within the nucleotide sequence of the molecule are encompassed within the term "variant" as used herein, as long as the sequence substantially retains its required function.

In other embodiments, a "variant", e.g. a "variant" of a cytotoxic or cytostatic gene product, as used herein, refers to a gene recognized in the art to be a product of another version of the same e.g. cytotoxic or cytostatic gene. Gene sequences and their products are routinely classified as being sequences of a particular gene in public databases such as the U.S. National Center for Biotechnology Information's PubMed database; thus, it is readily within the skill of those of average skill in the art to identify variants of e.g. a cytotoxic or cytostatic gene product of the present invention.

In another embodiment, "variants", e.g. of a cytotoxic or cytostatic gene product of the present invention, are at least 70% homologous, or, in other embodiments, share at least 75%, 80%, 82%, 84%, 86%, 88%, 90%, 92%, 94%, 96%, 98% or 99% sequence homology. Each possibility represents a separate embodiment of the present invention.

As used herein the phrase "Diphtheria toxin" (DT or DTX) refers to a Diphtheria toxin or a fragment thereof containing at least an active portion of the Diphtheria toxin, which promotes cell death, or which may work to promote cell death or to otherwise ameliorate a neoplastic disorder in a subject. DT is comprised of two polypeptide fragments, A and B [Zdanovskaia, M. V.; Zdanovsky, A. G.; Yankovsky, N. K. "Diphtheria toxin NAD affinity and ADP ribosyltransferase activity are reduced at tryptophan 153 substitutions for alanine or phenylalanine." *Research in Microbiology*, 2000, 151, 557-562; Bennet, M. J.; Choe, S.; Eisenberg, D. "Refined structure of dimeric diphtheria toxin at 2.0 angstrom resolution." *Protein Science*, 1994, 3, 1444-1463]. Fragment A (DTA) consists of the catalytic domain (C), whereas fragment B is made up of the receptor domain, (R), and the transmembrane domain, (T). The R domain contains a receptor portion which binds to the HB-EGF receptor on the cell surface [Raab, Gerhard; Klagsbrun, Michael "Heparin-binding EGF-like growth factor" *Biochimica et Biophysica Acta (BBA)/Reviews on Cancer* 1997, 1333, F179-F199]. The bound toxin then enters the cytoplasm by endocytosis. The C-terminus hydrophobic series of α-sheets, known as the T domain, then embeds itself into the membrane, causing the N-terminus C domain to be cleaved and translocated into the cytoplasm. Once cleaved, the C domain becomes an active enzyme, catalyzing the creation of ADP-ribose-EF-2 from the protein synthesis translocation peptide EF-2 and NAD+ (Hudson T H et al, Quantal entry of diphtheria toxin to the cytosol. J Biol Chem. 1985 Mar. 10; 260(5):2675-80). A single C domain can use a cell's entire supply of EF-2 within hours, bringing protein synthesis to a halt, resulting in cell death. Since the present invention envisages recombinant preferably intracellular expression of the toxin the minimal C domain may be used. According to presently known preferred embodiments of this aspect of the present invention the toxin is diphtheria A chain toxin (DTA).

In another embodiment, the DTA is encoded by a nucleic acid sequence as set forth in SEQ ID NO: 6:
atggatcctgatgatgttgttgattcttctaaatcttttgtgatggaaaacttttcttcgtaccacgggactaaacctggttatgtagattccattcaaaaaggtatacaaaagccaaaatctggtacacaaggaaattatgacgatgattggaaagggttttatagtaccgacaataaatacgacgctgcgggatactctgtagataatgaaaacccgctctctggaaaagctggaggcgtggtcaaagtgacgtatccaggactgacgaaggttctcgcactaaaagtggataatgccgaaactattaagaaagagttaggtttaagtctcactgaaccgttgatggagcaagtcggaacggaagagtttatcaaaaggttcggtgatggtgcttcgcgtgtagtgctcagccttcccttcgctgaggggagttctagcgttgaatatattaataactgggaacaggcgaaagcgttaagcgtagaacttgagattaattttgaaacccgtggaaaacgtggccaagatgcgatgtatgagtatatggctcaagcctgtgcaggaaatcgtgtcaggcgatctttgtga (SEQ ID NO: 6). In another embodiment, the DTA-encoding sequence comprises a nucleic acid sequence as set forth in SEQ ID NO: 6. In another embodiment, the DTA-encoding sequence consists of a nucleic acid sequence as set forth in SEQ ID NO: 6. In another embodiment, the DTA-encoding sequence is a homologue of SEQ ID NO: 6. In another embodiment, the DTA-encoding sequence is a variant of SEQ ID NO: 6. In another embodiment, the DTA-encoding sequence is a fragment of SEQ ID NO: 6. In another embodiment, the DTA-encoding sequence is a homologue of a fragment of SEQ ID NO: 6. In another embodiment, the DTA-encoding sequence is a variant of a fragment of SEQ ID NO: 6. Each possibility represents a separate embodiment of the present invention.

In another embodiment, the amino acid sequence of the DTA is as set forth in SEQ ID NO: 7:
MDPDDVVDSSKSFVMENFSSYHGTKPGYVDSIQ-KGIQKPKSGTQGNYDDDWKGFYSTDNKYDAAGYS-VDNENPLSGKAGGVVKVTYPGLTKVLALKVDNAE-TIKKELGLSLTEPLMEQVGTEEFIKRFGDGASRVVLS-LPFAEGSSSVEYINNWEQAKALSVELEINFETRGKR-GQDAMYEYMAQACAGNRVRRSL (SEQ ID NO: 7). In another embodiment, the DTA comprises a nucleic acid sequence as set forth in SEQ ID NO: 7. In another embodiment, the DTA consists of a nucleic acid sequence as set forth in SEQ ID NO: 7. In another embodiment, the DTA is a homologue of SEQ ID NO: 7. In another embodiment, the DTA is a variant of SEQ ID NO: 7. In another embodiment, the DTA is a fragment of SEQ ID NO: 7. In another embodiment, the DTA is a homologue of a fragment of SEQ. ID NO: 7. In another embodiment, the DTA is a variant of a fragment of SEQ ID NO: 7. Each possibility represents a separate embodiment of the present invention.

In another embodiment, the DTA is at least 60% homologous to SEQ ID NO: 7. In another embodiment, the DTA is at least 65% homologous to SEQ ID NO: 7. In another embodiment, the DTA is at least 70% homologous to SEQ ID NO: 7. In another embodiment, the DTA is at least 72% homologous to SEQ ID NO: 7. In another embodiment, the DTA is at least 74% homologous to SEQ ID NO: 7. In another embodiment, the DTA is at least 76% homologous to SEQ ID NO: 7. In another embodiment, the DTA is at least 78% homologous to SEQ ID NO: 7. In another embodiment, the DTA is at least 80% homologous to SEQ ID NO: 7. In another embodiment, the DTA is at least 82% homologous to SEQ ID NO: 7. In another embodiment, the DTA is at least 84% homologous to SEQ ID NO: 7. In another embodiment, the DTA is at least 86% homologous to SEQ ID NO: 7. In another embodiment, the DTA is at least 88% homologous to SEQ ID NO: 7. In another embodiment, the DTA is at least 90% homologous to SEQ ID NO: 7. In another embodiment, the DTA is at least 92% homologous to SEQ ID NO: 7. In another embodiment, the DTA is at least 94% homologous to SEQ ID NO: 7. In another embodiment, the DTA is at least 95% homologous to SEQ ID NO: 7. In another embodiment, the DTA is at least 96% homologous to SEQ ID NO: 7. In another embodiment, the DTA is at least 97% homologous to SEQ ID NO: 7. In another embodiment, the DTA is at least 98% homologous to SEQ ID NO: 7. In another embodiment, the DTA is at least 99% homologous to SEQ ID NO: 7. In another embodiment, the DTA is over 99% homologous to SEQ ID NO: 7. Each possibility represents a separate embodiment of the present invention.

Constructs of the invention contain, on the same construct, multiple expression cassettes, wherein expression of the cytotoxic or cytostatic gene product is directed by at least two of the following three transcription-regulating sequences: an H19, an IGF-II P3, and an IGF-II P4 regulatory sequence, i.e. the gene product-encoding nucleic acid sequence is under transcriptional control of at least two of these sequences. As used herein, the phrase "being under H19 (or IGF-II P3 or IGF-II P4) expression control" (or "transcriptional control") refers to the transcription of the encoded sequence from an H19-specific (or IGF-II P3 or IGF-II P4) promoter sequence, or a sequence derived therefrom, which is operably-linked thereto to regulate their expression pattern (including spatial and temporal expression pattern).

In another embodiment, the regulatory sequence of methods and compositions of the present invention is derived from an H19, IGF-II P3, or IGF-II P4 transcriptional regulatory sequence. As used herein, a description of a regulatory sequence "derived from an H19, IGF-II P3, or IGF-II P4 transcriptional regulatory sequence" refers to a sequence "derived" (see below) from a region of the gene that regulates and/or controls the expression of the H19 or IGF-II coding sequences. As such, a regulatory sequence includes, without limitation, a sequence derived from a promoter or enhancer of the H19, IGF-II P3, or IGF-II P4 sequences.

The term "derived" refers to the fact that a transcriptional regulatory sequence (for example, a promoter or enhancer) can be the complete native regulatory sequence of the gene, a portion of the native regulatory sequence, a chimeric construction of the native regulatory sequence, a combinatorial construction of one or more native regulatory sequences, or a variant of the native regulatory sequence obtained by, for example, deletion, addition or replacement of at least one nucleotide. A variant regulatory sequence can comprise modified nucleotides. The derived sequence preferably demonstrates properties of control/regulation (e.g., increase) of the expression of coding sequences operably linked thereto.

Described herein are H19 regulatory sequences that can be used in the nucleic acid constructs of the invention to direct the specific expression of a cytotoxic or cytostatic gene product. H19 regulatory sequences useful in the present invention include inter alia the upstream H19 promoter region and the downstream H19 enhancer region. In certain embodiments, H19 promoter and enhancer sequences which can be used in accordance with the present invention include, but are not limited to, those described in U.S. Pat. No. 6,306,833, as detailed herein.

The H19-specific transcription-regulating sequence of compositions of the present invention is, in another embodiment, an H19 promoter. In another embodiment, the H19 promoter comprises a nucleic acid sequence as set forth in any one of SEQ ID NOS: 1-2. In another embodiment, the H19 promoter consists of a nucleic acid sequence as set forth in any one of SEQ ID NOS: 1-2.

The nucleotide sequence of one H19 promoter region is shown in SEQ ID NO: 1:
ctgcagggccccaacaaccctcaccaaaggccaaggtggtgaccgacgga-cccacagcggggtggctgggggagtcgaaactcgccagtctccactccactcc-caaccgtggtgccccacgcgggcctgggagagtctgtgaggccgcccaccgct-tgtcagtagagtgcgcccgcgagccgtaagcacagcccggcaacatgcggtctt-cagacaggaaagtggccgcgaatgggaccggggtgcccagcggctgtgggg-actctgtcctgcggaaaccgcggtgacgagcacaagctcggtcaactggatggg-aatcggcctggggggctggcaccgcgcccaccaggggttgcggcacttccct-ctgcccctcagcaccccacccctactctccaggaacgtgaggtctgagccgtgat-ggtggcaggaaggggccctctgtgccatccgagtccccagggacccgcagctg-gcccccagccatgtgcaaagtatgtgcagggcgctggcaggcagggagcagc-aggcatggtgtccctgaggggagacagtggtctgggagggagaggtcctgga-ccctgagggaggtgatggggcaatgctcagccctgtctccggatgccaagga-ggggtgcggggaggccgtctttggagaattccaggatgggtgctgggtgagag-agacgtgtgctggaactgtccagggcggaggtgggccctgcggggggccctcgg-gagggccctgctctgattggccggcagggcagggggcgggaattctggcgggcc-accccagttagaaaaagcccgggctaggaccgagga (SEQ ID NO: 1). In another embodiment, the H19 sequence is a homologue of SEQ ID NO: 1. In another embodiment, the H19 sequence is a variant of SEQ ID NO: 1. In another embodiment, the H19 sequence is a fragment of SEQ ID NO: 1. In another embodiment, the H19 sequence is a homologue of a fragment of SEQ ID NO: 1. In another embodiment, the H19 sequence is a variant of a fragment of SEQ ID NO: 1. Each possibility represents a separate embodiment of the present invention.

In another embodiment, the H19 sequence is at least 60% homologous to SEQ ID NO: 1. In another embodiment, the H19 sequence is at least 65% homologous to SEQ ID NO: 1. In another embodiment, the H19 sequence is at least 70% homologous to SEQ ID NO: 1. In another embodiment, the H19 sequence is at least 72% homologous to SEQ ID NO: 1. In another embodiment, the H19 sequence is at least 74% homologous to SEQ ID NO: 1. In another embodiment, the H19 sequence is at least 76% homologous to SEQ ID NO: 1. In another embodiment, the H19 sequence is at least 78% homologous to SEQ ID NO: 1. In another embodiment, the H19 sequence is at least 80% homologous to SEQ ID NO: 1. In another embodiment, the H19 sequence is at least 82% homologous to SEQ ID NO: 1. In another embodiment, the H19 sequence is at least 84% homologous to SEQ ID NO: 1. In another embodiment, the H19 sequence is at least 86% homologous to SEQ ID NO: 1. In another embodiment, the H19 sequence is at least 88% homologous to SEQ ID NO: 1.

In another embodiment, the H19 sequence is at least 90% homologous to SEQ ID NO: 1. In another embodiment, the H19 sequence is at least 92% homologous to SEQ ID NO: 1. In another embodiment, the H19 sequence is at least 94% homologous to SEQ ID NO: 1. In another embodiment, the H19 sequence is at least 95% homologous to SEQ ID NO: 1. In another embodiment, the H19 sequence is at least 96% homologous to SEQ ID NO: 1. In another embodiment, the H19 sequence is at least 97% homologous to SEQ ID NO: 1. In another embodiment, the H19 sequence is at least 98% homologous to SEQ ID NO: 1. In another embodiment, the H19 sequence is at least 99% homologous to SEQ ID NO: 1. In another embodiment, the H19 sequence is over 99% homologous to SEQ ID NO: 1. Each possibility represents a separate embodiment of the present invention.

This 831 nucleotide sequence extends from −837 to −7 nucleotides from the cap site (as described in Brannan et al. 1990). A consensus TATA sequence occurs at nucleotides −27 to −35. Two consensus AP2 binding sites (8/9 matches) occur at approximately −500 and −40 nucleotides upstream from the initiation of transcription. When placed upstream of the coding region for a heterologous gene, approximately 831 base pairs of the regulatory region is sufficient to direct expression of the operatively linked heterologous gene in cancer cells that also express endogenous H19. In another embodiment, an additional H19 promoter region between nucleotides −819 to +14 (SEQ ID NO: 2) is also sufficient to direct expression of the operatively linked heterologous gene in cancer cells:

gacaaccctcaccaagggccaaggtggtgaccgacggacccacagcggg-gtggctgggggagtcgaaactcgccagtctccactccactcccaaccgtggtgc-cccacgcgggcctgggagagtctgtgaggccgccaccgcttgtcagtagagt-gcgcccgcgagccgtaagcacagcccggcaacatgcggtcttcagacaggaaa-gtggccgcgaatgggaccgggtgcccagcggctgtggggactctgtcctgcg-gaaaccgcggtgacgagcacaagctcggtcaactggatgggaatcggcctggg-gggctggcaccgcgcccaccaggggggtttgcggcacttccctctgccctcagc-accccaccctactctccaggaacgtgagttctgagccgtgatggtggcaggaag-gggccctctgtgccatccgagtccccagggacccgcagctggcccccagccat-gtgcaaagtatgtgcagggcgctggcaggcagggagcagcaggcatggtgtcc-cctgaggggagacagtggtctgggagggagaagtcctggccctgagggaggt-gatggggcaatgctcagccctgtctccggatgccaaggagggggtgcggggag-gccgtcttggagaattccaggatgggtgctgggtgagagagacgtgtgctgga-actgtccaggcggaggtgggccctgcggggccacgggagggccctgctct-gattggccggcagggcagggcggaattcgggcggggccacccagttaga-aaaagccgggctaggaccgaggagcagggtgagggag (SEQ ID NO: 2). In another embodiment, the H19 sequence is a homologue of SEQ ID NO: 2. In another embodiment, the H19 sequence is a variant of SEQ ID NO: 2. In another embodiment, the H19 sequence is a fragment of SEQ ID NO: 2. In another embodiment, the H19 sequence is a homologue of a fragment of SEQ ID NO: 2. In another embodiment, the H19 sequence is a variant of a fragment of SEQ ID NO: 2. Each possibility represents a separate embodiment of the present invention.

In another embodiment, the H19 sequence is at least 60% homologous to SEQ ID NO: 2. In another embodiment, the H19 sequence is at least 65% homologous to SEQ ID NO: 2. In another embodiment, the H19 sequence is at least 70% homologous to SEQ ID NO: 2. In another embodiment, the H19 sequence is at least 72% homologous to SEQ ID NO: 2. In another embodiment, the H19 sequence is at least 74% homologous to SEQ ID NO: 2. In another embodiment, the H19 sequence is at least 76% homologous to SEQ ID NO: 2. In another embodiment, the H19 sequence is at least 78% homologous to SEQ ID NO: 2. In another embodiment, the H19 sequence is at least 80% homologous to SEQ ID NO: 2. In another embodiment, the H19 sequence is at least 82% homologous to SEQ ID NO: 2. In another embodiment, the H19 sequence is at least 84% homologous to SEQ ID NO: 2. In another embodiment, the H19 sequence is at least 86% homologous to SEQ ID NO: 2. In another embodiment, the H19 sequence is at least 88% homologous to SEQ ID NO: 2. In another embodiment, the H19 sequence is at least 90% homologous to SEQ ID NO: 2. In another embodiment, the H19 sequence is at least 92% homologous to SEQ ID NO: 2. In another embodiment, the H19 sequence is at least 94% homologous to SEQ ID NO: 2. In another embodiment, the H19 sequence is at least 95% homologous to SEQ ID NO: 2. In another embodiment, the H19 sequence is at least 96% homologous to SEQ ID NO: 2. In another embodiment, the H19 sequence is at least 97% homologous to SEQ ID NO: 2. In another embodiment, the H19 sequence is at least 98% homologous to SEQ ID NO: 2. In another embodiment, the H19 sequence is at least 99% homologous to SEQ ID NO: 2. In another embodiment, the H19 sequence is over 99% homologous to SEQ ID NO: 2. Each possibility represents a separate embodiment of the present invention.

The downstream enhancer region of the human H19 gene can optionally be added to an H19 promoter/DTA construct of the present invention in order to provide enhanced levels of cell-specific expression of the DTA molecule. As expected from an enhancer sequence, the downstream enhancer is able to exert its effect when placed in either reverse or direct orientation (relative to the orientation of the H19 enhancer in the endogenous H19 gene) downstream from the coding region of a heterologous gene under the control of the H19 promoter.

In another embodiment, the H19 enhancer sequence comprises the sequence:

caaggacatggaatttcggaccttctgtccccaccctctctgctgagcctagga-acctctgagcagcaggaaggccttgggtctagagcctagaaatggacccccacg-tccacctgcccagcctagaccccagcattgaagggtggtcagacttcctgtgag-aggaagccactaagcgggatggacaccatcgcccactccacccggccctgccc-agccctgcccagtccagcccagtccagcccagccctgcccttcccagccctgcc-cagcccagctcatccctgccctaccagcccagccctgtcctgccctgcccagcc-cagcccagcccagccctgccctgccctgccctgcccttcccagccctgaccttcc-cagccctgcccagcccagctcatccctgccctaccagctcagccctgccctgcc-ctgccctgccctgcccagcccctaccagcccagccctgccctgccctgcccagc-tcagccctgcccacccagccagcccagcccagcatgcgttctctggatggtga-gcacaggcttgaccttagaaagaggctggcaacgagggctgaggccaccagg-ccactgggtgctcacgggtcagacaagcccagagcctgctccctgccacgggt-cggggctgtcaccgccagcatgctgtggatgtgcatggcctcagggctgctggc-tccaggctgcccccgccctggctcccgaggccacccctcttatgccatgaacct-gtgccacaccacctctgagctgtccccgctcctgccgcctgcaccccctgagca-gccccctgtgtgtttcatggagtcttagcaaggaagggagctcgaattcctgc-agcccggg (SEQ ID NO: 3). In another embodiment, the H19 sequence is a homologue of SEQ ID NO: 3. In another embodiment, the H19 sequence is a variant of SEQ ID NO: 3. In another embodiment, the H19 sequence is a fragment of SEQ ID NO: 3. In another embodiment, the H19 sequence is a homologue of a fragment of SEQ ID NO: 3. "Homologue" may refer to any degree of homology disclosed herein. In another embodiment, the H19 sequence is a variant of a fragment of SEQ ID NO: 3. Each possibility represents a separate embodiment of the present invention.

In another embodiment, the H19 enhancer sequence comprises the sequence:

ccgggtaccgagctcccaggaagataaatgatttcctcctctctagagatggg-ggtgggatctgagcactcagagccaagggcgcagtgggtccgggcggggc-cctcctcggcctcccaacatgggggccaggaggtcagcccctcaacctggac-cccggctgggtctcaggaatggtctcccccagtggcccagcttgcttgtgttttc-agatgggtgtgcatgggtgtgtgtgtgtgtgtgtgtgtgtgtgtgtgtgtgt-gtgatgcctgacaagcccagagagccaaagacctgagtggagatcttgtgact-tctcaaaaggggattggaaggttcgagaaagagctgtggtcagccttgctctcc-cttaaggctgtggtaaccacactaggcatagcataggcctgcgccccgtccctccttccctcctccgcgcctctcctttctctttctccccctctaccccgctccctggcctg-
ctcctggtgacaccgttggcccccttccagggctgagggaagccagcgggggc-
ccttcctgaaagcccacctgcaggccggcttgctgggaaggggctgctctcgc-
agaggctcccgcccgcctgcagccgtttcctggaagcagtcgctgtgggtattc-
tgttccttgtcagcactgtgcttgcaaagaaagcagacactgtgctccttgtccttag-
ggagccccgctccatcacccaacacctggctggacacaggcgggaggccggg-
tccgcggggagcggcgcggggctggggccggaccattaaacacacacgggc-
gccaggcactgcaggctcctcctcctcctcctgcccagcgcctctgctcacaggc-
acgtgccaagcccctaggccaggaggccagcagtgggtgcagaacaagctcct-
gggaaggggtgcagggcggaccccc ggggagaagggctggcagggctgtg-
ggggacgctgaccgtgggccccacgttgcagaaaactggntgcctggctggaa-
gatggggagatgccaagcctctgaggcagcacgagcagggtgcatggagc-
cggggcgcggggaggctgcactgcagcatgcacccc aaagcccanagggag-
tggagaccaggccctggaatcgagaagtagaaaggcggcttggaggcctcga-
accggctgacctccaacagagtgggtctccagcctggctctgccctgccgcagg-
tccctccctcattaccaggcctagagcctccagtcccggtggcccccagccc-
gagggtgaacggcctcaccctgggtcgtgggacagagggcacgttcatcaaga-
gtggctcccaagggacacgtggctgtttgcagttcacaggaagcattcgagataa-
cggagcttgttttcccagtgggcacggagccagcagggggcgctgtggggcagc-
caggctgcaaggccaggctgtggggctgcagctgccttgggccccactcca-
ggcctttgcgggaggtgggaggcggaggcggcagctgcacagtggcccag-
gcgaggctctcagcccagtcgctctccgggtgggcagcccaagagggtctgg-
ctgagcctcccacatctgggactccatcacccaacaacttaattaaggctgaatttc-
acgtgtcctgtgacttgggtagacaaagccctgtccaaaggggcagccagccta-
aggcagtggggacggctgggtggcgggcgacggggagatggacaacagg-
accgagggtgtgcgggcgatggggagatggacaacaggaccgagggtgc-
gggcgatggggagatggacaacaggaccgagggtgtgcgggacacgcatg-
tcactcatgcacgccaatggggggcgtggg aggctggggagcagacagactgg-
gctgggctgggcgggaaggacgggcagatg (SEQ ID NO: 4). In
another embodiment, the H19 sequence is a homologue of
SEQ ID NO: 4. In another embodiment, the H19 sequence is
a variant of SEQ ID NO: 4. In another embodiment, the H19
sequence is a fragment of SEQ ID NO: 4. In another embodi-
ment, the H19 sequence is a homologue of a fragment of SEQ
ID NO: 4. "Homologue" may refer to any degree of homology
disclosed herein. In another embodiment, the H19 sequence
is a variant of a fragment of SEQ ID NO: 4. Each possibility
represents a separate embodiment of the present invention.

In another embodiment, the H19 enhancer sequence com-
prises the sequence:
ccgggtaccgagctcccaggaagataaatgatttcctcctctagagatggg-
ggtgggatctgagcactcagagccaagggcgcagtgggtccgggcggggc-
cctcctcggccctccaacatgggggccaggaggtcagccctcaacctggac-
cccggctgggtctcagggaatggtctccccagtggcccagcttgcttgtgttttca-
gatgggtgtgcatgggtgtgtgtgtgtgtgtgtgtgtgtgtgtgtgtgtgtg-
tgatgcctgacaagccccagagagccaaagacctgagtggagatcttgtgacttc-
tcaaaaggggggattggaaggttcgagaaagagctgtggtcagccttgctctccct-
taaggctgtggtaaccacactaggcatagcataggcctgcgccccgtccctcctt-
ccctcctccgcgcctctccttctctttctccccctctaccccgctccctggcctgct-
cctggtgacaccgttggcccccttccagggctgagggaagccagcgggggcc-
ccttcctgaaagcccacctgcaggccggcttgctgggaaggggctgctacgca-
gaggctcccgcccgcctgcagccgtttcctggaagcagtcgctgtgggtattct-
gttccttgtcagcactgtgcttgcaaagaaagcagacactgtgctccttgtccttag-
ggagccccgctccatcacccaacacctggctggacacaggcgggaggccggg-
tccgcggggagcggcgcggggctggggccggaccattaaacacacacgggc-
gccaggcactgcaggctcctcctcctcctcctgcccagcgcctctgctcacagg-
cacgtgccaagcccctaggccaggaggccagcagtgggtgcagaacaagctc-
ctgggaaggggtgcagggcggaccccc ggggagaagggctggcagggctgtg-
ggggacgctgaccgtgggccccacgttgcagaaaactggntgcctggctgg-
aagatggggagatgccaagcctctgaggcagcacgagcagggtgcatggag-
gccggggcgcggggaggctgcactgcagcatgcacccc aaagcccanaggg-
agtggagaccaggccctggaatcgagaagtagaaaggcggcttggaggcctcg-
aaccggctgacctccaacagagtggggccggcctggaggcaaagaggtgc-
ccgggtccggccctgcctgggggagctatgtgtcatgggcaagccacaggat-
atgtagcccgctctgacctatggacccagggcagggctgcaaggcagggcag-
gggagacagcacgggggagcaaggagcagagaggggggcctcaggctctccc-
aggaggaacattctcccgacaggaggaagagacggcccaggggtgactgtgg-
ggagccatggtggcagctggggtcgtggcagatgggagagaggctggcgagg-
tgaaggtgcaggggtcagggctctgggg cccacatgcctgtgggagcaggcag-
gcccagggctctccgccactccccactcccgcttggctcataggctgggcccaag-
ggtggggtgggatgagcaggagatggggccaggggg caagcagggcccca-
aagacatttagaaaaaccggtttatgcaggcagcattcagagcaggcggcgtgc-
gtggcgggggccctgggagcacagagaggcacacgtagggcccccgagggg-
ctccccattggccggcagtgacatcaccccctgtgtcaacagtgatgtctgcgctc-
cggccagccagggtttatggagcgagacccagcccggcctgggccctcactcc-
ccaggcccacacactagccactgttcagggtccggggtggcggcatggcctgg-
gggtcctggcaccgctgctcctctgcccaccctaacttcccggcatcgcggctgc-
ccctctgagcgtccccaaccagtaagtgtggggcccagcaggcctgccgtcct-
cctcctcttccctctagagagaaacgtggaggtcctggggctgggggcgctcat-
agccctgtgacacaggtgcatgggtcagggtcccagaatggccctgggaa-
ggacctcagctggccggcggctctaggcttcagggtctgtctgcacagggg-
ntagcccctcccagacctctgtgaagccagtacgggcctcccctccctgccccgt-
gctctgtccggtgcttcctggactgcactgcgggccactggtgagagggtggaca-
gggaagggccgccgtggtgcctgttcctgcccacctggctgtgtggtcccctcca-
agtagggacaacccttctgagggcttgggggcacccctgggggttgccagggcctc-
ccagagccctgtgagccctggggggtctggcctgatgcccccctccacgtcca-
gggccggctgtggcccagaaccccagcttccagcaggccggtgtgcggtggt-
gacccaggagaggcctcgcctccactgaggggccaccgacctctgtcagacca-
cagagaccccaaggagtctgaaggctggagacccggggctgggaccaggtg-
ggactttcccacggagccgtcccc aggcccagctggggacacgtccccttctc-
tccagacacaccctgcctgccaccaggacacaccggcctgttgggggtctcttta-
agtgcttgccactctgaggtgactgtcccttccaaagaggtttctggggcccaggt-
gggatgcgtcggcctgagcaggaggatctgggccgccagggctggggactg-
tctcctggggaaggaagcgcctgggagcgtgtgtgctgacccaggaccatccag-
ggaggcccgtctgtggggcaagcgggaagggagcggctggagaggcttggcc-
gccccccgccctgcctcccattccttagctccatgcctgtcaacctctgtcacccagt-
gagtgatgtccaggggccctggaaaggtcacagcatgtttgagcggggtgagag-
agaggggaaaggcgggggcgggaaaagtacgtggaggaagattaggccca-
aggaaggagacagggttctgggagggagggagccactggggccgccgggaa-
ggtccctgatgctgctgccacccagaaccctcgcctcttagctagcccccgcagc-
cccagcctttctggcntgtggccctctcccccatcccaggtgtcctgtgcaacca-
ggccttggacccaaaccctcctgccccctcctctccctcctcacccctcccaatgca-
gtggtctccagcctggctctgccctgccgcaggtccacccctcattaccaggcc-
tagagcctccagtcccggtggccccc agcccgagggtgaacggcctcacc ctg-
ggtcgtgggacagagggcacgttcatcaagagtggctcccaagggacacgtgg-
ctgtttgcagttcacaggaagcattcgagataaggagcttgttttcccagtgggcac-
ggagccagcaggggggctgtggggcagcccagggtgcaaggccaggctgtg-
gggctgcagctgccttgggccccactcccaggcctttgcgggaggtgggaggc-
gggaggcggcagctgcacagtggcccaggcgaggctctcagcccagtcgc-
tctccgggtgggcagcccaagagggtctggctgagcctcccacatctgggactc-
catcacccaacaacttaattaaggctgaatttcacgtgtcctgtgacttgggtagaca-
aagccctgtccaaaggggcagccagcctaaggcagtggggacggcgtggt-
ggcgggcgacggggagatggacaacaggaccgagggtgtgcgggcgatgg-
gggagatgcacaacaggaccgagggtgtgcgggcgatggggagatggaca-
acaggaccgagggtgtgcgggacacgcatgtcactcatgcacgccaatggggg-
gcgtgggaggctggggagcagacagactgggctgggctgggcgggaaggac-
gggcagatg (SEQ ID NO: 5). In another embodiment, the H19
sequence is a homologue of SEQ ID NO: 5. In another
embodiment, the H19 sequence is a variant of SEQ ID NO: 5.
In another embodiment, the H19 sequence is a fragment of
SEQ ID NO: 5. In another embodiment, the H19 sequence is
a homologue of a fragment of SEQ ID NO: 5. "Homologue"
may refer to any degree of homology disclosed herein. In
another embodiment, the H19 sequence is a variant of a
fragment of SEQ ID NO: 5. Each possibility represents a
separate embodiment of the present invention.

In another embodiment, fragments of this enhancer, e.g.
fragments of the sequences set forth in any one of SEQ ID
NOS: 3-5 may also be used to facilitate gene expression. In
one embodiment, the enhancer consists of a sequence as set
forth in any one of SEQ ID NOs: 3-5.

Further described herein are IGF-II P3 regulatory
sequences that can be used in the nucleic acid constructs of
the invention to direct the specific expression of a cytotoxic or cytostatic gene product. In another embodiment, the IGF-II P3 transcription-regulating sequence of compositions of the present invention is an IGF-II P3 promoter. In another embodiment, the P3 promoter corresponds to nucleotide sequence −1229 to +140 of the IGF-II gene (one example of an IGF-II gene sequence is found in Chromosome 11, NC_000011.8, base pairs 2106926 . . . 2116578).

In another embodiment, an IGF-II gene sequence of methods and compositions of the present invention is:

```
                                            (SEQ ID NO: 10)
cccaaccccgcgcacagcgggcactggtttcgggcctctctgtctcctac gaagtccgtagagcaactcggatttgggaaatttctctctagcgttgccc aaacacacttgggtcggccgcgcgccctcaggacgtggacagggagggct tccccgtgtccaggaaagcgacccgggcattgcccccagtctcccccaaat ttgggcattgtccccgggtcttccaacggactgggcgnngctcccggaca ctgaggactggcccccggggtctcgctccaccttcagcagcgtccaccgcct gccacagagcgttcgatcgctcgctgcctgagctcctggtgcgcccgcgg acgcagcctccagcttcgcggtgagctccccgccgcgccgatcccctccg cctctgcgccctgaccggctctcggcccgcatctgctgctgtcccgccg gtgctggcgctcgtccgctgcgccggggaggccggcgtggggcgcgggac acggctgcggacttgcggctgcgctgcgctcgctcctgctgggcgccccg aaatccgcgccactttcgtttgctcattgcaaagatctcatttgtgggga aagcggctggagggtcccaaagtggggcgggcaggggggctggggcgaggg acgcggaggagaggcgctcccgccgggcggtaaagtgcctctagcccgcg ggcctaggactccgccgggagggcgcgcggagngcgaagtgattgatggc ggaagcgggggggcaagggggggcagggggggcgcgggattccgccggcgac cccttcccttggctaggcttaggcggcgggggggctggcggggtgcggga ttttgtgcgtggttttttgacttggtaaaaatcacagtgctttcttacatc gttcaaactctccaggagatggtttccccagacccccaaattatcgtggt ggccccccgagaccgaactcgcgtctatgcaagtccaacgcactgaggacg gggtaaccattatccagatattttgggtgggccgcaaaggcgagctactt agacgcaccccggtgagctcggccatgcaggtaggatttgagctgtgttt cccgccctgatcctctctcctctggcggccggagcctccgtaggctccaa gcctggcccagattcggcggcgcagccggccttccgcgcgtccgcaccta gcgggggctccgggctccggcgcggcaccgggggggcgctcgggatctgg ctgaggctccaaggcccgcgtggccggctcctcctgctggggcaggtggc ggctgcgcgcccgcccgagcccaggggcccctcagccgcaacaaccag caaggaccccccgactcagccccaagccacctgcatctgcactcagacgg ggcgcacccgcagtgcagcctcctggtggggcgctgggagcccgcctgcc cctgcctgcccggagaccccagctcacgagcacaggccgcccgggcaccc cagaaacccgggatggggcccctgaattctctaggacgggcattcagcat ggccttggcgctctgcggctcctgccccccaccccagcctcgcccccgcg cacccccccagccctgcgaccgcgccccccccccgggggccccagggcc ccagcccgcaccccccgcccgctcttggctcgggttgcggggggcgggcc
``` gggggcggggcgagggctccgcgggcgcccattggcgcgggcgcgaggcc agcggcccgcgcggccctgggccgcggctggcgcgactataagagccgg gcgtgggcgcccgcagttcgcctgctctccggcggagctgcgtgaggccc ggccggccccggccccccccttccggccgcccccgcctcctggcccacgc ctgcccgcgctctgcccaccagcgcctccatcgggcaaggcggcccccgcg tcgacgccgcccgctgcctcgctgctgactcccgtcccgggcgccgtccg cggggtcgcgctccgccgggcctgcggattccccgccgcctcctcttcat ctacctcaactcccccatccccgcttcgcccgaggaggcggttccccccc gcaggcagtccggctcgcaggccgccggcgttgtcaccccccccgcgctc cccctccagccctcccccggcgcgcagcctcgggccgctccccttccg cgctgcgtcccggagcggcccggtgccgccaccgcctgtcccctcccg aggcccgggctcgcgacggcagagggctccgtcggcccaaaccgagctgg gcgcccgcggtccgggtgcagcctccactccgccccccagtcaccgcctc ccccggccctcgacgtggcgcccttccctccgcttctctgtgctcccccg cgccctcttggcgtctgccccggccccgctctttctcccgcaaccttt cccttcgctccctcccgtccccccagctcctagcctccgactccctccc ccctcacgcccgccctctcgccttcgccgaaccaaagtggattaattac acgctttctgtttctctccgtgctgttctctcccgctgtgcgcctgcccg cctctcgctgtcctctctcccctcgccctctcttcggccccccctttc acgttcactctgtctctcccactatctctgccccctctatccttgatac aacagctgacctcatttcccgataccttttccccccgaaaagtacaaca tctggcccgccccagcccgaagacagcccgtcctccctggacaatcagac gaattctcccccccccccaaaaaaaagccatcccccgctctgccccgt cgcacattcggcccccgcgactcggccagagcggcgctggcagaggagtg tccggcaggagggccaacgcccgctgttcggtttgcgacacgcagcaggg aggtgggcggcagcgtcgccggcttccaggtaagcggcgtgtgcgggccg ggccggggccggggctggggcggcgcgggcttgcggcgacgcccggccct tcctccgcccgctcccggcccggggcctgcggggctcggcggggcggctg agcgggggggaggaggaggaggaggaggaggacggacggctgcgggtcc cgttccctgcgcggagcccgcgctaccnnnnnnnnnnnnnnnnnnnnnn nnngacgtccccgctgaagggggtcggtctgtgggtgcaggggtgccgc ctcacatgtgtgattcgtgccttgcgggccctggcctccggggtgctggg taacgaggaggggcgcggagccgcagaagcccaccctggtgtcgttgacg ccggtgccagcgagaccgcgagaggaagacggggcgggcgggccagga tggagaggggccgagttggcaggagtcatggcagacgccacactcgcgac catctccccacacccctctggcctctgtccgcaacatttccaaacagga gtcccgggagaggggagaggggctgctggtctgaggctaagaagggcag agccttcgaccggagagaggccgcggccgcctgccccagtggcaacgtt gaagttttccatacaacggaggtcgggaaggagacccccccccccccttca ctgcccgtgaagagatgagccggggtgcaggatgggagcccatggcac ttcgctacgggatgtccagggctccggttgggggtgcaggagagaagaga -continued

```
ctggctgggaggagggagagggcgggagcaaaggcgcggggggtgtggtca
gagggagaggggtggggggttaggtggagcccgggctggggaggagtcggct
cacacataaaactgaggcactgaccagcctgcaaactggatattagcttc
tcctgtgaaagagacttccagcttcctcctcctcctcttcctcctcctcc
tcctgccccagcgagccttctgctgagctgtaggtaaccagggctgtgga
gtgaaggaccccgctgccatcccactccagcctgaggcagggcagcagg
gggcacggcccacgcctgggcctcgggccctgcagccgccagcccgctgc
ctctcggacagcaccccctccccctcttttcctctgcccctgccccacc
tggcgtctctgctccctcacctgctccttccctttctgttccttcccttc
ggccccctccttgcccagctcaggacttttcctgggccctcacctgctcc
gcaccgctgcatgcttcctgtcctgctttctgccggtccctgacccgga
cctccaagcgcagagtggtggggcttgttgcggaagcgcggcgagggcta
gagtggccagctggcggagtgtgctcttagaatttggaagggggtggcag
aggggggcggtgagaggactggccagggtccgccatgtcaaggagatgacc
aaggaggctttcagatcctcggcgcagtcgcccactagtctttagagagg
gcatgcaaagttgtgcttctgtcccactgcctgctcagtcgctcacataa
tttattgcatcaaaaactccctgggtctgcggagcaaggctgggctgc
ccgcctggagggtaccaccttctgcaggagcagggccaacttgctgtggt
ggctcccggcctccaccccgagtgggtaacccggccctgtgacctgca
gcctgtggaggggtgtgcctaagactggcctcccttccagattgtagt
ctggggaacctggtgtcggacttccaggtggcctgagctggtctcttca
gctccacggggagagtttggtagcgcaaatagggagatgttctgggcccc
tggccttactggttcgatttgaggcctggaaaggaggctctgggcgtgtg
tgtgtgtgtttgggggtacccaaggcagactggagttggagaactgggtg
actgggaaaacaaggttttctagagcatgggtggcgtggttgtgttaacca
ttggagtcgcttgacccaggcctggctcagctgcagactggaaaggtgga
aaagccaggggggagggggcgggctgggcccagcaggactggcctgctgctt
tgagggcgatggtcctcctggacccccctgctcagctgggggttgtggg
gaggaaggggctggtcctccttggagcacatgctctgtaggggtggggct
gtctgccatcttggcggcgctggaggcctgagaagtggcgatgtaacgct
gggctggccctgccccatggtgtcataggacggaggcaggtcgggtgtc
cagcctgggcccctgcagctgtggatgccgctgagctcctgcaataatga
ccgtgcagatggtcaccctcgtgtaaaattactagtgcttcttgcaaat
ggaaggaactgggccttttctgtgtgcttctggacgcttcattctgcaca
tggccctgcgccctcacctcggcattatgacctgtgtgttacttttgtaa
taaaaataatgtttataggaaagccgtgctttcaattttcaactgaattt
gtaggttggcaaatttggtttgggaggggcacctctggcctggggcttgg
cctggctgccccgctcacgccacttctctcccgccccagacaccaatgg
gaatcccaatggggaagtcgatgctggtgcttctcaccttcttggccttc
gcctcgtgctgcattgctgcttaccgccccagtgagaccctgtgcggcgg
ggagctggtggacaccctccagttcgtctgtggggaccgcggcttctact
```

-continued

```
tcagtaagtagcagggaggggcttcctcagacctggtcaggcccctagag
tgaccggtgaggatctcccatcctcaagccaggggagcacactcctaggt
cagcagcccagccgcttgctctgagactttgaccttcccgccgcgtttct
gagcacgtgcggtgtcccagggcatccacaccagctgcctttcccatcac
acgcctccttcgaagggtgggccagaggtgcccctagacgtcaggggca
tctacaggggtctccctgggcatcagaatttctgttgggggccgtgaggc
tcctgctcctgaggcaccgcacgcctagtgcagggcttcaggctctggag
gaagagcctgccttcttcctgcaccttttggacattttgacaagggacg
tgcgttcggtgaatgatcagaattaaaatcaataaagtgatttatataat
taaaatcaataagacaagtgcagttggtgggtggcagggggtgagcggtgc
atgcgcctccttgggccccaaggctgccgtgggggggtgcccacctgctga
cctcaaggacgcttcagcctttcctcatgtttctctcttggttctccagc
ctggggctggcaggtgggtgcatggcccattgtccttgagacccccaccc
ccagatagggggggctgggtggatgcagaggcaggcatggtgcctgggcat
gcctgatggggcagggggaggggccgctccttactggcagaggccgcaact
tattccacctgacactcaccacgtgacatctttaccaccactgcttactc
acgctgtgaaatgggctcacaggatgcaaatgcacttcaaagcttctctc
tgaaaagttcctgctgcttgactctggaagccctgcccgccctggcctc
tcctgtgccctctctcttgcctgcccatttgggggtaggaagtggcact
gcagggcctggtgccagccagtccttgcccagggagaagcttccctgcac
caggctttcctgagaggagggagggccaagcccccacttggggcccc
gtgacggggcctcctgctccctcctccggctgatggcacctgccctttgg
cacccccaaggtggagccccagcgaccttcccctccagctgagcattgc
tgtggggagagggggaagacgggaggaaagaagggagtggttccatcac
gcctcctcagcctcctctcctcccgtcttctcctctcctgcccttgtctc
cctgtctcagcagctccaggggtggtgtgggcccctccagcctcccaggt
ggtgccaggccagagtccaagctcacggacagcagtcctcctgtggggc
cctgaactgggctcacatcccacacattttccaaaccactcccattgtga
gcctttggtcctggtggtgtccctctggttgtgggaccaagagcttgtgc
ccattttttcatctgaggaaggaggcagcagaagtcacgggctggtctggg
ccccactcacctcccctctcacctctcttcttcctgggacgcctctgcct
gccggctctcacttccctccctgacccgcagggtggctgcgnccttcca
gggcctggcctgagggcagggtggtttgctgggggttcggcctccgggg
gctggggtcggtgcggtgctaacacggctctctctgtgctgtgggactt
ccaggcaggccgcaagccgtgtgagccgtcgcagccgtggcatcgttga
ggagtgctgtttccgcagctgtgacctggccctcctggagacgtactgtg
ctaccccgccaagtccgagagggacgtgtcgacccctccgaccgtgctt
ccggtgagggtcctgggccccctttcccactctctagagacagagaaatag
ggcttcgggcgccagcgtttcctgtggcctctgggaccctcttggccagg
gacaaggacccgtgacttccttgcttgctgtgtggcccgggagcagctca
gacgctggctccttctgtccctctgcccgtggacattagctcaagtcact
```

-continued
```
gatcagtcacaggggtggcctgtcaggtcaggcgggcggctcaggcggaa gagcgtggagagcaggcacctgctgaccagcccctcccctcccaggaca acttccccgagataccccctgggcaagttcttccaatatgacacctggaag cagtccaccccagcgcctgcgcaggggcctgcctgccctcctgcgtgcccg ccggggtcacgtgctcgccaaggagctcgaggcgttcagggaggccaaac gtcaccgtccctgattgctctacccacccaagacccgcccacggggc gccccccagagatggccagcaatcggaagtgagcaaaactgccgcaagt ctgcagcccggcgccaccatcctgcagcctcctcctgaccacggacgttt ccatcaggttccatcccgaaaatctctcggttccacgtccctgggctt ctcctgacccagtccccgtgcccgcctcccgaaacaggctactctcct cggcccctccatcgggctgaggaagcacagcagcatcttcaaacatgta caaaatcgattggctttaaacacccttcatatccctcccccaaattat ccccaattatcccacacataaaaaatcaaaacattaaactaaccccctt cccccccccccacaacaaccctcttaaaactaattggcttttttagaaaca ccccacaaaagctcagaaattggctttaaaaaaaacaaccaccaaaaaa atcaattggctaaaaaaaaaagtattaaaaacgaattggctgagaaaca attggcaaaataaaggaatttggcactccccacccccctcttttctcttct cccttggactttgagtcaaattggcctggacttgagtccctgaaccagca aagagaaaagaagggccccagaaatcacaggtgggcacgtcgcgtctacc gccatctccttctcacgggaatttttcagggtaaact.
```

In another embodiment, the IGF-II sequence comprises a nucleic acid sequence as set forth in SEQ ID NO: 10. In another embodiment, the nucleic acid sequence of the IGF-II sequence consists of SEQ ID NO: 10. In another embodiment, the IGF-II sequence is homologous to SEQ ID NO: 10. In another embodiment, the IGF-II sequence is a variant of SEQ ID NO: 10. In another embodiment, the IGF-II sequence is a fragment of SEQ ID NO: 10. In another embodiment, the IGF-II sequence is a homologue of a fragment of SEQ ID NO: 10. In another embodiment, the IGF-II sequence is a variant of a fragment of SEQ ID NO: 10. Each possibility represents a separate embodiment of the present invention.

The IGF-II P3 transcription-regulating sequence of methods of the present invention is, in another embodiment, an IGF-II P3 promoter (also referred to herein as "P3"). In another embodiment, the sequence of the P3 promoter is:
gagctcggccatgcaggtaggatttgagctgtgtttcccgccctgatcctctctc-
ctctggcggccggagcctccgtaggctccaagcctggcccagattcggcggcg-
cagccggccttccgcgcgtccgcacctagcgggggctccggggctccggcgc-
ggcaccggggggcgctcgggatctggctgaggctccaaggcccgcgtggccg-
gctcctcctgctggggcaggtggcggctgcgcgccccgcccgagcccagggg-
cccccctcagccgcaacaaccagcaaggaccccccgactcagcccccaagccac-
ctgcatctgcactcagacggggcgcacccgcagtgcagcctcctggtggggcg-
ctgggagcccgcctgcccctgcctgcccggagacccccagctcacgagcacag-
gccgcccgggcaccccagaaacccgggatggggcccctgaattctctaggacg-
ggcattcagcatggccttggcgctctgcggctccctgccccccaccagcctcgc-
ccccgcgcaccccccagccctgcgaccgccgccccccccccggggcccca-
gggcccagcccgcacccccccgcccctctttggctcgggttgcgggggcgg-
gccggggcggggcgagggctccgcgggcgcccattggcgcgggcgcgag-
gccagccggccccgcgcggccctgggccgcggctggcgcgactataagagccg-
ggcgtgggcgcccgcagttcgcctgctctccggcggagctgcgtgaggcccgg-
ccggccccggccccccccttccggccgcccccgcctcctggcccacgcctgcc-
cgcgctctgcccaccagcgcctccatcgggcaaggcggcccccgcgtcgac (SEQ ID NO: 8; the first 6 base pairs [bp] are an added restriction site that can optionally be used in subcloning).

In another embodiment, the IGF-II P3 promoter comprises a nucleic acid sequence as set forth in SEQ ID NO: 8. In another embodiment, the nucleic acid sequence of the IGF-II P3 promoter consists of SEQ ID NO: 8. In another embodiment, the IGF-II P3 promoter is homologous to SEQ ID NO: 8. In another embodiment, the IGF-H P3 promoter is a variant of SEQ ID NO: 8. In another embodiment, the IGF-II P3 promoter is a fragment of SEQ ID NO: 8. In another embodiment, the IGF-II P3 promoter is a homologue of a fragment of SEQ ID NO: 8. In another embodiment, the IGF-II P3 promoter is a variant of a fragment of SEQ ID NO: 8. Each possibility represents a separate embodiment of the present invention.

In another embodiment, the sequence of the P3 promoter is:

```
                                    (SEQ ID NO: 12)
gacgggggtgggcggggccaggatggagaggggccgagttggcaggagtc atggcagacgccacattcgcgacactctccccacaccccctctggctctg tccgcaacatttccaaacaggagtcccgggagaggggagaggggctgct ggtctgaggctaagaagggcagagccttcgacccggagagaggccgcggc ccctgcccagtgggcagcgtggaagtttccatacaaggaggtgggaagga gaccccccccccttcactgccctgtgcagagatgagccgggggtgcag gatgggagcccatggcacttcgctacgggatggtcagggctcccggttgg gggtgcaggagagaagagactggctgggaggagggagagggcgggagcaa aggcgcggggagtggtcagcagggagagggtgggggtagggtggagc ccgggctgggaggagtcggctcacacataaaagctgaggcactgaccagc ctgcaaactggacattagcttctcctgtgaaagagacttccagcttcctc ctcctcctcttcctcctcctcctgccccagcgagccttctgctgagc tgtaggtaaccagggccgtggatgagactctc.
```

In another embodiment, the IGF-II P3 promoter comprises a nucleic acid sequence as set forth in SEQ ID NO: 12. In another embodiment, the nucleic acid sequence of the IGF-II P3 promoter consists of SEQ ID NO: 12. In another embodiment, the IGF-II P3 promoter is homologous to SEQ ID NO: 12. In another embodiment, the IGF-II P3 promoter is a variant of SEQ ID NO: 12. In another embodiment, the IGF-II P3 promoter is a fragment of SEQ ID NO: 12. In another embodiment, the IGF-II P3 promoter is a homologue of a fragment of SEQ ID NO: 12. In another embodiment, the IGF-II P3 promoter is a variant of a fragment of SEQ ID NO: 12. Each possibility represents a separate embodiment of the present invention.

In another embodiment, the IGF-II P3 promoter comprises an Sp1-binding site thereof. In another embodiment, the Sp1-binding site is residues 10-18 of SEQ ID NO: 12. In another embodiment, the Sp1-binding site is residues 388-399 of SEQ ID NO: 12. In another embodiment, the Sp1-binding site is another Sp1-binding site found in SEQ ID NO: 8 or SEQ ID NO: 12. In another embodiment, the IGF-II P3 promoter comprises a TATA box. In another embodiment, the TATA box is residues 476-482 of SEQ ID NO: 12. In another embodiment, the TATA box is another TATA box found in SEQ ID NO: 8 or SEQ ID NO: 12. Each possibility represents a separate embodiment of the present invention.

In another embodiment, the IGF-II P3 sequence is at least 60% homologous to a sequence selected from SEQ ID NO: 8, SEQ ID NO: 12, and SEQ ID NO: 17. In another embodiment, the IGF-II P3 sequence is at least 65% homologous to SEQ ID NO: 8 or SEQ ID NO: 12. In another embodiment, the IGF-II P3 sequence is at least 70% homologous to SEQ ID NO: 8 or SEQ ID NO: 12. In another embodiment, the IGF-II P3 sequence is at least 72% homologous to SEQ ID NO: 8 or SEQ ID NO: 12. In another embodiment, the IGF-II P3 sequence is at least 74% homologous to SEQ ID NO: 8 or SEQ ID NO: 12. In another embodiment, the IGF-II P3 sequence is at least 76% homologous to SEQ ID NO: 8 or SEQ ID NO: 12. In another embodiment, the IGF-II P3 sequence is at least 78% homologous to SEQ ID NO: 8 or SEQ ID NO: 12. In another embodiment, the IGF-II P3 sequence is at least 80% homologous to SEQ ID NO: 8 or SEQ ID NO: 12. In another embodiment, the IGF-II P3 sequence is at least 82% homologous to SEQ ID NO: 8 or SEQ ID NO: 12. In another embodiment, the IGF-II P3 sequence is at least 84% homologous to SEQ ID NO: 8 or SEQ ID NO: 12. In another embodiment, the IGF-II P3 sequence is at least 86% homologous to SEQ ID NO: 8 or SEQ ID NO: 12. In another embodiment, the IGF-II P3 sequence is at least 88% homologous to SEQ ID NO: 8 or SEQ ID NO: 12. In another embodiment, the IGF-II P3 sequence is at least 90% homologous to SEQ ID NO: 8 or SEQ ID NO: 12. In another embodiment, the IGF-II P3 sequence is at least 92% homologous to SEQ ID NO: 8 or SEQ ID NO: 12. In another embodiment, the IGF-II P3 sequence is at least 94% homologous to SEQ ID NO: 8 or SEQ ID NO: 12. In another embodiment, the IGF-II P3 sequence is at least 95% homologous to SEQ ID NO: 8 or SEQ ID NO: 12. In another embodiment, the IGF-II P3 sequence is at least 96% homologous to SEQ ID NO: 8 or SEQ ID NO: 12. In another embodiment, the IGF-H P3 sequence is at least 97% homologous to SEQ ID NO: 8 or SEQ ID NO: 12. In another embodiment, the IGF-II P3 sequence is at least 98% homologous to SEQ ID NO: 8 or SEQ ID NO: 12. In another embodiment, the IGF-II P3 sequence is at least 99% homologous to SEQ ID NO: 8 or SEQ ID NO: 12. In another embodiment, the IGF-II P3 sequence is over 99% homologous to SEQ ID NO: 8 or SEQ ID NO: 12. Each possibility represents a separate embodiment of the present invention.

In another embodiment, the IGF-II P3 promoter contains the promoter elements found in $^{-}291$-$^{+}130$, relative to the P3 start site. In another embodiment, the IGF-II P3 promoter contains the promoter elements found in $^{-}1232$-$^{-}812$, relative to the P3 start site. In another embodiment, the IGF-II P3 promoter contains the promoter elements found in $^{-}238$-$^{+}140$, relative to the P3 start site. In another embodiment, the IGF-II P3 promoter contains the promoter elements found 5' to residue $^{-}515$, relative to the P3 start site. In another embodiment, the IGF-II P3 promoter contains the promoter elements found 5' to residue $^{-}238$, relative to the P3 start site. Each possibility represents a separate embodiment of the present invention.

Further described herein are IGF-II P4 regulatory sequences that can be used in the nucleic acid constructs of the invention to direct the specific expression of a cytotoxic or cytostatic gene product. In another embodiment, the IGF-II P4 transcription-regulating sequence of compositions of the present invention is an IGF-II P4 promoter (also referred to herein as "P4"). In another embodiment, the sequence of the P4 promoter is set forth in SEQ ID NO: 9, as set forth hereinbelow.

In another embodiment, the IGF-II P4 promoter comprises a nucleic acid sequence as set forth in SEQ ID NO: 9. In another embodiment, the nucleic acid sequence of the IGF-II P4 promoter consists of SEQ ID NO: 9. In another embodiment, the IGF-II P4 promoter is homologous to SEQ ID NO: 9. In another embodiment, the IGF-II P4 promoter is a variant of SEQ ID NO: 9. In another embodiment, the IGF-II P4 promoter is a fragment of SEQ ID NO: 9. In another embodiment, the IGF-II P4 promoter is a homologue of a fragment of SEQ ID NO: 9. In another embodiment, the IGF-II P4 promoter is a variant of a fragment of SEQ ID NO: 9. Each possibility represents a separate embodiment of the present invention.

In another embodiment, the sequence of the P4 promoter is set forth in SEQ ID NO: 13:

```
                                        (SEQ ID NO: 13)
ggatccccaaaatgtgttccttgctttcatctgccaattttacgtaatat ggctctacggcaaaattcccaatttcatatggagaattttctttaactac ccctcctcacaaattggtcccccaagctagctggcccctatttgagacct ctttctctatgttcccaattgcatggagcaacttctctcatccccaaac ctgtaatctattttttctggagtctcgagtttagtcattaatcacggttcc cacattaacggagtccccgggggtcccctcctcaggacacccattcgcta agcccgcaaggcagaaagaactctgccttgcgttccccaaaatttgggca ttgttccggctcgccggccacccactgcagcttcccaacccgcgcaca gcgggcactggtttcgggcctctctgtctcctacgaagtccccagagcaa ctcggatttgggaaatttctctctagcgttgcccaaacacacttgggtcg gccgcgcgccctcaggacgtggacagggagggcttccccgtgtccaggaa agcgaccgggcattgcccccagtctcccccaaatttgggcattgtccccg ggtcttccaacggactgggcgttgctcccggacactgaggactggcccg gggtctcgctcaccttcagcagcgtccaccgcctgccacagagcgttcga tcgctcgctgcctgagctcctggtgcgcccgcggacgcagcctccagctt cgcggtgagctcccgccgcgccgatcccctccgcctctgcgccctgac cggctctcggcccgcatctgctgctgtcccgccggtgctggcgctcgtct ccggctgccgccggggaggc.
```

In another embodiment, the IGF-II P4 promoter comprises a nucleic acid sequence as set forth in SEQ ID NO: 13. In another embodiment, the nucleic acid sequence of the IGF-II P4 promoter consists of SEQ ID NO: 13. In another embodiment, the IGF-II P4 promoter is homologous to SEQ ID NO: 13. In another embodiment, the IGF-II P4 promoter is a variant of SEQ ID NO: 13. In another embodiment, the IGF-II P4 promoter is a fragment of SEQ ID NO: 13. In another embodiment, the IGF-II P4 promoter is a homologue of a fragment of SEQ ID NO: 13. In another embodiment, the IGF-II P4 promoter is a variant of a fragment of SEQ ID NO: 13. Each possibility represents a separate embodiment of the present invention.

In another embodiment, the IGF-II P4 sequence is at least 60% homologous to a sequence selected from SEQ ID NO: 9 and SEQ ID NO: 13. In another embodiment, the IGF-II P4 sequence is at least 65% homologous to SEQ ID NO: 9 or SEQ ID NO: 13. In another embodiment, the IGF-II P4 sequence is at least 70% homologous to SEQ ID NO: 9 or SEQ ID NO: 13. In another embodiment, the IGF-II P4 sequence is at least 72% homologous to SEQ ID NO: 9 or SEQ ID NO: 13. In another embodiment, the IGF-II P4 sequence is at least 74% homologous to SEQ ID NO: 9 or SEQ ID NO: 13. In another embodiment, the IGF-II P4 sequence is at least 76% homologous to SEQ ID NO: 9 or SEQ ID NO: 13. In another embodiment, the IGF-II P4 sequence is at least 78% homologous to SEQ ID NO: 9 or SEQ ID NO: 13. In another embodiment, the IGF-II P4 sequence is at least 80% homologous to SEQ ID NO: 9 or SEQ ID NO: 13. In another embodiment, the IGF-II P4 sequence is at least 82% homologous to SEQ ID NO: 9 or SEQ ID NO: 13. In another embodiment, the IGF-II P4 sequence is at least 84% homologous to SEQ ID NO: 9 or SEQ ID NO: 13. In another embodiment, the IGF-II P4 sequence is at least 86% homologous to SEQ ID NO: 9 or SEQ ID NO: 13. In another embodiment, the IGF-II P4 sequence is at least 88% homologous to SEQ ID NO: 9 or SEQ ID NO: 13. In another embodiment, the IGF-II P4 sequence is at least 90% homologous to SEQ ID NO: 9 or SEQ ID NO: 13. In another embodiment, the IGF-II P4 sequence is at least 92% homologous to SEQ ID NO: 9 or SEQ ID NO: 13. In another embodiment, the IGF-II P4 sequence is at least 94% homologous to SEQ ID NO: 9 or SEQ ID NO: 13. In another embodiment, the IGF-II P4 sequence is at least 95% homologous to SEQ ID NO: 9 or SEQ ID NO: 13. In another embodiment, the IGF-II P4 sequence is at least 96% homologous to SEQ ID NO: 9 or SEQ ID NO: 13. In another embodiment, the IGF-II P4 sequence is at least 97% homologous to SEQ ID NO: 9 or SEQ ID NO: 13. In another embodiment, the IGF-II P4 sequence is at least 98% homologous to SEQ ID NO: 9 or SEQ ID NO: 13. In another embodiment, the IGF-II P4 sequence is at least 99% homologous to SEQ ID NO: 9 or SEQ ID NO: 13. In another embodiment, the IGF-II P4 sequence is over 99% homologous to SEQ ID NO: 9 or SEQ ID NO: 13. Each possibility represents a separate embodiment of the present invention.

In another embodiment, the P4 promoter corresponds to nucleotide sequence −546 to +102 of the IGF-II gene, relative to the IGF-P4 start site.

In another embodiment, these regulatory sequences from genomically imprinted and non-imprinted genes that are expressed in cancer cells can be further delineated to define the minimal regulatory sequences required to obtain the desired tumor specific expression. For example, the promoter region may be altered by additions, substitutions or deletions and assayed for retention of tumor specific expression function. Various portions of the H19 downstream enhancer may be tested individually for the ability to enhance transcription from the H19 promoter.

The TNF-alpha protein of methods and compositions of the present invention is, in another embodiment, encoded by a nucleotide molecule having the sequence:

tcatgagcaccgagagcatgatcagggatgtggagctggccgaggaggccc-tgcccaagaaaacaggcggccctcagggcagcagaagatgcctgttcctgagcc-tgttcagcttcctgatcgtggccggagccaccaccctgcctgcctgctgaacttcg-gcgtgatcggcccccagagagaggagttccccagagacctgagcctgatctccc-ccctggcccaggctgtgagaagcagcagcagaaccccagcgacaagcccgt-ggcccacgtggtggccaaccccaggccgagggccagctgcagtggctgaac-agaagagccaacgccctgctggccaacggcgtggagctgagagacaaccagc-tggtggtgcccagcgagggcctgtacctgatctacagccaggtgctgttcaaggg-ccagggctgccccagcacccacgtgctgctgacccacaccatcagcagaatcgc-cgtgtcctaccagaccaaggtgaacctgctgtccgccatcaagagcccttgccag-agagagaccccccgagggcgccgaggccaagcccttggtacgagcctatctacct-gggcggcgtgttccagctggagaagggcgacagactgagcgccgagatcaaca-gacccgactacctggatttcgccgagagcggccaggtgtacttcggcatcatcgc-cctgtgataatctagaaccatgg (SEQ ID NO: 14). In another embodiment, the nucleic acid sequence encoding the TNF-alpha consists of SEQ ID NO: 14. In another embodiment, the sequence encoding the TNF-alpha is homologous to SEQ ID NO: 14. In another embodiment, the sequence encoding the TNF-alpha is a variant of SEQ ID NO: 14. In another embodiment, the sequence encoding the TNF-alpha is a fragment of SEQ ID NO: 14. In another embodiment, the sequence encoding the TNF-alpha is a homologue of a fragment of SEQ ID NO: 14. In another embodiment, the sequence encoding the TNF-alpha is a variant of a fragment of SEQ ID NO: 14. Each possibility represents a separate embodiment of the present invention.

In another embodiment, the amino acid sequence of the TNF-alpha is
MSTESMIRDVELAEEALPKKTGGPQGSRRCLFLSL-FSFLIVAGATTLFCLLNFGVIGPQREEFPRDLSLISPLA-QAVRSSSRTPSDKPVAHVVANPQAEGQLQWLNRRA-NALLANGVELRDNQLVVPSEGLYLIYSQVLFKGQG-CPSTHVLLTHTISRIAVSYQTKVNLLSAIKSPCQRETP-EGAEAKPWYEPIYLGGVFQLEKGDRLSAEINRPDYL-DFAESGQVYFGIIAL (SEQ ID NO: 15). In another embodiment, the sequence of the TNF-alpha consists of SEQ ID NO: 15. In another embodiment, the sequence of the TNF-alpha is homologous to SEQ ID NO: 15. In another embodiment, the sequence of the TNF-alpha is a variant of SEQ ID NO: 15. In another embodiment, the sequence of the TNF-alpha is a fragment of SEQ ID NO: 15. In another embodiment, the sequence of the TNF-alpha is a homologue of a fragment of SEQ ID NO: 15. In another embodiment, the sequence of the TNF-alpha is a variant of a fragment of SEQ ID NO: 15. Each possibility represents a separate embodiment of the present invention.

Alterations in a regulatory sequences of the present invention or (e.g. a sequence encoding a cytotoxic or cytostatic gene product) can be generated using a variety of chemical and enzymatic methods which are well known to those skilled in the art. For example, regions of the sequences defined by restriction sites can be deleted. Oligonucleotide-directed mutagenesis can be employed to alter the sequence in a defined way and/or to introduce restriction sites in specific regions within the sequence. Additionally, deletion mutants can be generated using DNA nucleases such as Bal31 or ExoIII and S1 nuclease. Progressively larger deletions in the regulatory sequences are generated by incubating the DNA with nucleases for increased periods of time.

The altered sequences are evaluated for their ability to fulfill the required function, e.g. to direct tumor specific expression of heterologous coding sequences in appropriate host cells. It is within the scope of the present invention that any altered regulatory sequences which retain their ability to direct tumor specific expression be incorporated into the nucleic acid constructs of the present invention for further use.

The constructs of the present invention may be produced using standard recombinant and synthetic methods well known in the art. An isolated nucleic acid sequence can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis (see e.g. Sambrook et al., 2001, Molecular Cloning: A Laboratory Manual, Cold Springs Harbor Laboratory, New York; Ausubel, et al., 1989, Chapters 2 and 4). Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional oligonucleotide of the invention.

A nucleic acid molecule analog can be produced using a number of methods known to those skilled in the art (see, for example, Sambrook et al., 2001, ibid). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. For example, nucleic acid molecule analogs can be selected from a mixture of modified nucleic acids by screening for the function of the oligonucleic acid encoded by the nucleic acid with respect to tumor progression, for example by the methods described herein.

Optionally, the construct may further comprise one or more sequences encoding additional gene products under a cancer-specific (e.g. an H19-specific) transcriptional control. The construct may also comprise other regulatory sequences or selectable markers, as known in the art. The nucleic acid construct (also referred to herein as an "expression vector") or construct system of the present invention may include additional sequences that render this vector suitable for replication and integration in prokaryotes, eukaryotes, or preferably both (e.g., shuttle vectors). In addition, a typical cloning vector may also contain transcription and translation initiation sequences, transcription and translation terminators, and a polyadenylation signal.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancers that are suitable for the present invention include those derived from polyoma virus, human or murine cytomegalovirus (CMV), the long term repeat from various retroviruses such as murine leukemia virus, murine or Rous sarcoma virus and HIV.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase RNA stability. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Exemplary termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, and pNMT81, which are available from Invitrogen, pCI which is available from Promega, pMbac, pPbac, pBK-RSV and pBK-CMV, which are available from Strategene, pTRES which is available from Clontech, and their derivatives. These may serve as vector backbone for the constructs of the present invention.

Expression vectors containing regulatory elements from eukaryotic viruses such as retroviruses can be also used. SV40 vectors include pSVT7 and pMT2, for instance. Vectors derived from bovine papilloma virus include pBV-1MTHA, and vectors derived from Epstein-Barr virus include pHEBO and p2O5. Other exemplary vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells. These may serve as vector backbone for the constructs of the present invention.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinarily skilled artisan and as such, no general description of selection considerations is provided herein. For example, bone marrow cells can be targeted using the human T-cell leukemia virus type I (HTLV-I) and kidney cells may be targeted using the heterologous promoter present in the baculovirus *Autographa californica* multiple nucleopolyhedrovirus (AcMNPV), as described by Liang, C. Y. et al. (2004). High efficiency gene transfer into mammalian kidney cells using baculovirus vectors. Arch Virol 149, 51-60.

Recombinant viral vectors are useful for in vivo expression of the genes of the present invention since they offer advantages such as lateral infection and targeting specificity. Lateral infection is inherent in the life cycle of retrovirus, for example, and is the process by which a single infected cell produces many progeny virions that bud off and infect neighboring cells. The result is the rapid infection of a large area of cells, most of which were not initially infected by the original viral particles. This is in contrast to vertical-type infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of the present invention into cells. Such methods are generally described in Sambrook et al, ibid; Ausubel et al., Current Protocols in Molecular Biology, John Wiley and Sons, Baltimore, Md. (1989); Chang et al., Somatic Gene Therapy, CRC Press, Ann Arbor, Mich. (1995); Vega et al., Gene Targeting, CRC Press, Ann Arbor Mich. (1995), Vectors: A Survey of Molecular Cloning Vectors and Their Uses, Butterworths, Boston Mass. (1988); and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Gene Therapy

Gene therapy approaches can be used in accordance with the present invention to prevent or treat cancer. Gene therapy refers to therapy performed by the administration to a subject of an expressed or expressible nucleic acid.

Any of the methods for gene therapy available in the art can be used in accordance with the present invention. Long-term effective use of a gene therapy vector to ameliorate disease in large mammals has been demonstrated. For example, administration of an adeno-associated virus ("AAV") containing a wild-type gene to dogs suffering from Leber congenital amaurosis, a condition that results in blindness due to a mutation of a gene (RPE65) in the retinal pigment epithelium, has successfully corrected the genetic defect (Ackland et al., 2001, Nature Genetics 28:92). Expression of the wild-type RPE65 gene was confirmed by RT PCR. Furthermore, restoration of function was demonstrated by electrophysiological studies of the retina, as well as by unbiased observations of the treated animals. The treatment was shown to be effective for at least four months.

Gene therapy has also proven useful in treatment of a complication of diabetes. Gene therapy with functional therapeutic angiogenesis VEGF (Vascular Endothelial Growth Factor) and other proteins are already in clinical trials for treating polygenic and complex diseases such as myocardial ischemia, hypertension, atherosclerosis and restenosis (Pachori A S et al, Gene therapy: role in myocardial protection. Handb Exp Pharmacol. 2006; (176 Pt 2):335-50). Further, VEGF-expressing plasmids were shown to have efficacy in a phase III study comparing intramuscular delivery of ANG1 with placebo in diabetic patients with critical limb ischemia was carried out on thirteen patients (Kusumanto et al., Molecular Therapy 3:S73).

Gene therapy has also been successfully used to treat an inherited disorder of the X-chromosome, namely severe combined immunodeficiency (SCID), and chronic granulomatous disease (CGD), as reviewed in Blaese R M, Immunol Res. 2007; 38(1-3):274-84.

Further, recent studies have shown that, p53 can successfully and therapeutically be expressed in normal and malignant tissues (Fischer U, Janssen K, Schulze-Osthoff K, BioDrugs. 2007; 21(5):273-97).

Accordingly, gene therapy approaches using the vectors of the invention, which comprise a heterologous polynucleotide operatively linked to more than one transcriptional regulatory sequences, can be used to prevent or treat cancer and hyperproliferative diseases.

A vector of the invention can be delivered in vivo (i.e., directly into a subject). Accordingly, in one embodiment, a vector of the invention is injected directly into the target tissue or cell derivation site. In another embodiment, a vector of the invention can be introduced into the target tissue as an implant such as, for example, in a polymer formulation (See, e.g., U.S. Pat. No. 5,702,717). In another embodiment, a vector of the invention is targeted to the desired cells or tissues.

In certain embodiments, in vivo nucleic acid transfer techniques (i.e., in vivo gene therapy) include transfection with viral or non-viral constructs, such as adenovirus, lentivirus, Herpes simplex I virus, or adeno-associated virus (AAV) and lipid-based systems.

The vector of the invention can be injected directly into a target tissue as naked DNA. In another embodiment, a vector of the invention can be introduced intracellularly using microparticle bombardment, for example, by using a Biolistic gene gun (DuPont). Plasmid DNA can be delivered with the help of, for example, cationic polymers, cationic liposomes (e.g. lipofectin, cholesterol derivatives such as D.D.A.B. and cationic phospholipids) or derivatized (e.g., antibody conjugated), polylysine conjugates, gramicidin S, artificial viral envelopes or other such intracellular carriers, as well as direct injection of the naked gene construct, electroporation or $CaPO_4$ precipitation carried out in vivo as well as polyethylenimine-based non-viral gene delivery systems. Reviews on nucleic acid transfer and expression systems for cancer gene therapy include Lungwitz (2005) Eur. J. Phar. Biopharm. 60 (2):247-66; Aigner (2006) J. Biotechnol. 254:12-25; Christopher and Wong (2006) Curr. Pharm. Des. 1995-2006; and Wolff (2005) Acta Myol. 24:202-8.

Measuring Expression of Genes in Tumor Cells

Expression driven by H19, IGF-II P3, and IGF-II P4 in tumors and cell lines can be determined, for example, using the techniques of RNA analysis, in situ hybridization, or reporter gene constructs. In addition, tumor cells with activated IGF-1 gene expression can be similarly determined and targeted in gene therapy using the IGF-1 promoter to direct expression of a heterologous polynucleotide.

For most RNA analysis applications, a labeled probe that specifically hybridizes to the gene transcript of interest is prepared using any number of techniques well known in the art. The labeled probe can contain at least 15-30 bases complementary to the H19 nucleotide sequence, and more preferably contains at least 50 to 150 bases complementary to the H19 transcript. A particularly preferred hybridization probe for H19 expression is a polynucleotide complementary to the 3' end of the H19 message from approximately 800 base pairs upstream of the poly A site to the poly A site.

In a specific embodiment of the invention, a labeled antisense RNA probe is generated in vitro using a T7 or T3 expression plasmid. H19 probes can also be labeled by random priming in the presence of labeled nucleotide, for example, using the Prime-It kit (Stratagene™, La Jolla, Calif.; Catalog No. 300392). Alternatively, labeled probes can be generated in a PCR reaction using a cDNA clone of the H19 coding region and primers designed to amplify a region of the coding region, or by a standard nick translation reaction.

Labels appropriate for polynucleotide probes include nucleotides incorporating radioactive isotopes (such as $^{35}S$ and $^{32}P$), fluorescent, luminescent and color tags, and enzymatic moieties.

The labeled probe is hybridized in situ to a cell or tissue sample using standard techniques such as described in U.S. Pat. No. 5,955,273, incorporated herein by reference. Alternatively, if a sufficient quantity of the appropriate cells can be obtained, standard RNA analysis (e.g., Northern analysis, RNase protection, or primer extension) can be performed to determine the level of mRNA expression of the gene of interest.

Additionally, such gene expression assays can be performed "in situ," i.e., directly upon tissue sections (fixed and/or frozen) of patient tissue obtained from biopsies or resections, such that no nucleic acid purification is necessary. Nucleic acid reagents such as those described above can be used as probes and/or primers for such in situ procedures (See, e.g., Nuovo, 1992, "PCR In Situ Hybridization: Protocols And Applications," Raven Press, NY).

An alternative method to determine if a cell type or tumor will be capable of specifically activating expression constructs containing the particular transcriptional regulatory sequences operatively linked to a heterologous polynucleotide is to actually transfect such expression constructs into the cell. For these purposes, the heterologous polynucleotide is preferably a marker gene product. A positive result in an assay for the marker gene product reveals that the cell or cell line is capable of activating expression from the transcriptional regulatory sequences.

In addition, various amplification methods, which are sensitive enough to detect to minute amounts of RNA, can also be used to determine whether the tumor expresses H19 and/or IGF-II. Such methods include, PCR, RT-PCR and in situ PCR (all the above referring also to "nested" PCR, and nested RT-PCR), LCR (ligase chain reaction) and 3SR (self sustained sequence replication). In accordance with a preferred embodiment RT-PCR and nested RT-PCR are used. The amplification products are identified by methods used in the art such as by separation on a gel.

Pharmaceutical Compositions and Kits

In another aspect, the invention provides a pharmaceutical composition comprising a nucleic acid construct of the invention, and optionally one or more pharmaceutically acceptable carriers, excipients or diluents.

According to one aspect, the invention provides a pharmaceutical composition comprising i) a nucleic acid construct containing at least two nucleic acid sequences encoding a cytotoxic gene protein, wherein one nucleic acid sequence is operably linked to an H19-specific transcription-regulating sequence and another nucleic acid sequence is operably linked to an IGF-II P4 transcription-regulating sequence; and ii) a pharmaceutically acceptable carrier, excipient or diluent.

In another aspect, the invention provides a pharmaceutical composition comprising i) a nucleic acid construct containing at least two nucleic acid sequences encoding a cytotoxic gene protein, wherein one nucleic acid sequence is operably linked to an IGF-II P3 transcription-regulating sequence and another nucleic acid sequence is operably linked to an IGF-II P4 transcription-regulating sequence; and ii) a pharmaceutically acceptable carrier, excipient or diluent.

In another aspect, the invention provides a pharmaceutical composition comprising i) a nucleic acid construct containing at least two nucleic acid sequences encoding a cytotoxic gene protein, wherein one nucleic acid sequence is operably linked to an H19-specific transcription-regulating sequence and another nucleic acid sequence is operably linked to an IGF-II P3 transcription-regulating sequence; and ii) a pharmaceutically acceptable carrier, excipient or diluent.

According to one embodiment, the invention provides a pharmaceutical composition comprising i) a nucleic acid construct containing a first open reading frame encoding a diphtheria toxin, the first open reading frame being operably linked to an H19-specific transcription-regulating sequence, and a second open reading frame encoding a diphtheria toxin, the second open reading frame being operably linked to an IGF-II P4 transcription-regulating sequence; and ii) a pharmaceutically acceptable carrier, excipient or diluent. In one embodiment, said nucleic acid construct further comprises a third open reading frame encoding a diphtheria toxin, said third open reading frame being operably linked to an IGF-II P3 transcription-regulating sequence.

In another embodiment, the invention provides a pharmaceutical composition comprising i) a nucleic acid construct containing a first open reading frame encoding a diphtheria toxin, the first open reading frame being operably linked to an H19-specific transcription-regulating sequence, and a second open reading frame encoding a diphtheria toxin, the second open reading frame being operably linked to an IGF-II P3 transcription-regulating sequence; and ii) a pharmaceutically acceptable carrier, excipient or diluent. In another embodiment, said nucleic acid construct further comprises a third open reading frame encoding a diphtheria toxin, said third open reading frame being operably linked to an IGF-II P4 transcription-regulating sequence.

In another embodiment, the invention provides a pharmaceutical composition comprising i) a nucleic acid construct containing a first open reading frame encoding a diphtheria toxin, the first open reading frame being operably linked to an IGF-II P3 transcription-regulating sequence, and a second open reading frame encoding a diphtheria toxin, the second open reading frame being operably linked to an IGF-II P4 transcription-regulating sequence; and ii) a pharmaceutically acceptable carrier, excipient or diluent. In another embodiment, said nucleic acid construct further comprises a third open reading frame encoding a diphtheria toxin, said third open reading frame being operably linked to an H19-specific transcription-regulating sequence.

In another embodiment, the diphtheria toxin is diphtheria toxin A (DTA). In another embodiment, said diphtheria toxin comprises a sequence as set forth in SEQ ID NO: 7.

In another embodiment, the H19-specific transcription-regulating sequence is a promoter comprising a nucleic acid sequence set forth in any one of SEQ ID NOS: 1-2.

In another embodiment, the IGF-II P4 transcription-regulating sequence is a promoter comprising a nucleic acid sequence set forth in SEQ ID NO: 9.

In another embodiment, the IGF-II P3 transcription-regulating sequence is a promoter comprising a nucleic acid sequence as set forth in a sequence selected from SEQ ID NO: 8, SEQ ID NO: 12, and SEQ ID NO: 17.

In another embodiment, said nucleic acid construct is a plasmid or a eukaryotic expression vector.

In another embodiment, there is provided a pharmaceutical pack containing a course of anti-neoplastic treatment for one individual mammal comprising a container having a unit of a nucleic acid construct of the invention in unit dosage form.

In some embodiments, the constructs of the invention are provided in packs in a form ready for administration. In other embodiments, the constructs of the invention are provided in concentrated form in packs, optionally with the diluent required to make final solution(s) for administration. In still other embodiments, the product contains a compound useful in the invention in solid form and, optionally, a separate container with a suitable solvent or carrier for the compound useful in the invention.

In still other embodiments, the above packs/kits include other components, e.g., instructions for dilution, mixing and/or administration of the product, other containers, syringes, needles, etc. Other such pack/kit components will be readily apparent to one of skill in the art.

In a particular embodiment, the kits further comprise instructions for administering said nucleic acid construct to a subject afflicted with cancer, particularly with a tumor characterized by expression of H19 RNA and/or expression of IGF-II from the P3 and/or P4 promoter in at least a portion of the cells of the tumor, as detailed herein.

As used herein, a "pharmaceutical composition" refers to a preparation of one or more of the active ingredients described herein, e.g. a construct encoding a DTA molecule, with other components such as physiologically suitable carriers and excipients. The purpose of a pharmaceutical composition is to facilitate administration of a compound to a subject.

Hereinafter, the phrases "therapeutically acceptable carrier" and "pharmaceutically acceptable carrier," which may be used interchangeably, refer to a carrier or a diluent that does not cause significant irritation to an organism and does not abrogate the biological activity and properties of the administered compound. As used herein, a "pharmaceutically acceptable carrier, excipient or diluent" may refer to a single auxiliary material or to various mixtures and combinations of such therapeutically inert ingredients.

Herein, the term "excipient" refers to an inert substance added to a pharmaceutical composition to further facilitate administration of an active ingredient. Examples, without limitation, of excipients particularly suitable for administering nucleic acid agents include calcium carbonate, calcium phosphate, various sugars and types of starch, cellulose derivatives, gelatin, vegetable oils, and polyethylene glycols.

In another embodiment of the present invention, a therapeutic composition further comprises a pharmaceutically acceptable carrier. As used herein, a "carrier" refers to any substance suitable as a vehicle for delivering a therapeutic agent, e.g. a nucleic acid molecule of the present invention to a suitable in vivo or in vitro site. As such, carriers can act as a pharmaceutically acceptable excipient of a therapeutic composition containing a nucleic acid molecule of the present invention. Preferred carriers particularly suitable for administering nucleic acid agents are capable of maintaining a nucleic acid molecule of the present invention in a form that, upon arrival of the nucleic acid molecule to a cell, the nucleic acid molecule is capable of entering the cell and being expressed by the cell. Carriers of the present invention include: (1) excipients or formularies that transport, but do not specifically target a nucleic acid molecule to a cell (referred to herein as non-targeting carriers); and (2) excipients or formularies that deliver a nucleic acid molecule to a specific site in a subject or a specific cell (i.e., targeting carriers). Examples of non-targeting carriers include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- and o-cresol, formalin and benzol alcohol. Preferred auxiliary substances for aerosol delivery include surfactant substances non-toxic to a subject, for example, esters or partial esters of fatty acids containing from about six to about twenty-two carbon atoms. Examples of esters include caproic, octanoic, lauric, palmitic, stearic, linoleic, linolenic, olesteric, and oleic acids. Other carriers can include metal particles (e.g., gold particles) for use with, for example, a biolistic gun through the skin. Therapeutic compositions of the present invention can be sterilized by conventional methods.

Targeting carriers are herein referred to as "delivery vehicles". Delivery vehicles of the present invention are capable of delivering a therapeutic composition of the present invention to a target site in a subject. A "target site" refers to a site in a subject to which one desires to deliver a therapeutic composition. Examples of delivery vehicles particularly suitable for administering nucleic acid agents include, but are not limited to, artificial and natural lipid-containing delivery vehicles. Natural lipid-containing delivery vehicles include cells and cellular membranes. Artificial lipid-containing delivery vehicles include liposomes and micelles. A delivery vehicle of the present invention can be modified to target to a particular site in a subject, thereby targeting and making use of a nucleic acid molecule of the present invention at that site. Suitable modifications include manipulating the chemical formula of the lipid portion of the delivery vehicle and/or introducing into the vehicle a compound capable of specifically targeting a delivery vehicle to a preferred site, for example, a preferred cell type. Specifically targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. For example, an antibody specific for an antigen found on the surface of a target cell can be introduced to the outer surface of a liposome delivery vehicle so as to target the delivery vehicle to the target cell. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

In certain particular embodiments, a delivery vehicle particularly suitable for administering nucleic acid agents is a liposome. A liposome is capable of remaining stable in a subject for a sufficient amount of time to deliver a nucleic acid molecule of the present invention to a preferred site in the subject. A liposome of the present invention is preferably stable in the subject into which it has been administered for at least about 30 minutes, more preferably for at least about 1 hour and even more preferably for at least about 24 hours.

A liposome of the present invention comprises a lipid composition that is capable of targeting a nucleic acid molecule of the present invention to a particular, or selected, site in a subject.

Suitable liposomes for use with the present invention include any liposome. Preferred liposomes of the present invention include those liposomes standardly used in, for example, gene delivery methods known to those of skill in the art. In certain embodiments, more preferred liposomes comprise liposomes having a polycationic lipid composition and/or liposomes having a cholesterol backbone conjugated to polyethylene glycol.

Preferably the pharmaceutical composition can also include a transfection agent such as DOTMA, DOPE, and DC-Chol (Tonkinson et al., 1996). A preferred example of a transfection agent is poly(ethylamine) (PEI).

Other agents particularly suitable for administering nucleic acid agents can be used are e.g. cationic lipids, polylysine, and dendrimers. Alternatively, naked DNA can be administered.

Therapeutic Use

In another aspect, the invention provides a method for treating cancer in a subject in need thereof, comprising administering to the subject a therapeutically effective amount of a nucleic acid molecule of the present invention, wherein said subject is afflicted with a tumor characterized by expression of H19 RNA and/or IGF-II from the P3 and/or P4 promoter, in at least a portion of the cells of the tumor.

In another aspect, there is provided a method for inhibiting tumor progression in a subject in need thereof, comprising administering to the subject a therapeutically effective amount of a nucleic acid molecule of the present invention, wherein said subject is afflicted with a tumor characterized by expression of H19 RNA and/or IGF-II from the P3 and/or P4 promoter, in at least a portion of the cells of the tumor.

In another aspect, there is provided a method for inhibiting or preventing tumor metastasis in a subject in need thereof, comprising administering to the subject a therapeutically effective amount of a nucleic acid molecule of the present invention, wherein the tumor is characterized by expression of H19 RNA and/or IGF-II from the P3 and/or P4 promoter, in at least a portion of the cells of the tumor.

In another aspect, there is provided a method for reducing or alleviating symptoms associated with a neoplastic disorder in a subject in need thereof, wherein the subject is afflicted with a tumor characterized by expression of H19 RNA and/or IGF-II from the P3 and/or P4 promoter, in at least a portion of the cells of the tumor, the method comprising administering to the subject a therapeutically effective amount of a nucleic acid molecule of the present invention.

In another embodiment, the nucleic acid construct contains a first open reading frame encoding a diphtheria toxin, the first open reading frame being operably linked to an H19-specific transcription-regulating sequence, and a second open reading frame encoding a diphtheria toxin, the second open reading frame being operably linked to an IGF-II P4 transcription-regulating sequence. In another embodiment, a cell of said tumor is capable of expressing a transcript directed by the H19 promoter and/or a transcript directed by the IGF-II P4 promoter. In one embodiment, said nucleic acid construct further comprises a third open reading frame encoding a diphtheria toxin, said third open reading frame being operably linked to an IGF-II P3 transcription-regulating sequence.

In another embodiment, the nucleic acid construct contains a first open reading frame encoding a diphtheria toxin, the first open reading frame being operably linked to an H19-specific transcription-regulating sequence, and a second open reading frame encoding a diphtheria toxin, the second open reading frame being operably linked to an IGF-II P3 transcription-regulating sequence. In another embodiment, a cell of said tumor is capable of expressing a transcript directed by the H19 promoter and/or a transcript directed by the IGF-II P3 promoter. In another embodiment, said nucleic acid construct further comprises a third open reading frame encoding a diphtheria toxin, said third open reading frame being operably linked to an IGF-II P4 transcription-regulating sequence.

In another embodiment, the nucleic acid construct contains a first open reading frame encoding a diphtheria toxin, the first open reading frame being operably linked to an IGF-II P3 transcription-regulating sequence, and a second open reading frame encoding a diphtheria toxin, the second open reading frame being operably linked to an IGF-II P4 transcription-regulating sequence. In another embodiment, a cell of said tumor is capable of expressing a transcript directed by the IGF-II P3 promoter and/or a transcript directed by the IGF-II P4 promoter. In another embodiment, said nucleic acid construct further comprises a third open reading frame encoding a diphtheria toxin, said third open reading frame being operably linked to an H19-specific transcription-regulating sequence.

In another embodiment, the diphtheria toxin is diphtheria toxin A (DTA). In another embodiment, said diphtheria toxin comprises a sequence as set forth in SEQ ID NO: 7.

In another embodiment, the H19-specific transcription-regulating sequence is a promoter comprising a nucleic acid sequence set forth in any one of SEQ ID NOS: 1-2.

In another embodiment, the IGF-II P4 transcription-regulating sequence is a promoter comprising a nucleic acid sequence set forth in SEQ ID NO: 9.

In another embodiment, the IGF-II P3 transcription-regulating sequence is a promoter comprising a nucleic acid sequence as set forth in a sequence selected from SEQ ID NO: 8, SEQ ID NO: 12, and SEQ ID NO: 17.

The present invention also relates to a method for increasing a subject's sensitivity to a therapeutic agent, comprising administering to a subject in need thereof an effective amount of a nucleic acid molecule of the present invention.

As used herein, "treating" cancer (or treating a subject with cancer) refers to taking steps to obtain beneficial or desired results, including but not limited to, alleviation or amelioration of one or more symptoms of cancer, diminishment of extent of disease, delay or slowing of disease progression, amelioration, palliation or stabilization of the disease state, partial or complete remission, prolonged survival and other beneficial results known in the art.

In another embodiment, the subject is human.

In another embodiment, tumors that may be treated according to the method of the present invention are those express H19 RNA and/or express IGF-II from the P3 and/or P4 promoter during tumor onset or progression. In another embodiment, a cell of a target tumor of a method of the present invention expresses endogenously a transcript directed by the H19 promoter (e.g. an H19 transcript) and a transcript directed by the IGF-II P3 promoter (e.g. an IGF-II transcript). In another embodiment, a cell of the target tumor expresses endogenously a transcript directed by the H19 promoter and a transcript directed by the IGF-II P4 promoter (e.g. an IGF-II transcript). In another embodiment, a cell of the target tumor expresses endogenously a transcript directed by the IGF-II P3 promoter and a transcript directed by the IGF-II P4 promoter. In another embodiment, the target tumor is a tumor that endogenously expresses the P3-driven IGF-II transcript, P4-driven IGF-II transcript, and H19 transcript. In another embodiment, the target tumor endogenously expresses at least two of the IGF-II-P3, IGF-II-P4 and H19 driven transcripts. Each possibility represents a separate embodiment of the present invention.

In another embodiment, the target tumor has been genotyped for expression of H19 and/or expression of IGF-II under control of the P3 or P4 promoter, or both. In another embodiment, the target tumor has not been genotyped. Each possibility represents a separate embodiment of the present invention.

For example, in some embodiments, the tumor is selected from Wilm's tumor, hepatoblastoma, embryonal rhabdomyosarcoma, germ cell tumors and trophoblastic tumors, testicular germ cell tumors, testicular seminoma, teratoma, immature teratoma of ovary, sacrococcygeal tumor, choriocarcinoma, placental site trophoblastic tumors, bladder carcinoma, hepatocellular carcinoma, ovarian carcinoma, cervical carcinoma, lung carcinoma, breast carcinoma, squamous cell carcinoma in head and neck, esophageal carcinoma, thyroid carcinoma, neurogenic tumors, astrocytoma, ganglioblastoma, neuroblastoma, osteosarcoma, melanoma, pancreatic canrcinoma, prostate cancer, uterus cancer, renal cell carcinoma, colorectal carcinoma, colon cancer, medulloblastoma, glioblastoma, adrenocortical tumors, small cell lung cancer, non-small cell lung cancer, acute lymphoblastic leukemia (ALL), head and neck cancers, oral cancers, gestational trophoblastic tumors, meningioma and hepatoma. In some particular embodiments, the tumor is selected from head and neck cancers, oral cancers and gestational trophoblastic tumors.

In another embodiment, the subject is afflicted with Beckwith-Wiedermann syndrome (BWS), thus having a predisposition for developing an H19 and/or IGF-II-associated tumor such as Wilm's tumor or hepatoblastoma.

In another embodiment, the target tumor is a solid tumor. In another embodiment, the target tumor is a carcinoma. In certain particular embodiments, the tumor may be a bladder cancer (e.g. bladder carcinoma), liver cancer (e.g. hepatocellular carcinoma) ovarian cancer (e.g. clear cell carcinoma), pancreatic cancer (e.g. pancreatic ductal carcinoma, epithelioid carcinoma).

In certain other preferable embodiments, the tumor is selected from the group consisting of a bladder carcinoma, a hepatocellular carcinoma, an ovarian carcinoma, and a pancreatic carcinoma. In another embodiment, the target tumor is a bladder carcinoma. In another embodiment, the target tumor is a hepatocellular carcinoma. In another embodiment, the target tumor is a colon carcinoma. In another embodiment, the target tumor is a superficial bladder cancer. In another embodiment, the target tumor is a cervical carcinoma. In another embodiment, the target tumor is lung carcinoma. In another embodiment, the target tumor is lung adenocarcinoma. In another embodiment, the target tumor is small cell lung carcinoma. In another embodiment, the target tumor is a breast carcinoma. In another embodiment, the target tumor is a squamous cell carcinoma in head and neck. In another embodiment, the target tumor is a renal cell carcinoma. In another embodiment, the target tumor is an esophageal carcinoma. In another embodiment, the target tumor is a pancreatic cancer. In another embodiment, the target tumor is a hepatoblastoma. In another embodiment, the target tumor is a rhabdomyosarcoma. In another embodiment, the target tumor is a thyroid carcinoma. In another embodiment, the target tumor is a ganglioblastoma. In another embodiment, the target tumor is an ovarian carcinoma. In another embodiment, the target tumor is a squamous cell bronchogenic carcinoma. In another embodiment, the target tumor is a liver neoplasm. In another embodiment, the target tumor is a colorectal carcinoma. In another embodiment, the target tumor is an endometrial carcinoma. In another embodiment, the target tumor is a testicular tumor. In another embodiment, the target tumor is a testicular germ cell tumor. In another embodiment, the target tumor is a squamous cell bronchogenic carcinoma. In another embodiment, the target tumor is prostate cancer. In another embodiment, the target tumor is Wilm's tumor. In another embodiment, the target tumor is an astrocytoma. In another embodiment, the target tumor is a neuroblastoma. Each possibility represents a separate embodiment of the present invention.

In another embodiment, the target disease of a method of the present invention is a cell-proliferative disorder wherein at least some of the cells are capable of expressing a transcript under the control of the H19 promoter and/or the IGF-II P4 promoter. In another embodiment, the target disease is a cell-proliferative disorder wherein at least some of the cells are capable of expressing a transcript under the control of the H19 promoter and/or the IGF-II P3 promoter. In another embodiment, the target disease is a cell-proliferative disorder wherein at least some of the cells are capable of expressing a transcript under the control of the IGF-II P4 promoter and/or the IGF-II P3 promoter. Each possibility represents a separate embodiment of the present invention.

In another embodiment, the methods of the invention further comprise a step of detecting the presence of H19 RNA and/or IGF-II RNA in tumor cells obtained from the subject, wherein the presence of the RNA in at least a portion of the tumor cells is indicative that said tumor is treatable by the methods of the present invention. For example, the presence of H19 RNA and/or IGF-II RNA may be detected by methods known in the art such as PCR, RT-PCR, in situ PCR, in situ RT-PCR, LCR and, 3SR, and hybridization with a probe comprising a detectable moiety. In other embodiments, the presence of an RNA may be determined in a cell or tissue sample derived from the tumor, or, in alternate embodiments, in cell-containing specimens of body fluids, rinse fluids that were in contact with the primary tumor site, or tissues or organs other than the tissue primary tumor site (e.g. for detecting tumor metastases).

Exemplary metastasizing tumors include, e.g. colorectal cancer metastasizing to the liver and metastasizing breast cancer. In a particular embodiment, the constructs of the invention are used to prevent or inhibit the formation of liver metastases.

In order to treat a subject with a disease, pharmaceutical compositions of the present invention are administered to the subject in an effective manner such that the compositions are capable of treating that subject from disease. According to the present invention, treatment of a disease refers to alleviating a disease and/or associated symptoms and/or preventing the development of a secondary disease resulting from the occurrence of a primary disease.

Thus, the term "therapeutically effective amount" referred to herein means that the nucleic acid constructs of the invention are administered to the subject in an amount that is effective, when administered to said subject, to treat that subject.

An effective administration protocol (i.e., administering a pharmaceutical composition in an effective manner) comprises suitable dose parameters and modes of administration that result in treatment of a disease. Effective dose parameters and modes of administration can be determined using methods standard in the art for a particular disease. Such methods include, for example, determination of survival rates, side effects (i.e., toxicity) and progression or regression of disease.

In accordance with the present invention, a suitable single dose size is a dose that is capable of treating a subject with disease when administered one or more times over a suitable time period. For example, a suitable single dose size may induce a reduction in tumor cell mass in a subject in need thereof. Doses of a pharmaceutical composition of the present invention suitable for use with direct injection techniques can be used by one of skill in the art to determine appropriate single dose sizes for systemic administration based on the size of a subject.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, intraarterial, intravesicle (into the bladder) or intraocular injections.

Alternatively, one may administer a preparation in a local rather than systemic manner, for example, via injection of the preparation directly into a specific region of a patient's body or by direct administration into a body cavity such as the bladder, uterus etc. in another particular embodiment, intralesional administration, e.g. intratumoral injection, is contemplated.

Solutions or suspensions used for parenteral, intradermal, or subcutaneous application can include the following components: a sterile diluent such as water for injection, saline solution, fixed oils, polyethylene glycols, glycerine, propylene glycol (or other synthetic solvents), antibacterial agents (e.g., benzyl alcohol, methyl parabens), antioxidants (e.g., ascorbic acid, sodium bisulfite), chelating agents (e.g., ethylenediaminetetraacetic acid), buffers (e.g., acetates, citrates, phosphates), and agents that adjust tonicity (e.g., sodium chloride, dextrose). The pH can be adjusted with acids or bases, such as hydrochloric acid or sodium hydroxide, for example. The parenteral preparation can be enclosed in ampules, disposable syringes or multiple dose vials made of glass or plastic.

Pharmaceutical compositions adapted for parenteral administration include, but are not limited to, aqueous and non-aqueous sterile injectable solutions or suspensions, which can contain antioxidants, buffers, bacteriostats and solutes that render the compositions substantially isotonic with the blood of an intended recipient. Such compositions can also comprise water, alcohols, polyols, glycerine and vegetable oils, for example. Extemporaneous injection solutions and suspensions can be prepared from sterile powders, granules and tablets. Such compositions should comprise a therapeutically effective amount of a vector of the invention and/or other therapeutic agent, together with a suitable amount of carrier so as to provide the form for proper administration to the subject. The formulation should suit the mode of administration.

In certain embodiments, the compositions of the present invention can be used to treat cancer alone or with other established or experimental therapeutic regimens against cancer. Therapeutic methods for treatment of cancer suitable for combination with the present invention include, but are not limited to, chemotherapy, radiotherapy, phototherapy and photodynamic therapy, surgery, nutritional therapy, ablative therapy, combined radiotherapy and chemotherapy, brachiotherapy, proton beam therapy, immunotherapy, cellular therapy, and photon beam radiosurgical therapy.

Anti-cancer drugs that can be co-administered with the constructs of the invention include, but are not limited to the following: acivicin; aclarubicin; acodazole hydrochloride; acronine; adriamycin; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; taxol; tecogalan sodium; tegafur; teloxantrone hydrochloride; temoporfin; teniposide; teroxirone; testolactone; thiamiprine; thioguanine; thiotepa; tiazofuirin; tirapazamine; topotecan hydrochloride; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride. Additional antineoplastic agents include those disclosed in Chapter 52, "Antineoplastic Agents" (Calabresi, P. and Chabner, B. A.), and the introduction thereto, pp. 1202-1263, of Goodman and Gilman, The Pharmacological Basis of Therapeutics, Eighth Edition, 1990, McGraw-Hill, Inc. (Health Professions Division). Each possibility represents a separate embodiment of the present invention.

The following examples are presented in order to more fully illustrate some embodiments of the invention. They should, in no way be construed, however, as limiting the broad scope of the invention.

EXPERIMENTAL DETAILS SECTION

Overview of Multiple-promoter Vectors

Double promoter expression vectors were created, carrying on a single construct two separate genes expressing the DTA toxin, from two different regulatory sequences, as follows:

H19+IGF-II-P4 promoters (hereinafter "H19-DTA-P4-DTA"; depicted in FIG. 1);
IGF-II-P3+IGF-II-P4 promoters (hereinafter "P4-DTA-P3-DTA"; described subsequently); and
H19+IGF-II-P3 promoters; (hereinafter "H19-DTA-P3-DTA"; described subsequently).

Transfections

Transfections were performed using the in vitro jetPEI™ transfection reagent (Polyplus Transfection) as recommended by the manufacturer. After 48 hours, cells were harvested and luciferase activity was determined using the Luciferase Assay System kit (Promega). Light output was measured using a Lumac Biocounter apparatus. Total protein content of the lysates was determined by the Bio-Rad protein assay reagent, and results were normalized to the total protein and expressed as Light units/pg protein. A plasmid that expresses luciferase under SV40 transcription control, LucSV40 (Promega) was used as a positive control for the efficiency of transfection, as it contains the SV40 promoter and enhancer, while a plasmid containing Luc1 but lacking regulatory sequences (Promega) was used as a negative control to determine the basal nonspecific luciferase expression (this was negligible in all cell lines). All experiments were performed in triplicate.

Creation of H19-DTA-P4-DTA

The synthetic DTA cassette and synthetic P4 cassette were each assembled from PCR products and subcloned into pGA4 (ampR, available from GeneArt, Regensburg, Germany) using SacI and KpnI restriction sites. Plasmid DNA was purified (Pure Yield™ Plasmid Midiprep, Promega) from transformed K12 XL10 gold bacteria and concentration determined by UV spectroscopy. The final constructs were verified by sequencing and were named 0704870 (SEQ ID NO: 21) and 0704867 (SEQ ID NO: 23), respectively. Sequence congruence was 100%.

The P4 promoter that was utilized had the following sequence:

(SEQ ID NO: 9)
acttcccggtcggtctgtgggtgcaggggtgccgcctcacatgtgtgat tcgtgccttgcgggccctggcctccggggtgctgggtaacgaggagggc gcggagccgcagaagcccaccctggtatgttgacgcggtgccagcgagac cgcgagaggaagacgggggtgggcggggccaggatggagaggggccgagt tggcaggagtcatggcagacgccacattcgcgacatctcccccacaccccc ctctggctctgtccgcaacatttccaaacaggagtcccgggagaggggga gaggggctgctggtctgaggctaagaagggcagagccttcgaccccggaga gaggccgcggcccctgcccagtgggcagcgtggaagtttccatacaagga ggtgggaaggagaccccccccccccttcactgccctgtgcagagatgagc cgggggtgcaggatgggagcccatggcacttcgctacgggatggtccagg gctcccggttggggtgcaggagagaagagactggctgggaggagggaga gggcgggagcaaaggcgcggggggagtggtcagcagggagaggggtgggggg gtagggtggagcccgggctggggaggagtcggctcacacatacaaagctgag gcactgaccagcctgcaaactggacattagcttctcctgtgaaagagact tccagcttcctcctcctctatcctcctcctcctcctgccccagcgagcc ttctgctgagctgtagggggatcttctagagtcg.

Next, a vector that expressed DTA from the IGF-II P4 promoter alone was created. To create this vector, the DTA sequence was amplified from 0704870 and subcloned into 0704867 using NheI and KpnI restriction sites. The plasmid DNA was purified from transformed K12 KH10B bacteria and concentration determined by UV spectroscopy. The final construct (0704877) was verified by sequencing. The sequence congruence was 100%.

To create the H19-DTA-P4-DTA vector, the P4-DTA cassette was amplified from 0704877, and subcloned into 052966, a vector that expresses DTA from the H19 promoter, using NotI and KpnI restriction sites. 052966 is referred to hereinafter as "H19-DTA" and has the following sequence:

(SEQ ID NO: 16)
ggtaccgacaaccctcaccaagggccaaggtggtgaccgacggacccaca gcggggtggctgggggagtcgaaactcgccagtctccactccactcccaa ccgtggtgccccacgcgggcctgggagagtctgtgaggccgcccaccgct tgtcagtagagtgcgcccgcgagccgtaagcacagcccggcaacatgcgg tcttcagacaggaaagtggccgcgaatgggaccggggtgcccagcggctg tggggactctgtcctgcggaaaccgcggtgacgagcacaagctcggtcaa ctggatgggaatcggcctgggggggctggcaccgcgcccaccaggggttt gcggcacttccctctgcccctcagcaccccacccctactctccaggaacg tgagttctgagccgtgatggtggcaggaaggggccctctgtgccatccga gtccccagggaccccgcagctggccccccagccatgtgcaaagtatgtgcag ggcgctggcaggcagggagcagcaggcatggtgtccctgagggagaca gtggtctgggagggagaagtcctggaccctgagggaggtgatgggcaat gctcagccctgtctccggatgccaaaggaggggtgcggggaggccgtctt tggagaattccaggatgggtgctgggtgagagagacgtgtgctggaactg tccaggcggaggtgggccctgcggggccctcgggagggccctgctctg attggccggcagggcagggcgggaatcctgggcggggccaccccagtta gaaaaagcccgggctaggaccgaggagcagggtgagggagaagcttggca ttccggtactgttggtaaagccaccatggatcctgatgatgttgttgatt cttctaaatcttttgtgatggaaaacttttcttcgtaccacgggactaaa cctggttatgtagattccattcaaaaaggtatacaaaagccaaaatctgg tacacaaggaaattatgacgatgattggaaagggttttatagtaccgaca ataaatacgacgctgcgggatactctgtagataatgaaaacccgctctct ggaaaagctggaggcgtggtcaaagtgacgtatccaggactgacgaaggt tctcgcactaaaagtggataatgccgaaactattaagaaagagttaggtt taagtctcactgaaccgttgatggagcaagtcggaacggaagagtttatc aaaaggttcggtgatggtgcttcgcgtgtagtgctcagccttcccttcgc tgaggggagttctagcgttgaatatattaataactgggaacaggcgaaag cgttaagcgtagaacttgagattaattttgaaacccgtggaaaacgtggc caagatgcgatgtatgagtatatggctcaagcctgtgcaggaaatcgtgt caggcgatctttgtgaaggaaccttacttctgtggtgtgacataattgga caaactacctacagagatttggggatcctctagagtcggggcggccggcc gcttcgagcagacatgataagatacattgatgagtttggacaaaccacaa ctagaatgcagtgaaaaaaatgctttatttgtgaaatttgtgatgctatt gctttatttgtaaccattataagctgcaataaacaagttaacaacaacaa ttgcattcattttatgtttcaggttcagggggaggtgtgggaggttttt aaagcaagtaaaacctctacaaatgtggtaaaatcgataaggatccgtcg accgatgcccttgagagccttcaacccagtcagctccttccggtgggcgc ggggcatgactatcgtcgccgcacttatgactgtcttctttatcatgcaa ctcgtaggacaggtgccggcagcgctcttccgcttcctcgctcactgact cgctgcgctcggtcgttcggctgcggcgagcgggtatcagctcactcaaag -continued

```
gcggtaatacggttatccacagaatcaggggataacgcaggaaagaacat
gtgagcaaaaggccagcaaaaggccaggaaccgtaaaaaggccgcgttgc
tggcgttttttccataggctccgcccccctgacgagcatcacaaaaatcga
cgctcaagtcagaggtggcgaaacccgacaggactataaagataccaggc
gtttccccctggaagctccctcgtgcgctctcctgttccgaccctgccgc
ttaccggatacctgtccgcctttctcccttcgggaagcgtggcgctttct
catagctcacgctgtaggtatctcagttcggtgtaggtcgttcgctccaa
gctgggctgtgtgcacgaaccccccgttcagcccgaccgctgcgcttat
ccggtaactatcgtcttgagtccaacccggtaagacacgacttatcgcca
ctggcagcagccactggtaacaggattagcagagcgaggtatgtaggcgg
tgctacagagttcttgaagtggtggcctaactacggctacactagaagaa
cagtatttggtatctgcgctctgctgaagccagttaccttcggaaaaaga
gttggtagctcttgatccggcaaacaaaccaccgctggtagcggtggttt
ttttgtttgcaagcagcagattacgcgcagaaaaaaaggatctcaagaag
atcctttgatcttttctacggggtctgacgctcagtggaacgaaaactca
cgttaagggattttggtcatgagattatcaaaaaggatcttcacctagat
ccttttaaattaaaaatgaagttttaaatcaatctaaagtatatatgagt
aaacttggtctgacagttagaaaaactcatcgagcatcaaatgaaactgc
aatttattcatatcaggattatcaataccatattttgaaaaagccgttt
ctgtaatgaaggagaaaactcaccgaggcagttccataggatggcaagat
cctggtatcggtctgcgattccgactcgtccaacatcaatacaacctatt
aatttcccctcgtcaaaataaggttatcaagtgagaaatcaccatgagt
gacgactgaatccggtgagaatggcaaaagtttatgcatttctttccaga
cttgttcaacaggccagccattacgctcgtcatcaaaatcactcgcatca
accaaaccgttattcattcgtgattgcgcctgagcgagacgaaatacgcg
atcgctgttaaaaggacaattacaaacaggaatcgaatgcaaccggcgca
ggaacactgccagcgcatcaacaatattttcacctgaatcaggatattct
tctaatacctggaatgctgttttcccggggatcgcagtggtgagtaacca
tgcatcatcaggagtacggataaaatgcttgatggtcggaagaggcataa
attccgtcagccagtttagtctgaccatctcatctgtaacatcattggca
acgctaccttgccatgtttcagaaacaactctggcgcatcgggcttccc
atacaatcgatagattgtcgcacctgattgcccgacattatcgcgagccc
atttatacccatataaatcagcatccatgttggaatttaatcgcggccta
gagcaagacgtacccgttgaatatggctcatactcttcatttcaatatt
attgaagcatttatcagggttattgtctcatgagcggatacatatttgaa
tgtatttagaaaaataaacaaatagggtccgcgcacatttccccgaaa
agtgccacctgacgcgccctgtagcggcgcattaagcgcggcgggtgtg
tggttacgcgcagcgtgaccgctacacttgccagcgccctagcgcccgct
cctttcgctttcttcccttcctttctcgccacgttcgccggctaccccgt
caagctctaaatcggggcctctttaggttccgatttagtgattacgg
cacctcgaccccaaaaaacttgattagggtgatggttcacgtagtgggcc
```

-continued

```
atcgccctgatagacggtttttcgccctttgacgttggagtccacgttct
ttaatagtggactcttgttccaaactggaacaacactcaaccctatctcg
gtctattcttttgatttataagggattttgccgatttcggcctattggtt
aaaaaatgagctgatttaacaaaaatttaacgcgaattttaacaaaatat
taacgcttacaatttgccattcgccattcaggctgcgcaactgttgggaa
gggcgatcggtgcgggcctcttcgctattacgccagcccaagctaccatg
ataagtaagtaatattaaggtacgggaggtacttggagcggccgcaataa
aatatctttattttcattacatctgtgtgttggttattgtgtgaatcgat
agtactaacatacgctctccatcaaaacaaaacgaaacaaaacaaactag
caaaataggctgtccccagtgcaagtgcaggtgccagaacatttctctat
cgata.
```

The plasmid DNA was purified from transformed K12 KH10B bacteria and concentration determined by UV spectroscopy. The final construct was verified by sequencing. The sequence congruence was 100%.

The sequence of H19-DTA-P4-DTA was:

```
                                    (SEQ ID NO: 11)
ccctcaccaagggccaaggtggtgaccgacggacccacagcggggtggct
gggggagtcgaaactcgccagtctccactccactcccaaccgtggtgccc
cacgcgggcctgggagagtctgtgaggccgcccaccgcttgtcagtagag
tgcgcccgcgagccgtaagcacagcccggcaacatgcggtcttcagacag
gaaagtggccgcgaatgggaccggggtgcccagcggctgtggggactctg
tcctgcggaaaccgcggtgacgagcacaagctcggtcaactggatgggaa
tcggcctgggggggctggcaccgcgcccaccaggggggtttgcggcacttcc
ctctgcccctcagcaccccacccctactctccaggaacgtgagttctgag
ccgtgatggtggcaggaagggccctctgtgccatccgagtccccaggga
cccgcagctggcccccagccatgtgcaaagtatgtgcagggcgctggcag
gcagggagcagcaggcatggtgtccctgaggggagacagtggtctggga
gggagaagtcctggaccctgagggaggtgatgggcaatgctcagccctg
tctccggatgccaaaggagggtgcggggaggccgtcttggagaattcc
aggatgggtgctgggtgagagagacgtgtgctggaactgtccagggcgga
ggtgggccctgcgggggccctcgggagggccctgctctgattggccggca
gggcaggggcgggaatcctgggcggggccaccccagttagaaaaagcccg
ggctaggaccgaggagcagggtgagggagaagcttggcattccggtactg
ttggtaaagccaccatggatcctgatgatgttgttgattcttctaaatct
tttgtgatggaaaacttttcttcgtaccacgggactaaacctggttatgt
agattccattcaaaaaggtatacaaaagccaaaatctggtacacaaggaa
attatgacgatgattggaaagggtttttatagtaccgacaataaatacgac
gctgcgggatactctgtagataatgaaaacccgctctctggaaaagctgg
aggcgtggtcaaagtgacgtatccaggactgacgaaggttctcgcactaa
aagtggataatgccgaaactattaagaaagagttaggtttaagtctcact
gaaccgttgatggagcaagtcggaacggaagagtttatcaaaaggttcgg
```

-continued tgatggtgcttcgcgtgtagtgctcagccttcccttcgctgaggggagtt
ctagcgttgaatatattaataactgggaacaggcgaaagcgttaagcgta
gaacttgagattaatttttgaaacccgtggaaaacgtggccaagatgcgat
gtatgagtatatggctcaagcctgtgcaggaaatcgtgtcaggcgatctt
tgtgaaggaaccttacttctgtggtgtgacataattggacaaactaccta
cagagatttggggatcctctagagtcggggcggccggccgcttcgagcag
acatgataagatacattgatgagtttggacaaaccacaactagaatgcag
tgaaaaaaatgctttatttgtgaaatttgtgatgctattgctttatttgt
aaccattataagctgcaataaacaagttaacaacaacaattgcattcatt
ttatgtttcaggttcaggggggaggtgtgggaggttttttaaagcaagtaa
aacctctacaaatgtggtaaaatcgataaggatccgtcgaccgatgccct
tgagagccttcaacccagtcagctccttccggtgggcgcggggcatgact
atcgtcgccgcacttatgactgtcttcttatcatgcaactcgtaggaca
ggtgccggcagcgctcttccgcttcctcgctcactgactcgctgcgctcg
gtcgttcggctgcggcgagcggtatcagctcactcaaaggcggtaatacg
gttatccacagaatcaggggataacgcaggaaagaacatgtgagcaaaag
gccagcaaaaggccaggaaccgtaaaaaggccgcgttgctggcgtttttc
cataggctccgcccccctgacgagcatcacaaaaatcgacgctcaagtca
gaggtggcgaaacccgacaggactataaagataccaggcgtttccccctg
gaagctccctcgtgcgctctcctgttccgaccctgccgcttaccggatac
ctgtccgcctttctcccttcgggaagcgtggcgctttctcatagctcacg
ctgtaggtatctcagttcggtgtaggtcgttcgctccaagctgggctgtg
tgcacgaaccccccgttcagcccgaccgctgcgccttatccggtaactat
cgtcttgagtccaacccggtaagacacgacttatcgccactggcagcagc
cactggtaacaggattagcagagcgaggtatgtaggcggtgctacagagt
tcttgaagtggtggcctaactacggctacactagaagaacagtatttggt
atctgcgctctgctgaagccagttaccttcggaaaaagagttggtagctc
ttgatccggcaaacaaaccaccgctggtagcggtggtttttttgtttgca
agcagcagattacgcgcagaaaaaaaggatctcaagaagatcctttgatc
ttttctacggggtctgacgctcagtggaacgaaaactcacgttaagggat
tttggtcatgagattatcaaaaaggatcttcacctagatccttttaaatt
aaaaatgaagttttaaatcaatctaaagtatatatgagtaaacttggtct
gacagttagaaaaactcatcgagcatcaaatgaaactgcaatttattcat
atcaggattatcaataccatatttttgaaaaagccgtttctgtaatgaag
gagaaaactcaccgaggcagttccataggatggcaagatcctggtatcgg
tctgcgattccgactcgtccaacatcaatacaacctattaatttcccctc
gtcaaaataaggttatcaagtgagaaatcaccatgagtgacgactgaat
ccggtgagaatggcaaaagtttatgcatttattccagacttgttcaacag
gccagccattacgctcgtcatcaaaatcactcgcatcaaccaaaccgtta
ttcattcgtgattgcgcctgagcgagacgaaatacgcgatcgctgttaaa
aggacaattacaaacaggaatcgaatgcaaccggcgcaggaacactgcca -continued gcgcatcaacaatattttcacctgaatcaggatattcttctaatacctgg
aatgctgttttcccggggatcgcagtggtgagtaaccatgcatcatcagg
agtacggataaaatgcttgatggtcggaagaggcataaattccgtcagcc
agtttagtctgaccatctcatctgtaacatcattggcaacgctacattgc
catgtttcagaaacaactctggcgcatcgggcttcccatacaatcgatag
attgtcgcacctgattgcccgacattatcgcgagcccatttatacccata
taaatcagcatccatgttggaatttaatcgcggcctagagcaagacgttt
cccgttgaatatggctcatactcttcctttttcaatattattgaagcatt
tatcagggttattgtctcatgagcggatacatatttgaatgtatttagaa
aaataaacaaatagggghttccgcgcacatttccccgaaaagtgccacctg
acgcgcccgtagcggcgcattaagcgcggcgggtgtggtggttacgcgc
agcgtgaccgctacacttgccagcgccctagcgcccgctcctttcgcttt
cttcccttcctttctcgccacgttcgccggctttccccgtcaagctctaa
atcggggggctccctttagggttccgatttagtgctttacggcacctcgac
cccaaaaaacttgattagggtgatggttcacgtagtgggccatcgccctg
atagacggtttttcgccctttgacgttggagtccacgttctttaatagtg
gactcttgttccaaactggaacaacactcaacccctatctcggtctattct
tttgatttataagggattttgccgatttcggcctattggttaaaaaatga
gctgatttaacaaaaatttaacgcgaattttaacaaaatattaacgctta
caatttgccattcgccattcaggctgcgcaactgttgggaagggcgatcg
gtgcgggcctcttcgctattacgccagcccaagctaccatgataagtaag
taatattaaggtacgggaggtacttggagcggccgcaataaaaatatcttt
attttcattacatctgtgtgttggttttttgtgtgaatcgatagtactaa
catacgctctccatcaaaacaaaacgaaacaaaacaaactagcaaaatag
gctgtcccagtcaagtgcaggtgccagaacatttctctatcgataact
tcccggtcggtctgtgggtgcaggggtgccgcctcacatgtgtgattcg
tgccttgcgggccctggcctccggggtgctgggtaacgaggaggggcgcg
gagccgcagaagcccaccctggtatgttgacgcggtgccagcgagaccgc
gagaggaagacgggggtgggcgggccaggatggagaggggccgagttgg
caggagtcatggcagacgccacattcgcgacatctcccccacaccccctc
tggctctgtccgcaacatttccaaacaggagtcccgggagaggggagag
gggctgctggtctgaggctaagaagggcagagccttcgacccggagagag
gccgcggccctgcccagtgggcagcgtggaagtttccatacaaggaggt
gggaaggagaccccccccccccttcactgccctgtgcagagatgagccgg
gggtgcaggatgggagcccatggcacttcgctacgggatggtccagggct
cccggttggggtgcaggagagaagagactggctgggaggagggagaggg
cgggagcaaaggcgcggggagtggtcagcagggagagggtgggggta
gggtggagcccgggctgggaggagtcggctcacacataaaagctgaggca
ctgaccagcctgcaaactggacattagcttctcctgtgaaagagacttcc
agcttcctcctcctcctcttcctcctcctcctcctgccccagcgagcctt
ctgctgagctgtaggggatcttctagagtcggctagcggcattccggta -continued ctgttggtaaagccaccatggatcctgatgatgttgttgattcttctaaa tcttttgtgatggaaaacttttcttcgtaccacgggactaaacctggtta tgtagattccattcaaaaaggtatacaaaagccaaaatctggtacacaag gaaattatgacgatgattggaaagggttttatagtaccgacaataaatac gacgctgcgggatactctgtagataatgaaaacccgctctctggaaaagc tggaggcgtggtcaaagtgacgtatccaggactgacgaaggttctcgcac taaaagtggataatgccgaaactattaagaaagagttaggtttaagtctc actgaaccgttgatggagcaagtcggaacggaagagtttatcaaaaggtt cggtgatggtgcttcgcgtgtagtgctcagccttccttcgctgagggga gttctagcgttgaatatattaataactgggaacaggcgaaagcgttaagc gtagaacttgagattaattttgaaacccgtggaaaacgtggccaagatgc gatgtatgagtatatggctcaagcctgtgcaggaaatcgtgtcaggcgat ctttgtgaaggaaccttacttctgtggtgtgacataattggacaaactac ctacagagatttggggatccctcgagacgtagggtaccgacaa.

Creation P4-DTA-P3-DTA

The P4-DTA-P3-DTA construct was created using a strategy very similar to that used to create the H19-DTA-P4-DTA construct. The final construct was verified by sequencing. Sequence congruence was 100%. The IGF-II P3 promoter had the following sequence:

(SEQ ID NO: 17)
ggccatgcaggtaggatttgagctgtgtttcccgccctgatcctctctcc tctggcggccggagcctccgtaggctccaagcctggcccagattcggcgg cgcagccggccttccgcgcgtccgcacctagcgggggctccggggctccg gcgcggcaccggggggcgctcgggatctggctgaggctccaaggcccgcg tggccggctcctcctgctggggcaggtggcggctgcgcgccccgcccgag cccagggcccctcagccgcaacaaccagcaaggaccccccgactcagc ccaagccacctgcatctgcactcagacggggcgcaccgcagtgcagcc tcctggtggggcgctgggagcccgcctgcccctgcctgcccggagacccc agctcacgagcacaggccgcccgggcaccccagaaacccgggatggggcc cctgaattctctaggacgggcattcagcatggccttggcgctctgcggct ccctgccccccacccagcctcgcccccgcgcaccccccagccctgcgac cgccgcccccccccggggcccagggcccagcccgcacccccgccc cgctcttggctcgggttgcggggcgggccgggggcggggcgagggctcc gcgggcgccattggcgcgggcgcgaggccagcggcccgcgcggccctg ggccgcggctggcgcgactataagagccgggcgtgggcgccgcagttcg cctgctctccgcggagctgcgtgaggcccggccggcccggccccccc ttccggccgccccgcctcctggcccacgctgcccgcgctctgcccacc agcgcctccatcgggcaaggcggcccgcgtcgac.

P4-DTA-P3-DTA had the following sequence:

(SEQ ID NO: 24)
gcggccgcaataaaatatcttattttcattacatctgtgtgttggtttt tgtgtgaatcgatagtactaacatacgctctccatcaaaacaaaacgaaa caaaacaaactagcaaaataggctgtccccagtgcaagtgcaggtgccag aacatttctctatcgataacttcccggtcggtctgtgggtcagggggtg ccgcctcacatgtgtgattcgtgccttgcgggccctggcctccggggtgc tgggtaacgaggaggggcgcggagccgcagaagcccaccctggtatgttg acgcggtgccagcgagaccgcgagaggaagacggggtgggcggggccag gatggagagggccgagttggcaggagtcatggcagacgccacattcgcg acatctcccccacacccctctggctctgtccgcaacatttccaaacagg agtcccgggagaggggagaggggctgctggtctgaggctaagaagggca gagccttcgacccggagagaggccgcggcccctgcccagtgggcagcgtg gaagtttccatacaaggaggtgggaaggagaccccccccccccttcactg ccctgtgcagagatgagccggggtgcaggatgggagcccatggcacttc gctacgggatggtccagggctcccggttgggggtgcaggagagaagagac tggctgggaggagggagagggcgggagcaaaggcgcgggggagtggtcag cagggagagggtggggggtagggtggagcccgggctgggaggagtcggc tcacacataaaagctgaggcactgaccagcctgcaaactggacatttagc ttctcctgtgaaagagacttccagcttcctcctcctcctcttcctcctcc tcctcctgccccagcgagccttctgctgagctgtaggggatcttctaga gtcggctagcggcattccggtactgttggtaaagccaccatggatcctga tgatgttgattcttctaaatcttttgtgatggaaaacttttcttcgt accacgggactaaacctggttatgtagattccattcaaaaaggtatacaa aagccaaaatctggtacacaaggaaattatgacgatgattggaaagggtt ttatagtaccgacaataaatacgacgctgcgggatactctgtagataatg aaaacccgctctctggaaaagctggaggcgtggtcaaagtgacgtatcca ggactgacgaaggttctcgcactaaaagtggataatgccgaaactatta gaaagagttaggttagtctcactgaaccgttgatggagcaagtcggaac ggaagagtttatcaaaaggttcggtgatggtgcttcgcgtgtagtgctca gccttcccttcgctgaggggagttctagcgttgaatatattaataactgg gaacaggcgaaagcgttaagcgtagaacttgagattaattttgaaacccg tggaaaacgtggccaagatgcgatgtatgagtatatggctcaagcctgtg caggaaatcgtgtcaggcgatctttgtgaaggaaccttacttctgtggtg tgacataattggacaaactacctacagagatttggggatccctcgaggc catgcaggtaggatttgagctgtgtttcccgccctgatcctctctcctct ggcggccggagcctccgtaggctccaagcctggcccagattcggcggcgc agccgcttccgcgcgtccgcacctagcgggggctccggggctccggcgc ggcaccggggggcgctcgggatctggctgaggctccaaggcccgcgtggc cggctcctcctgctggggcaggtggcggctgcgcgccccgcccgagccca ggggcccctcagccgcaacaaccagcaaggaccccccgactcagccca agccacctgcatctgcactcagacggggcgcaccgcagtgcagcctcct ggtggggcgctgggagcccgcctgcccctgcctgcccggagaccccagct cacgagcacaggccgcccgggcaccccagaaacccgggatggggcccctg aattctctaggacgggcattcagcatggccttggcgctctgcggctccct -continued

```
gcccccacccagcctcgccccgcgcaccccccagccctgcgaccgcc
gccccccccccggggcccagggccccagcccgcaccccccgcccgct
cttggctcgggttgcggggcgggccggggcggggcgagggctccgcgg
gcgcccattggcgcgggcgcgaggccagcggcccgcgcggccctgggcc
gcggctggcgcgactataagagccgggcgtgggcgcccgcagttcgcctg
ctctccggcggagctgcgtgaggcccggccggccccggcccccccttcc
ggccgccccgcctcctggcccacgcctgcccgcgctctgcccaccagcg
cctccatcgggcaaggcggccccgcgtcgacaagcttggcattccggtac
tgttggtaaagccaccatggatcctgatgatgttgttgattcttctaaat
cttttgtgatggaaaacttttcttcgtaccacgggactaaacctggttat
gtagattccattcaaaaaggtatacaaaagccaaaatctggtacacaagg
aaatatgacgatgattggaaagggttttatagtaccgacaataaatacg
acgctgcgggatactctgtagataatgaaaacccgctctctggaaaagct
ggaggcgtggtcaaagtgacgtatccaggactgacgaaggttctcgcact
aaaagtggataatgccgaaactattaagaaagagttaggtttaagtctca
ctgaaccgttgatggagcaagtcggaacggaagagtttatcaaaaggttc
ggtgatggtgcttcgcgtgtagtgctcagccttcccttcgctgaggggag
ttctagcgttgaatatattaataactgggaacaggcgaaagcgttaagcg
tagaacttgagattaattttgaaaccgtggaaaacgtggccaagatgcg
atgtatgagtatatggctcaagcctgtgcaggaaatcgtgtcaggcgatc
tttgtgaaggaaccttacttctgtggtgtgacataattggacaaactacc
tacagagatttggggatcctctagagtcggggcggccggccgcttcgagc
agacatgataagatacattgatgagtttgacaaaccacaactagaatgc
agtgaaaaaaatgctttatttgtgaaatttgtgatgctattgctttatt
gtaaccattataagctgcaataaacaagttaacaacaacaattgcattca
ttttatgtttcaggttcaggggaggtgtgggaggttttttaaagcaagt
aaaacctctacaaatgtggtaaaatcgataaggatccgtcgaccgatgcc
cttgagagccttcaacccagtcagctccttccggtgggcgcggggcatga
ctatcgtcgccgcacttatgactgtcttctttatcatgcaactcgtagga
caggtgccggcagcgctcttccgcttcctcgctcactgactcgctgcgct
cggtcgttcggctgcggcgagcggtatcagctcactcaaaggcggtaata
cggttatccacagaatcaggggataacgcaggaaagaacatgtgagcaaa
aggccagcaaaaggccaggaaccgtaaaaaggccgcgttgctggcgtttt
tccataggctccgcccccctgacgagcatcacaaaaatcgacgctcaagt
cagaggtggcgaaacccgacaggactataaagataccaggcgtttccccc
tggaagctccctcgtgcgctctcctgttccgaccctgccgcttaccggat
acctgtccgcctttctcccttcgggaagcgtggcgctttctcatagctca
cgctgtaggtatctcagttcggtgtaggtcgttcgctccaagctgggctg
tgtgcacgaaccccccgttcagcccgaccgctgcgccttatccggtaact
atcgtcttgagtccaacccggtaagacacgacttatcgccactggcagca
gccactggtaacaggattagcagagcgaggtatgtaggcggtgctacaga
```

```
gttcttgaagtggtggcctaactacggctacactagaagaacagtatttg
gtatctgcgctctgctgaagccagttaccttcggaaaaagagttggtagc
tcttgatccggcaaacaaaccaccgctggtagcggtggtttttttgtttg
caagcagcagattacgcgcagaaaaaaaggatctcaagaagatcctttga
tcttttctacggggtctgacgctcagtggaacgaaaactcacgttaaggg
attttggtcatgagattatcaaaaaggatcttcacctagatcctttttaaa
ttaaaaatgaagttttaaatcaatctaaagtatatatgagtaaacttggt
ctgacagttagaaaaactcatcgagcatcaaatgaaactgcaatttattc
atatcaggattatcaataccatatttttgaaaaagccgtttctgtaatga
aggagaaaactcaccgaggcagttccataggatggcaagatcctggtatc
ggtctgcgattccgactcgtccaacatcaatacaacctattaatttcccc
tcgtcaaaaataaggttatcaagtgagaaatcaccatgagtgacgactga
atccggtgagaatggcaaaagtttatgcatttctttccagacttgttcaa
caggccagccattacgctcgtcatcaaaatcactcgcatcaaccaaaccg
ttattcattcgtgattgcgcctgagcgagacgaaatacgcgatcgctgtt
aaaaggacaattacaaacaggaatcgaatgcaaccggcgcaggaacactg
ccagcgcatcaacaatattttcacctgaatcaggatattcttctaatacc
tggaatgctgttttcccggggatcgcagtggtgagtaaccatgcatcatc
aggagtacggataaaatgcttgatggtcggaagaggcataaattccgtca
gccagtttagtctgaccatctcatctgtaacatcattggcaacgctacct
ttgccatgtttcagaaacaactctggcgcatcgggcttcccatacaatcg
atagattgtcgcacctgattgcccgacattatcgcgagcccatttatacc
catataaatcagcatccatgttggaatttaatcgcggcctagagcaagac
gtttcccgttgaatatggctcatactcttccttttcaatattattgaag
catttatcagggttattgtctcatgagcggatacatatttgaatgtattt
agaaaaataaacaaataggggttccgcgcacatttccccgaaaagtgcca
cctgacgcgccctgtagcggcgcattaagcgcggcgggtgtggtggttac
gcgcagcgtgaccgctacacttgccagcgccctagcgcccgctcctttcg
ctttcttcccttcctttctcgccacgttcgccggctttccccgtcaagct
ctaaatcggggggctccctttagggttccgatttagtgctttacggcacct
cgaccccaaaaaacttgattagggtgatggttcacgtagtgggccatcgc
cctgatagacggtattcgcccttcgacgttggagtccacgttctttaata
gtggactcttgttccaaactggaacaacactcaaccctatctcggtctat
tcttttgatttataagggattttgccgatttcggcctattggttaaaaaa
tgagctgatttaacaaaaatttaacgcgaattttaacaaaatattaacgc
ttacaatttgccattcgccattcaggctgcgcaactgttgggaagggcga
tcggtgcgggcctcttcgctattacgccagcccaagctaccatgataagt
aagtaatattaaggtacgggaggtacttgga.
```

P3-DTA, expressing DTA under the P3 promoter alone, had the following sequence:

(SEQ ID NO: 19)
```
tctatcgataggtaccgacaaccctcaccaagggccaaggtggtgaccgg
ccatgcaggtaggatttgagctgtgtttcccgccctgatcctctctcctc
tggcggccggagcctccgtaggctccaagcctggcccagattcggcggcg
cagccggccttccgcgcgtccgcacctagcgggggctccggggctccggc
gcggcaccgggggcgctcgggatctggctgaggctccaaggccgcgtg
gccggctcctcctgctggggcaggtggcggctgcgcgccccgcccgagcc
caggggcccctcagccgcaacaaccagcaaggaccccccgactcagccc
caagccacctgcatctgcactcagacggggcgcaccgcagtgcagcctc
ctggtggggcgctgggagcccgcctgcccctgcctgcccggagacccag
ctcacgagcacaggccgcccgggcaccccagaaaccgggatgggcccc
tgaattctctaggacgggcattcagcatggccttggcgctctgcggctcc
ctgccccccacccagcctcgccccgcgcaccccccagccctgcgaccg
ccgccccccccccggggcccagggcccagcccgcacccccgcccg
ctcttggctcgggttgcggggcgggccggggcggggcgagggctccgc
gggcgcccattggcgcgggcgcgaggccagcggccccgcgcggccctggg
ccgcggctggcgcgactataagagccgggcgtgggcgcccgcagttcgcc
tgctctccggcggagctgcgtgaggccggccggccccggccccccctt
ccggccgccccgcctcctggcccacgcctgcccgcgctctgcccaccag
cgcctccatcgggcaaggcggcccccgcaagcttggcattccggtactgtt
ggtaaagccaccatggatcctgatgatgttgttgattcttctaaatcttt
tgtgatggaaacttttcttcgtaccacgggactaaacctggttatgtag
attccattcaaaaaggtatacaaaagccaaatctggtacacaaggaaat
tatgacgatgattggaaagggttttatagtaccgacaataaatacgacgc
tgcgggatactctgtagataatgaaaaccgctctctggaaaagctggag
gcgtggtcaaagtgacgtatccaggactgacgaaggttctcgcactaaaa
gtggataatgccgaaactattaagaaagagttaggtttaagtctcactga
accgttgatggagcaagtcggaacggaagagtttatcaaaaggttcggtg
atggtgcttcgcgtgtagtgctcagccttcccttcgctgaggggagttct
agcgttgaatatattaataactgggaacaggcgaaagcgttaagcgtaga
acttgagattaattttgaaacccgtggaaaacgtggccaagatgcgatgt
atgagtatatggctcaagcctgtgcaggaaatcgtgtcaggcgatctttg
tgaaggaaccttacttctgtggtgtgacataattggacaaactacctaca
gagatttggggatcctctagagtcggggcggccggccgcttcgagcagac
atgataagatacattgatgagtttggacaaaccacaactagaatgcagtg
aaaaaaatgctttatttgtgaaatttgtgatgctattgctttatttgtaa
ccattataagctgcaataaacaagttaacaacaacaattgcattcatttt
atgtttcaggttcaggggaggtgtgggaggttttttaaagcaagtaaaa
cctctacaaatgtggtaaaatcgataaggatccgtcgaccgatgcccttg
agagccttcaacccagtcagctccttccggtgggcgcggggcatgactat
cgtcgccgcacttatgactgtcttctttatcatgcaactcgtaggacagg
```
-continued
```
tgccggcagcgctcttccgcttcctcgctcactgactcgctgcgctcggt
cgttcggctgcggcgagcggtatcagctcactcaaaggcggtaatacggt
tatccacagaatcaggggataacgcaggaaagaacatgtgagcaaaaggc
cagcaaaaggccaggaaccgtaaaaaggccgcgttgctggcgttttttcca
taggctccgcccccctgacgagcatcacaaaaatcgacgctcaagtcaga
ggtggcgaaacccgacaggactataaagataccaggcgtttccccctgga
agctccctcgtgcgctctcctgttccgaccctgccgcttaccggatacct
gtccgcctttctcccttcgggaagcgtggcgctttctcatagctcacgct
gtaggtatctcagttcggtgtaggtcgttcgctccaagctgggctgtgtg
cacgaaccccccgttcagcccgaccgctgcgccttatccggtaactatcg
tcttgagtccaacccggtaagacacgacttatcgccactggcagcagcca
ctggtaacaggattagcagagcgaggtatgtaggcggtgctacagagttc
ttgaagtggtggcctaactacggctacactagaagaacagtatttggtat
ctgcgctctgctgaagccagttaccttcggaaaaagagttggtagctctt
gatccggcaaacaaaccaccgctggtagcggtggtttttttgtttgcaag
cagcagattacgcgcagaaaaaaaggatctcaagaagatcctttgatctt
ttctacggggtctgacgctcagtggaacgaaaactcacgttaagggattt
tggtcatgagattatcaaaaaggatcttcacctagatccttttaaattaa
aaatgaagttttaaatcaatctaaagtatatatgagtaaacttggtctga
cagttagaaaaactcatcgagcatcaaatgaaactgcaatttattcatat
caggattatcaataccatattttgaaaaagccgtttctgtaatgaagga
gaaaactcaccgaggcagttccataggatggcaagatcctggtatcggtc
tgcgattccgactcgtccaacatcaatacaacctattaatttccctcgt
caaaaataaggttatcaagtgagaaatcaccatgagtgacgactgaatcc
ggtgagaatggcaaaagtttatgcatttctttccagacttgttcaacagg
ccagccattacgctcgtcatcaaaatcactcgcatcaaccaaaccgttat
tcattcgtgattgcgcctgagcgagacgaaatacgcgatcgctgttaaaa
ggacaattacaaacaggaatcgaatgcaaccggcgcaggaacactgccag
cgcatcaacaatattttcacctgaatcaggatattcttctaatacctgga
atgctgttttcccggggatcgcagtggtgagtaaccatgcatcatcagga
gtacgataaaatgcttgatggtcggaagaggcataaattccgtcagcca
gtttagtctgaccatctcatctgtaacatcattggcaacgctacctttgc
catgtttcagaaacaactctggcgcatcgggcttcccatacaatcgatag
attgtcgcacctgattgcccgacattatcgcgagcccatttatacccata
taaatcagcatccatgttggaatttaatcgcggcctagagcaagacgttt
cccgttgaatatggctcatactcttcctttttcaatattattgaagcatt
tatcagggttattgtctcatgagcggatacatatttgaatgtatttagaa
aaataaacaaatagggggttccgcgcacatttccccgaaaagtgccacctg
acgcgccctgtagcggcgcattaagcgcggcgggtgtggtggttacgcgc
agcgtgaccgctacacttgccagcgccctagcgcccgctcctttcgcttt
cttcccttcctttctcgccacgttcgccggctttccccgtcaagctctaa
```

-continued

```
atcgggggctccctttagggttccgatttagtgctttacggcacctcgac
cccaaaaaacttgattagggtgatggttcacgtagtgggccatcgcctg
atagacggttttcgccctttgacgttggagtccacgttctttaatagtg
gactcttgttccaaactggaacaacactcaaccctatctcggtctattct
tttgatttataagggattttgccgatttcggcctattggttaaaaaatga
gctgatttaacaaaaatttaacgcgaattttaacaaaatattaacgctta
caatttgccattcgccattcaggctgcgcaactgttgggaagggcgatcg
gtgcgggcctcttcgctattacgccagcccaagctaccatgataagtaag
taatattaaggtacgggaggtacttggagcggccgcaataaaaatatcttt
attttcattacatctgtgtgttggttttttgtgtgaatcgatagtactaa
catacgctctccatcaaaacaaaacgaaacaaaacaaactagcaaaatag
gctgtccccagtgcaagtgcaggtgccagaacatttctctatcgataggt
accgaca.
```

P4-DTA, a plasmid expressing DTA under the P4 promoter, was created by replacing the P3 promoter with the P4 promoter (SEQ ID NO: 9).

In addition, a control construct, P4-Luc-P3-Luc, was created using the same strategy. The sequence of P4-Luc-P3-Luc is as follows:

(SEQ ID NO: 22)
```
ggtgcgggcctcttcgctattacgccagcccaagctaccatgataagtaa
gtaatattaaggtacgggaggtacttggagcggccgcaataaaaatatctt
tattttcattacatctgtgtgttggttttttgtgtgaatcgatagtacta
acatacgctctccatcaaaacaaaacgaaacaaaacaaactagcaaaata
ggctgtccccagtgcaagtgcaggtgccagaacatttctctatcgataac
ttcccggtcggtctgtgggtgcaggggtgccgcctcacatgtgtgattc
gtgccttgcgggccctggcctccggggtgctgggtaacgaggaggggcgc
ggagccgcagaagcccaccctggtatgttgacgcggtgccagcgagaccg
cgagaggaagacgggggtgggcggggccaggatggagaggggccgagttg
gcaggagtcatggcagacgccacattcgcgacatctcccccacaccccct
ctggctctgtccgcaacatttccaaacaggagtcccgggagaggggaga
gggctgctggtctgaggctaagaagggcagagccttcgacccggagaga
ggccgcggccctgcccagtgggcagcgtggaagtttccatacaaggagg
tgggaaggagaccccccccccttcactgccctgtgcagagatgagccg
ggggtgcaggatgggagcccatggcacttcgctacgggatggtccagggc
tcccggttgggggtgcaggagagaagagactggctgggaggagggagagg
gcgggagcaaaggcgcgggggagtggtcagcagggagaggggtgggggt
agggtggagcccgggctggaggagtcggctcacacataaaagctgaggc
actgaccagcctgcaaactggacattagcttctcctgtgaaagagacttc
cagcttcctcctcctcttcctcctcctcctgccccagcgagcct
tctgctgagctgtaggggatcttctagagtcggctagcggcattccggt
actgttggtaaagccaccatggaagacgccaaaaacataaagaaaggccc
```

-continued
```
ggcgccattctatccgctggaagatggaaccgctggagagcaactgcata
aggctatgaagagatacgcccgttcctggaacaattgcttttacagat
gcacatatcgaggtggacatcacttacgctgagtacttcgaaatgtccgt
tcggttggcagaagctatgaaacgatatgggctgaatacaaatcacagaa
tcgtcgtatgcagtgaaaactctcttcaattctttatgccggtgttgggc
gcgttatttatcggagttgcagttgcgcccgcgaacgacatttataatga
acgtgaattgctcaacagtatgggcatttcgcagcctaccgtggtgttcg
tttccaaaaaggggttgcaaaaaattttgaacgtgcaaaaaaagctccca
atcatccaaaaaattattatcatggattctaaaacggattaccagggatt
tcagtcgatgtacacgttcgtcacatctcatctacctcccggttttaatg
aatacgattttgtgccagagtccttcgatagggacaagacaattgcactg
atcatgaactcctctggatctactggtctgcctaaaggtgtcgctctgcc
tcatagaactgcctgcgtgagattctcgcatgccagagatcctattttg
gcaatcaaatcattccggatactgcgattttaagtgttgttccattccat
cacggttttggaatgtttactacactcggatatttgatatgtggatttcg
agtcgtcttaatgtatagatttgaagaagagctgtttctgaggagccttc
aggattacaagattcaaagtgcgctgctggtgccaaccctattctcttc
ttcgccaaaagcactctgattgacaaatacgatttatctaatttacacga
aattgcttctggtggcgctccctctctaaggaagtcggggaagcggttg
ccaagaggttccatctgccaggtatcaggcaaggatatgggctcactgag
actacatcagctattctgattacacccgagggggatgataaaccgggcgc
ggtcggtaaagttgttccatttttgaagcgaaggttgtggatctggata
ccgggaaaacgctgggcgttaatcaaagaggcgaactgtgtgtgagaggt
cctatgattatgtccggttatgtaaacaatccggaagcgaccaacgcctt
gattgacaaggatggatggctacattctggagacatagcttactgggacg
aagacgaacacttcttcatcgttgaccgcctgaagtctctgattaagtac
aaaggctatcaggtggctcccgctgaattggaatccatcttgctccaaca
ccccaacatcttcgacgcaggtgtcgcaggtcttcccgacgatgacgccg
gtgaacttcccgccgccgttgttgttttggagcacggaaagacgatgacg
gaaaaagagatcgtggattacgtcgccagtcaagtaacaaccgcgaaaaa
gttgcgcggaggagttgtgtttgtggacgaagtaccgaaaggtcttaccg
gaaaactcgacgcaagaaaaatcagagagatcctcataaaggccaagaag
ggcggaaagatcgccgtgtaatctcgagggccatgcaggtaggatttgag
ctgtgtttcccgccctgatcctctctcctctggcggccggagcctccgta
ggctccaagcctggcccagattcggcggcgcagccggccttccgcgcgtc
cgcacctagcggggctccggggctccggcgcggcaccgggggcgctcg
ggatctggctgaggctccaaggcccgcgtggccggctcctcctgctgggg
caggtggcggctgcgcgccccgcccgagcccaggggcccctcagccgca
acaaccagcaaggacccccgactcagcccaagccacctgcatctgcac
tcagacggggcgcaccccgcagtgcagcctcctggtggggcgctgggagcc
cgcctgcccctgcctgcccggagaccccagctcacgagcacaggccgccc
```

-continued gggcacccagaaacccgggatggggcccctgaattctctaggacgggca
ttcagcatggccttggcgctctgcggctccctgcccccacccagcctcg
ccccgcgcaccccagccctgcgaccgccgcccccccccggggcc
ccagggcccagcccgcaccccgccccgctcttggctcgggttgcggg
ggcgggccggggcggggcgagggctccgcgggcgcccattggcgcggc
gcgaggccagcggcccgcgcggccctgggccgcggctggcgcgactata
agagccgggcgtgggcgcccgcagttcgcctgctctccgcggagctgcg
tgaggcccggccggccccggccccccccttccggccgcccccgcctcctg
gcccacgcctgcccgcgctctgcccaccagcgcctccatcgggcaaggcg
gccccgcgtcgacaagcttggcattccggtactgttggtaaagccaccat
ggaagacgccaaaaacataaagaaaggcccggcgccattctatccgctgg
aagatggaaccgctggagagcaactgcataaggctatgaagagatacgcc
tggttcctggaacaattgcttttacagatgcacatatcgaggtggacatc
acttacgctgagtacttcgaaatgtccgttcggttggcagaagctatgaa
acgatatgggctgaatacaaatcacagaatcgtcgtatgcagtgaaaact
ctcttcaattctttatgccggtgttgggcgcgttatttatcggagttgca
gttgcgcccgcaacgacatttataatgaacgtgaattgctcaacagtat
gggcatttcgcagcctaccgtggtgttcgtttccaaaaaggggttgcaaa
aaattttgaacgtgcaaaaaaagctcccaatcatccaaaaaattattatc
atggattctaaaacggattaccagggatttcagtcgatgtacacgttcgt
cacatctcatctacctcccggttttaatgaatacgattttgtgccagagt
ccttcgatagggacaagacaattgcactgatcatgaactcctctggatct
actggtctgcctaaaggtgtcgctctgcctcatagaactgcctgcgtgag
attctcgcatgccagagatcctatttttggcaatcaaatcattccggata
ctgcgattttaagtgttgttccattccatcacggttttggaatgtttact
acactcggatatttgatatgtggatttcgagtcgtcttaatgtatagatt
tgaagaagagctgtttctgaggagccttcaggattacaagattcaaagtg
cgctgctggtgccaaccctattctccttcttcgccaaaagcactctgatt
gacaaatacgatttatctaatttacacgaaattgcttctggtggcgctcc
cctctctaaggaagtcggggaagcggttgccaagaggttccatctgccag
gtatcaggcaaggatatgggctcactgagactacatcagctattctgatt
acacccgaggggatgataaaccgggcgcggtcggtaaagttgttccatt
ttttgaagcgaaggttgtggatctggataccgggaaaacgctgggcgtta
atcaaagaggcgaactgtgtgtgagaggtcctatgattatgtccggttat
gtaaacaatccggaagcgaccaacgccttgattgacaaggatggatggct
acattctggagacatagcttactgggacgaagacgaacacttcttcatcg
ttgaccgcctgaagtctctgattaagtacaaaggctatcaggtggctccc
gctgaattggaatccatcttgctccaacaccccaacatcttcgacgcagg
tgtcgcaggtcttcccgacgatgacgccggtgaacttcccgccgccgttg
ttgttttggagcacggaaagacgatgacgaaaagagatcgtggattac
gtcgccagtcaagtaacaaccgcgaaaaagttgcgcggaggagttgtgtt -continued tgtggacgaagtaccgaaaggtcttaccggaaaactcgacgcaagaaaaa
tcagagagatcctcataaaggccaagaagggcggaaagatcgccgtgtaa
ttctagagtcggggcggccggccgcttcgagcagacatgataagatacat
tgatgagtttggacaaaccacaactagaatgcagtgaaaaaaatgcttta
tttgtgaaatttgtgatgctattgctttatttgtaaccattataagctgc
aataaacaagttaacaacaacaattgcattcattttatgtttcaggttca
gggggaggtgtgggaggttttttaaagcaagtaaaacctctacaaatgtg
gtaaaatcgataaggatccgtcgaccgatgcccttgagagccttcaaccc
agtcagctccttccggtgggcgcggggcatgactatcgtcgccgcactta
tgactgtcttctttatcatgcaactcgtaggacaggtgccggcagcgctc
ttccgcttcctcgctcactgactcgctgcgctcggtcgttcggctgcggc
gagcggtatcagctcactcaaaggcggtaatacggttatccacagaatca
ggggataacgcaggaaagaacatgtgagcaaaaggccagcaaaaggccag
gaaccgtaaaaaggccgcgttgctggcgtttttccataggctccgccccc
ctgacgagcatcacaaaaatcgacgctcaagtcagaggtggcgaaacccg
acaggactataaagataccaggcgtttccccctggaagctccctcgtgcg
ctctcctgttccgaccctgccgcttaccggatacctgtccgcctttctcc
cttcgggaagcgtggcgctttctcatagctcacgctgtaggtatctcagt
tcggtgtaggtcgttcgctccaagctgggctgtgtgcacgaaccccccgt
tcagcccgaccgctgcgccttatccggtaactatcgtcttgagtccaacc
cggtaagacacgacttatcgccactggcagcagccactggtaacaggatt
agcagagcgaggtatgtaggcggtgctacagagttcttgaagtggtggcc
taactacggctacactagaagaacagtatttggtatctgcgctctgctga
agccagttaccttcggaaaaagagttggtagctcttgatccggcaaacaa
accaccgctggtagcggtggtttttttgtttgcaagcagcagattacgcg
cagaaaaaaaggatctcaagaagatcctttgatcttttctacggggtctg
acgctcagtggaacgaaaactcacgttaagggattttggtcatgagatta
tcaaaaaggatcttcacctagatccttttaaattaaaaatgaagttttaa
atcaatctaaagtatatatgagtaaacttggtctgacagttagaaaaact
catcgagcatcaaatgaaactgcaatttattcatatcaggattatcaata
ccatatttttgaaaaagccgtttctgtaatgaaggagaaaactcaccgag
gcagttccataggatggcaagatcctggtatcggtctgcgattccgactcg
tccaacatcaatacaacctattaatttcccctcgtcaaaaataaggttat
caagtgagaaatcaccatgagtgacgactgaatccggtgagaatggcaaa
agtttatgcatttctttccagacttgttcaacaggccagccattacgctc
gtcatcaaaatcactcgcatcaaccaaaccgttattcattcgtgattgcg
cctgagcgagacgaaatacgcgatcgctgttaaaaggacaattacaaaca
ggaatcgaatgcaaccggcgcaggaacactgccagcgcatcaacaatatt
ttcacctgaatcaggatattcttctaatacctggaatgctgttttcccgg
ggatcgcagtggtgagtaaccatgcatcatcaggagtacggataaaatgc
ttgatggtcggaagaggcataaattccgtcagccagtttagtctgaccat -continued ctcatctgtaacatcattggcaacgctacctttgccatgtttcagaaaca
actctggcgcatcgggcttccatacaatcgatagattgtcgcacctgatt
gcccgacattatcgcgagcccatttatacccatataaatcagcatccatg
ttggaatttaatcgcggcctagagcaagacgtttcccgttgaatatggct
catactcttcctttttcaatattattgaagcatttatcagggttattgtc
tcatgagcggatacatatttgaatgtatttagaaaaataaacaaataggg
gttccgcgcacatttccccgaaaagtgccacctgacgcgccctgtagcgg
cgcattaagcgcggcgggtgtggtggttacgcgcagcgtgaccgctacac
ttgccagcgccctagcgcccgctcctttcgctttcttccttcctttctc
gccacgttcgccggctttccccgtcaagctctaaatcggggctcccttt
agggttccgatttagtgctttacggcacctcgaccccaaaaaacttgatt
agggtgatggttcacgtagtgggccatcgccctgatagacggttttcgc
cctttgacgttggagtccacgttctttaatagtggactcttgttccaaac
tggaacaacactcaaccctatctcggtctattcttttgatttataaggga
ttttgccgatttcggcctattggttaaaaaatgagctgatttaacaaaaa
tttaacgcgaattttaacaaaatattaacgcttacaatttgccattcgcc
attcaggctgcgcaactgttgggaagggcgatc.

Creation of H19-DTA-P3-DTA

The H19-DTA-P3-DTA construct was created using a strategy very similar to that used to create the H19/P4 construct. The final construct was verified by sequencing. Sequence congruence was 100%.

H19-DTA-P3-DTA had the following sequence:

(SEQ ID NO: 18)
ccctcaccaagggccaaggtggtgaccgacggacccacagcggggtggct
gggggagtcgaaactcgccagtctccactccactcccaaccgtggtgccc
cacgcgggcctgggagagtctgtgaggccgccaccgcttgtcagtagag
tgcgcccgcgagccgtaagcacagcccggcaacatgcggtcttcagacag
gaaagtggccgcgaatgggaccggggtgcccagcggctgtggggactctg
tcctgcggaaaccgcggtgacgagcacaagctcggtcaactggatgggaa
tcggcctgggggctggcaccgcgccaccaggggtttgcggcacttcc
ctctgcccctcagcaccccaccctactctccaggaacgtgagttctgag
ccgtgatggtggcaggaaggggccctctgtgccatccgagtccccaggga
cccgcagctggcccccagccatgtgcaaagtatgtgcagggcgctggcag
gcagggagcagcaggcatggtgtccctgaggggagacagtggtctggga
gggagaagtcctggaccctgagggaggtgatggggcaatgctcagccctg
tctccggatgccaaaggaggggtgcggggaggccgtctttggagaattcc
aggatgggtgctgggtgagagagacgtgtgctggaactgtccagggcgga
ggtgggcctgcggggggccctcggggagggccctgctctgattggccggca
gggcaggggcgggaatcctgggcggggccaccccagttagaaaagcccg
ggctaggaccgaggagcagggtgagggagaagcttggcattccggtactg
ttggtaaagccaccatggatcctgatgatgttgttgattcttctaaatct -continued tttgtgatggaaaacttttcttcgtaccacgggactaaacctggttatgt
agattccattcaaaaaggtatacaaaagccaaaatctggtacacaaggaa
attatgacgatgattggaaagggttttatagtaccgacaataaatacgac
gctgcgggatactctgtagataatgaaaacccgctctctggaaaagctgg
aggcgtggtcaaagtgacgtatccaggactgacgaaggttctcgcactaa
agtggataatgccgaaactattaagaaagagttaggtttaagtctcactg
aaccgttgatggagcaagtcggaacggaagagtttatcaaaaggttcggt
gatggtgcttcgcgtgtagtgctcagccttccttcgctgagggagttc
tagcgttgaatatattaataactgggaacaggcgaaagcgttaagcgtag
aacttgagattaaattttgaaacccgtggaaaacgtggccaagatgcgat
gtatgagtatatggctcaagcctgtgcaggaaatcgtgtcaggcgatctt
tgtgaaggaaccttacttctgtggtgtgacataattggacaaactaccta
cagagatttggggatcctctagagtcggggcggccgccgcttcgagcag
acatgataagatacattgatgagtttggacaaaccacaactagaatgcag
tgaaaaaatgctttatttgtgaaatttgtgatgctattgctttatttgt
aaccattataagctgcaataaacaagttaacaacaacaattgcattcatt
ttatgtttcaggttcaggggaggtgtgggaggttttttaaagcaagtaa
aacctctacaaatgtggtaaaatcgataaggatccgtcgaccgatgccct
tgagagccttcaacccagtcagctccttccggtgggcgcggggcatgact
atcgtcgccgcacttatgactgtcttctttatcatgcaactcgtaggaca
ggtgccggcagcgctcttccgcttcctcgctcactgactcgctgcgctcg
gtcgttcggctgcggcgagcggtatcagctcactcaaaggcggtaatacg
gttatccacagaatcaggggataacgcaggaaagaacatgtgagcaaaag
gccagcaaaaggccaggaaccgtaaaaaggccgcgttgctggcgtttttc
cataggctccgcccccctgacgagcatcacaaaaatcgacgctcaagtca
gaggtggcgaaacccgacaggactataaagataccaggcgtttccccctg
gaagctccctcgtgcgctctcctgttccgaccctgccgcttaccggatac
ctgtccgcctttctcccttcgggaagcgtggcgctttctcatagctcacg
ctgtaggtatctcagttcggtgtaggtcgttcgctccaagctgggctgtg
tgcacgaaccccccgttcagcccgaccgctgcgccttatccggtaactat
cgtcttgagtccaacccggtaagacacgacttatcgccactggcagcagc
cactggtaacaggattagcagagcgaggtatgtaggcggtgctacagagt
tcttgaagtggtggcctaactacggctacactagaagaacagtatttggt
atctgcgctctgctgaagccagttaccttcggaaaaagagttggtagctc
ttgatccggcaaacaaaccaccgctggtagcggtggtttttttgtttgca
agcagcagattacgcgcagaaaaaaaggatctcaagaagatcctttgatc
ttttctacggggtctgacgctcagtggaacgaaaactcacgttaagggat
tttggtcatgagattatcaaaaaggatcttcacctagatccttttaaatt
aaaaatgaagttttaaatcaatctaaagtatatatgagtaaacttggtct
gacagttagaaaaactcatcgagcatcaaatgaaactgcaatttattcat
atcaggattatcaataccatatttttgaaaaagccgtttctgtaatgaag -continued

```
gagaaaactcaccgaggcagttccataggatggcaagatcctggtatcgg
tctgcgattccgactcgtccaacatcaatacaacctattaatttcccctc
gtcaaaaataaggttatcaagtgagaaatcaccatgagtgacgactgaat
ccggtgagaatggcaaaagtttatgcatttctttccagacttgttcaaca
ggccagccattacgctcgtcatcaaaatcactcgcatcaacaaaccgtta
ttcattcgtgattgcgcctgagcgagacgaaatacgcgatcgctgttaaa
aggacaattacaaacaggaatcgaatgcaaccggcgcaggaacactgcca
gcgcatcaacaatattttcacctgaatcaggatattcttctaatacctgg
aatgctgttttcccggggatcgcagtggtgagtaaccatgcatcatcagg
agtacggataaaatgcttgatggtcggaagaggcataaattccgtcagcc
agtttagtctgaccatctcatctgtaacatcattggcaacgctacctttg
ccatgtttcagaaacaactctggcgcatcgggcttcccatacaatcgata
gattgtcgcacctgattgcccgacattatcgcgagccatttataccccat
ataaatcagcatccatgttggaatttaatcgcggcctagagcaagacgtt
tcccgttgaatatggctcatactcttccttttcaatattattgaagcat
ttatcagggttattgtctcatgagcggatacatattgaatgtatttagaa
aaataaacaaatagggttccgcgcacatttccccgaaaagtgccacctg
acgcgccctgtagcggcgcattaagcgcggcgggtgtggtggttacgcgc
agcgtgaccgctacacttgccagcgccctagcgcccgctcctttcgcttt
cttcccttcctttctcgccacgttcgccggctttccccgtcaagctctaa
atcggggctcccttagggttccgatttagtgctttacggcacctcgac
cccaaaaaacttgattagggtgatggttcacgtagtgggccatcgccctg
atagacggttttcgccctttgacgttggagtccacgttcttaatagtg
gactcttgttccaaactggaacaacactcaaccctatctcggtctattct
ttgatttataagggattttgccgatttcggcctattggttaaaaaatgag
ctgatttaacaaaaatttaacgcgaattttaacaaaatattaacgcttac
aatttgccattcgccattcaggctgcgcaactgttgggaagggcgatcgg
tgcgggcctcttcgctattacgccagcccaagctaccatgataagtaagt
aatattaaggtacgggaggtacttggagcggccgcaataaaatatcttta
ttttcattacatctgtgtgttggttttttgtgtgaatcgatagtactaac
atacgctctccatcaaaacaaaacgaaacaaaacaaactagcaaaatagg
ctgtccccagtgcaagtgcaggtgccagaacatttctctatcgatactcg
agggccatgcaggtaggatttgagctgtgtttcccgccctgatcctctct
cctctggcggccggagcctccgtaggctccaagcctggcccagattcggc
ggcgcagccggccttccgcgcgtccgcacctagcgggggctccggggctc
cggcgcggcaccggggggcgctcgggatctggctgaggctccaaggcccg
cgtggccggctcctcctgctggggcaggtggcggctgcgcgccccgcccg
agcccaggggccccctcagccgcaacaaccagcaaggaccccccgactca
gccccaagccacctgcatctgcactcagacggggcgcacccgcagtgcag
cctcctggtggggcgctgggagcccgcctgcccctgcctgcccgagacc
ccagctcacgagcacaggccgcccggcaccccagaaacccgggatggggg
```

-continued

```
cccctgaattctctaggacgggcattcagcatggccttggcgctctgcgg
ctccctgccccccaccagcctcgccccgcgcacccccagccctgcg
aggcggcccccccccccggggccccagggcccagcccgcacccccgc
cccgctcttggctcgggttgcgggggcgggccggggcggggcgagggct
ccgcgggcgcccattggcgcgggcgcgaggccagcggcccgcgcggccc
tgggccgcggctggcgcgactataagagccgggcgtgggcgcccgcagtt
cgcctgctctccggcggagctgcgtgaggcccggccggccccggccccc
ccttccggccgccccgcctcctggcccacgcctgcccgcgctctgccca
ccagcgcctccatcgggcaaggcggccccgcgtcgacaagcttagctacg
ctagcggcattccggtactgttggtaaagccaccatggatcctgatgatg
ttgttgattcttctaaatcttttgtgatggaaaacttttcttcgtaccac
gggactaaacctggttatgtagattccattcaaaaaggtatacaaaagcc
aaaatctggtacacaaggaaattatgacgatgattggaaagggttttata
gtaccgacaataaatacgacgctgcgggatactctgtagataatgaaaac
ccgctctctggaaaagctggaggcgtggtcaaagtgacgtatccaggact
gacgaaggttctgcactaaaagtggataatgccgaaactattaagaaaga
gttaggtttaagtctcactgaaccgttgatggagcaagtcggaacggaag
agtttatcaaaaggttcggtgatggtgcttcgcgtgtagtgctcagcctt
cccttcgctgaggggagttctagcgttgaatatattaataactgggaaca
ggcgaaagcgttaagcgtagaacttgagattaattttgaaacccgtggaa
aacgtggccaagatgcgatgtatgagtatatggctcaagcctgtgcagga
aatcgtgtcaggcgatctttgtgaaggaaccttacttctgtggtgtgaca
taattggacaaactacctacagagatttggggatccctcgagacgtaggt
accgacaa.
```

In addition, a control construct, H19-Luc-P3-Luc, was created using the same strategy. The sequence of H19-Luc-P3-Luc is as follows:

(SEQ ID NO: 20)
```
gacaaccctcaccaagggccaaggtggtgaccgacggacccacagcgggg
tggctggggagtcgaaactcgccagtctccactccactcccaaccgtgg
tgccccacgcgggcctgggagagtctgtgaggccgcccaccgcttgtcag
tagagtgcgcccgcgagccgtaagcacagcccggcaacatgcggtcttca
gacaggaaagtggccgcgaatgggaccggggtgcccagcggctgtgggga
ctctgtcctgcggaaaccgcggtgacgagcacaagctcggtcaactggat
gggaatcggcctgggggctggcaccgcgcccaccaggggtttgcggca
cttccctctgcccctcagcaccccaccctactctccaggaacgtgagtt
ctgagccgtgatggtggcaggaaggggccctctgtgccatccgagtcccc
agggacccgcagctggcccccagccatgtgcaaagtatgtgcagggcgct
ggcaggcagggagcagcaggcatggtgtcccctgaggggagacagtggtc
tgggagggagaagtcctgccctgagggaggtgatgggcaatgctcagc
cctgtctccggatgccaaaggaggggtgcggggaggccgtctttggagaa
```

```
ttccaggatgggtgctgggtgagagagacgtgtgctggaactgtccaggg
cggaggtgggccctgcgggggccctcgggagggccctgctctgattggcc
ggcagggcaggggcgggaattctgggcggggccaccccagttagaaaaag
cccgggctaggaccgaggagcagggtgagggaagcttggcattccggtac
tgttggtaaagccaccatggaagacgccaaaaacataaagaaaggcccgg
cgccattctatccgctggaagatggaaccgctggagagcaactgcataag
gctatgaagagatacgccctggttcctggaacaattgcttttacagatgc
acatatcgaggtggacatcacttacgctgagtacttcgaaatgtccgttc
ggttggcagaagctatgaaacgatatgggctgaatacaaatcacagaatc
gtcgtatgcagtgaaaactctcttcaattctttatgccggtgttgggcgc
gttatttatcggagttgcagttgcgcccgcgaacgacatttataatgaac
gtgaattgctcaacagtatgggcatttcgcagcctaccgtggtgttcgtt
tccaaaaaggggttgcaaaaaattttgaacgtgcaaaaaaagctcccaat
catccaaaaaattattatcatggattctaaaacggattaccagggatttc
agtcgatgtacacgttcgtcacatctcatctacctcccggttttaatgaa
tacgattttgtgccagagtccttcgatagggacaagacaattgcactgat
catgaactcctctggatctactggtctgcctaaaggtgtcgctctgcctc
atagaactgcctgcgtgagattctcgcatgccagagatcctattttttggc
aatcaaatcattccggatactgcgattttaagtgttgttccattccatca
cggttttggaatgtttactacactcggatatttgatatgtggatttcgag
tcgtcttaatgtatagatttgaagaagagctgtttctgaggagccttcag
gattacaagattcaaagtgcgctgctggtgccaaccctattctccttctt
cgccaaaagcactctgattgacaaatacgatttatctaatttacacgaaa
ttgcttctggtggcgctcccctctctaaggaagtcggggaagcggttgcc
aagaggttccatctgccaggtatcaggcaaggatatgggctcactgagac
tacatcagctattctgattacacccgaggggatgataaaccgggcgcgg
tcggtaaagttgttccattttttgaagcgaaggttgtggatctggatacc
gggaaaacgctgggcgttaatcaaagaggcgaactgtgtgtgagaggtcc
tatgattatgtccggttatgtaaacaatccggaagcgaccaacgccttga
ttgacaaggatggatggctacattctggagacatagcttactgggacgaa
gacgaacacttcttcatcgttgaccgcctgaagtctctgattaagtacaa
aggctatcaggtggctcccgctgaattggaatccatcttgctccaacacc
ccaacatcttcgacgcaggtgtcgcaggtcttcccgacgatgacgccggt
gaacttcccgccgccgttgttgttttggagcacggaaagacgatgacgga
aaaagagatcgtggattacgtcgccagtcaagtaacaaccgcgaaaagt
tgcgcggaggagttgtgtttgtggacgaagtaccgaaaggtcttaccgga
aaactcgacgcaagaaaaatcagagagatcctcataaaggccaagaaggg
cggaaagatcgccgtgtaattctagagtcggggcggccggccgcttcgag
cagacatgataagatacattgatgagtttggacaaaccacaactagaatg
cagtgaaaaaaatgctttatttgtgaaatttgtgatgctattgctttatt
tgtaaccattataagctgcaataaacaagttaacaacaacaattgcattc
```

```
attttatgtttcaggttcaggggaggtgtgggaggttttttaaagcaag
taaaacctctacaaatgtggtaaaatcgataaggatccgtcgaccgatgc
ccttgagagccttcaacccagtcagctccttccggtgggcgcggggcatg
actatcgtcgccgcacttatgactgtcttctttatcatgcaactcgtagg
acaggtgccggcagcgctcttccgcttcctcgctcactgactcgctgcgc
tcggtcgttcggctgcggcgagcggtatcagctcactcaaaggcggtaat
acggttatccacagaatcaggggataacgcaggaaagaacatgtgagcaa
aaggccagcaaaaggccaggaaccgtaaaaaggccgcgttgctggcgttt
ttccataggctccgcccccctgacgagcatcacaaaaatcgacgctcaag
tcagaggtggcgaaacccgacaggactataaagataccaggcgtttcccc
ctggaagctccctcgtgcgctctcctgttccgaccctgccgcttaccgga
tacctgtccgcctttctcccttcgggaagcgtggcgctttctcatagctc
acgctgtaggtatctcagttcggtgtaggtcgttcgctccaagctgggct
gtgtgcacgaaccccccgttcagcccgaccgctgcgccttatccggtaac
tatcgtcttgagtccaacccggtaagacacgacttatcgccactggcagc
agccactggtaacaggattagcagagcgaggtatgtaggcggtgctacag
agttcttgaagtggtggcctaactacggctacactagaagaacagtattt
ggtatctgcgctctgctgaagccagttaccttcggaaaaagagttggtag
ctcttgatccggcaaacaaaccaccgctggtagcggtggtttttttgttt
gcaagcagcagattacgcgcagaaaaaaaggatctcaagaagatcctttg
atcttttctacggggtctgacgctcagtggaacgaaaactcacgttaagg
gattttggtcatgagattatcaaaaaggatcttcacctagatccttttaa
attaaaaatgaagttttaaatcaatctaaagtatatatgagtaaacttgg
tagacagttagaaaaactcatcgagcatcaaatgaaactgcaatttattc
atatcaggattatcaataccatatttttgaaaaagccgtttctgtaatga
aggagaaaactcaccgaggcagttccataggatggcaagatcctggtatc
ggtctgcgattccgactcgtccaacatcaatacaacctattaatttcccc
tcgtcaaaaataaggttatcaagtgagaaatcaccatgagtgacgactga
atccggtgagaatggcaaaagtttatgcatttattccagacttgttcaac
aggccagccattacgctcgtcatcaaaatcactcgcatcaaccaaaccgt
tattcattcgtgattgcgcctgagcgagacgaaatacgcgatcgctgtta
aaaggacaattacaaacaggaatcgaatgcaaccggcgcaggaacactgc
cagcgcatcaacaatattttcacctgaatcaggatattcttctaatacct
ggaatgctgttttcccggggatcgcagtggtgagtaaccatgcatcatca
ggagtacggataaaatgcttgatggtcggaagaggcataaattccgtcag
ccagtttagtctgaccatctcatctgtaacatcattggcaacgctacctt
tgccatgtttcagaaacaactctggcgcatcgggcttcccatacaatcga
tagattgtcgcacctgattgcccgacattatcgcgagcccatttatacc
atataaatcagcatccatgttggaatttaatcgcggcctagagcaagacg
tttcccgttgaatatggctcatactcttcctttttcaatattattgaagc
atttatcagggttattgtctcatgagcggatacatatttgaatgtattta
```

-continued
gaaaaataaacaaataggggttccgcgcacatttccccgaaaagtgccac
ctgacgcgccctgtagcggcgcattaagcgcggcgggtgtggtggttacg
cgcagcgtgaccgctacacttgccagcgccctagcgcccgctcctttcgc
tttcttcccttcctttctcgccacgttcgccggctttccccgtcaagctc
taaatcggggctccctttagggttccgatttagtgctttacggcacctc
gaccccaaaaaacttgattagggtgatggttcacgtagtgggccatcgcc
ctgatagacggttttcgccctttgacgttggagtccacgttctttaata
gtggactcttgttccaaactggaacaacactcaaccctatctcggtctat
tcttttgatttataagggattttgccgatttcggcctattggttaaaaaa
tgagctgatttaacaaaaatttaacgcgaattttaacaaaatattaacgc
ttacaatttgccattcgccattcaggctgcgcaactgttgggaagggcga
tcggtgcgggcctcttcgctattacgccagcccaagctaccatgataagt
aagtaatattaaggtacgggaggtacttggagcggccgcaataaaatata
ttattttcattacatctgtgtgttggttattgtgtgaatcgatagtacta
acatacgctctccatcaaaacaaaacgaaacaaaacaaactagcaaaata
ggctgtccccagtgcaagtgcaggtgccagaacatttctctatcgatact
cgagggccatgcaggtaggatttgagctgtgtttcccgccctgatcctct
ctcctctggcggccggagcctccgtaggctccaagcctggcccagattcg
gcggcgcagccggcctccgcgcgtccgcacctagcggggggctccggggct
ccggcgcggcaccggggggcgctcgggatctggctgaggctccaaggccc
gcgtggccggctcctcctgctggggcaggtggcggctgcgcgccccgccc
gagcccaggggcccctcagccgcaacaaccagcaaggaccccccgactc
agccccaagccacctgcatctgcactcagacggggcgcaccgcagtgca
gcctcctggtggggcgctgggagcccgcctgcccctgcctgcccggagac
cccagctcacgagcacaggccgcccgggcaccccagaaacccgggatggg
gcccctgaattctctaggacgggcattcagcatggccttggcgctctgcg
gctccctgcccccagcctcgccccgcgcacccccagccctgcgacc
gccgccccccccggggcccagggcccagcccgcaccccgcccc
gctcttggctcgggttgcggggcgggccggggcggggcgagggctccg
cgggcgccattggcgcgggcgcgaggccagcggcccgcgcggccctgg
gccgcggctggcgcgactataagagccgggcgtgggcgccgcagttcgc
ctgctctccggcggagctgcgtgaggccggccggcccggcccccccct
tccggccgccccgcctcctggcccacgcctgcccgcgctctgcccacca
gcgcctccatcgggcaaggcggccccgcgtcgacaagcttagctacgcta
gcggcattccggtactgttggtaaagccaccatggaagacgccaaaaaca
taaagaaaggcccggcgccattctatccgctggaagatggaaccgctgga
gagcaactgcataaggctatgaagagatacgccctggttcctggaacaat
tgcttttacagatgcacatatcgaggtggacatcacttacgctgagtact
tcgaaatgtccgttcggttggcagaagctatgaaacgatatgggctgaat
acaaatcacagaatcgtcgtatgcagtgaaaactctcttcaattctttat
gccggtgttgggcgcgttatttatcggagttgcagttgcgcccgcgaacg acatttataatgaacgtgaattgctcaacagtatgggcatttcgcagcct
accgtggtgttcgtttccaaaaagggggttgcaaaaaattttgaacgtgca
aaaaaagctcccaatcatccaaaaaattattatcatggattctaaaacgg
attaccagggatttcagtcgatgtacacgttcgtcacatctcatctacct
cccggttttaatgaatacgattttgtgccagagtccttcgatagggacaa
gacaattgcactgatcatgaactcctctggatctactggtctgcctaaag
gtgtcgctctgcctcatagaactgcctgcgtgagattctcgcatgccaga
gatcctatttttggcaatcaaatcattccggatactgcgattttaagtgt
tgttccattccatcacggttttggaatgtttactacactcggatatttga
tatgtggatttcgagtcgtcttaatgtatagatttgaagaagagctgttt
ctgaggagccttcaggattacaagattcaaagtgcgctgctggtgccaac
cctattctccttcttcgccaaaagcactctgattgacaaatacgatttat
ctaatttacacgaaattgcttctggtggcgctcccctctctaaggaagtc
ggggaagcggttgccaagaggttccatctgccaggtatcaggcaaggata
tgggctcactgagactacatcagctattctgattacacccgaggggatg
ataaaccgggcgcggtcggtaaagttgttccatttttttgaagcgaaggtt
gtggatctggataccgggaaaacgctgggcgttaatcaaagaggcgaact
gtgtgtgagaggtcctatgattatgtccggttatgtaaacaatccggaag
cgaccaacgccttgattgacaaggatggatggctacattctggagacata
gcttactgggacgaagacgaacacttcttcatcgttgaccgcctgaagtc
tctgattaagtacaaaggctatcaggtggctcccgctgaattggaatcca
tcttgctccaacaccccaacatcttcgacgcaggtgtcgcaggtcttccc
gacgatgacgccggtgaacttcccgccgccgttgttgttttggagcacgg
aaagacgatgacggaaaaagagatcgtggattacgtcgccagtcaagtaa
caaccgcgaaaaagttgcgcggaggagttgtgtttgtggacgaagtaccg
aaaggtcttaccggaaaactcgacgcaagaaaaatcagagagatcctcat
aaaggccaagaagggcggaaagatcgccgtgtaatctcgagacgtagggt
acc.

EXAMPLE 1

Superior Anti-Bladder Carcinoma Activity by a Single Construct Containing DTA Genes Separately Expressed from H19 and P4 Promoters First, the anti-cancer therapeutic effect of the double promoter construct H19-DTA-P4-DTA was tested in vitro by determining its ability to lyse three different human bladder carcinoma lines, relative to the single promoter constructs. Anti-tumor activity was determined by measurement of inhibition of luciferase activity following co-transfection with LucSV40. T24P, Umuc3 and HT-1376 bladder cancer cell lines were co-transfected with H19-DTA, P4-DTA, or H19-DTA-P4-DTA at the indicated concentrations and 2 µg of LucSV40. Luciferase activity as an indicator of survival of the transfected cells was determined and compared to that of cells transfected with LucSV40 alone. H19-DTA and P4-DTA were able to drive the expression of the DTA gene and thus reduce luciferase activity in a dose-response manner.

Figure 2A:
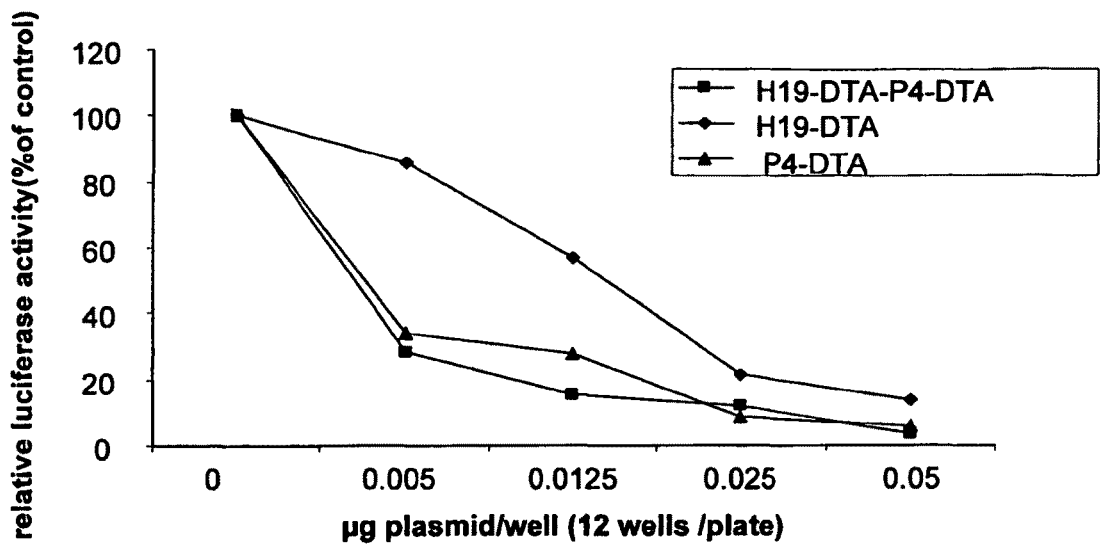
FIG. 2. Relative in-vitro activity of DTA-expressing constructs with H19, P4, and H19+P4 regulatory sequences in T24P cells. Human T24P cells were co-transfected with 2 µg of LucSV40 and the indicated concentrations of H19-DTA, P4-DTA, or H19-DTA-P4-DTA. A. Luciferase activity at various dosages compared to cells transfected with LucSV40 alone. B. Additional repetition of the experiment described in (A). C. Bar graph of 0.005 µg data. Y axis (for A-C): luciferase activity (% of control). X axis (for A-B): µg plasmid/well. Error bars in this Figure and throughout the Figures reflect 1 standard error of the mean.
Figure 2B:
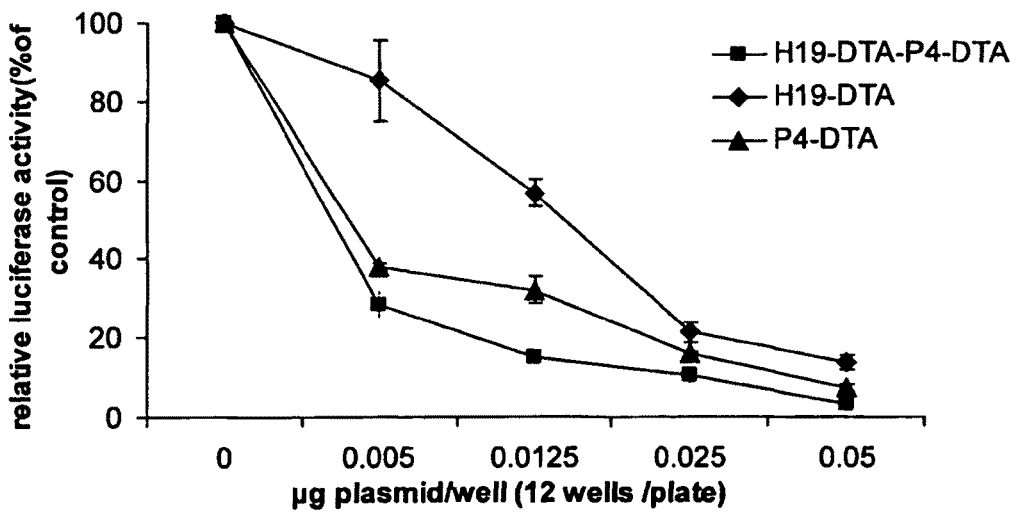
Figure 2C:
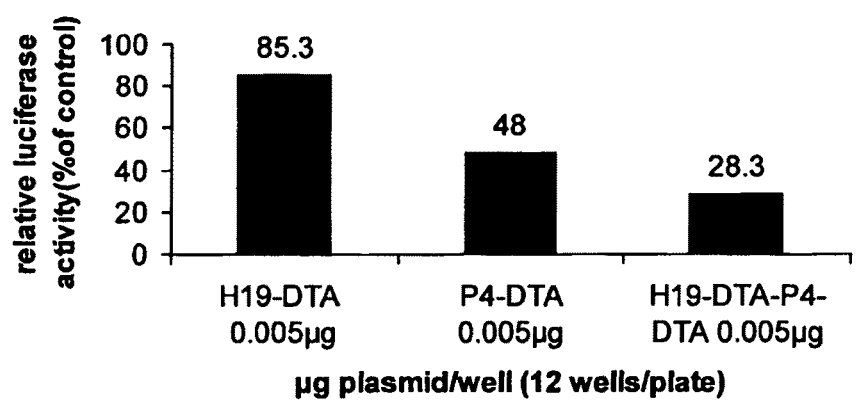
Figure 3A:
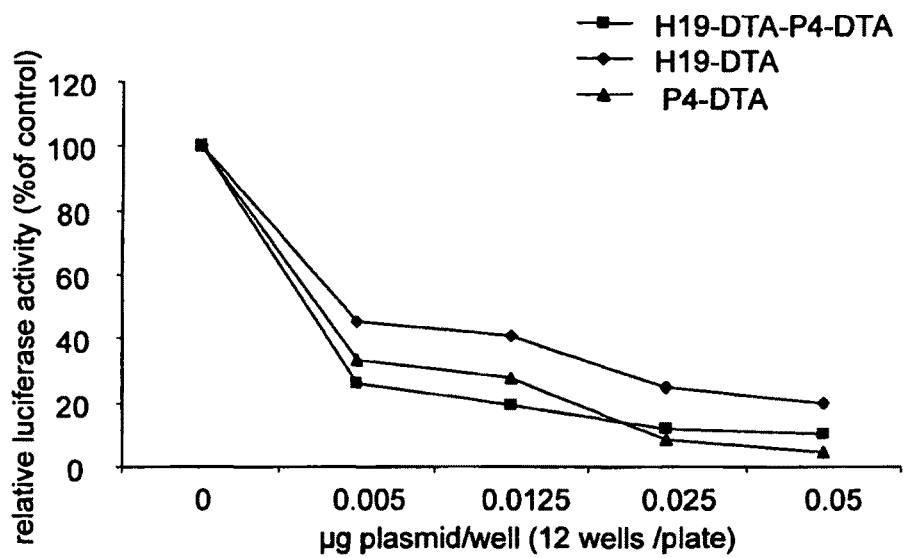
FIG. 3. Relative activity of DTA-expressing constructs in UMUC3 cells. Experiment was performed as described for FIG. 2; axes are same as FIG. 2. A. Luciferase activity at various dosages compared to cells transfected with LucSV40 alone. B. Additional repetition of the experiment described in (A). C. Bar graph of 0.005 µg data.
Figure 3B:
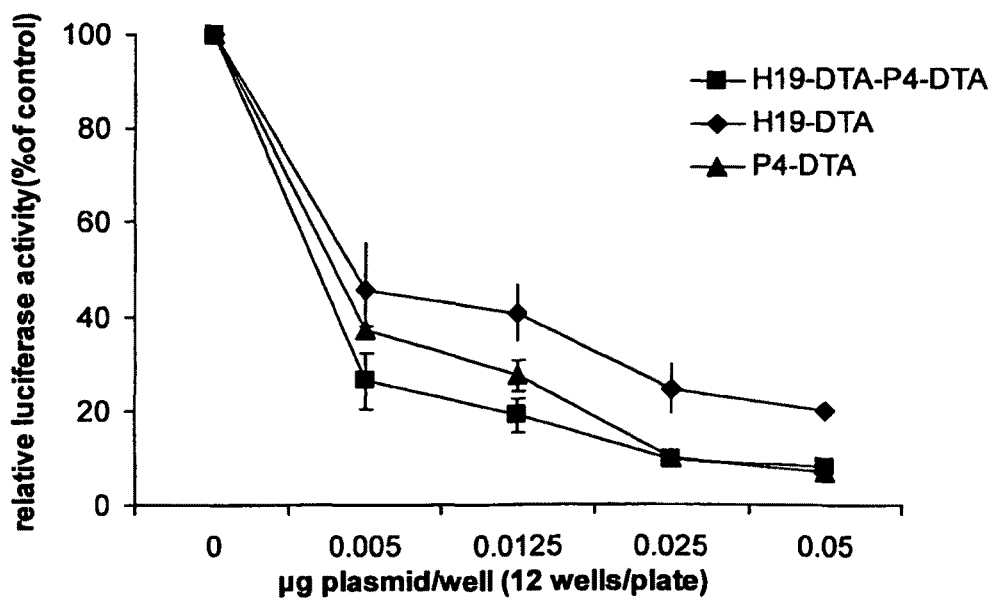
Figure 3C:
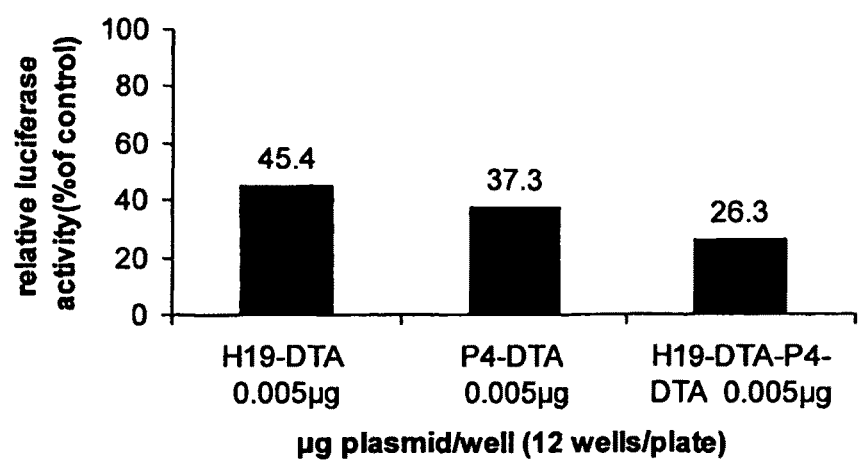
Figure 40A:
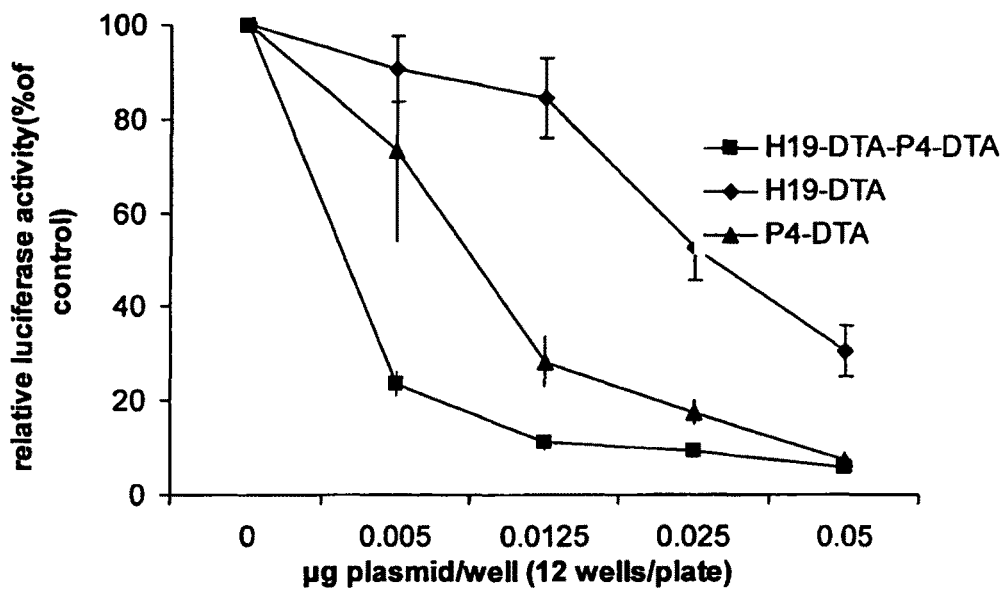
Figure 40B:
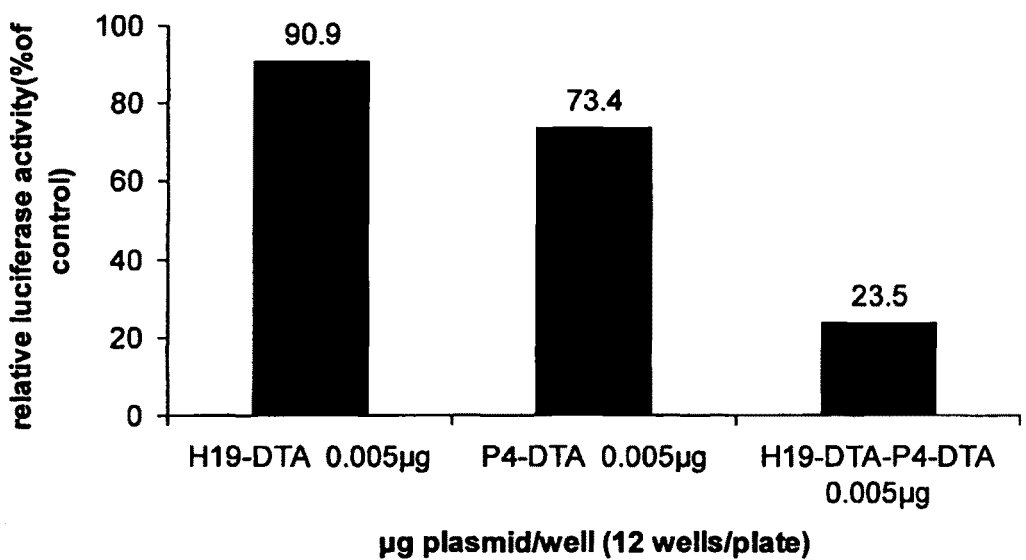

H19-DTA-P4-DTA, however, exhibited far superior efficiency in lysing the cancer cell lines, relative to each of the single promoter constructs, in T24P cells (FIGS. 2A-C). Very similar results were obtained when the experiment was repeated with UMUC3 cells (FIGS. 3A-C) and HT-1376 (FIGS. 40A-B).

Thus, a DTA expression vector, carrying on the same construct two separate genes expressing the DTA toxin from H19 and P4, exhibited significantly superior ability to lyse various human bladder cancer cell lines, relative to expression vectors carrying either gene alone.

EXAMPLE 2

Figure 4A:
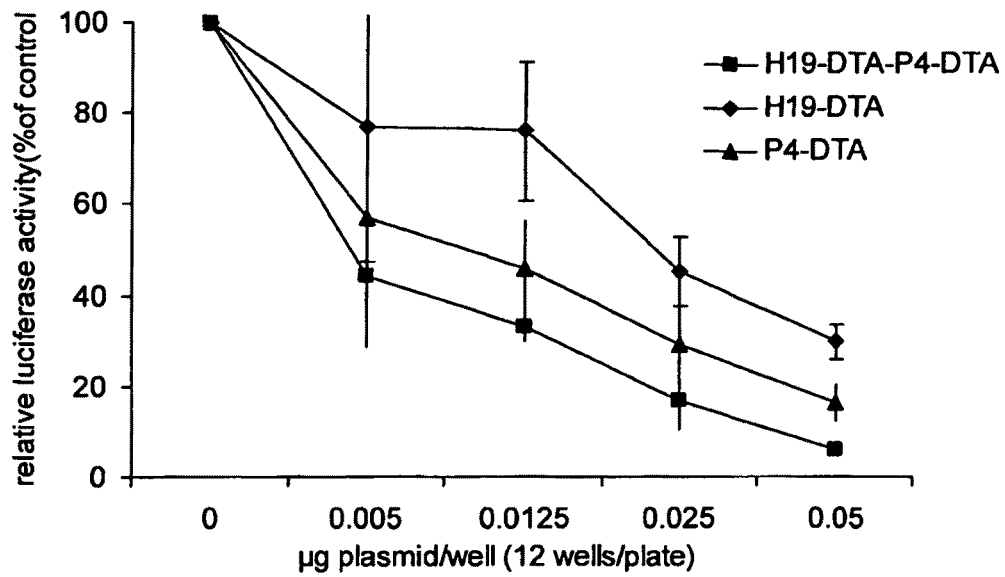
FIG. 4. Relative activity of DTA-expressing constructs in Hep3B cells. Experiment was performed as described for FIG. 2; axes are same as FIG. 2. A. Luciferase activity at various dosages compared to cells transfected with LucSV40 alone. B. Bar graph of 0.005 µg data.
Figure 4B:
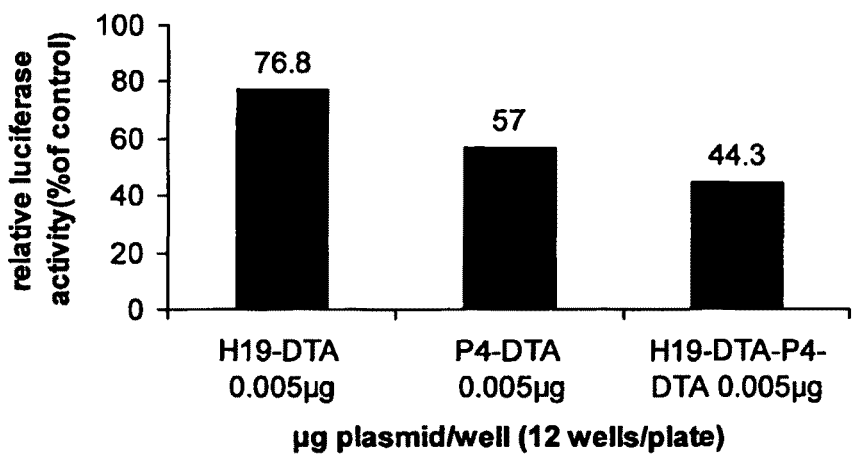

Superior Anti-Liver Carcinoma Activity by a Single Construct Containing DTA Genes Separately Expressed from H19 and P4 Promoters The anti-cancer therapeutic effect of the constructs described in Example 1 was tested in vitro on Hep3B human liver cancer (hepatocellular carcinoma) cells. As seen with the bladder carcinoma cell lines, the double promoter construct H19-DTA-P4-DTA exhibited far superior efficiency in lysing the cancer cell lines, relative to each of the single promoter constructs (FIGS. 4A-B).

Thus, H19-DTA-P4-DTA double promoter expression vectors of the present invention exhibit significantly superior ability to lyse liver carcinoma cells, relative to either gene alone.

EXAMPLE 3

Figure 5A:
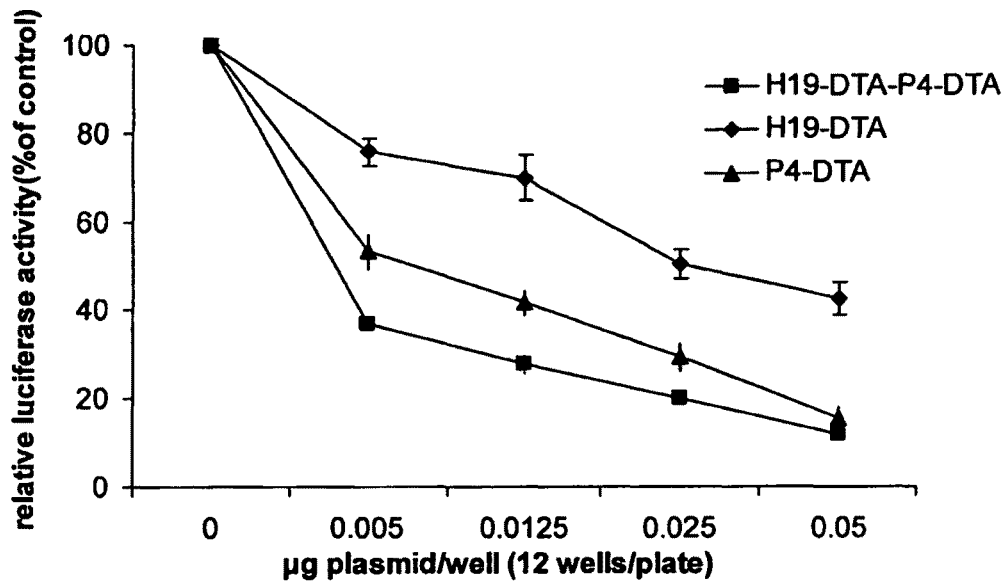
FIG. 5. Relative activity of DTA-expressing constructs in ES-2 cells. Experiment was performed as described for FIG. 2; axes are same as FIG. 2. A. Luciferase activity at various dosages compared to cells transfected with LucSV40 alone. B. Bar graph of 0.005 µg data.
Figure 5B:
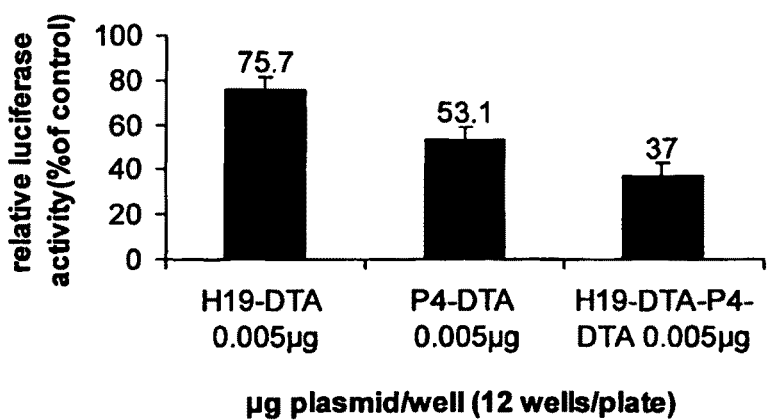

Superior Anti-Ovarian Carcinoma Activity by a Single Construct Containing DTA Genes Separately Expressed from H19 and P4 Promoters The anti-cancer therapeutic effect of the constructs described in Example 1 was tested in vitro on ES-2 human ovarian cancer (clear cell carcinoma) cells. As seen with the bladder carcinoma cell lines, the double promoter construct H19-DTA-P4-DTA exhibited far superior efficiency in lysing the cancer cell lines, relative to each of the single promoter constructs (FIGS. 5A-B).

Thus, H19-DTA-P4-DTA double promoter expression vectors of the present invention exhibit significantly superior ability to lyse ovarian carcinoma cells, relative to either gene alone.

EXAMPLE 4

Figure 6A:
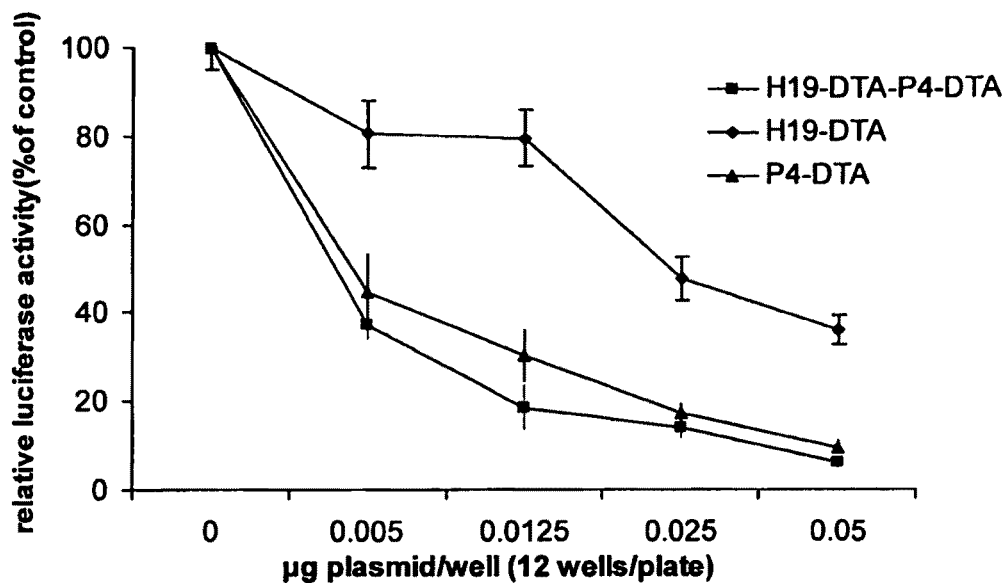
FIG. 6. Relative activity of DTA-expressing constructs in PC-1 cells. Experiment was performed as described for FIG. 2; axes are same as FIG. 2. A. Luciferase activity at various dosages compared to cells transfected with LucSV40 alone. B. Bar graph of 0.005 µg data.
Figure 6B:
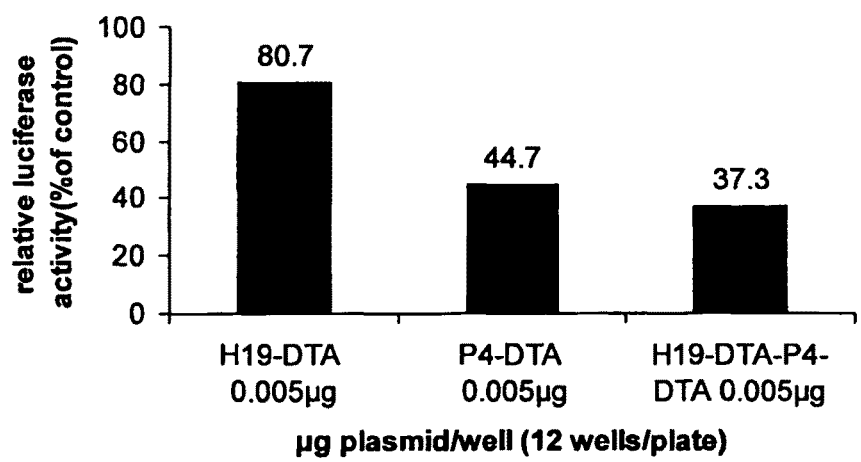
Figure 7A:
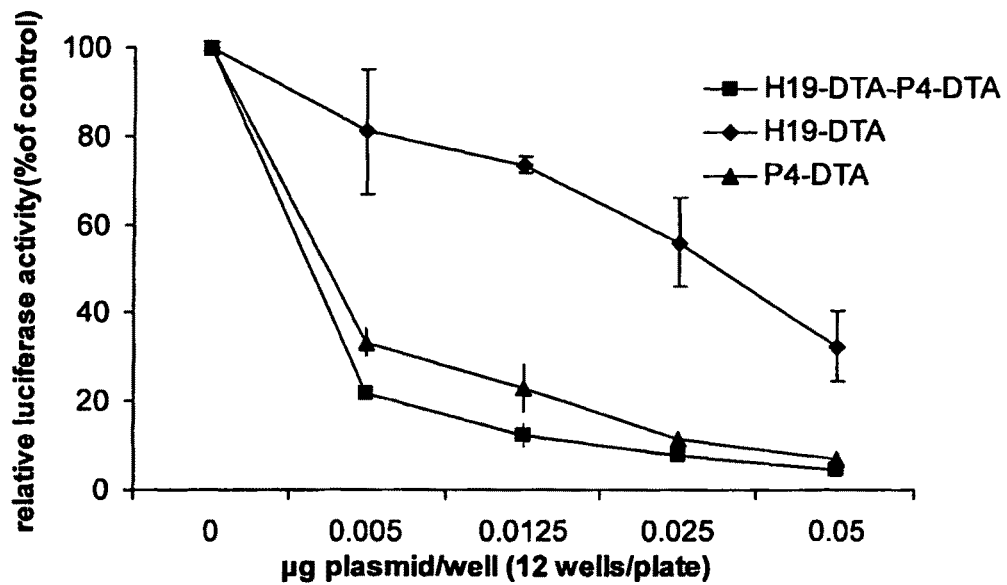
FIG. 7. Relative activity of DTA-expressing constructs in CRL-1469 cells. Experiment was performed as described for FIG. 2; axes are same as FIG. 2. A. Luciferase activity at various dosages compared to cells transfected with LucSV40 alone. B. Bar graph of 0.005 µg data.
Figure 7B:
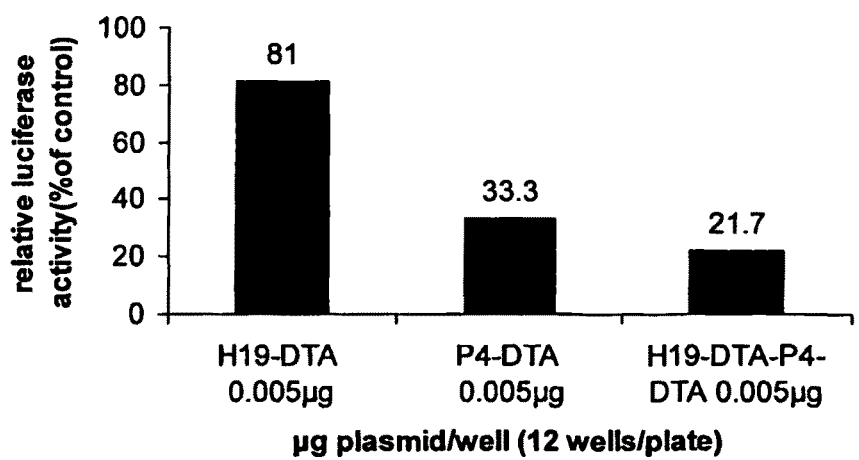

Superior Anti-Pancreatic Carcinoma Activity by a Single Construct Containing DTA Genes Separately Expressed from H19 and P4 Promoters The anti-cancer therapeutic effect of the constructs described in Example 1 was tested in vitro on PC-1 hamster pancreatic cancer (pancreatic ductal carcinoma) and CRL-1469 human pancreatic cancer (epithelioid carcinoma) cells. As seen with the bladder carcinoma cell lines, the double promoter construct H19-DTA-P4-DTA exhibited far superior efficiency in lysing the hamster (FIGS. 6A-B) and human (FIGS. 7A-B) pancreatic cancer cell lines, relative to each of the single promoter constructs.

Thus, H19-DTA-P4-DTA double promoter expression vectors of the present invention exhibit significantly superior ability to lyse pancreatic carcinoma cells, relative to either gene alone.

Overall, H19-DTA-P4-DTA expression vectors consistently exhibited significantly superior ability when tested against a broad spectrum of tumor cells, relative to expression vectors carrying either gene alone. The consistency of these results across each of these cancer cell lines demonstrates the superior ability of H19-DTA-P4-DTA constructs of the present invention against cancer in general.

EXAMPLE 5

Figure 9A:
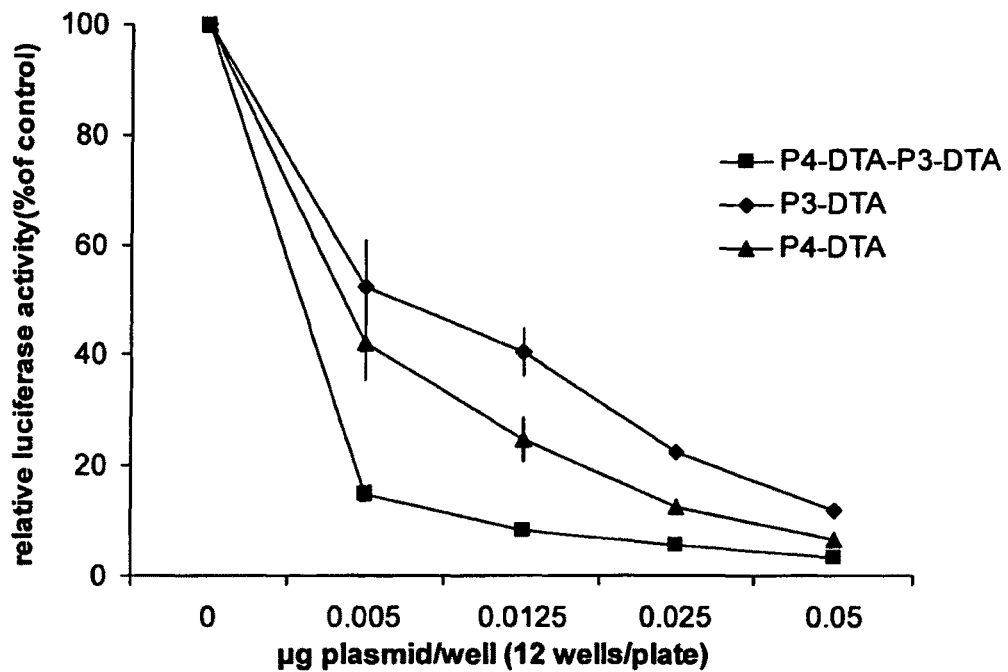
Figure 9B:
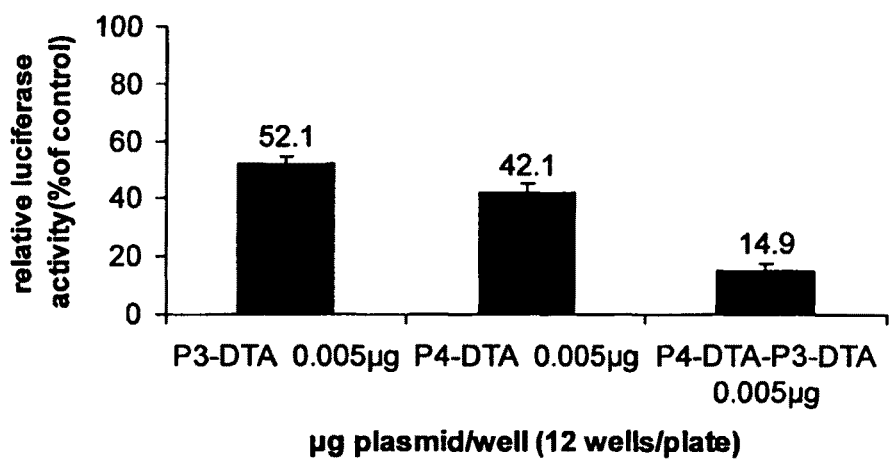
Figure 10A:
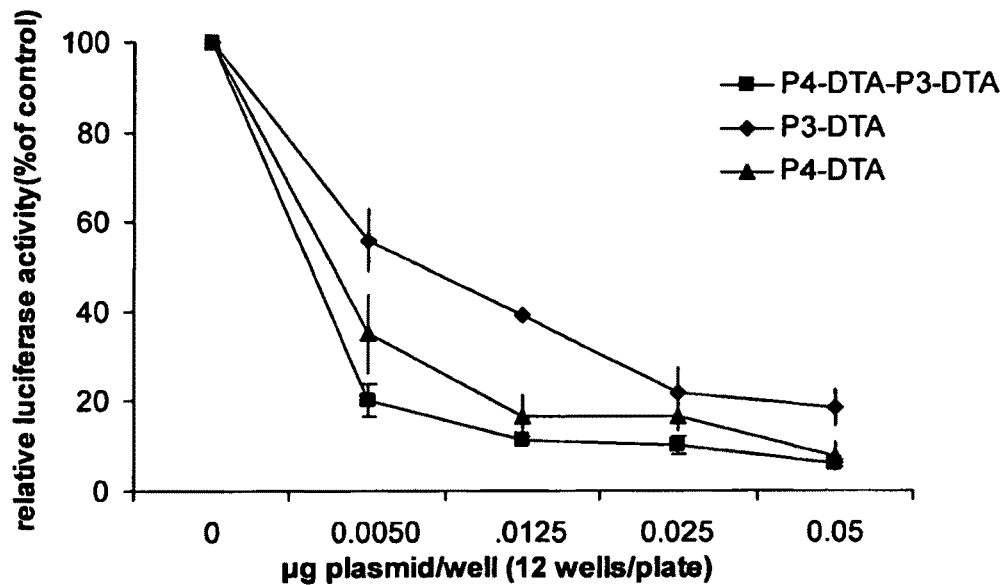
Figure 10B:
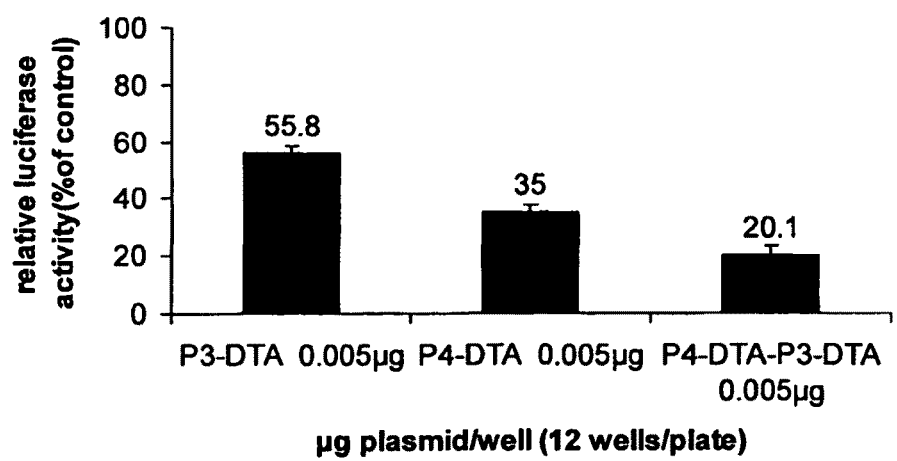
Figure 11A:
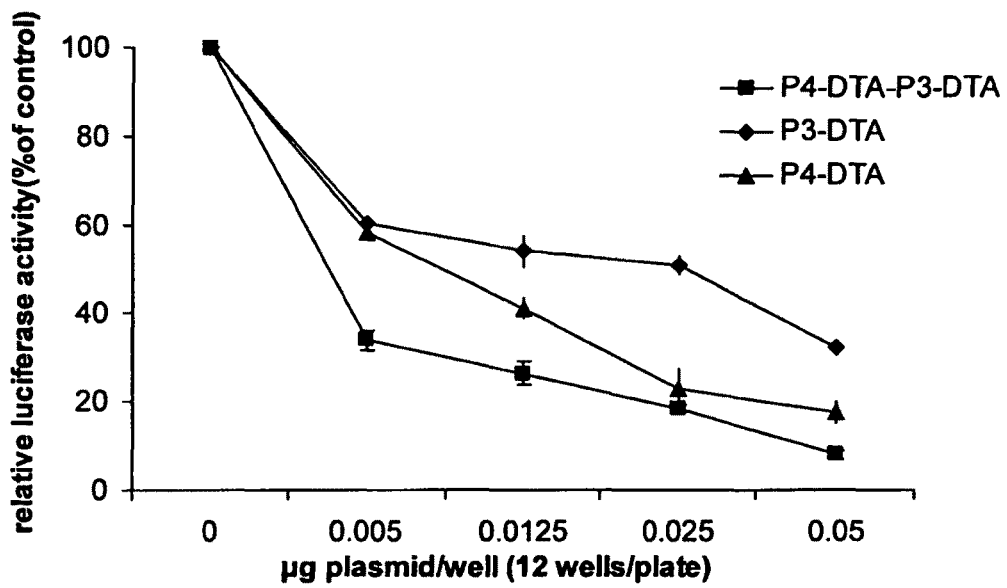
Figure 11B:
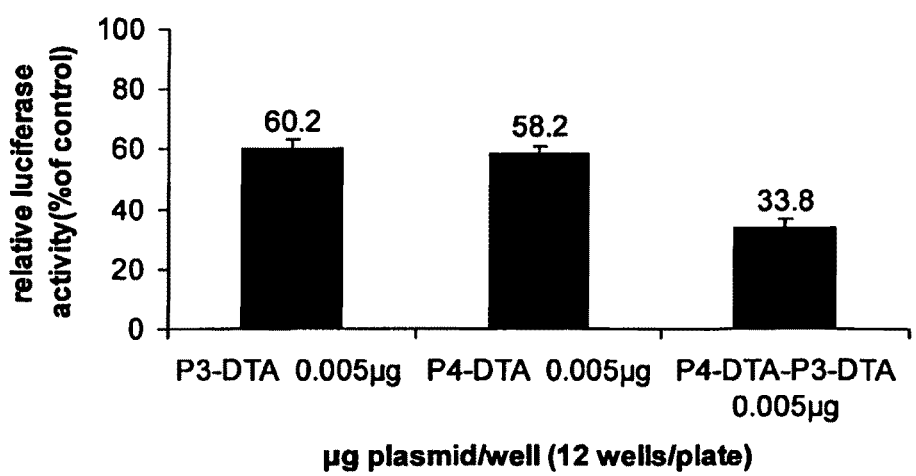
Figure 13A:
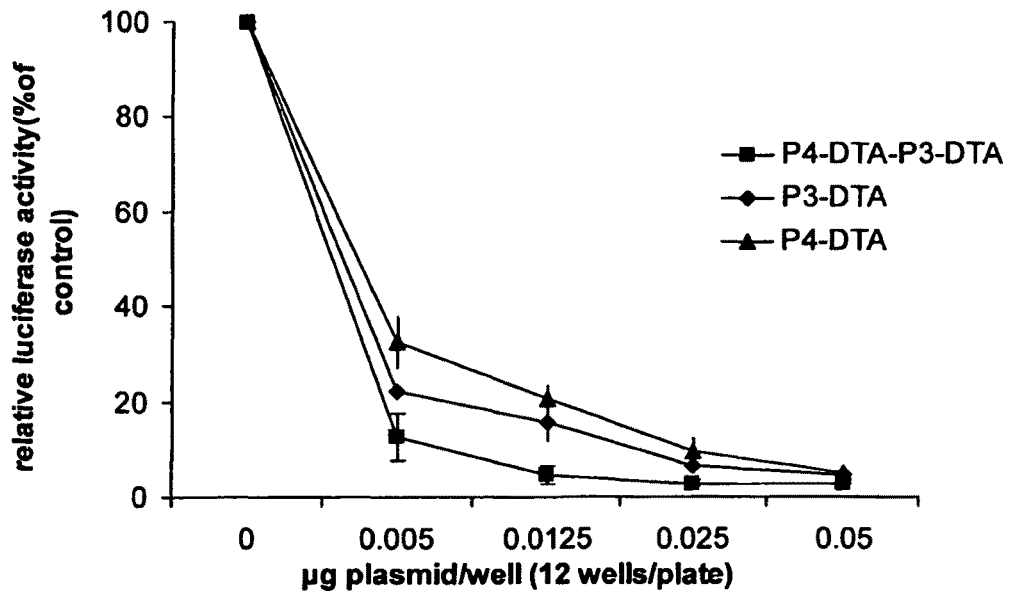
Figure 13B:
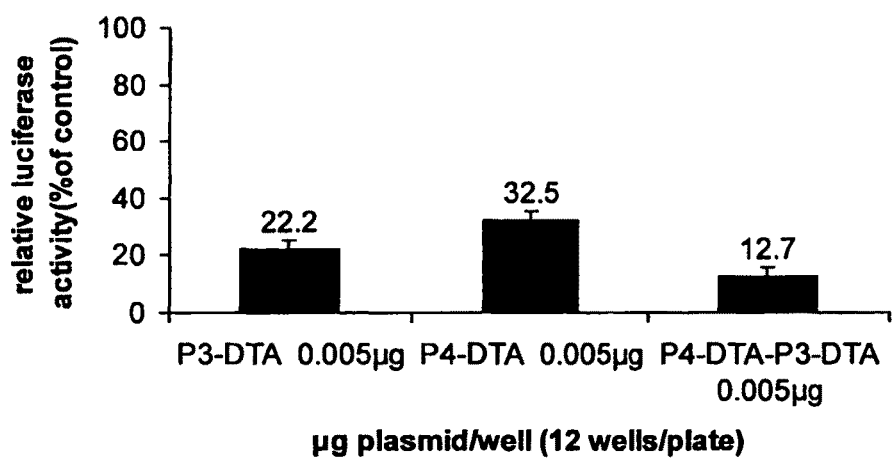

Superior Activity by a Single Construct Containing Separate P3- and P4-Driven DTA Genes Against Six Different Carcinoma Types Next, the activity of the double promoter expression construct, expressing DTA from the IGF-II-P3 and IGF-II-P4 promoters, P4-DTA-P3-DTA, was tested against two different human bladder carcinoma cell lines (T24P and HT-1376), compared to the corresponding single-promoter constructs. Cells were co-transfected with 2 μg of LucSV40 and P3-DTA, P4-DTA, or P4-DTA-P3-DTA at the concentrations indicated in the figures. Luciferase activity was determined and compared to that of cells transfected with LucSV40 alone. P3-DTA and P4-DTA were able to drive the expression of the DTA gene and thus reduce luciferase activity in a dose-response manner in both cell lines. The double promoter construct P4-DTA-P3-DTA however, exhibited superior efficiency in lysing the cancer cell lines, relative to each of the single promoter constructs, in T24P cells (FIGS. 8A-B) and HT-1376 cells (FIGS. 9A-B). Very similar results were obtained as well in Hep3B human liver carcinoma cells (FIGS. 10A-B). Very similar results were obtained as well in ES-2 human ovarian carcinoma cells (FIGS. 11A-B). Very similar results were obtained as well in PC-1 hamster pancreatic carcinoma cells (FIGS. 12A-B) and CRL-1469 human pancreatic carcinoma cells (FIGS. 13A-B).

Thus, DTA expression vectors, carrying on the same construct two separate genes expressing the DTA toxin from IGF-II-P3 and IGF-II-P4 promoters, consistently exhibited significantly superior ability when tested against six different cancer cell lines, relative to expression vectors carrying either gene alone. The consistency of these results across a broad spectrum of tumor cells demonstrates the superior ability of P4-DTA-P3-DTA constructs of the present invention against cancers in general.

EXAMPLE 6

Superior Activity by a Single Construct Containing Separate H19- and P3-Driven DTA Genes Against Bladder Carcinoma Cells Next, the ability of the double promoter expression construct, H19-DTA-P3-DTA was tested against the human bladder carcinoma cell lines T24P, compared to the corresponding single-promoter constructs.

The therapeutic effect of the constructs was tested in vitro by determining their ability to lyse human bladder cancer cell lines, as determined by co-transfection with LucSV40 and measurement of inhibition of luciferase activity. The human bladder cancer cell line T24P was co-transfected with 2 μg of LucSV40 and H19-DTA, P3-DTA, or H19-DTA-P3-DTA at the concentrations indicated in the figures. Luciferase activity was determined and compared to that of cells transfected with LucSV40 alone. H19-DTA and P3-DTA were able to drive the expression of the DTA gene and thus reduce luciferase activity in a dose-response manner in all the three cell lines.

Figure 14A:
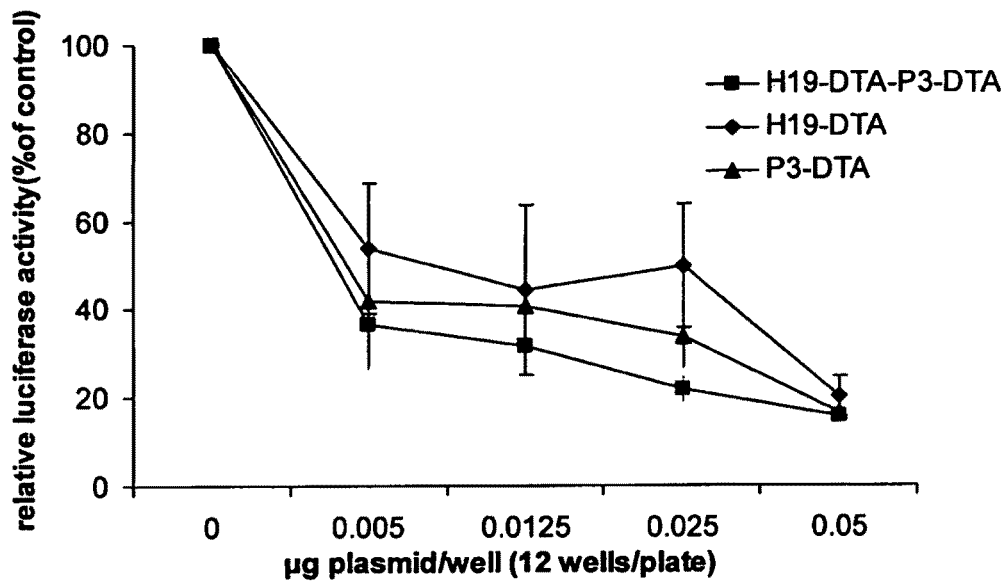
Figure 14B:
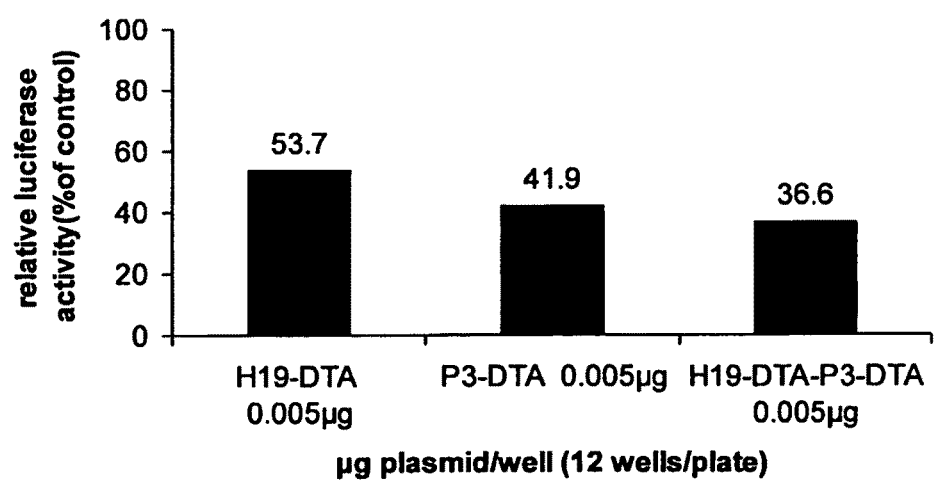

The double promoter construct H19-DTA-P3-DTA, however, exhibited superior efficiency in lysing the cancer cell lines, relative to each of the single promoter constructs (FIGS. 14A-B).

Thus, DTA expression vectors, carrying on the same construct two separate genes expressing the DTA toxin from H19 and IGF-II-P3 promoters, exhibited significantly superior ability when tested against bladder carcinoma cells, relative to expression vectors carrying either gene alone.

EXAMPLE 7

Figure 15A:
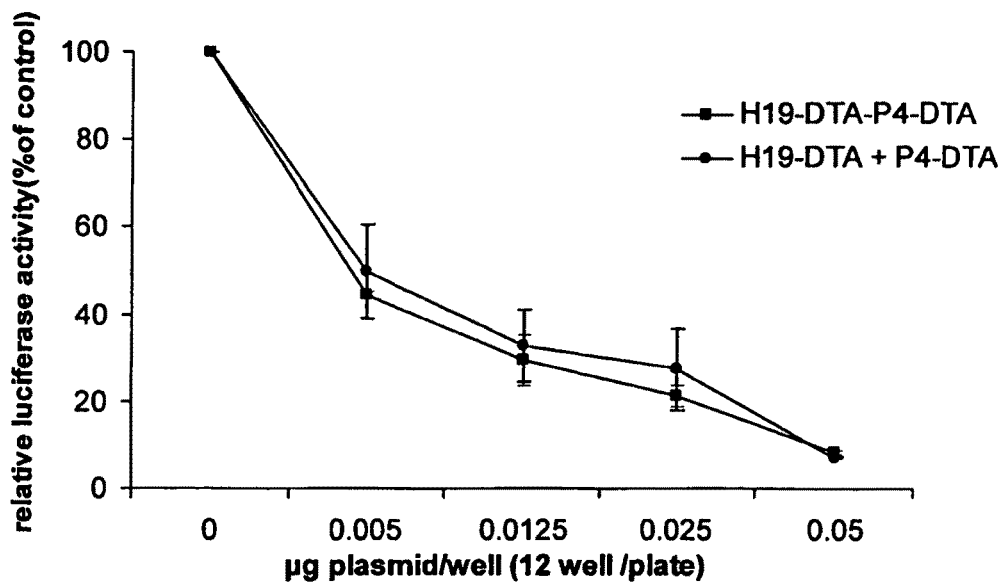
Figure 15B:
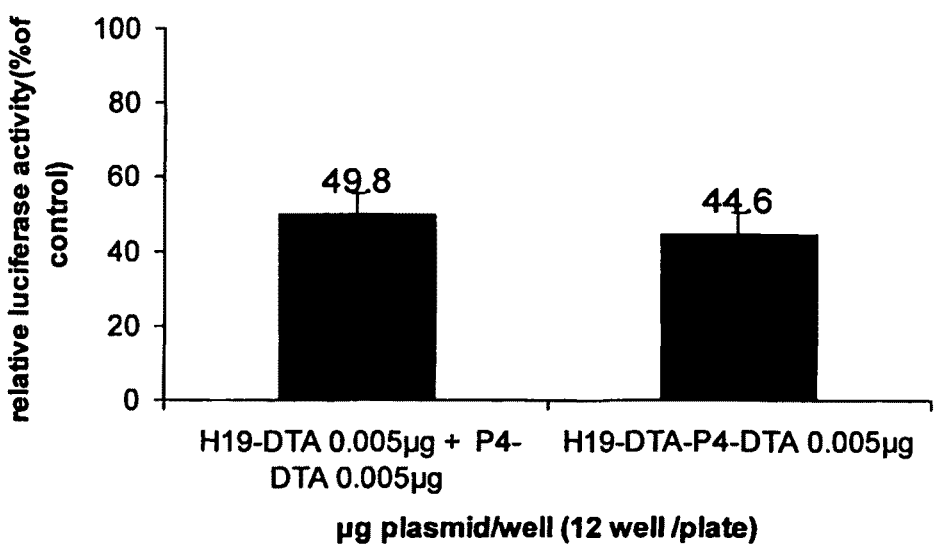
Figure 16A:
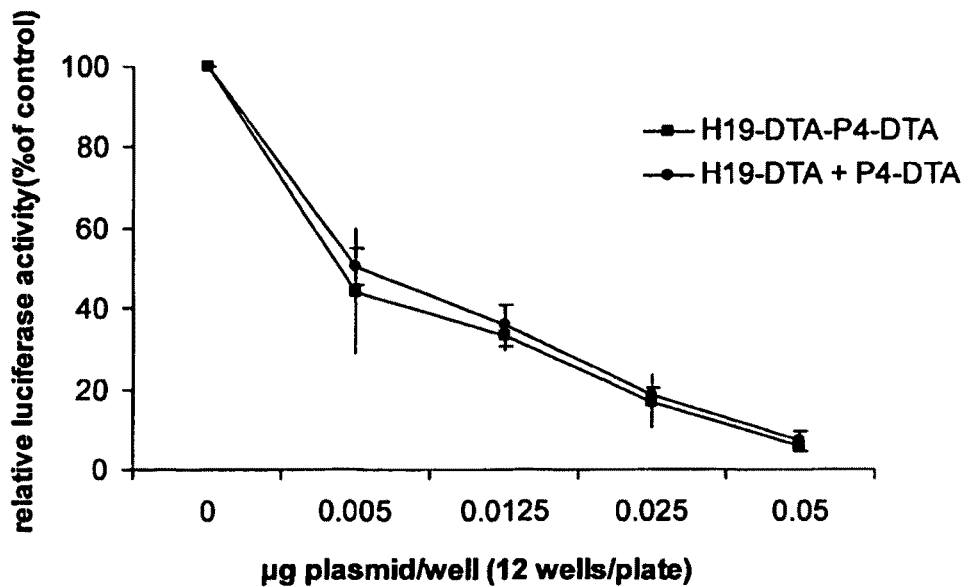
Figure 16B:
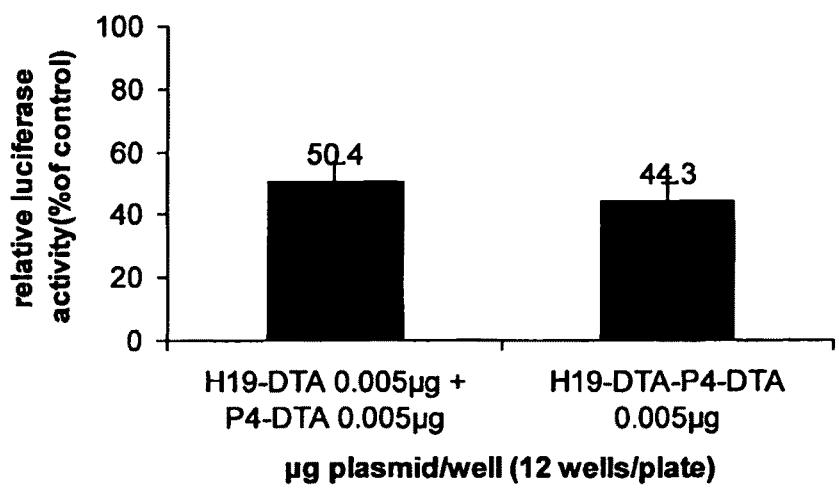
Figure 23A:
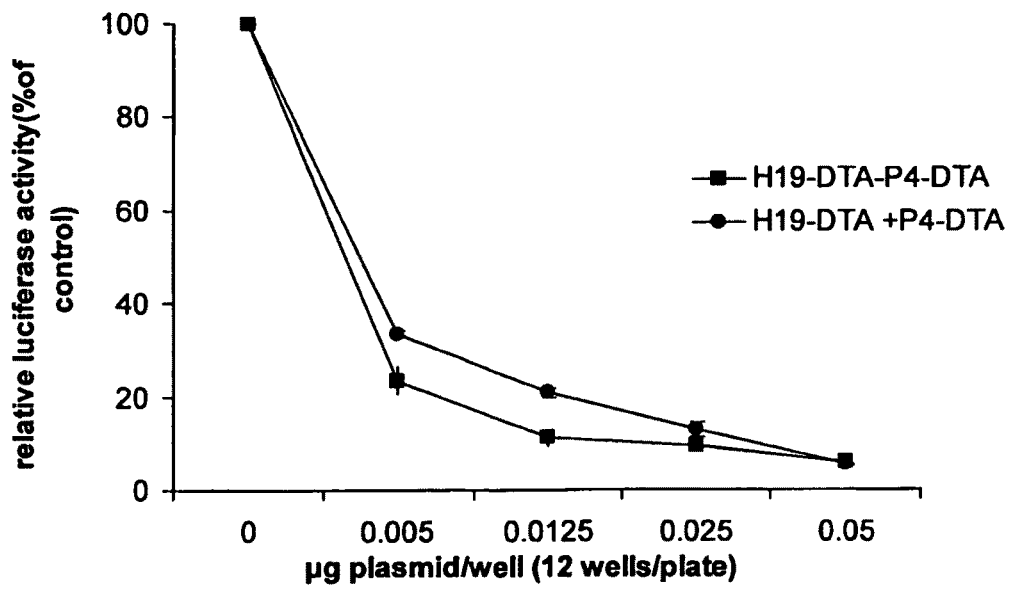
Figure 23B:
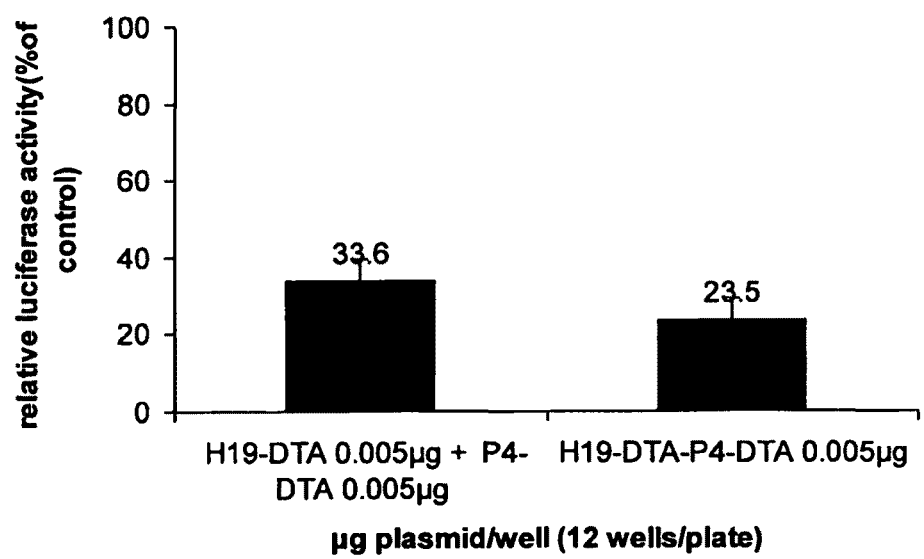

DTA Genes Separately Expressed from H19 and P4 Promoters Exhibit Greater-Than-Additive Anti-Cancer Activity when Present on a Single Construct Next, the presence of a greater-than-additive anti-cancer effect of the double promoter construct H19-DTA-P4-DTA was tested in the human bladder cancer cell lines T24P and HT-1376, the human ovarian cancer cell line ES-2, the human liver cancer cell line Hep3B, the hamster pancreatic cell line PC-1, and the human pancreatic cancer cell line CRL-1469. T24P, ES-2, Hep3B, PC-1 and CRL-1469 were co-transfected with 2 µg of LucSV40 and either (a) the concentrations indicated in the figures of single-promoter constructs H19-DTA+P4-DTA in combination, or (b) the same amount of H19-DTA-P4-DTA as for one of the single-promoter constructs. The total amount of DNA co-transfected in samples receiving both single promoter constructs was therefore twice than the cells transfected with H19-DTA-P4-DTA. Luciferase activity was determined and compared to that of cells transfected with LucSV40 alone. Double-promoter construct H19-DTA-P4-DTA exhibited superior efficiency in lysing the cancer cell lines, relative to the combined activity of both single promoter constructs (H19-DTA+P4-DTA), in T24P cells (FIGS. 15A-B). Very similar results were obtained in Hep3B human liver cancer cells (FIGS. 16A-B), ES-2 human ovarian cancer cells (FIGS. 17A-B), PC-1 hamster pancreatic cells (FIGS. 18A-B), CRL-1469 human pancreatic cancer cells (FIGS. 19A-B) and HT-1376 cells (FIG. 23A-B).

Thus, H19-driven and IGF-II P4-driven DTA-encoding genes present on a single expression vector exhibited greater-than-additive anti-cancer activity relative to expression vectors carrying either gene alone when tested against a broad spectrum of tumor cells. The consistency of these results across each of these cancer cell lines demonstrates the superior ability of H19/P4 constructs of the present invention against cancer in general.

EXAMPLE 8

Figure 20A:
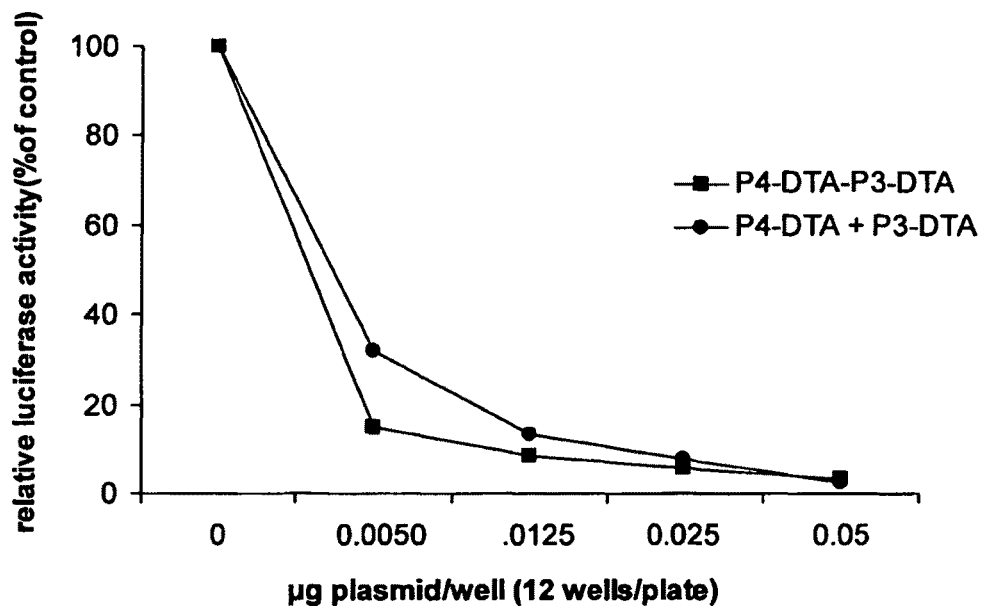
Figure 20B:
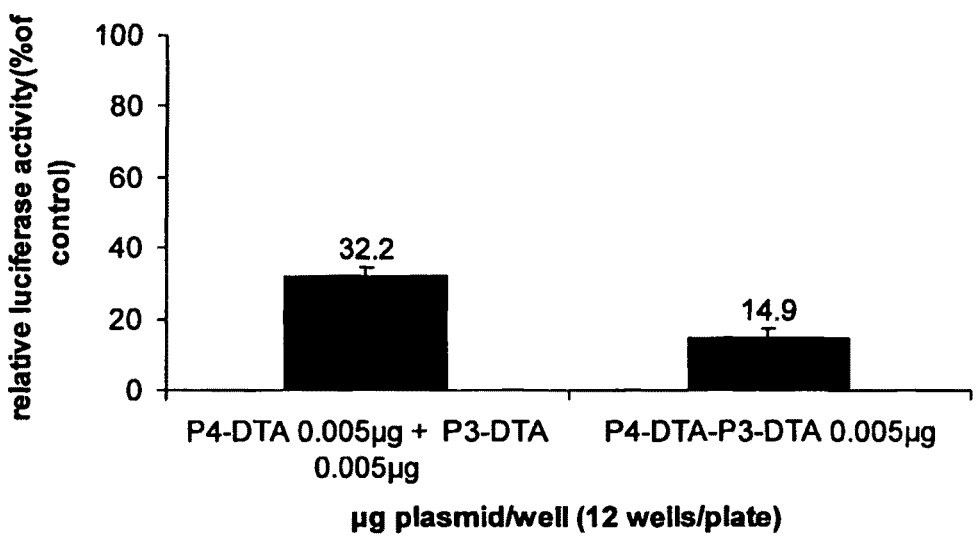
Figure 24A:
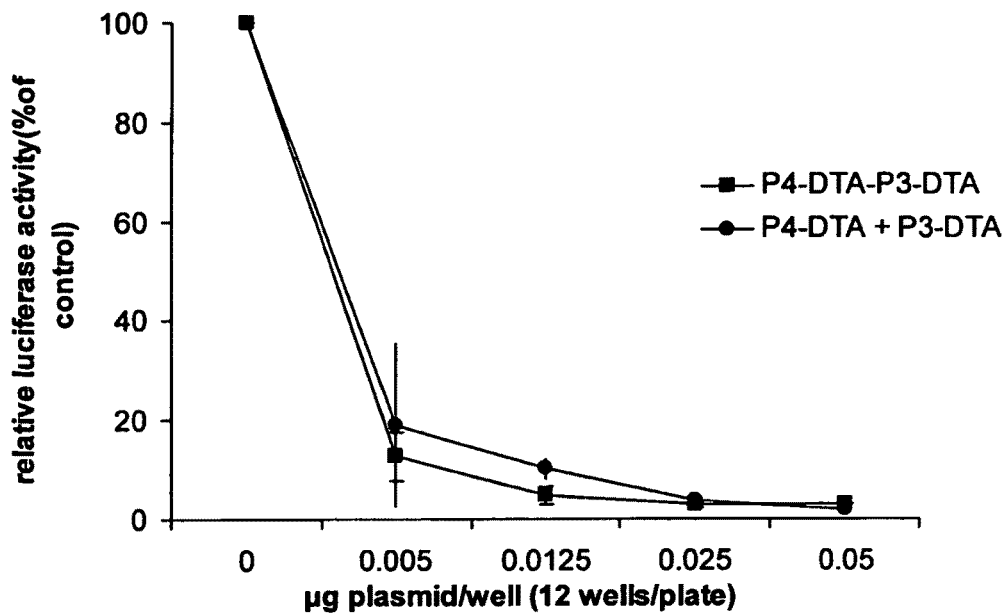
Figure 24B:
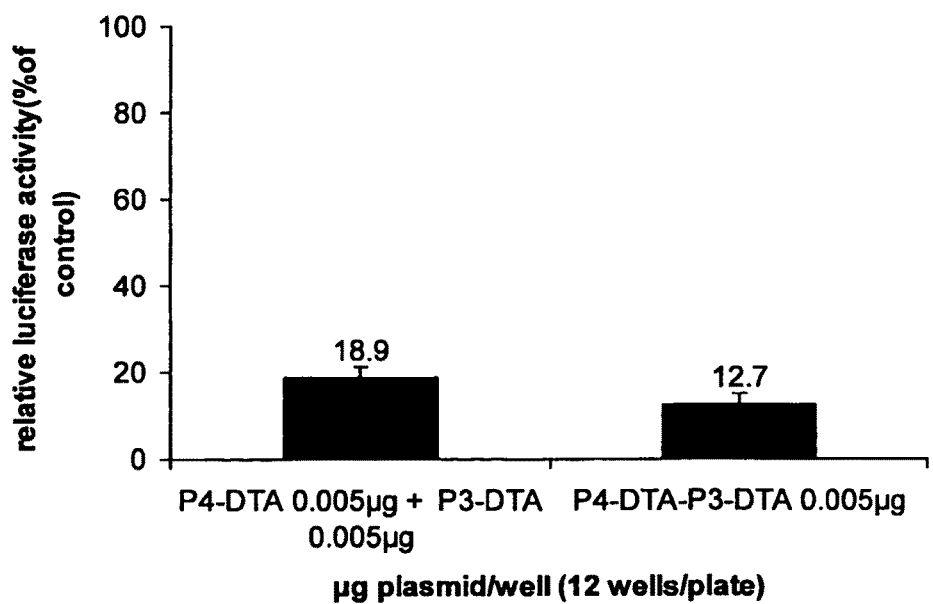

DTA Genes Separately Expressed from P3 and P4 Promoters Exhibit Greater-Than-Additive Anti-Cancer Activity when Present on a Single Construct Next, the presence of a greater-than-additive anti-cancer effect of the P4-DTA-P3-DTA double promoter plasmids was tested in HT-1376, ES-2, Hep3B, PC-1, and CRL-1469 cells, exactly as described in the previous Example. The double promoter construct P4-DTA-P3-DTA exhibited superior efficiency in lysing the cancer cell lines, relative to the combined activity of both single promoter constructs (P3-DTA+P4-DTA), in HT-1376 cells (FIGS. 20A-B). Very similar results were obtained in ES-2 cells (FIGS. 21A-B), Hep3B cells (FIG. 22) and CRL-1469 cells (FIGS. 24A-B).

Thus, IGF-II P3-driven and IGF-II P4-driven DTA-encoding genes present on a single expression vector exhibited greater-than-additive anti-cancer activity relative to expression vectors carrying either gene alone when tested against a broad spectrum of tumor cells. The consistency of these results across each of these cancer cell lines demonstrates the superior ability of P3-DTA-P4-DTA constructs of the present invention against cancer in general.

EXAMPLE 9

Bladder Carcinoma Animal Model

The Heterotopic Model for Subcutaneous Bladder Tumors
$2 \times 10^6$ T24P or $3 \times 10^6$ HT-1376 human bladder carcinoma cells in phosphate-buffered saline were subcutaneously injected into the dorsa of 6-7 weeks old nude female mice in order to establish heterotopic bladder tumors. 10 days after inoculation, measurable tumors appeared that were treated with the H19-DTA-P4-DTA, P4-DTA-P3-DTA and H19-DTA-P3-DTA expression vectors.

Treatment of the Heterotopic Subcutaneous Tumors
Animals were separated into groups of the same size (n=6). 3 injections of 25 µg/tumor of the expression vectors (P4-DTA-P3-DTA, H19-DTA-P4-DTA, or H19-DTA-P3-DTA respectively) or the control vector (P4-Luc-P3-Luc, H19-Luc-P4-Luc, or H19-Luc-P3-Luc respectively) were administered into each tumor. At each time point, tumor dimensions were measured using a caliper, and tumor volume was calculated according to the formula width$^2 \times$length$\times 0.5$. Animals were sacrificed 3 days after the last injection, tumors were excised, and their ex-vivo weight and volume were measured.

EXAMPLE 10

The H19-DTA-P4-DTA Construct Exhibits Greater-Than-Additive Anti-Cancer Activity in Several in Vivo Bladder Cancer Models T24P Results
The anti-cancer therapeutic activity of H19-DTA-P4-DTA was tested in an in vivo bladder cancer model. T24P human bladder carcinoma cells were subcutaneously injected into the dorsa of athymic female mice in order to model heterotopic bladder cancer. 10 days later, mice developed measurable heterotopic tumors. The therapeutic potency of the vectors was tested by directly administering 3 injections of 25 µg of the expression vectors or the control vector (H19-Luc, P4-Luc, and H19-Luc-P4-Luc, expressing luciferase under the H19 promoter, P4 promoter or both promoters, respectively) into each heterotopic bladder cancer tumor. Tumor size was determined and in-vivo fold increase of the tumor size was calculated at the end of each treatment.

Three injections of H19-DTA (FIG. 25) and P4-DTA (FIG. 26) at two-day intervals were able to inhibit tumor development by at least 49% and 57%, respectively compared to H19-Luc and P4-Luc treatment, respectively. However, three injections of the double promoter plasmid H19-DTA-P4-DTA at two-day intervals inhibited tumor development by at least 70% compared to H19-Luc-P4-Luc treatment (FIG. 27). The double promoter construct thus exhibited enhanced ability to inhibit tumor development in vivo, compared to each of the single-promoter constructs (H19-DTA and P4-DTA).

To confirm the difference between the H19-DTA-P4-DTA and H19-Luc-P4-Luc groups, tumors were excised and their weight and volume determined ex vivo. Mice treated with H19-DTA-P4-DTA exhibited at least a 61% reduction of the ex-vivo tumor volume (FIG. 28) and at least a 54% reduction of ex-vivo tumor weight (FIG. 29) compared to H19-Luc-P4-Luc treatment.

To test whether the in vivo anti-cancer activity of H19-DTA-P4-DTA was greater-than-additive, an additional group of T24P tumor-containing mice were treated with three injections of 25 µg each of single-promoter constructs H19-DTA+ P4-DTA in combination. The total amount of DNA co-transfected administered was therefore twice than the H19-DTA-P4-DTA group. As can be seen in FIG. 30, tumor development in mice receiving both H19-DTA and P4-DTA plasmids was inhibited by 63% compared to combined H19-Luc+P4-Luc treated mice. An enhanced effect was observed in mice treated with the double-promoter construct H19-DTA-P4-DTA, wherein tumor development was inhibited by 70% compared to the mice treated with the control plasmid H19-Luc-P4-Luc (FIG. 27). Thus, the H19-DTA-P4-DTA vector exhibits greater-than-additive in vivo anti-cancer activity.

FIG. 31 summarizes all the T24P bladder cancer model data. H19-DTA-P4-DTA clearly exhibits activity superior to each of the single promoter plasmids alone and also superior to their combined activity.

HT-1376 Results

The therapeutic ability of H19-DTA-P4-DTA was tested in another bladder cancer, model, HT-1376. Experiments were conducted as described for the T24P model. Mice containing HT-1376 tumors were administered 25 µg each of H19-DTA and P4-DTA in combination or 25 µg of H19-DTA-P4-DTA. Administration of H19-DTA and P4-DTA in combination inhibited tumor development by at least 64.5% compared to combined H19-Luc+P4-Luc treated tumors (FIG. 32), while H19-DTA-P4-DTA inhibited tumor development by at least 67% compared to H19-Luc-P4-Luc treatment (FIG. 33). Thus, H19-DTA-P4-DTA exhibited enhanced anti-tumor activity, compared to the combined activity of the single-promoter constructs.

EXAMPLE 11

The P4-DTA-P3-DTA Construct Exhibits Greater-Than-Additive Anti-Cancer Activity in an in Vivo Bladder Cancer Model Next, the anti-cancer therapeutic activity of P4-DTA-P3-DTA was tested in the T24P in vivo bladder cancer model described hereinabove in Examples 9-10. Experiments were performed as described above.

Three injections of P3-DTA at two-day intervals were able to inhibit the tumor growth by at least 50.5% compared to P3-Luc treatment (FIG. 34), while P4-DTA administered in the same manner inhibited tumor growth by at least 57% compared to P4-Luc treatment (FIG. 35). In contrast, 3 injections of the double promoter plasmid P4-DTA-P3-DTA at two-day intervals inhibited tumor development by at least 70% compared to P3-Luc/P4-Luc treatment (FIG. 36). Thus, P4-DTA-P3-DTA exhibited enhanced anti-tumor activity, compared to each of the single-promoter constructs (P3-DTA and P4-DTA).

To test whether the in vivo anti-cancer activity of P4-DTA-P3-DTA was greater-than-additive, an additional group of T24P tumor-containing mice was treated with 3 injections of 25 µg each of single-promoter constructs P3-DTA+P4-DTA in combination. The total amount of DNA co-transfected administered was therefore twice than the P4-DTA-P3-DTA group. Tumor development was inhibited by at least 63.3% compared to combined P3-Luc+P4-Luc treatment (FIG. 37), an amount less than the 70% observed with P4-DTA-P3-DTA treatment (FIG. 36). Thus, the P4-DTA-P3-DTA vector exhibits greater-than-additive in vivo anti-cancer activity.

EXAMPLE 12

In Vivo Tumor Growth Inhibition by H19-DTA-P3-DTA Expression Vectors

Next, the anti-cancer therapeutic activity of the double promoter plasmid H19-DTA-P3-DTA was tested in the T24P in vivo bladder cancer model described hereinabove in Examples 9-10. Experiments were performed as described above.

Three injections of H19-DTA at two-day intervals were able to inhibit the tumor growth by at least 49% compared to H19-Luc treatment (FIG. 25), and P3-DTA administered in the same manner inhibited tumor growth by at least 50.5% compared to P3-Luc treatment (FIG. 38). In contrast, 3 injections of H19-DTA-P3-DTA at two-day intervals inhibited tumor development by at least 59% compared to H19-Luc-P3-Luc treatment (FIG. 39). Thus, H19-DTA-P3-DTA exhibited enhanced anti-tumor activity, compared to each of the single-promoter constructs (H19-DTA and P3-DTA).

Overall, the results presented herein demonstrate that multiple promoter constructs of the present invention exhibit enhanced, greater-than-additive ability to inhibit tumor development, compared to the corresponding single-promoter constructs.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. An isolated nucleic acid construct, comprising:
   a) a first open reading frame encoding a diphtheria toxin, the first open reading frame being operably linked to an H19 promoter; and
   b) a second open reading frame encoding a diphtheria toxin, the second open reading frame being operably linked to an IGF-II-promoter selected from IGF-II P3 and IGF-II P4 promoter sequences; and
   wherein the diphtheria toxin is diphtheria toxin A (DTA) or comprises a sequence that is at least 90% homologous to the sequence set forth in SEQ ID NO: 7; and
   wherein the nucleic acid sequence of the H19 promoter exhibits H19 promoter activity and is at least 90% homologous to SEQ ID NOS: 1 or 2, and the nucleic acid sequence of the IGF-II P4 promoter exhibits IGF-II P4 promoter activity and is at least 90% homologous to SEQ ID NO: 9, the nucleic acid sequence of the IGF-II P3 promoter exhibits IGF-II P3 promoter activity and is at least 90% homologous to the sequence selected from SEQ ID NO: 8, SEQ ID NO: 12, and SEQ ID NO: 17.

2. The nucleic acid construct of claim 1, wherein the H19 promoter comprises the nucleic acid sequence as set forth in any one of SEQ ID NOS: 1 or 2, or wherein the IGF-II P4 promoter comprises the nucleic acid sequence as set forth in SEQ ID NO: 9, or wherein the IGF-II P3 promoter comprises the nucleic acid sequence as set forth in a sequence selected from SEQ ID NO: 8, SEQ ID NO: 12, and SEQ ID NO: 17.

3. The nucleic acid construct of claim 1, wherein the nucleic acid construct is a plasmid.

4. The nucleic acid construct of claim 1, wherein the IGF-II promoter-is an IGF-II P3 promoter.

5. The nucleic acid construct of claim 4, further comprising a third open reading frame encoding a diphtheria toxin, with the third open reading frame being operably linked to an IGF-II P4 promoter.

6. The nucleic acid construct of claim 1, wherein the IGF-II promoter-is an IGF-II P4 promoter.

7. The nucleic acid construct of claim 6, further comprising a third open reading frame encoding a diphtheria toxin, with the third open reading frame being operably linked to an IGF-II P3 promoter.

8. An isolated eukaryotic expression vector comprising the nucleic acid construct of claim 1.

9. An isolated nucleic acid construct, comprising:
   a) a first open reading frame encoding a diphtheria toxin, said first open reading frame being operably linked to an IGF-II P3 promoter; and
   b) a second open reading frame encoding the diphtheria toxin, said second open reading frame being operably linked to an IGF-II P4 promoter;
   wherein the IGF-II P3-promoter comprises the nucleic acid sequence as set forth in the sequence selected from SEQ ID NO: 8, SEQ ID NO: 12, and SEQ ID NO: 17, or wherein the IGF-II P4-promoter comprises the nucleic acid sequence as set forth in SEQ ID NO: 9.

10. The nucleic acid construct of claim 9, wherein the diphtheria toxin is diphtheria toxin A (DTA), or wherein the diphtheria toxin comprises the sequence set forth in SEQ ID NO: 7.

11. An isolated eukaryotic expression vector comprising the nucleic acid construct of claim 9.

12. The nucleic acid construct of claim 9, further comprising a third open reading frame encoding the diphtheria toxin, with the third open reading frame being operably linked to an H19 promoter.

13. An isolated nucleic acid construct, comprising:
   a first open reading frame encoding a cytotoxic or cytostatic gene product, the first open reading frame being operably linked to a first promoter; and
   a second open reading frame encoding the cytotoxic or cytostatic gene product, the second open reading frame being operably linked to a second promoter;
   wherein the first promoter and the second promoter are selected from the group consisting of:
   i) the first promoter being an H19 promoter comprising the nucleic acid sequence as set forth in any one of SEQ ID NOS: 1 or 2, and the second promoter being an IGF-II P4 promoter comprising the nucleic acid sequence as set forth in SEQ ID NO: 9;
   ii) the first promoter being an H19 promoter comprising the nucleic acid sequence as set forth in any one of SEQ ID NOS: 1 or 2, and the second promoter being an IGF-II P3 promoter comprising the nucleic acid sequence as set forth in a sequence selected from SEQ ID NO: 8, SEQ ID NO: 12, and SEQ ID NO: 17; and
   iii) the first promoter being an IGF-II P4 promoter comprising the nucleic acid sequence as set forth in SEQ ID NO: 9, and the second promoter being an IGF-II P3 promoter comprising the nucleic acid sequence as set forth in the sequence selected from SEQ ID NO: 8, SEQ ID NO: 12, and SEQ ID NO: 17.

14. The nucleic acid construct of claim 2, wherein the H19 promoter comprises the nucleic acid sequence set forth in SEQ ID NO: 2.

15. An isolated nucleic acid construct comprising:
   a) a first open reading frame encoding a diphtheria toxin, the first open reading frame being operably linked to an H19 promoter; and
   b) a second open reading frame encoding a diphtheria toxin, the second open reading frame being operably linked to an IGF-II promoter selected from IGF-II P3 and IGF-II P4 promoter sequences, and wherein the nucleic acid sequence of the diphtheria toxin is at least 90% homologous to SEQ ID NO: 7, and
wherein the H19 promoter comprises the nucleic acid sequence as set forth in any one of SEQ ID NOS: 1 or 2, and wherein the IGF-II P4 promoter comprises the nucleic acid sequence as set forth in SEQ ID NO: 9, or wherein the IGF-II P3 promoter comprises the nucleic acid sequence as set forth in the sequence selected from SEQ ID NO: 8, SEQ ID NO: 12, and SEQ ID NO: 17.

* * * * *